(12) United States Patent
Celeste et al.

(10) Patent No.: US 10,077,319 B2
(45) Date of Patent: Sep. 18, 2018

(54) ANTI-PCSK9-GLP-1 FUSIONS AND METHODS FOR USE

(71) Applicants: MedImmune, LLC, Gaithersburg, MD (US); MedImmune Limited, Cambridge (GB)

(72) Inventors: Anthony Celeste, Gaithersburg, MD (US); Matthieu Chodorge, Cambridge (GB); Andrew Buchanan, Cambridge (GB); Cristina Rondinone, Gaithersburg, MD (US); Joseph Grimsby, Gaithersburg, MD (US); Peter Ravn, Cambridge (GB); Jonathan Seaman, Cambridge (GB); David Fairman, Cambridge (GB)

(73) Assignees: MedImmune, LLC, Gaithersburg, MD (US); MedImmune Limited, Cambridge (GB)

( * ) Notice: Subject to any disclaimer, the term of this patent is extended or adjusted under 35 U.S.C. 154(b) by 0 days.

(21) Appl. No.: 15/117,985

(22) PCT Filed: Feb. 20, 2015

(86) PCT No.: PCT/US2015/016911
§ 371 (c)(1),
(2) Date: Aug. 10, 2016

(87) PCT Pub. No.: WO2015/127273
PCT Pub. Date: Aug. 27, 2015

(65) Prior Publication Data
US 2016/0369010 A1 Dec. 22, 2016

Related U.S. Application Data

(60) Provisional application No. 61/943,300, filed on Feb. 21, 2014, provisional application No. 61/944,550, filed on Feb. 25, 2014.

(51) Int. Cl.
| | | |
|---|---|---|
| *A61K 39/00* | (2006.01) |
| *A61K 38/00* | (2006.01) |
| *C07K 16/40* | (2006.01) |
| *A61K 38/26* | (2006.01) |
| *A61K 39/395* | (2006.01) |
| *C07K 14/605* | (2006.01) |

(52) U.S. Cl.
CPC .............. *C07K 16/40* (2013.01); *A61K 38/26* (2013.01); *A61K 39/3955* (2013.01); *C07K 14/605* (2013.01); *A61K 38/00* (2013.01); *A61K 39/00* (2013.01); *A61K 2039/505* (2013.01); *C07K 2317/24* (2013.01); *C07K 2317/92* (2013.01); *C07K 2317/94* (2013.01); *C07K 2319/00* (2013.01)

(58) Field of Classification Search
CPC .............................. C07K 16/40; C07K 14/605
See application file for complete search history.

(56) References Cited

U.S. PATENT DOCUMENTS

| | | | |
|---|---|---|---|
| 2008/0269130 A1* | 10/2008 | Stoffers ................. | A61K 38/26 514/1.1 |
| 2010/0009904 A1 | 1/2010 | Lv et al. | |
| 2011/0034373 A1 | 2/2011 | Coskun et al. | |
| 2012/0100141 A1* | 4/2012 | Herring ................. | C07K 16/18 424/134.1 |
| 2012/0238496 A1 | 9/2012 | Fan et al. | |
| 2013/0071390 A1 | 3/2013 | Stadheim et al. | |
| 2013/0302399 A1 | 11/2013 | Feldhaus et al. | |
| 2013/0330336 A1 | 12/2013 | Darling et al. | |

FOREIGN PATENT DOCUMENTS

| | | |
|---|---|---|
| CN | 101665799 | 3/2010 |
| WO | WO 2011/111007 | 9/2011 |
| WO | WO 2012/154999 | 11/2012 |
| WO | WO 2015/155139 | 10/2015 |
| WO | WO 2015/155140 | 10/2015 |
| WO | WO 2015/155141 | 10/2015 |

OTHER PUBLICATIONS

Murage, E.N., et al., Search for alpha-helical propensity in the receptor-bound conformation of glucagon-like peptide-1, *Bioorg Med Chem.* Dec. 1, 2008;16(23):10106-101112. Epub Oct. 5, 2008.
International Search Report for International Patent Application PCT/US2015/016911, dated Jul. 7, 2015, pp. 1-4.
Written Opinion of the International Searching Authority for International Patent Application PCT/US2015/016911, dated Jul. 7, 2015, pp. 1-6.

* cited by examiner

*Primary Examiner* — Gyan Chandra

(57) ABSTRACT

This application provides anti-PCSK9~GLP-1 fusions and methods for use.

20 Claims, 72 Drawing Sheets
Specification includes a Sequence Listing.

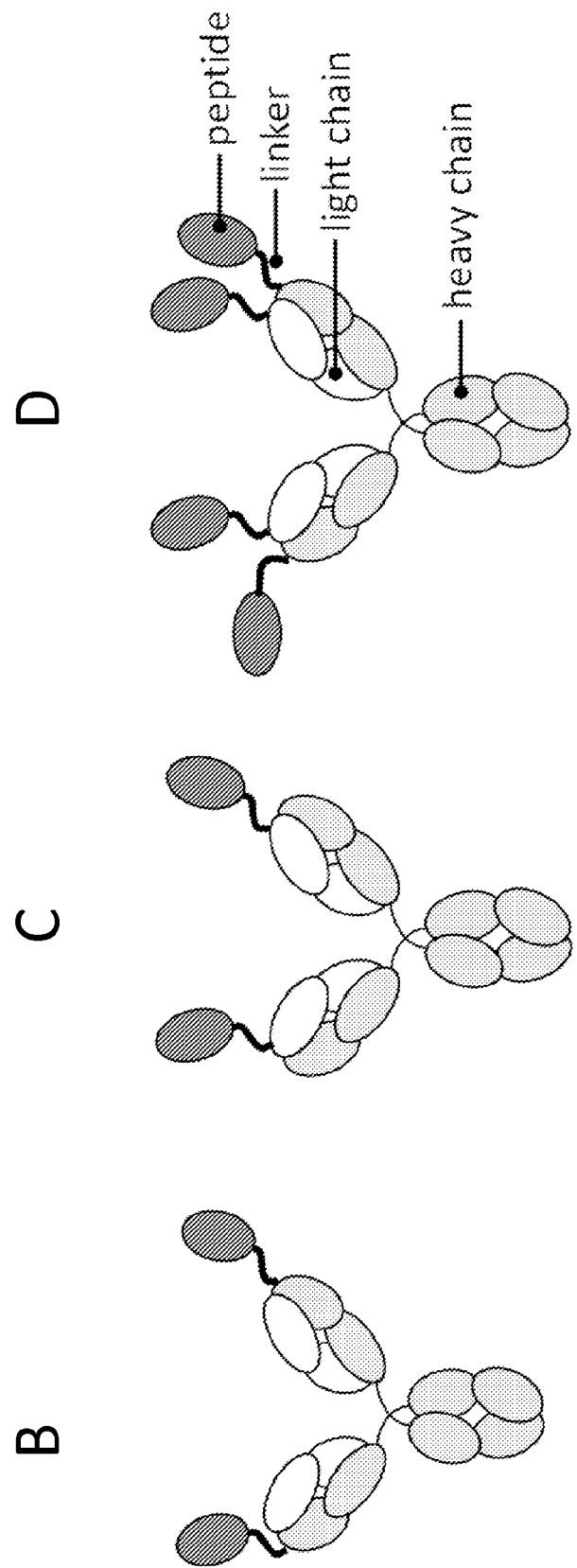
FIG. 1B-D

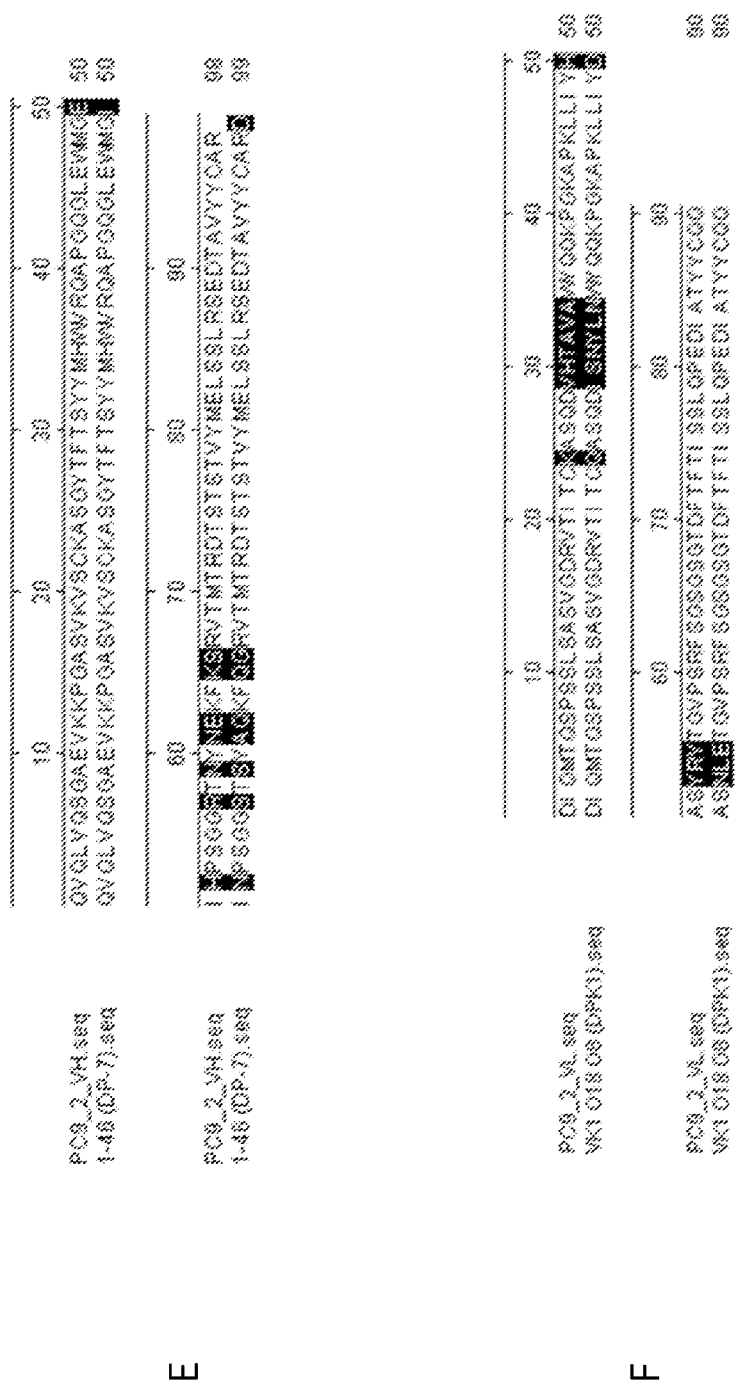
FIG. 1E-F

FIGS. 2A-B
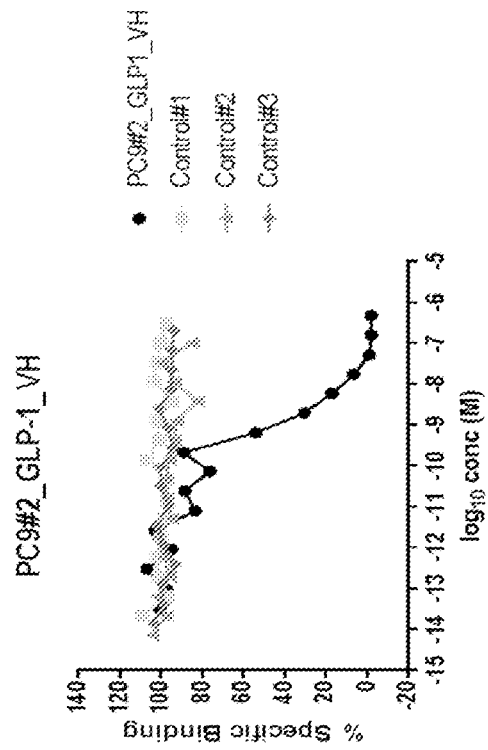
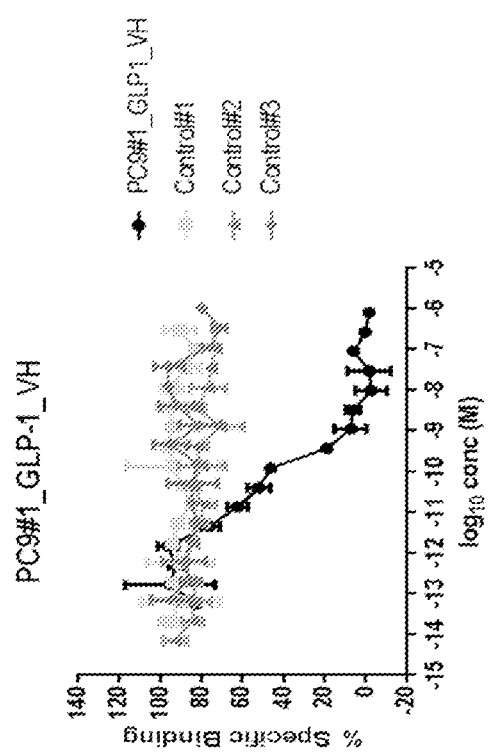

FIGS. 2C-D
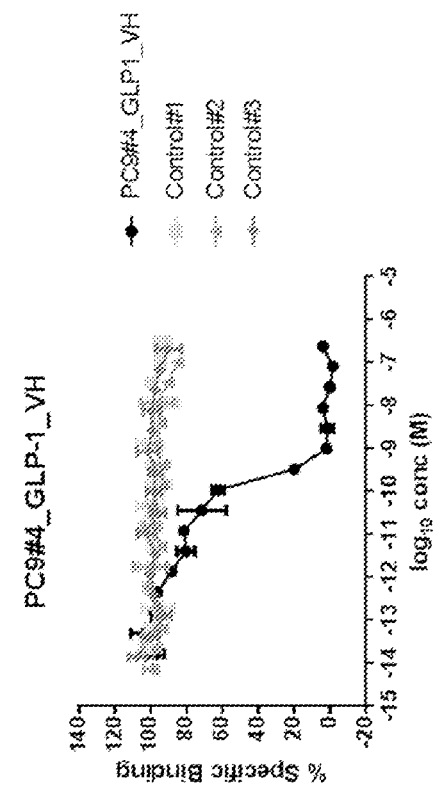
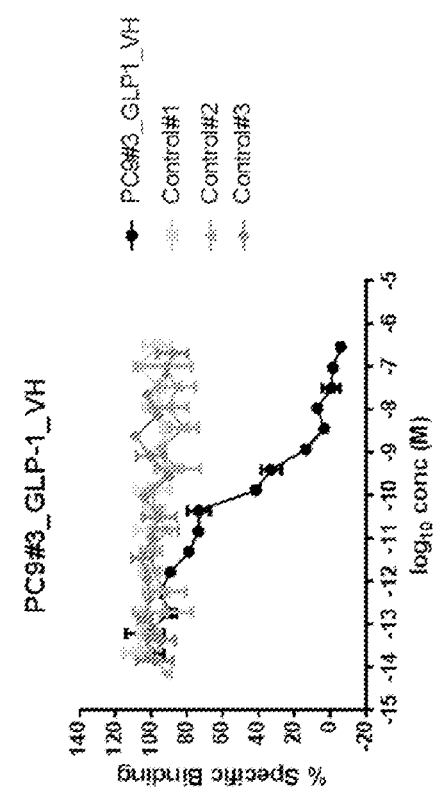

FIGS. 2E-F
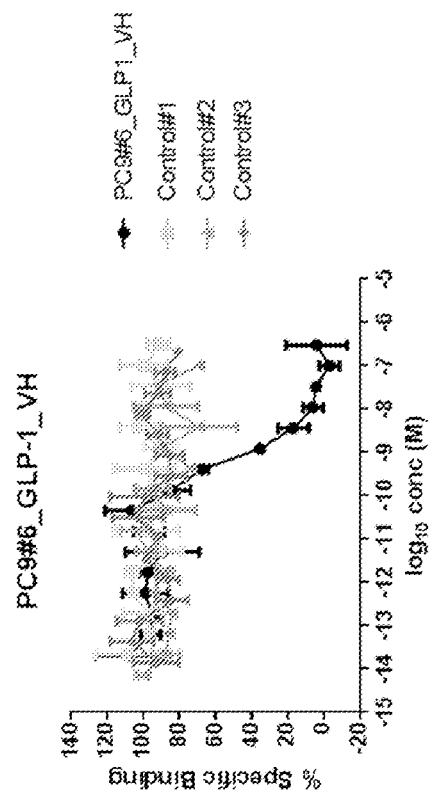
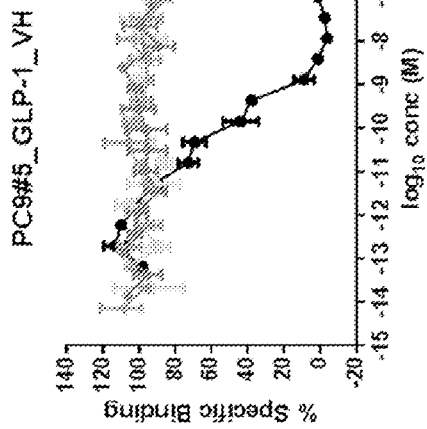

FIGS. 3A-B
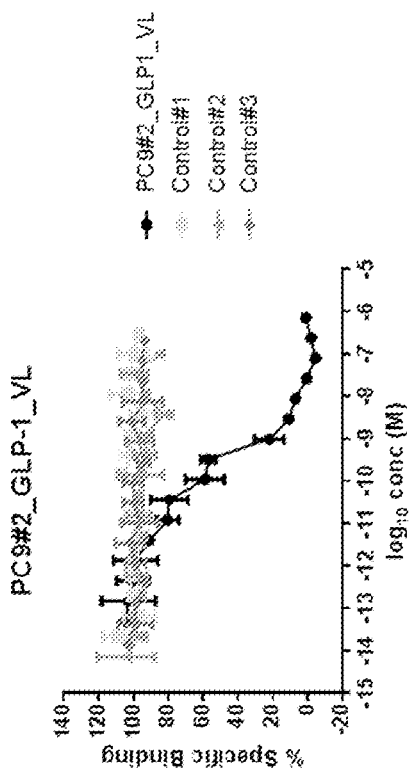
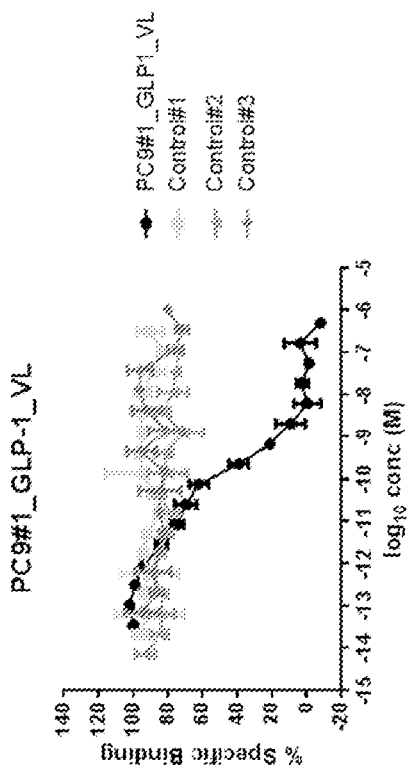

FIGS. 3C-D
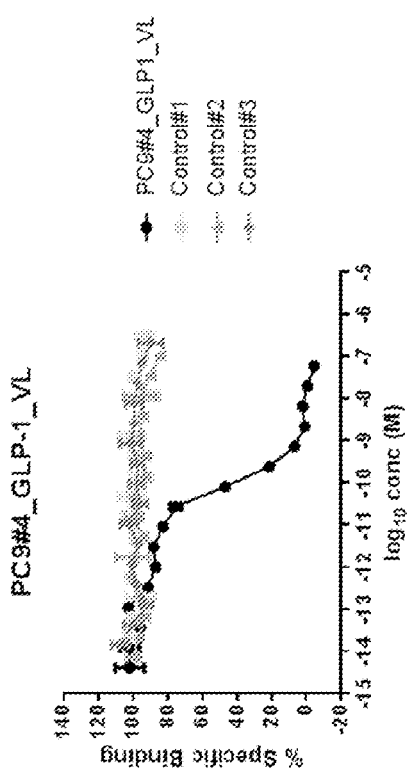
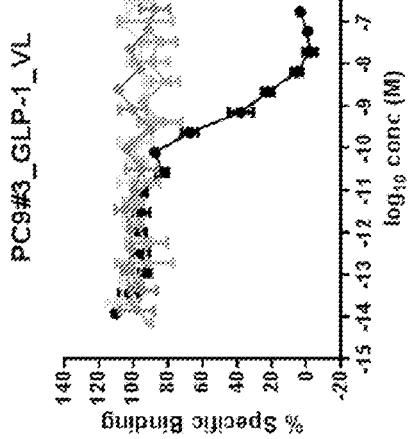

FIGS. 3E-F
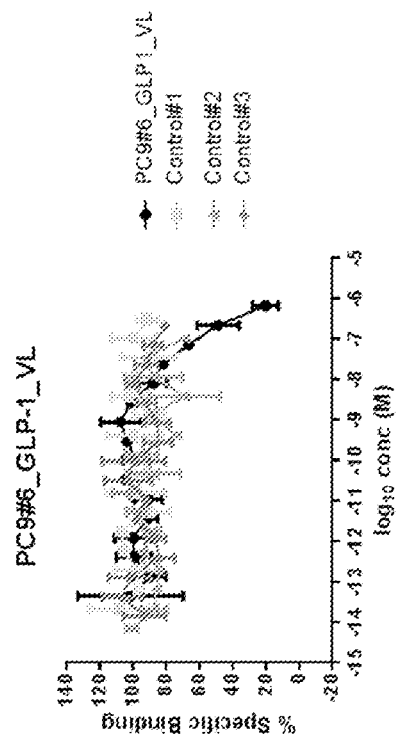
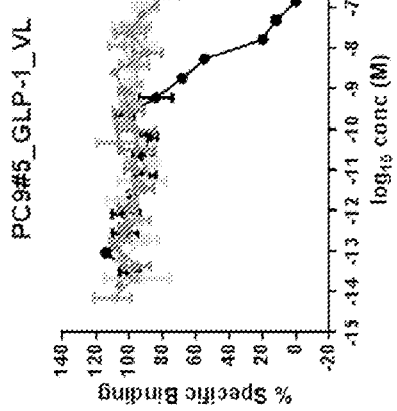

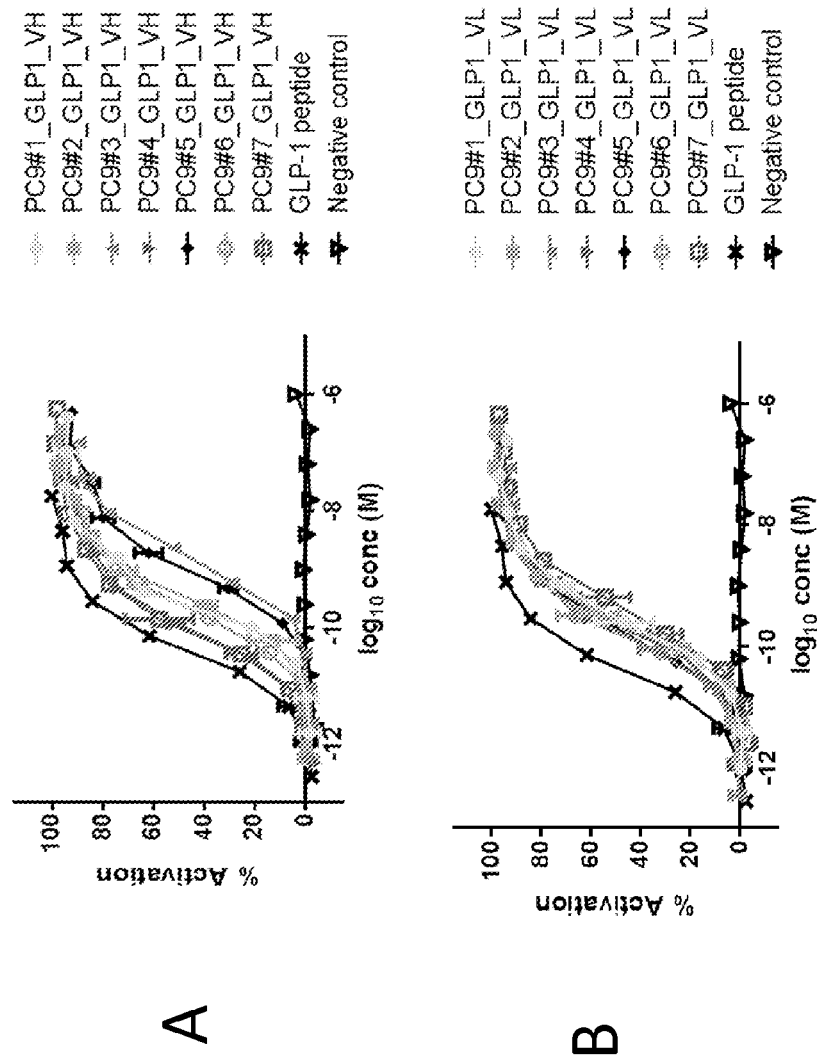
FIGS. 4A-B

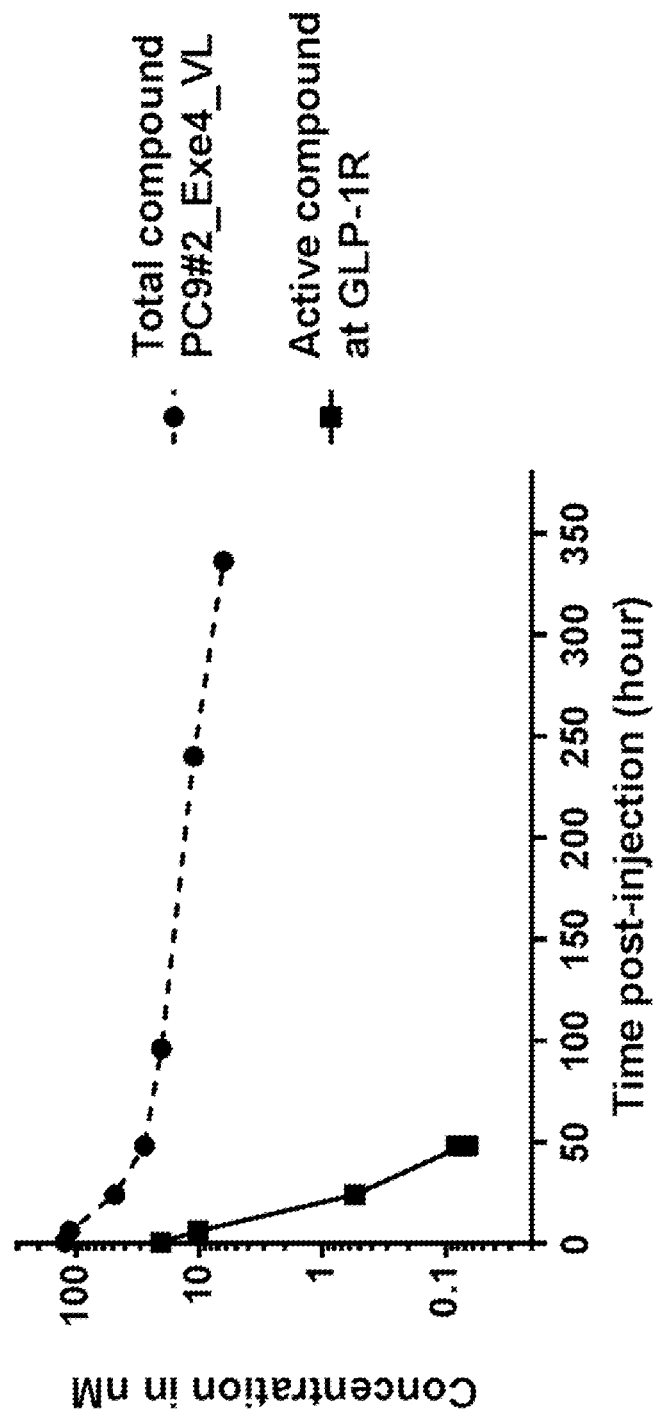

| | Peptide sequence | Linker sequence | SEQ ID NO. |
|---|---|---|---|
| GLP-1 analogue | HGEGTFTSDVSSYLEEQAAKEFIAWLVKGG | GGGGSGGGGSGGGGSGGGGSA | 501 |
| NGS#1 | HGEGTFTSDVSSYLEEQNASEFIAWLVKGG | GGGGSGGGGSGGGGSGGGGSA | 502 |
| NGS#2 | HGEGTFTSDVSSYLEEQAAKEFIAWLVNGS | GGGGSGGGGSGGGGSGGGGSA | 503 |
| NGS#3 | HGEGTFTSDVSSYLEEQAAKEFIAWLVKNG | SGGGGSGGGGSGGGGSGGGGSA | 504 |
| NGS#4 | HGEGTFTSDVSSYLEEQAAKEFIAWLVKGN | GSGGGGSGGGGSGGGGSGGGGSA | 505 |
| NGS#5 | HGEGTFTSDVSSYLEEQAAKEFIAWLVKGG | NGSGGGGSGGGGSGGGGSGGGGSA | 506 |
| NGS#6 | HGEGTFTSDVSSYLEEQAAKEFIAWLVKGG | GNGSGGGGSGGGGSGGGGSGGGGSA | 507 |
| NGS#7 | HGEGTFTSDVSSYLEEQAAKEFIANLSKGG | GGGGSGGGGSGGGGSGGGGSA | 508 |
| NGS#8 | HGEGTFTSDVSSYLEEQAAKEFIANLTKGG | GGGGSGGGGSGGGGSGGGGSA | 509 |

B

| Peptide name | 1 | 11 | 21 | 31 | 41 | 51 | |
|---|---|---|---|---|---|---|---|
| Exendin-4 | HGEGTFTSDL | SKQMEEEAVR | LFIEWLKNGG | PSSGAPPPS | | | SEQ ID NO. 12 |
| DS8#1 | HGEGTFTSDL | SKQMEEEAVR | LFIEWLKNGG | PSSGAPPPS | C | | SEQ ID NO. 30 |
| DS8#2 | HGECTFTSDL | SKQMEEEAVR | LFIEWLKNGG | PSSGAPPPS | C | | SEQ ID NO. 31 |
| DS8#3 | HGEGTFTSDL | SKQMEEEEVR | LFIEWLKNGG | PSSGAPPG | | | SEQ ID NO. 32 |

FIG. 8A-B
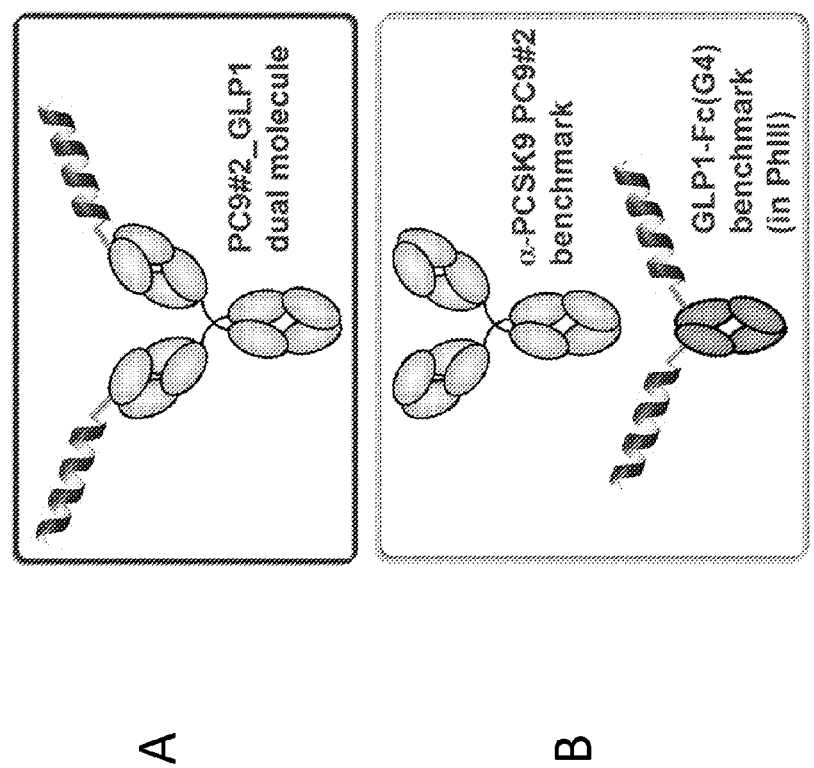

PC9#2_GLP-1_VL

FIG. 11
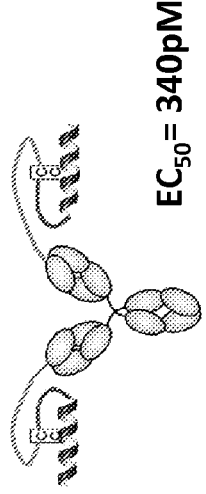
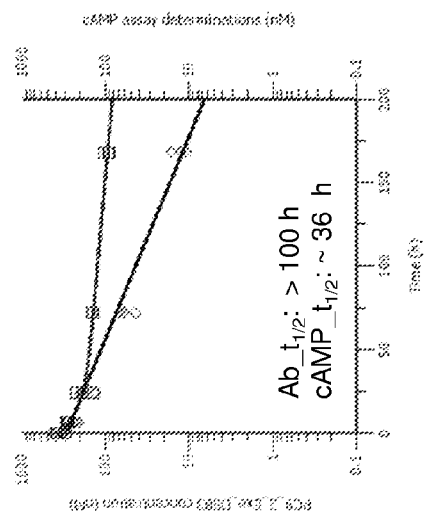

FIG. 14A
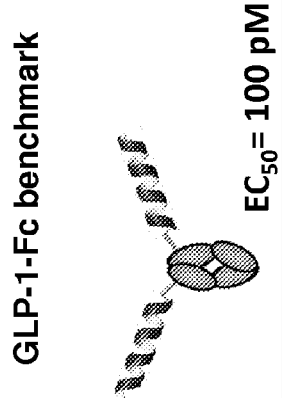
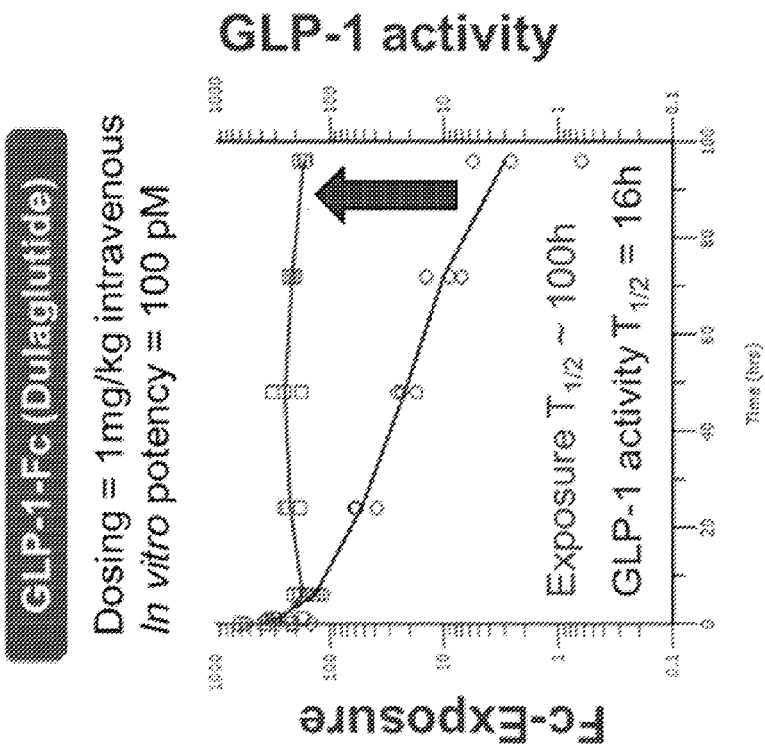

FIG. 17

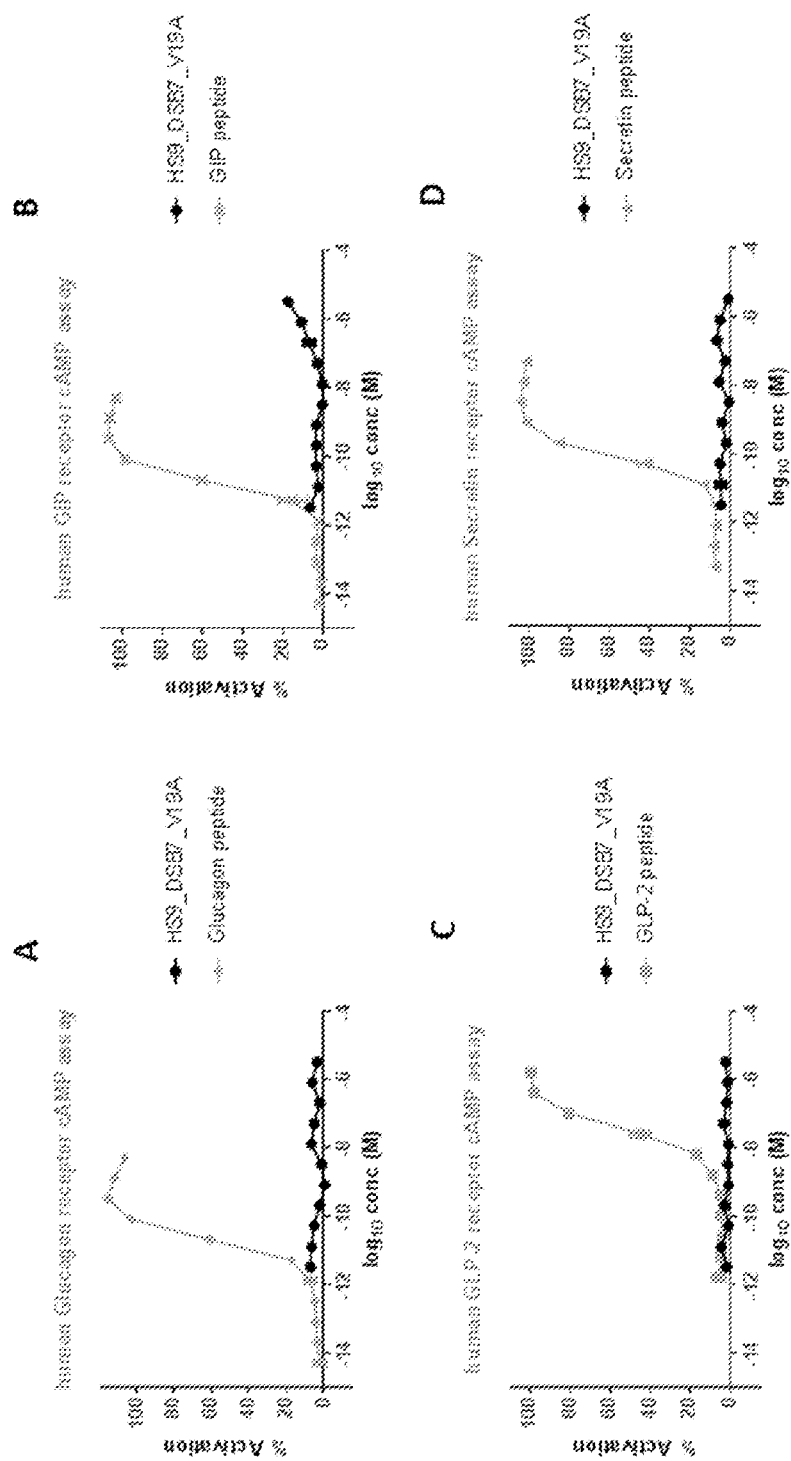
FIG. 29A-D

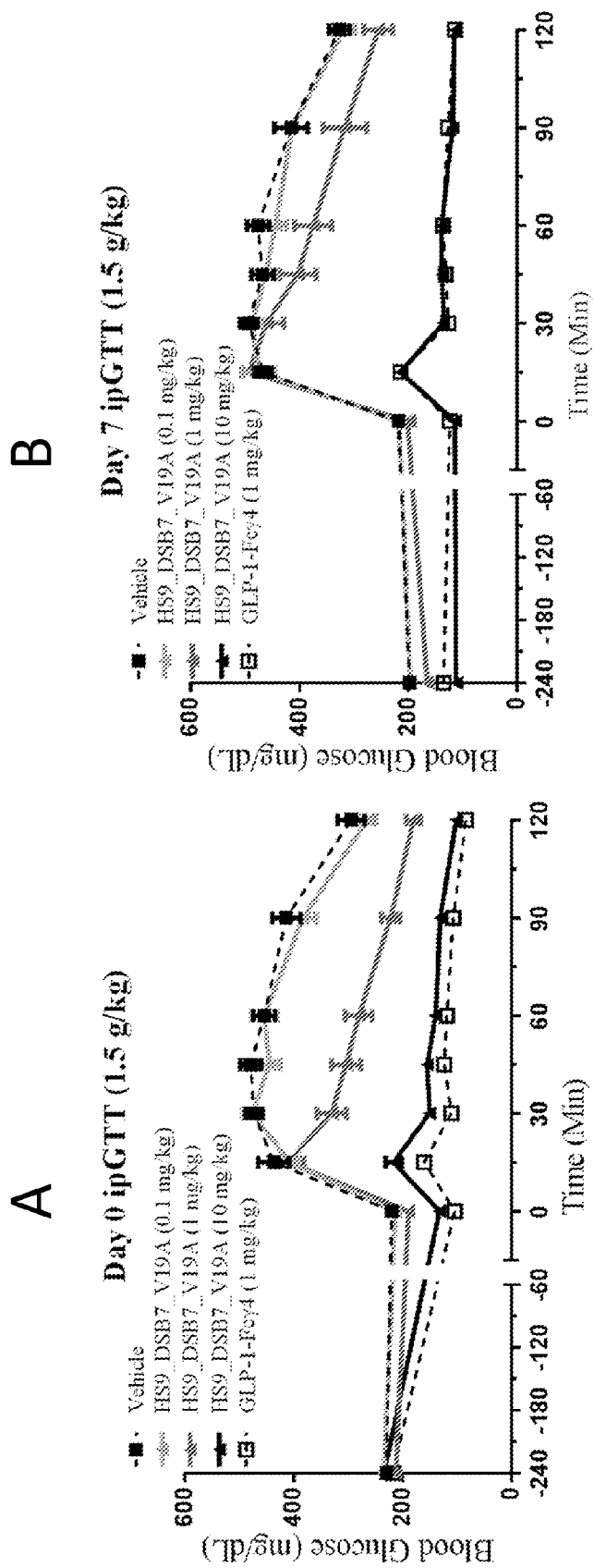
FIG. 47A-B

FIG. 48A-B
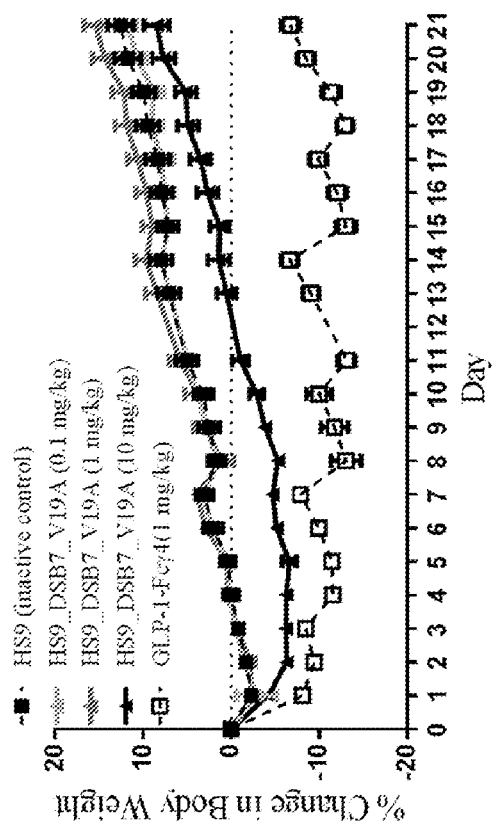
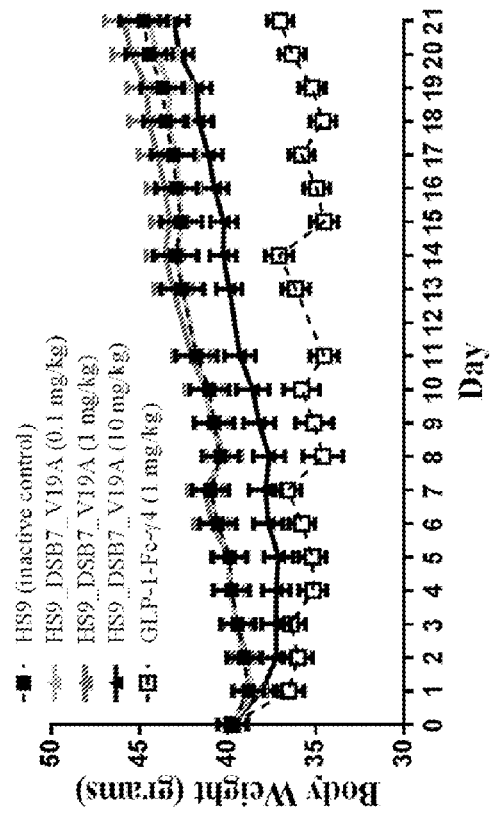

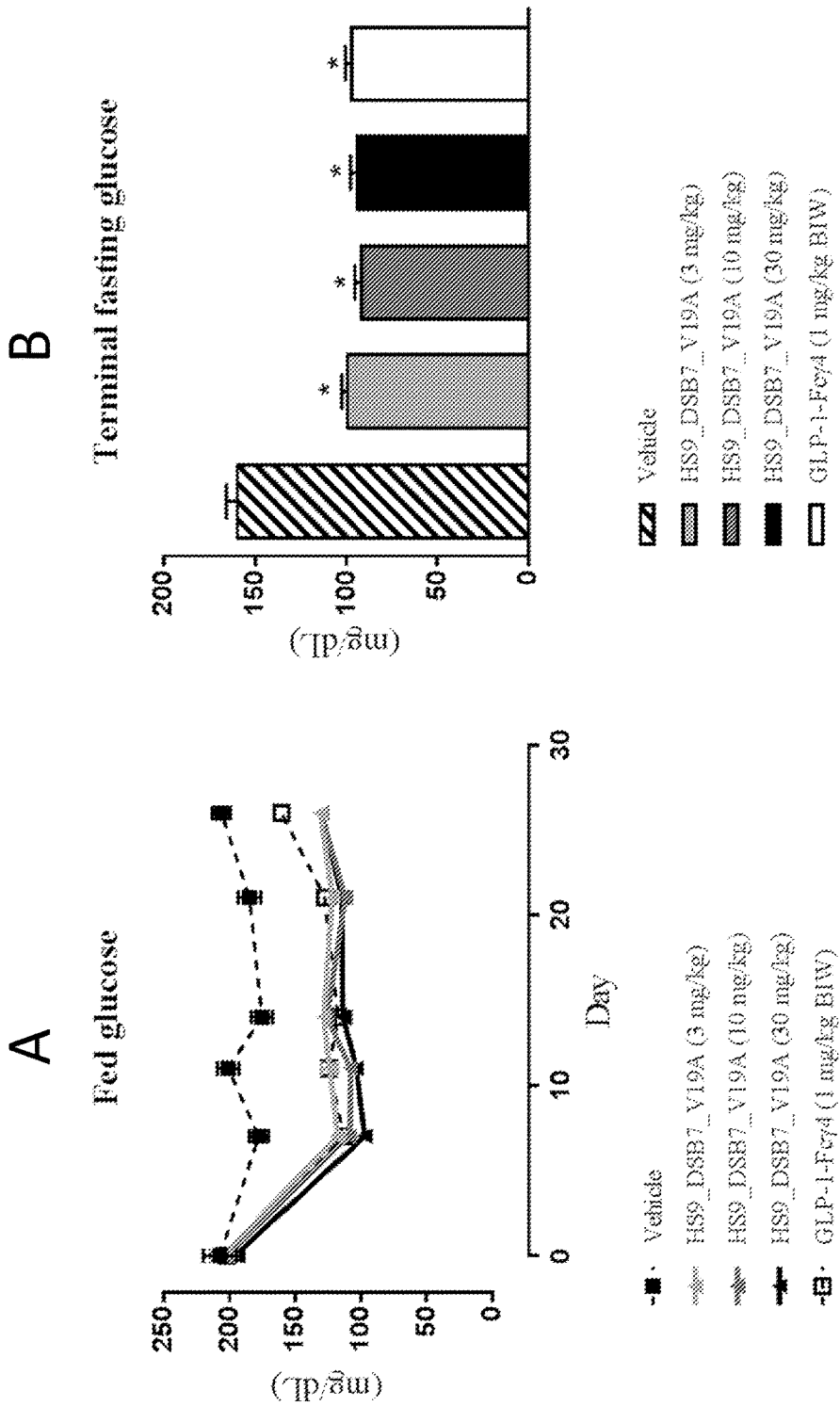
FIG. 50A-B

SEQUENCE LISTING

```
<160> NUMBER OF SEQ ID NOS: 510

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Glu Ile Ser Pro Ser Gly Gly Ser Thr Ser Tyr Asn Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
                100                 105                 110

Thr Val Thr Val Ser Ser
            115

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Lys Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
                100                 105

<210> SEQ ID NO 3
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

His Gly Glu Gly Thr Phe Thr Ser Asp Leu Ser Lys Gln Met Glu Glu
1               5                   10                  15

Glu Cys Ala Arg Leu Phe Ile Glu Trp Leu Lys Asn Gly Gly Pro Ser
                20                  25                  30

Ser Gly Ala Pro Pro Pro Gly Cys Gly
            35                  40

<210> SEQ ID NO 4
<211> LENGTH: 16

-continued

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Gly Ser Gly Gly Gly Ser Gly Gly Gly Gly Ser Ala
1               5                   10                  15

<210> SEQ ID NO 5
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile His Pro Ser Gly Gly Ser Thr Ser Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
        115

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val His Thr Ala
            20                  25                  30

Val Ala Trp Tyr Gln Gln Lys Pro Gly Lys Ala Pro Lys Leu Leu Ile
        35                  40                  45

Tyr His Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

```
<210> SEQ ID NO 7
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

His Gly Glu Gly Thr Phe Thr Ser Asp Leu Ser Lys Gln Met Glu Glu
1               5                   10                  15

Glu Cys Val Arg Leu Phe Ile Glu Trp Leu Lys Asn Gly Gly Pro Ser
                20                  25                  30

Ser Gly Ala Pro Pro Pro Ser Cys Gly
            35                  40

<210> SEQ ID NO 8
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Glu Ile His Pro Ser Gly Gly Arg Thr Asn Tyr Asn Glu Lys Phe
        50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
                100                 105                 110

Thr Val Thr Val Ser Ser
            115

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val His Thr Ala
                20                  25                  30

Val Ala Trp Tyr Gln Gln Lys Pro Gly Lys Ala Pro Lys Leu Leu Ile
            35                  40                  45

Tyr His Ala Ser Tyr Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80
```

```
Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105
```

<210> SEQ ID NO 10
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Ser Pro Phe Gly Gly Arg Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
        115
```

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105
```

<210> SEQ ID NO 12
<211> LENGTH: 39
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 13
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

His Gly Glu Gly Thr Phe Thr Ser Asp Leu Ser Lys Gln Met Glu Glu
1               5                   10                  15

Glu Cys Val Arg Leu Phe Ile Glu Trp Leu Lys Asn Gly Gly Pro Ser
            20                  25                  30

Ser Gly Ala Pro Pro Pro Gly Cys Gly Gly Gly Gly Ser Gly Gly
        35                  40                  45

Gly Gly Ser Gly Gly Gly Gly Ser Ala
    50                  55

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Tyr Tyr Met His
1               5

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Ile Ser Pro Ser Gly Gly Ser Thr Ser Tyr Asn Gln Lys Phe Gln
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16
```

```
Glu Ile His Pro Ser Gly Gly Ser Thr Ser Tyr Asn Gln Lys Phe Gln
1               5                   10                  15

Gly
```

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Glu Ile His Pro Ser Gly Gly Arg Thr Asn Tyr Asn Glu Lys Phe Lys
1               5                   10                  15

Ser
```

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Glu Ile Ser Pro Phe Gly Gly Arg Thr Asn Tyr Asn Glu Lys Phe Lys
1               5                   10                  15

Ser
```

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Glu Arg Pro Leu Tyr Ala Ser Asp Leu
1               5
```

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Gln Ala Ser Gln Asp Val Lys Thr Ala Val Ala
1               5                   10
```

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Gln Ala Ser Gln Asp Val His Thr Ala Val Ala
1               5                   10
```

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Ala Ser Gln Asp Val His Thr Ala Val Ala
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ala Ser Gln Gly Ile Ser Ser Ala Leu Ala
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Ala Ser Tyr Arg Tyr Thr
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

His Ala Ser Tyr Arg Tyr Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Gln Arg Tyr Ser Leu Trp Arg Thr
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 27

Gly Gly Gly Gly Ser
1               5

<210> SEQ ID NO 28
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 29
<211> LENGTH: 31
<212> TYPE: PRT
<213> ORGANISM: Homo sapiens

<400> SEQUENCE: 29

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 30
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

His Gly Glu Gly Thr Phe Thr Ser Cys Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Gly Gly Gly Gly Gly
        35                  40                  45

Gly Gly Cys Gly Gly
    50

<210> SEQ ID NO 31
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

His Gly Glu Cys Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Gly Gly Gly Gly Gly
        35                  40                  45
```

```
Gly Gly Gly Cys Gly
        50

<210> SEQ ID NO 32
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

His Gly Glu Gly Thr Phe Thr Ser Asp Leu Ser Lys Gln Met Glu Glu
1               5                   10                  15

Glu Cys Val Arg Leu Phe Ile Glu Trp Leu Lys Asn Gly Gly Pro Ser
            20                  25                  30

Ser Gly Ala Pro Pro Gly Cys
        35

<210> SEQ ID NO 33
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

His Gly Glu Gly Thr Phe Thr Ser Asp Leu Ser Lys Gln Met Glu Glu
1               5                   10                  15

Glu Ala Val Arg Cys Phe Ile Glu Trp Leu Lys Asn Gly Gly Pro Ser
            20                  25                  30

Ser Gly Ala Gly Gly Cys Ser
        35

<210> SEQ ID NO 34
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

His Gly Glu Gly Thr Phe Thr Ser Cys Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Gly Gly Gly Gly Gly
        35                  40                  45

Cys Gly Gly
        50

<210> SEQ ID NO 35
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

His Gly Glu Gly Thr Phe Thr Ser Cys Leu Ser Lys Gln Met Glu Glu
1               5                   10                  15
```

```
Glu Ala Val Arg Leu Phe Ile Glu Trp Leu Lys Asn Gly Gly Pro Ser
            20                  25                  30

Ser Gly Ala Pro Pro Ser Gly Gly Gly Gly Gly Gly Gly
        35                  40                  45

Gly Cys Gly Gly Gly
    50
```

```
<210> SEQ ID NO 36
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

His Gly Glu Gly Thr Phe Thr Ser Asp Leu Ser Lys Gln Met Glu Glu
1               5                   10                  15

Glu Cys Val Arg Leu Phe Ile Glu Trp Leu Lys Asn Gly Gly Pro Ser
            20                  25                  30

Ser Gly Ala Pro Pro Pro Gly Cys Gly
        35                  40
```

```
<210> SEQ ID NO 37
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

His Gly Glu Gly Thr Phe Thr Ser Asp Leu Ser Lys Gln Met Glu Glu
1               5                   10                  15

Glu Cys Val Arg Leu Phe Ile Glu Trp Leu Lys Asn Gly Gly Pro Ser
            20                  25                  30

Ser Gly Ala Pro Pro Gly Gly Cys Gly
        35                  40
```

```
<210> SEQ ID NO 38
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

His Gly Glu Gly Thr Phe Thr Ser Asp Leu Ser Lys Gln Met Glu Glu
1               5                   10                  15

Glu Ala Val Arg Cys Phe Ile Glu Trp Leu Lys Asn Gly Gly Pro Ser
            20                  25                  30

Ser Gly Ala Pro Pro Cys Gly Gly
        35                  40
```

```
<210> SEQ ID NO 39
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 39

His Gly Glu Gly Thr Phe Thr Ser Asp Leu Ser Lys Gln Met Glu Glu
1               5                   10                  15

Glu Ala Val Arg Cys Phe Ile Glu Trp Leu Lys Asn Gly Gly Pro Ser
            20                  25                  30

Ser Gly Ala Pro Pro Gly Cys Gly
        35                  40

<210> SEQ ID NO 40
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

His Gly Glu Gly Thr Phe Thr Ser Asp Leu Ser Lys Gln Met Glu Glu
1               5                   10                  15

Glu Ala Val Arg Leu Phe Ile Glu Cys Leu Lys Asn Gly Gly Pro Ser
            20                  25                  30

Ser Gly Ala Cys Gly Gly Ser
        35

<210> SEQ ID NO 41
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

His Gly Glu Gly Thr Phe Thr Ser Asp Leu Ser Lys Gln Met Glu Glu
1               5                   10                  15

Glu Ala Val Arg Leu Phe Ile Glu Cys Leu Lys Asn Gly Gly Pro Ser
            20                  25                  30

Ser Gly Ala Pro Cys Pro Ser
        35

<210> SEQ ID NO 42
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

His Gly Glu Gly Thr Phe Thr Ser Asp Leu Ser Lys Gln Met Glu Glu
1               5                   10                  15

Glu Ala Val Arg Leu Phe Ile Glu Cys Leu Lys Asn Gly Gly Pro Ser
            20                  25                  30

Ser Gly Ala Pro Pro Cys Ser
        35

<210> SEQ ID NO 43
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 43

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Ala Asp
        35                  40                  45

Ile Gln Met Thr Gln Ser Pro Ser Ser Leu Ser Ala Ser Val Gly Asp
    50                  55                  60

Arg Val Thr Ile Thr Cys Lys Ala Ser Gln Asp Val His Thr Ala Val
65                  70                  75                  80

Ala Trp Tyr Gln Gln Lys Pro Gly Lys Ala Pro Lys Leu Leu Ile Tyr
                85                  90                  95

His Ala Ser Tyr Arg Tyr Thr Gly Val Pro Ser Arg Phe Ser Gly Ser
                100                 105                 110

Gly Ser Gly Thr Asp Phe Thr Phe Thr Ile Ser Ser Leu Gln Pro Glu
            115                 120                 125

Asp Ile Ala Thr Tyr Tyr Cys Gln Gln Arg Tyr Ser Leu Trp Arg Thr
    130                 135                 140

Phe Gly Gln Gly Thr Lys Leu Glu Ile Lys Arg
145                 150                 155

<210> SEQ ID NO 44
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

His Val Glu Gly Thr Phe Thr Ser Asp Leu Ser Lys Gln Met Glu Glu
1               5                   10                  15

Glu Cys Val Arg Leu Phe Ile Glu Trp Leu Lys Asn Gly Gly Pro Ser
            20                  25                  30

Ser Gly Ala Pro Pro Pro Gly Cys Gly
        35                  40

<210> SEQ ID NO 45
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

His Gly Glu Gly Thr Phe Thr Ser Asp Leu Ser Lys Gln Met Ala Glu
1               5                   10                  15

Glu Cys Val Arg Leu Phe Ile Glu Trp Leu Lys Asn Gly Gly Pro Ser
            20                  25                  30

Ser Gly Ala Pro Pro Pro Gly Cys Gly
        35                  40

<210> SEQ ID NO 46
<211> LENGTH: 41
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 46

His Gly Glu Gly Thr Phe Thr Ser Asp Leu Ser Lys Gln Met Glu Glu
1               5                   10                  15

Glu Cys Val Arg Leu Phe Ile Glu Trp Ile Lys Asn Gly Gly Pro Ser
            20                  25                  30

Ser Gly Ala Pro Pro Pro Gly Cys Gly
        35                  40

<210> SEQ ID NO 47
<211> LENGTH: 164
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 47

His Gly Glu Gly Thr Phe Thr Ser Asp Leu Ser Lys Gln Met Glu Glu
1               5                   10                  15

Glu Cys Ala Arg Leu Phe Ile Glu Trp Leu Lys Asn Gly Gly Pro Ser
            20                  25                  30

Ser Gly Ala Pro Pro Pro Gly Cys Gly Gly Gly Gly Ser Gly Gly
        35                  40                  45

Gly Gly Ser Gly Gly Gly Ser Ala Asp Ile Gln Met Thr Gln Ser
        50                  55                  60

Pro Ser Ser Leu Ser Ala Ser Val Gly Asp Arg Val Thr Ile Thr Cys
65              70                  75                  80

Gln Ala Ser Gln Asp Val Lys Thr Ala Val Ala Trp Tyr Gln Gln Lys
            85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 48
<211> LENGTH: 177
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 48

His Gly Glu Gly Thr Phe Thr Ser Cys Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Gly Gly Gly Gly Gly
        35                  40                  45

Gly Gly Cys Gly Gly Gly Gly Ser Gly Gly Gly Gly Ser Gly
        50                  55                  60

```
Gly Gly Gly Ser Ala Asp Ile Gln Met Thr Gln Ser Pro Ser Ser Leu
 65                  70                  75                  80

Ser Ala Ser Val Gly Asp Arg Val Thr Ile Thr Cys Lys Ala Ser Gln
                 85                  90                  95

Asp Val His Thr Ala Val Ala Trp Tyr Gln Gln Lys Pro Gly Lys Ala
            100                 105                 110

Pro Lys Leu Leu Ile Tyr His Ala Ser Tyr Arg Tyr Thr Gly Val Pro
        115                 120                 125

Ser Arg Phe Ser Gly Ser Gly Ser Gly Thr Asp Phe Thr Phe Thr Ile
130                 135                 140

Ser Ser Leu Gln Pro Glu Asp Ile Ala Thr Tyr Tyr Cys Gln Gln Arg
145                 150                 155                 160

Tyr Ser Leu Trp Arg Thr Phe Gly Gln Gly Thr Lys Leu Glu Ile Lys
                165                 170                 175

Arg
```

<210> SEQ ID NO 49
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
His Gly Glu Gly Thr Phe Thr Ser Asp Leu Ser Lys Gln Met Glu Glu
 1               5                  10                  15

Glu Cys Val Arg Leu Phe Ile Glu Trp Leu Lys Asn Gly Gly Pro Ser
                20                  25                  30

Ser Gly Ala Pro Pro Gly Cys Gly Gly Gly Ser Gly Gly Gly Gly
             35                  40                  45

Ser Gly Gly Gly Ser Ala Asp Ile Gln Met Thr Gln Ser Pro Ser
 50                  55                  60

Ser Leu Ser Ala Ser Val Gly Asp Arg Val Thr Ile Thr Cys Lys Ala
 65                  70                  75                  80

Ser Gln Asp Val His Thr Ala Val Ala Trp Tyr Gln Gln Lys Pro Gly
                 85                  90                  95

Lys Ala Pro Lys Leu Leu Ile Tyr His Ala Ser Tyr Arg Tyr Thr Gly
            100                 105                 110

Val Pro Ser Arg Phe Ser Gly Ser Gly Ser Gly Thr Asp Phe Thr Phe
        115                 120                 125

Thr Ile Ser Ser Leu Gln Pro Glu Asp Ile Ala Thr Tyr Tyr Cys Gln
130                 135                 140

Gln Arg Tyr Ser Leu Trp Arg Thr Phe Gly Gln Gly Thr Lys Leu Glu
145                 150                 155                 160

Ile Lys Arg
```

<210> SEQ ID NO 50
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

His Gly Glu Gly Thr Phe Thr Ser Asp Val Ser Ser Tyr Leu Glu Glu

```
                 1               5                  10                 15
Gln Ala Ala Lys Glu Phe Ile Ala Asn Leu Ser Lys Gly Gly Gly Gly
                20                 25                 30
Gly Gly Gly Ser Gly Gly Gly Ser Gly Gly Gly Ser Ala Asp
                35                 40                 45
Ile Gln Met Thr Gln Ser Pro Ser Ser Leu Ser Ala Ser Val Gly Asp
    50                 55                 60
Arg Val Thr Ile Thr Cys Lys Ala Ser Gln Asp Val His Thr Ala Val
65                 70                 75                 80
Ala Trp Tyr Gln Gln Lys Pro Gly Lys Ala Pro Lys Leu Leu Ile Tyr
                85                 90                 95
His Ala Ser Tyr Arg Tyr Thr Gly Val Pro Ser Arg Phe Ser Gly Ser
                100                105                110
Gly Ser Gly Thr Asp Phe Thr Phe Thr Ile Ser Ser Leu Gln Pro Glu
                115                120                125
Asp Ile Ala Thr Tyr Tyr Cys Gln Gln Arg Tyr Ser Leu Trp Arg Thr
                130                135                140
Phe Gly Gln Gly Thr Lys Leu Glu Ile Lys Arg
145                 150                155
```

<210> SEQ ID NO 51
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
His Gly Glu Gly Thr Phe Thr Ser Asp Leu Ser Lys Gln Met Glu Glu
1               5                  10                 15
Glu Cys Val Arg Leu Phe Ile Glu Trp Leu Lys Asn Gly Gly Pro Ser
                20                 25                 30
Ser Gly Ala Pro Pro Gly Cys Gly Gly Gly Gly Ser Gly Gly
                35                 40                 45
Gly Gly Ser Gly Gly Gly Gly Ser Ala Asp Ile Gln Met Thr Gln Ser
    50                 55                 60
Pro Ser Ser Leu Ser Ala Ser Val Gly Asp Arg Val Thr Ile Thr Cys
65                 70                 75                 80
Lys Ala Ser Gln Asp Val His Thr Ala Val Ala Trp Tyr Gln Gln Lys
                85                 90                 95
Pro Gly Lys Ala Pro Lys Leu Leu Ile Tyr His Ala Ser Tyr Arg Tyr
                100                105                110
Thr Gly Val Pro Ser Arg Phe Ser Gly Ser Gly Ser Gly Thr Asp Phe
                115                120                125
Thr Phe Thr Ile Ser Ser Leu Gln Pro Glu Asp Ile Ala Thr Tyr Tyr
                130                135                140
Cys Gln Gln Arg Tyr Ser Leu Trp Arg Thr Phe Gly Gln Gly Thr Lys
145                 150                155                160
Leu Glu Ile Lys Arg
                165
```

<210> SEQ ID NO 52
<211> LENGTH: 164
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 52

His Gly Glu Gly Thr Phe Thr Ser Asp Leu Ser Lys Gln Met Glu Glu
1               5                   10                  15

Glu Cys Val Arg Leu Phe Ile Glu Trp Leu Lys Asn Gly Gly Pro Ser
            20                  25                  30

Ser Gly Ala Pro Pro Gly Cys Gly Gly Gly Gly Ser Gly Gly
        35                  40                  45

Gly Gly Ser Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65              70                  75                  80

Gln Ala Ser Gln Asp Val Lys Thr Ala Val Ala Trp Tyr Gln Gln Lys
            85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 53
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile His Pro Ser Gly Gly Arg Thr Asn Tyr Asn Glu Lys Phe
    50                  55                  60

Lys Ser Arg Val Thr Met Thr Arg Asp Thr Ser Thr Ser Thr Val Tyr
65              70                  75                  80

Met Glu Leu Ser Ser Leu Arg Ser Glu Asp Thr Ala Val Tyr Tyr Cys
            85                  90                  95

Ala Arg Glu Arg Pro Leu Tyr Ala Ser Asp Leu Trp Gly Gln Gly Thr
            100                 105                 110

Thr Val Thr Val Ser Ser
        115

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val His Thr Ala
            20                  25                  30

Val Ala Trp Tyr Gln Gln Lys Pro Gly Lys Ala Pro Lys Leu Leu Ile
        35                  40                  45

Tyr His Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Ser Pro Phe Gly Gly Arg Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
        115

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 57
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Thr Tyr Asn Gln Lys Phe
    50                  55                  60

Lys Gly Lys Ala Thr Leu Thr Val Asp Lys Ser Tyr Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Trp Leu Leu Phe Ala Tyr Trp Gly Gln Gly Thr Leu Val Thr
            100                 105                 110

Val Ser Ala
        115

<210> SEQ ID NO 58
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Leu Ser
65                  70                  75                  80

Glu Asp Leu Ala Glu Tyr Phe Cys Gln Gln Phe Tyr Ser Tyr Pro Tyr
                85                  90                  95

Thr Phe Gly Gly Gly Thr Lys Leu Glu Ile Lys Arg
            100                 105

```
<210> SEQ ID NO 59
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Arg Pro Leu Tyr Ala Met Asp Tyr Trp Gly Gln Gly Thr
            100                 105                 110

Ser Val Thr Val Ser Ser
        115

<210> SEQ ID NO 60
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Arg Tyr Ser Thr Pro Arg
                85                  90                  95

Thr Phe Gly Gly Gly Thr Lys Leu Glu Ile Lys Arg
            100                 105

<210> SEQ ID NO 61
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61
```

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Gly Thr Ser Tyr Asn Gln Lys Phe
        50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Gly Gly Gly Ile Tyr Tyr Arg Tyr Asp Arg Asn Tyr Phe Asp Tyr
                100                 105                 110

Trp Gly Gln Gly Thr Thr Leu Thr Val Ser Ser
            115                 120
```

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Ser Leu His Ser Gly Val Pro Ser Arg Phe Ser Gly
        50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Phe
                85                  90                  95

Thr Phe Gly Ser Gly Thr Lys Leu Glu Ile Lys
            100                 105
```

<210> SEQ ID NO 63
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Glu Val Lys Leu Val Glu Ser Gly Gly Leu Val Gln Pro Gly Ser
1               5                   10                  15

Ser Met Lys Leu Ser Cys Thr Ala Ser Gly Phe Thr Phe Ser Asp Tyr
                20                  25                  30

Tyr Met Ala Trp Val Arg Gln Val Pro Glu Lys Gly Leu Glu Trp Val
            35                  40                  45

Ala Asn Ile Asn Tyr Asp Gly Ser Asn Thr Ser Tyr Leu Asp Ser Leu
        50                  55                  60
```

```
Lys Ser Arg Phe Ile Ile Ser Arg Asp Asn Ala Lys Asn Ile Leu Tyr
 65                  70                  75                  80

Leu Gln Met Ser Ser Leu Lys Ser Glu Asp Thr Ala Thr Tyr Tyr Cys
                 85                  90                  95

Ala Arg Glu Lys Phe Ala Ala Met Asp Tyr Trp Gly Gln Gly Thr Ser
            100                 105                 110

Val Thr Val Ser Ser
            115

<210> SEQ ID NO 64
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Val Met Thr Gln Ser His Lys Phe Met Ser Thr Ser Phe Gly
  1               5                  10                  15

Asp Arg Val Ser Ile Thr Cys Lys Ala Ser Gln Asp Val Ser Asn Ala
                 20                  25                  30

Leu Ala Trp Tyr Gln Gln Lys Pro Gly His Ser Pro Lys Leu Leu Ile
             35                  40                  45

Phe Ser Ala Ser Tyr Arg Tyr Thr Gly Val Pro Asp Arg Phe Thr Gly
 50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Trp
                 85                  90                  95

Thr Phe Gly Gly Gly Thr Lys Leu Glu Ile Lys Arg
            100                 105

<210> SEQ ID NO 65
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asp Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Thr Gly Leu Pro Lys Leu Tyr Tyr Gly Met Asp Val
            100                 105                 110

Trp Gly Gln Gly Thr Thr Val Thr Val Ser Ser
            115                 120
```

```
<210> SEQ ID NO 66
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Ser
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Ile Thr Ile Ser Val Asp Thr Ser Lys Asn Leu Phe
65                  70                  75                  80

Ser Leu Lys Leu Ser Ser Val Thr Ala Ala Asp Thr Ala Val Tyr Tyr
                85                  90                  95

Cys Ala Arg Gly Gly Val Thr Thr Tyr Tyr Tyr Ala Met Asp Val Trp
            100                 105                 110

Gly Gln Gly Thr Thr Val Thr Val Ser Ser
        115                 120

<210> SEQ ID NO 67
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Gly Ser Gly Asp Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Phe Val Leu Met Val Tyr Ala Met Leu Asp Tyr Trp Gly
            100                 105                 110

Gln Gly Thr Leu Val Thr Val Ser Ser
        115                 120

<210> SEQ ID NO 68
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Gly Ser Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Phe Val Leu Met Val Tyr Ala Met Leu Asp Tyr Trp Gly
            100                 105                 110

Gln Gly Thr Leu Val Thr Val Ser Ser
        115                 120

<210> SEQ ID NO 69
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Asp Tyr Asp Phe Trp Ser Ala Tyr Tyr Asp Ala Phe Asp Val
            100                 105                 110

Trp Gly Gln Gly Thr Met Val Thr Val Ser Ser
        115                 120

<210> SEQ ID NO 70
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu

```
                35                  40                  45
Trp Ile Gly Tyr Ile Tyr Asn Ser Gly Ser Thr Tyr Tyr Asn Pro Ser
         50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Glu Asp Thr Ala Met Val Pro Tyr Phe Asp Tyr Trp Gly
            100                 105                 110
Gln Gly Thr Leu Val Thr Val Ser Ser
            115                 120

<210> SEQ ID NO 71
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Val Gln Ser Gly Ala Glu Val Lys Lys Pro Gly Ala
1               5                  10                  15
Ser Val Lys Val Ser Cys Lys Ala Ser Gly Tyr Thr Phe Pro Ser Tyr
                20                  25                  30
Gly Ile Ser Trp Val Arg Gln Ala Pro Gly Gln Gly Leu Glu Trp Met
            35                  40                  45
Gly Trp Ile Ser Ala Tyr Asn Gly Asn Thr Asn Tyr Ala Glu Lys Leu
         50                  55                  60
Gln Gly Arg Val Thr Met Thr Thr Asp Thr Ser Thr Ser Thr Ala Tyr
65                  70                  75                  80
Met Glu Val Arg Ser Leu Arg Ser Asp Asp Thr Ala Val Phe Tyr Cys
                85                  90                  95
Ala Arg Gly Tyr Val Met Asp Val Trp Gly Gln Gly Thr Thr Val Thr
            100                 105                 110
Val Ser Ser
            115

<210> SEQ ID NO 72
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Val Gln Ser Gly Ala Glu Val Lys Arg Pro Gly Ala
1               5                  10                  15
Ser Val Lys Val Ser Cys Lys Ala Ser Gly Tyr Thr Leu Thr Ser Tyr
                20                  25                  30
Gly Ile Ser Trp Val Arg Gln Ala Pro Gly Gln Gly Leu Glu Trp Met
            35                  40                  45
Gly Trp Ile Ser Val Tyr Asn Gly Asn Thr Asn Tyr Ala Gln Lys Val
         50                  55                  60
Gln Gly Arg Val Thr Met Thr Thr Asp Thr Ser Thr Ser Thr Val Tyr
65                  70                  75                  80
Met Glu Leu Arg Ser Leu Ser Ser Asp Asp Thr Ala Val Tyr Tyr Cys
```

85                  90                  95

Ala Arg Gly Tyr Gly Met Asp Val Trp Gly Gln Gly Thr Thr Val Thr
                100                 105                 110

Val Ser Ser
        115

<210> SEQ ID NO 73
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
                20                  25                  30

Gly Ile Ser Trp Val Arg Gln Ala Pro Gly Gln Gly Leu Glu Trp Met
            35                  40                  45

Gly Trp Ile Ser Phe Tyr Asn Gly Asn Thr Asn Tyr Ala Gln Lys Val
    50                  55                  60

Gln Gly Arg Val Thr Met Thr Thr Asp Thr Ser Thr Ser Thr Val Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
                100                 105                 110

Val Ser Ser
        115

<210> SEQ ID NO 74
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
                20                  25                  30

Gly Ile Ser Trp Val Arg Gln Ala Pro Gly Gln Gly Leu Glu Trp Met
            35                  40                  45

Gly Trp Ile Ser Phe Tyr Asn Gly Asn Thr Asn Tyr Ala Gln Lys Val
    50                  55                  60

Gln Gly Arg Val Thr Met Thr Thr Asp Thr Ser Thr Ser Thr Val Tyr
65                  70                  75                  80

Met Glu Leu Arg Ser Leu Arg Ser Asp Asp Thr Ala Val Tyr Phe Cys
                85                  90                  95

Ala Arg Gly Tyr Gly Met Asp Val Trp Gly Gln Gly Thr Thr Val Thr
                100                 105                 110

Val Ser Ser
        115

```
<210> SEQ ID NO 75
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Pro Leu Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Val
        50                  55                  60

Gln Gly Ser Val Thr Met Thr Thr Asp Thr Ser Thr Ser Thr Val Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
                100                 105                 110

Val Ser Ser
        115

<210> SEQ ID NO 76
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Val Gln Leu Val Gln Ser Gly Ala Glu Val Lys Lys Pro Gly Ala
1               5                   10                  15

Ser Leu Lys Val Ser Cys Lys Ala Ser Gly Tyr Ser Leu Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Val
        50                  55                  60

Gln Gly Arg Val Thr Met Thr Thr Asp Thr Ser Thr Ser Thr Val Tyr
65                  70                  75                  80

Met Glu Val Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
                100                 105                 110

Val Ser Ser
        115

<210> SEQ ID NO 77
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Val
    50                  55                  60

Gln Gly Arg Val Thr Met Thr Thr Asp Thr Ser Thr Ser Thr Val Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 78
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Val
    50                  55                  60

Gln Gly Arg Val Thr Met Thr Thr Asp Thr Ser Thr Ser Thr Val Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 79
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
            50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 80
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Gly Ile Ser Trp Val Arg Gln Ala Pro Gly Gln Gly Leu Glu Trp Met
        35                  40                  45

Gly Trp Val Ser Ala Tyr Asn Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Val Met Asp Val Trp Gly Gln Gly Thr Thr Val Thr
            100                 105                 110

Val Ser Ser
        115

<210> SEQ ID NO 81
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115

<210> SEQ ID NO 82
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Lys Asn Tyr Ser
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Gly Asp Thr Ala Val
                85                  90                  95

Tyr Tyr Cys Ala Arg Gly Gly Pro Thr Ala Ala Phe Asp Tyr Trp Gly
            100                 105                 110

Gln Gly Thr Leu Val Thr Val Ser Ser
        115                 120

<210> SEQ ID NO 83
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Asn Trp Gly Phe Ala Phe Asp Ile Trp Gly Gln Gly
            100                 105                 110

Thr Met Val Thr Val Ser Ser
        115

<210> SEQ ID NO 84

```
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys His Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Asn Trp Gly Phe Ala Phe Asp Val Trp Gly His Gly
            100                 105                 110

Thr Met Val Thr Val Ser Ser
        115

<210> SEQ ID NO 85
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Ala Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Arg Thr Asp Tyr Asn Pro Ser Leu Lys
    50                  55                  60

Ser Arg Val Thr Ile Ser Val Asp Thr Ser Lys Lys Gln Phe Ser Leu
65                  70                  75                  80

Lys Leu Asn Ser Val Thr Ala Ala Asp Thr Ala Val Tyr Tyr Cys Ala
                85                  90                  95

Arg Gly Gln Leu Val Pro Phe Asp Tyr Trp Gly Gln Gly Thr Leu Val
            100                 105                 110

Thr Val Ser Ser
        115

<210> SEQ ID NO 86
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Phe
            20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
50                      55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Ser Cys
            85                  90                  95

Thr Arg Glu Ser Asn Trp Gly Phe Ala Phe Asp Ile Trp Gly Gln Gly
            100                 105                 110

Thr Met Val Thr Val Ser Ser
            115

<210> SEQ ID NO 87
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Val His Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Ser Phe
            20                  25                  30

Gly Met His Trp Val Arg Gln Ala Pro Gly Lys Gly Leu Glu Trp Val
            35                  40                  45

Ala Leu Ile Trp Ser Asp Gly Ser Asp Glu Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ala Ile Ala Ala Leu Tyr Tyr Tyr Tyr Gly Met Asp Val Trp
            100                 105                 110

Gly Gln Gly Thr Thr Val Thr Val Ser Ser
            115                 120

<210> SEQ ID NO 88
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
            35                  40                  45

Ala Leu Ile Trp Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ile Ala Ala Leu Tyr Tyr Tyr Tyr Gly Met Asp Val Trp
            100                 105                 110

Gly Gln Gly Thr Thr Val Thr Val Ser Ser
        115                 120

<210> SEQ ID NO 89
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Val His Leu Val Glu Ser Gly Gly Val Val Gln Pro Gly Arg
1               5                   10                  15

Ser Leu Arg Leu Ser Cys Ala Ala Ser Gly Phe Thr Phe Asn Ser Phe
            20                  25                  30

Gly Met His Trp Val Arg Gln Ala Pro Gly Lys Gly Leu Glu Trp Val
        35                  40                  45

Ala Leu Ile Trp Ser Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ile Ala Ala Leu Tyr Tyr Tyr Tyr Gly Met Asp Val Trp
            100                 105                 110

Gly Gln Gly Thr Thr Val Thr Val Ser Ser
        115                 120

<210> SEQ ID NO 90
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Leu Ile Trp Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ile Ala Ala Leu Tyr Tyr Tyr Tyr Gly Met Asp Val Trp
            100                 105                 110

Gly His Gly Thr Thr Val Thr Val Ser Ser
        115                 120

<210> SEQ ID NO 91
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Leu Ile Trp Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ala Ile Ala Ala Leu Tyr Tyr Tyr Tyr Gly Met Asp Val Trp
            100                 105                 110

Gly Gln Gly Thr Thr Val Thr Val Ser Ser
        115                 120

<210> SEQ ID NO 92
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Leu Ile Trp His Asp Gly Ser Asn Thr Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Ile Ala Val Ala Tyr Tyr Tyr Tyr Gly Met Asp Val Trp
            100                 105                 110

Gly Gln Gly Thr Thr Val Thr Val Ser Ser
        115                 120

<210> SEQ ID NO 93
<211> LENGTH: 117

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Val Gly Ser Pro Phe Asp Tyr Trp Gly Gln Gly Thr Leu
            100                 105                 110

Val Thr Val Ser Ser
        115

<210> SEQ ID NO 94
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gly Leu Ala Ala Arg Pro Gly Gly Met Asp Val Trp
            100                 105                 110

Gly Gln Gly Thr Thr Val Thr Val Ser Ser
        115                 120

<210> SEQ ID NO 95
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Val Gln Leu Val Gln Ser Gly Ala Glu Val Lys Lys Pro Gly Ala

```
            1               5                  10                 15
Ser Val Lys Val Ser Cys Lys Ala Ser Gly Tyr Thr Phe Thr Ser Tyr
                  20                  25                 30

Gly Ile Ser Trp Val Arg Gln Ala Pro Gly Gln Gly Leu Glu Trp Met
            35                  40                 45

Gly Trp Ile Ser Thr Tyr Asn Gly Asn Thr Asn Tyr Ala Gln Lys Val
      50                  55                 60

Gln Gly Arg Val Thr Met Thr Thr Asp Thr Ser Thr Ser Thr Ala Tyr
65                  70                  75                 80

Met Glu Leu Arg Ser Leu Arg Ser Asp Asp Thr Ala Val Tyr Tyr Cys
                  85                  90                 95

Ala Arg Gly Tyr Thr Arg Asp Tyr Trp Gly Gln Gly Thr Leu Val Thr
                  100                 105                110

Val Ser Ser
            115
```

<210> SEQ ID NO 96
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

```
Asp Ile Val Met Thr Gln Ser Pro Leu Ser Leu Ser Val Thr Pro Gly
1               5                  10                 15

Glu Pro Pro Ser Ile Ser Cys Arg Ser Ser Gln Ser Leu Leu His Ser
                  20                  25                 30

Asn Gly Tyr Asn Phe Leu Asn Trp Tyr Leu Gln Lys Pro Gly Gln Ser
            35                  40                 45

Pro Gln Leu Leu Ile Tyr Leu Gly Ser His Arg Ala Ser Gly Val Pro
      50                  55                 60

Asp Arg Phe Ser Gly Ser Gly Ser Gly Thr Asp Phe Thr Leu Glu Ile
65                  70                  75                 80

Ser Arg Val Glu Ala Glu Asp Val Gly Val Tyr Tyr Cys Met Gln Val
                  85                  90                 95

Leu Gln Thr Pro Phe Thr Phe Gly Pro Gly Thr Lys Val Asp Ile Lys
                  100                 105                110
```

<210> SEQ ID NO 97
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Asp Ile Gln Met Thr Gln Ser Pro Ser Ser Leu Ser Ala Ser Val Gly
1               5                  10                 15

Asp Arg Val Thr Ile Thr Cys Arg Ala Ser Gln Arg Ile Ser Asn Tyr
                  20                  25                 30

Leu Ser Trp Tyr Leu Gln Lys Pro Gly Ile Ala Pro Lys Leu Leu Ile
            35                  40                 45

Tyr Ala Ala Ser Ser Leu Gln Ser Gly Val Pro Ser Arg Phe Ser Gly
      50                  55                 60

Ser Gly Ser Gly Thr Asp Phe Thr Leu Thr Ile Ser Ser Leu Gln Ser
```

```
                65                  70                  75                  80
Glu Asp Phe Ala Thr Tyr Tyr Cys Gln Gln Ser Tyr Ser Thr Pro Leu
                    85                  90                  95
Ile Phe Gly Gly Gly Thr Lys Val Glu Ile Lys
                100                 105

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Leu Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Val Leu Ile
                35                  40                  45

Tyr Ala Ala Ser Leu Gln Ser Gly Val Pro Ser Arg Phe Ser Gly
            50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Ser Pro Ile
                85                  90                  95

Thr Phe Gly Gln Gly Thr Arg Leu Glu Ile Lys
                100                 105

<210> SEQ ID NO 99
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ile Tyr
                20                  25                  30

Leu Asn Trp Tyr Gln Gln Lys Pro Gly Lys Ala Pro Tyr Leu Leu Ile
                35                  40                  45

Tyr Ala Ala Ala Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Ile
                85                  90                  95

Thr Phe Gly Gln Gly Thr Arg Leu Glu Ile Lys
                100                 105

<210> SEQ ID NO 100
<211> LENGTH: 111
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 100

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Ser Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
            100                 105                 110

<210> SEQ ID NO 101
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala His
            20                  25                  30

Tyr Asp Val His Trp Tyr Gln Gln Val Pro Gly Thr Ala Pro Lys Leu
        35                  40                  45

Leu Ile Tyr Gly Asn Thr Tyr Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Ser
                85                  90                  95

Leu Ser Gly Val Val Phe Gly Gly Gly Thr Lys Leu Thr Val Leu
            100                 105                 110

<210> SEQ ID NO 102
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Arg Tyr
            20                  25                  30

Asn Ser Val Ser Trp Tyr Gln His His Pro Gly Lys Ala Pro Lys Val
        35                  40                  45

Met Ile Tyr Glu Val Ser Asn Arg Pro Ser Gly Val Ser Thr Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Val Val Phe Gly Gly Gly Thr Lys Leu Thr Val Leu
            100                 105

<210> SEQ ID NO 103
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Pro Pro Lys Leu
            35                  40                  45

Met Ile Tyr Glu Val Ser Asn Arg Pro Ser Gly Val Ser Ile Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105

<210> SEQ ID NO 104
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Pro Pro Lys Leu
            35                  40                  45

Met Ile Tyr Glu Val Ser Asn Arg Pro Ser Gly Val Ser Ile Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105

<210> SEQ ID NO 105
<211> LENGTH: 109
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 105

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Pro Pro Lys Leu
        35                  40                  45

Met Ile Tyr Glu Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Ala Val Leu
            100                 105

<210> SEQ ID NO 106
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln Tyr Pro Gly Lys Pro Pro Lys Leu
        35                  40                  45

Lys Ile Tyr Glu Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105

<210> SEQ ID NO 107
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Pro Pro Lys Leu
        35                  40                  45
```

```
Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
 65                 70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105
```

<210> SEQ ID NO 108
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Pro Pro Lys Leu
                35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
 65                 70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105
```

<210> SEQ ID NO 109
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Asn Ser Asp Val Gly Gly Tyr
                20                  25                  30

Asn Ser Val Ser Trp Tyr Gln Gln His Pro Gly Lys Pro Pro Lys Leu
                35                  40                  45

Met Ile Tyr Glu Val Ser Asn Arg Pro Ser Gly Ile Ser Asn Arg Phe
    50                  55                  60

Ser Gly Ser Lys Ser Gly Asn Thr Ala Ser Leu Thr Ile Ser Gly Leu
 65                 70                  75                  80

Gln Ala Glu Asp Glu Ala Asp Tyr Phe Cys Ser Ser Tyr Thr Ser Thr
                85                  90                  95

Ser Met Val Phe Gly Gly Gly Thr Lys Leu Thr Val Leu
            100                 105
```

<210> SEQ ID NO 110
<211> LENGTH: 109

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu
            100                 105

<210> SEQ ID NO 111
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Ser Val Ser Trp Tyr Gln Gln His Pro Gly Lys Ala Pro Lys Arg
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Thr
                85                  90                  95

Asn Met Val Phe Gly Gly Gly Thr Lys Leu Thr Val Leu
            100                 105

<210> SEQ ID NO 112
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu

```
                35                  40                  45
Met Ile Tyr Glu Val Thr Asn Arg Pro Ser Gly Val Ser Asn Arg Phe
         50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                 85                  90                  95

Ser Met Val Phe Gly Gly Gly Thr Lys Leu Thr Val Leu
             100                 105

<210> SEQ ID NO 113
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Leu Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asn Tyr
                 20                  25                  30

Asn Leu Val Ser Trp Tyr Gln Gln Tyr Ser Gly Lys Ala Pro Lys Leu
             35                  40                  45

Met Ile Tyr Glu Val Ser Lys Arg Pro Ser Gly Val Ser Asn Arg Phe
         50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                 85                  90                  95

Ser Thr Leu Val Phe Gly Gly Gly Thr Lys Leu Thr Val Leu
             100                 105                 110

<210> SEQ ID NO 114
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Lys
                 20                  25                  30

Thr Val Asn Trp Tyr Gln Gln Val Pro Gly Thr Ala Pro Lys Leu Leu
             35                  40                  45

Ile Tyr Arg Asn Asn Gln Arg Pro Leu Gly Val Pro Asp Arg Phe Ser
         50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                 85                  90                  95

Asn Trp Val Phe Gly Gly Gly Thr Lys Leu Thr Val Leu
             100                 105
```

<210> SEQ ID NO 115
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Ser Val Leu Thr Gln Pro Pro Ser Ala Ser Gly Pro Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Arg Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Trp Val Phe Gly Gly Gly Thr Lys Leu Thr Val Leu
            100                 105

<210> SEQ ID NO 116
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Val Trp Asp Asp Ser Leu
                85                  90                  95

Asn Gly Trp Val Phe Gly Gly Gly Thr Lys Leu Thr Val Leu
            100                 105                 110

<210> SEQ ID NO 117
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Lys
            20                  25                  30

Thr Val Asn Trp Tyr Gln Gln Phe Pro Gly Thr Ala Pro Lys Leu Leu
            35                  40                  45

Ile Tyr Ser Asn Asn Arg Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Trp Val Phe Gly Ala Gly Thr Lys Leu Thr Val Leu
            100                 105

<210> SEQ ID NO 118
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Ser Val Leu Thr Gln Pro Pro Ser Val Ser Ala Ala Pro Gly Gln
 1               5                   10                  15

Lys Val Thr Ile Ser Cys Ser Gly Ser Ser Ser Asn Ile Gly Asn Asn
                 20                  25                  30

Phe Val Ser Trp Tyr Gln Gln Leu Pro Gly Thr Ala Pro Lys Leu Leu
            35                  40                  45

Ile Tyr Asp Tyr Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Tyr Val Phe Gly Thr Gly Thr Arg Val Thr Val Leu
            100                 105                 110

<210> SEQ ID NO 119
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Ser Val Leu Thr Gln Pro Pro Ser Val Ser Ala Ala Pro Gly Gln
 1               5                   10                  15

Lys Val Thr Ile Ser Cys Ser Gly Ser Ser Ser Asn Ile Gly Asn Asn
                 20                  25                  30

Phe Val Ser Trp Tyr Gln Gln Leu Pro Gly Thr Ala Pro Lys Leu Leu
            35                  40                  45

Ile Tyr Asp Tyr Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Gly Tyr Val Phe Gly Thr Gly Thr Arg Val Thr Val Leu
            100                 105                 110

-continued

<210> SEQ ID NO 120
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Phe Val Ser Trp Tyr Gln Gln Phe Pro Gly Thr Ala Pro Lys Leu Leu
        35                  40                  45

Ile Tyr Asp Tyr Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ser Tyr Val Phe Gly Thr Gly Thr Arg Val Thr Val Leu
            100                 105                 110

<210> SEQ ID NO 121
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Phe Val Ser Trp Tyr Gln Gln Leu Pro Gly Thr Ala Pro Lys Leu Leu
        35                  40                  45

Ile Tyr Asp Tyr Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Tyr Val Phe Gly Thr Gly Thr Arg Val Thr Val Leu
            100                 105                 110

<210> SEQ ID NO 122
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Ser Val Leu Thr Gln Pro Pro Thr Val Ser Ala Ala Pro Gly Gln
1               5                   10                  15

Lys Val Thr Ile Ser Cys Ser Gly Ser Ser Asn Ile Gly Asn Asn
                20                  25                  30

Phe Val Ser Trp Tyr Gln Gln Leu Pro Gly Thr Ala Pro Lys Leu Leu
            35                  40                  45

Ile Tyr Asp Tyr Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Tyr Val Phe Gly Thr Gly Thr Arg Val Thr Val Leu
                100                 105                 110

<210> SEQ ID NO 123
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Phe Val Ser Trp Tyr Gln Gln Leu Pro Gly Thr Ala Pro Lys Leu Leu
            35                  40                  45

Ile Tyr Asp Ser Asn Lys Arg Pro Ser Gly Ile Pro Asp Arg Phe Ser
50                  55                  60

Gly Ser Lys Ser Gly Thr Ser Ala Thr Leu Asp Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu
                100                 105                 110

<210> SEQ ID NO 124
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gln Ser Val Leu Thr Gln Pro Pro Ser Val Ser Ala Ala Pro Gly Gln
1               5                   10                  15

Lys Val Thr Ile Ser Cys Ser Gly Ser Asn Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
50                  55                  60

Gly Ser Asn Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu
            100                 105                 110

<210> SEQ ID NO 125
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Ser Tyr Glu Leu Thr Gln Pro Pro Ser Val Ser Val Ser Pro Gly Gln
1               5                   10                  15

Thr Ala Arg Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asn Thr Lys Trp Pro Leu Gly Ile Pro Glu Arg Phe Ser Gly Ser
50                  55                  60

Lys Ser Gly Asn Thr Val Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

<210> SEQ ID NO 126
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Pro Val Leu Thr Gln Pro Leu Phe Ala Ser Ala Ser Leu Gly Ala
1               5                   10                  15

Ser Val Thr Leu Thr Cys Thr Leu Ser Ser Gly Tyr Ser Ser Tyr Glu
            20                  25                  30

Val Asp Trp Tyr Gln Gln Arg Pro Gly Lys Gly Pro Arg Phe Val Met
        35                  40                  45

Arg Val Asp Thr Gly Gly Ile Val Gly Ser Lys Gly Glu Gly Ile Pro
50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Thr Asn Phe Val Val Val Phe Gly Gly Gly Thr Lys
            100                 105                 110

Leu Thr Val Leu
        115

<210> SEQ ID NO 127
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Val Gln Leu Val Glu Ser Gly Gly Val Val Gln Pro Gly Arg
1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Gly Phe Asp Gly Ser Asn Ile Tyr Tyr Gly Asp Ser Val
    50                  55                  60

Arg Gly Arg Ile Ile Ile Ser Arg Asp Asn Ser Glu Asn Thr Leu Tyr
65                  70                  75                  80

Leu Glu Met Asn Ser Leu Arg Ala Glu Asp Thr Ala Val Tyr Tyr Cys
                85                  90                  95

Ala Arg Glu Lys Gly Leu Asp Trp Gly Gln Gly Thr Leu Val Thr Val
            100                 105                 110

Ser Ser

<210> SEQ ID NO 128
<211> LENGTH: 118
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 128

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
        35                  40                  45

Ser Thr Ile Ser Gly Ser Gly Gly Thr Thr Asn Tyr Ala Asp Ser Val
    50                  55                  60

Lys Gly Arg Phe Ile Ile Ser Arg Asp Ser Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Leu Val Thr Val Ser Ser
        115

<210> SEQ ID NO 129
<211> LENGTH: 128
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 129

Gln Val Gln Leu Gln Glu Ser Gly Pro Gly Leu Val Lys Pro Ser Glu
1               5                  10                  15

Thr Leu Ser Leu Thr Cys Thr Val Ser Gly Asp Ser Ile Asn Thr Tyr
            20                  25                  30

Tyr Trp Ser Trp Phe Arg Gln Pro Pro Gly Lys Gly Leu Glu Trp Ile
        35                  40                  45

```
Gly Tyr Ile Tyr Tyr Ser Gly Thr Thr Asn Tyr Asn Pro Ser Leu Lys
            50                  55                  60

Ser Arg Val Thr Ile Ser Ile Asp Thr Pro Arg Asn Gln Phe Ser Leu
65                  70                  75                  80

Lys Leu Ile Ser Val Thr Ala Ala Asp Thr Ala Val Tyr Tyr Cys Ala
                85                  90                  95

Arg Glu Arg Ile Thr Met Ile Arg Gly Val Thr Leu Tyr Tyr Tyr Ser
            100                 105                 110

Tyr Gly Met Asp Val Trp Gly Gln Gly Thr Thr Val Thr Val Ser Ser
                115                 120                 125

<210> SEQ ID NO 130
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Met Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Lys Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Ile Val Leu Met Val Tyr Asp Met Asp Tyr Tyr Tyr Tyr
            100                 105                 110

Gly Met Asp Val Trp Gly Gln Gly Thr Thr Val Thr Val Ser Ser
        115                 120                 125

<210> SEQ ID NO 131
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ser Thr Gly Lys Gly Leu Glu Trp Val
        35                  40                  45

Ser Ala Ile Gly Ser Thr Gly Asp Thr Tyr Tyr Pro Gly Ser Val Lys
    50                  55                  60

Gly Arg Phe Thr Ile Thr Arg Glu Lys Ala Lys Asn Ser Val Tyr Leu
65                  70                  75                  80

Gln Met Asn Ser Leu Arg Ala Gly Asp Thr Ala Val Tyr Tyr Cys Val
                85                  90                  95
```

Arg Glu Gly Trp Glu Val Pro Phe Asp Tyr Trp Gly Gln Gly Thr Leu
                100                 105                 110

Val Thr Val Ser Ser
        115

<210> SEQ ID NO 132
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ser Thr Gly Lys Gly Leu Glu Trp Val
        35                  40                  45

Ser Ala Ile Gly Ser Thr Gly Asp Thr Tyr Tyr Pro Gly Ser Val Lys
    50                  55                  60

Gly Arg Phe Thr Ile Thr Arg Glu Lys Ala Lys Asn Ser Val Tyr Leu
65                  70                  75                  80

Gln Met Asn Ser Leu Arg Ala Gly Asp Thr Ala Val Tyr Tyr Cys Val
                85                  90                  95

Arg Glu Gly Trp Glu Val Pro Phe Asp Tyr Trp Gly Gln Gly Thr Leu
                100                 105                 110

Val Thr Val Ser Ser
        115

<210> SEQ ID NO 133
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Val
                85                  90                  95

Arg Glu Gly Trp Glu Val Pro Phe Asp Tyr Trp Gly Gln Gly Thr Leu
                100                 105                 110

Val Thr Val Ser Ser
        115

<210> SEQ ID NO 134

<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Gly Phe Asp Gly Ser Asn Ile His Tyr Gly Asp Ser Val
    50                  55                  60

Arg Gly Arg Ile Ile Ile Ser Arg Asp Asn Ser Glu Asn Thr Leu Tyr
65                  70                  75                  80

Leu Glu Met Asn Ser Leu Arg Ala Glu Asp Thr Ala Met Tyr Tyr Cys
                85                  90                  95

Ala Arg Glu Lys Gly Leu Asp Trp Gly Gln Gly Thr Thr Val Thr Val
            100                 105                 110

Ser Ser

<210> SEQ ID NO 135
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Gly Phe Asp Gly Ser Asn Ile His Tyr Gly Asp Ser Val
    50                  55                  60

Arg Gly Arg Ile Ile Ile Ser Arg Asp Asn Ser Glu Asn Thr Leu Tyr
65                  70                  75                  80

Leu Glu Met Asn Ser Leu Arg Ala Glu Asp Thr Ala Met Tyr Tyr Cys
                85                  90                  95

Ala Arg Glu Lys Gly Leu Asp Trp Gly Gln Gly Thr Leu Val Thr Val
            100                 105                 110

Ser Ser

<210> SEQ ID NO 136
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Gly Phe Asp Gly Ser Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Gly Leu Asp Trp Gly Gln Gly Thr Leu Val Thr Val
            100                 105                 110

Ser Ser

<210> SEQ ID NO 137
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Gln Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Gly Phe Asp Gly Ser Asn Ile Tyr Tyr Gly Asp Ser Val
    50                  55                  60

Arg Gly Arg Ile Ile Ile Ser Arg Asp Asn Ser Glu Asn Thr Leu Tyr
65                  70                  75                  80

Leu Glu Met Asn Ser Leu Arg Ala Glu Asp Thr Ala Val Tyr Tyr Cys
                85                  90                  95

Ala Arg Glu Lys Gly Leu Asp Trp Gly Gln Gly Thr Leu Val Thr Val
            100                 105                 110

Ser Ser

<210> SEQ ID NO 138
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Gly Phe Asp Gly Ser Asn Ile Tyr Tyr Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Ala Arg Glu Lys Gly Leu Asp Trp Gly Gln Gly Thr Leu Val Thr Val
                100                 105                 110

Ser Ser

<210> SEQ ID NO 139
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
                100                 105                 110

Leu Val Thr Val Ser Ser
            115

<210> SEQ ID NO 140
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Val Gln Leu Val Gln Ser Gly Gly Gly Leu Val Gln Pro Gly Gly
1               5                   10                  15

Ser Leu Arg Leu Ser Cys Ala Val Ser Gly Phe Thr Leu Ser Ser Tyr
                20                  25                  30

Asp Met His Trp Val Arg Gln Pro Thr Gly Lys Gly Leu Glu Trp Val
            35                  40                  45

Ser Ala Ile Gly Ser Thr Gly Asp Thr Tyr Tyr Pro Gly Ser Val Lys
        50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Trp Asp Val Pro Phe Asp Phe Trp Gly Gln Gly Thr Leu
                100                 105                 110

Val Thr Val Ser Ser
            115
```

<210> SEQ ID NO 141
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Leu Ser Ser Tyr
            20                  25                  30

Asp Met His Trp Val Arg Gln Pro Thr Gly Lys Gly Leu Glu Trp Val
        35                  40                  45

Ser Ala Ile Gly Ser Thr Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Trp Asp Val Pro Phe Asp Phe Trp Gly Gln Gly Thr Leu
            100                 105                 110

Val Thr Val Ser Ser
        115

<210> SEQ ID NO 142
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Trp Asp Val Pro Phe Asp Phe Trp Gly Gln Gly Thr Leu
            100                 105                 110

Val Thr Val Ser Ser
        115

<210> SEQ ID NO 143
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Thr Tyr
            20                  25                  30

Tyr Trp Ser Trp Phe Arg Gln Pro Pro Gly Lys Gly Leu Glu Trp Ile
        35                  40                  45

Gly Tyr Ile Tyr Tyr Ser Gly Thr Thr Asn Tyr Asn Pro Ser Leu Lys
50                  55                  60

Ser Arg Val Thr Ile Ser Ile Asp Thr Pro Arg Asn Gln Phe Ser Leu
65                  70                  75                  80

Lys Leu Ile Ser Val Thr Ala Ala Asp Thr Ala Val Tyr Tyr Cys Ala
                85                  90                  95

Arg Glu Arg Ile Thr Met Ile Arg Gly Val Thr Leu Tyr Tyr Tyr Ser
            100                 105                 110

Tyr Gly Met Asp Val Trp Gly Gln Gly Thr Thr Val Thr Val Ser Ser
        115                 120                 125

<210> SEQ ID NO 144
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Thr Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Thr Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Ile Thr Met Ile Arg Gly Val Thr Leu Tyr Tyr Tyr Ser
            100                 105                 110

Tyr Gly Met Asp Val Trp Gly Gln Gly Thr Thr Val Thr Val Ser Ser
        115                 120                 125

<210> SEQ ID NO 145
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Leu Met
            35                  40                  45

Gly Trp Ile Ser Gly Tyr Asn Gly Asn Thr Asn Tyr Ala Gln Glu Leu
    50                  55                  60

Gln Ala Arg Val Thr Met Thr Thr Asp Thr Ser Thr Ser Thr Ala Tyr
65                  70                  75                  80

Met Glu Leu Arg Asn Leu Arg Ser Asp Asp Thr Ala Val Tyr Tyr Cys
                85                  90                  95

Ala Arg Asp Arg Val Val Val Ala Ala Ala Asn Tyr Tyr Phe Tyr Ser
                100                 105                 110

Met Asp Val Trp Gly Gln Gly Thr Thr Val Thr Val Ser Ser
            115                 120                 125

<210> SEQ ID NO 146
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Ile Ser Trp Val Arg Gln Ala Pro Gly Gln Gly Leu Glu Leu Met
            35                  40                  45

Gly Trp Ile Ser Gly Tyr Asn Gly Asn Thr Asn Tyr Ala Gln Glu Leu
    50                  55                  60

Gln Ala Arg Val Thr Met Thr Thr Asp Thr Ser Thr Ser Thr Ala Tyr
65                  70                  75                  80

Met Glu Leu Arg Asn Leu Arg Ser Asp Asp Thr Ala Val Tyr Tyr Cys
                85                  90                  95

Ala Arg Asp Arg Val Val Val Ala Ala Ala Asn Tyr Tyr Phe Tyr Ser
                100                 105                 110

Met Asp Val Trp Gly Gln Gly Thr Thr Val Thr Val Ser Ser
            115                 120                 125

<210> SEQ ID NO 147
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Ile Ser Trp Val Arg Gln Ala Pro Gly Gln Gly Leu Glu Trp Met
            35                  40                  45

Gly Trp Ile Ser Gly Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Asp Arg Val Val Val Ala Ala Asn Tyr Tyr Phe Tyr Ser
        100                 105                 110

Met Asp Val Trp Gly Gln Gly Thr Thr Val Thr Val Ser Ser
        115                 120                 125

<210> SEQ ID NO 148
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Gln Val His Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ile Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Gly Asp Lys Arg Tyr Ser Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Ile Thr Glu Thr Ser Tyr Tyr Phe Tyr Tyr Gly Met
            100                 105                 110

Asp Val Trp Gly Gln Gly Thr Thr Val Thr Val Ser Ser
        115                 120                 125

<210> SEQ ID NO 149
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ile Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Gly Asp Lys Arg Tyr Ser Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Ile Thr Glu Thr Ser Tyr Tyr Phe Tyr Tyr Gly Met
            100                 105                 110

Asp Val Trp Gly Gln Gly Thr Thr Val Thr Val Ser Ser
        115                 120                 125

<210> SEQ ID NO 150
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ile Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Gly Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Ile Thr Glu Thr Ser Tyr Tyr Phe Tyr Tyr Gly Met
            100                 105                 110

Asp Val Trp Gly Gln Gly Thr Thr Val Thr Val Ser Ser
        115                 120                 125

<210> SEQ ID NO 151
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Ile Thr Leu Lys Glu Ser Gly Pro Thr Leu Val Lys Pro Ser Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Ser Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg His Asp Ser Ser Tyr Tyr Phe Tyr Tyr Gly Met
            100                 105                 110

Asp Val Trp Gly Gln Gly Ile Thr Val Thr Val Ser Ser
        115                 120                 125

<210> SEQ ID NO 152
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gln Ile Thr Leu Lys Glu Ser Gly Pro Thr Leu Val Lys Pro Ser Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Ser Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg His Asp Ser Ser Tyr Tyr Phe Tyr Tyr Gly Met
            100                 105                 110

Asp Val Trp Gly Gln Gly Thr Thr Val Thr Val Ser Ser
            115                 120                 125

<210> SEQ ID NO 153
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Ser Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg His Asp Ser Ser Tyr Tyr Phe Tyr Tyr Gly Met
            100                 105                 110

Asp Val Trp Gly Gln Gly Thr Thr Val Thr Val Ser Ser
            115                 120                 125

<210> SEQ ID NO 154
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Lys Trp Val Arg Gln Ala Pro Gly Lys Gly Leu Glu Trp Val

```
                35                  40                  45

Ala Asn Ile Asn Gln Asp Gly Ser Glu Lys Tyr Tyr Val Asp Ser Val
            50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                85                  90                  95

Ala Arg Asp Ile Val Leu Met Val Tyr Asp Met Asp Tyr Tyr Tyr Tyr
               100                 105                 110

Gly Met Asp Val Trp Gly Gln Gly Thr Thr Val Thr Val Ser Ser
               115                 120                 125

<210> SEQ ID NO 155
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser His
                20                  25                  30

Trp Met Ser Trp Val Arg Gln Ala Pro Gly Lys Gly Leu Glu Trp Val
                35                  40                  45

Ala Asn Ile Asn Gln Asp Gly Ser Glu Lys Tyr Tyr Val Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Ile Val Leu Met Val Tyr Asp Met Asp Tyr Tyr Tyr Tyr
               100                 105                 110

Gly Met Asp Val Trp Gly Gln Gly Thr Thr Val Thr Val Ser Ser
               115                 120                 125

<210> SEQ ID NO 156
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Gln Val Gln Leu Val Glu Ser Gly Gly Gly Val Val Gln Pro Gly Arg
 1               5                  10                  15

Ser Leu Arg Leu Ser Cys Ala Val Ser Gly Phe Thr Phe Ser Ser Tyr
                20                  25                  30

Gly Met His Trp Val Arg Gln Ala Pro Gly Lys Gly Leu Glu Trp Val
                35                  40                  45

Ala Ala Ile Ser Tyr Asp Gly Ser Asn Lys Tyr Tyr Val Asp Ser Val
            50                  55                  60

Lys Gly Arg Phe Thr Ile Ser Arg Asp Asn Ser Lys Lys Thr Leu Tyr
 65                  70                  75                  80

Leu Gln Met Asn Ser Leu Arg Ala Glu Asp Thr Ala Val Tyr Asn Cys
```

```
                    85                  90                  95

Ala Lys Asn Ile Val Leu Val Met Tyr Asp Ile Asp Tyr His Tyr Tyr
                100                 105                 110

Gly Met Asp Val Trp Gly Gln Gly Thr Thr Val Thr Val Ser Ser
            115                 120                 125

<210> SEQ ID NO 157
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gln Val Gln Leu Val Glu Ser Gly Gly Gly Val Val Gln Pro Gly Arg
1               5                   10                  15

Ser Leu Arg Leu Ser Cys Ala Val Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Asn Cys
                85                  90                  95

Ala Lys Asn Ile Val Leu Val Met Tyr Asp Ile Asp Tyr His Tyr Tyr
                100                 105                 110

Gly Met Asp Val Trp Gly Gln Gly Thr Thr Val Thr Val Ser Ser
            115                 120                 125

<210> SEQ ID NO 158
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Gln Val Gln Leu Val Glu Ser Gly Gly Gly Val Val Gln Pro Gly Arg
1               5                   10                  15

Ser Leu Arg Leu Ser Cys Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ile Val Leu Val Met Tyr Asp Ile Asp Tyr His Tyr Tyr
                100                 105                 110

Gly Met Asp Val Trp Gly Gln Gly Thr Thr Val Thr Val Ser Ser
            115                 120                 125
```

```
<210> SEQ ID NO 159
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Gln Val Gln Leu Val Glu Ser Gly Gly Val Val Gln Pro Gly Arg
1               5                   10                  15

Ser Leu Arg Leu Ser Cys Ala Val Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ala Ile Ser Tyr Asp Gly Ser Asn Lys Tyr Tyr Val Asp Ser Val
        50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Asn Cys
                85                  90                  95

Ala Lys Asn Ile Val Leu Val Met Tyr Asp Ile Asp Tyr His Tyr Tyr
                100                 105                 110

Gly Met Asp Val Trp Gly Gln Gly Thr Thr Val Thr Val Ser Ser
            115                 120                 125

<210> SEQ ID NO 160
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gln Val Gln Leu Val Glu Ser Gly Gly Val Val Gln Pro Gly Arg
1               5                   10                  15

Ser Leu Arg Leu Ser Cys Ala Val Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ala Ile Ser Tyr Asp Gly Ser Asn Lys Tyr Tyr Val Asp Ser Val
        50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Asn Cys
                85                  90                  95

Ala Lys Asn Ile Val Leu Val Met Tyr Asp Ile Asp Tyr His Tyr Tyr
                100                 105                 110

Gly Met Asp Val Trp Gly Gln Gly Thr Thr Val Thr Val Ser Ser
            115                 120                 125

<210> SEQ ID NO 161
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ile Val Leu Val Met Tyr Asp Ile Asp Tyr His Tyr Tyr
            100                 105                 110

Gly Met Asp Val Trp Gly Gln Gly Thr Thr Val Thr Val Ser Ser
        115                 120                 125
```

<210> SEQ ID NO 162
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 162

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Ala Ser
            20                  25                  30

Gly Val Gly Val Gly Trp Phe Arg Gln Pro Pro Gly Lys Ala Leu Glu
        35                  40                  45

Trp Leu Ala Leu Ile Tyr Trp Asn Asp Asp Lys Arg Tyr Ser Pro Ser
50                  55                  60

Leu Lys Asn Ser Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Ile His Leu Trp Ser Tyr Phe Tyr Tyr Gly Met Asp
            100                 105                 110

Val Trp Gly Gln Gly Thr Thr Val Thr Val Ser Ser
        115                 120
```

<210> SEQ ID NO 163
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 163

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Ala Ser
            20                  25                  30

Gly Val Gly Val Gly Trp Phe Arg Gln Pro Pro Gly Lys Ala Leu Glu
        35                  40                  45
```

```
Trp Leu Ala Leu Ile Tyr Trp Asn Asp Asp Lys Arg Tyr Ser Pro Ser
         50                  55                  60

Leu Lys Asn Ser Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Arg Ile His Leu Trp Ser Tyr Phe Tyr Tyr Gly Met Asp
                100                 105                 110

Val Trp Gly Gln Gly Thr Thr Val Thr Val Ser Ser
            115                 120

<210> SEQ ID NO 164
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Ala Ser
                20                  25                  30

Gly Val Gly Val Gly Trp Ile Arg Gln Pro Pro Gly Lys Ala Leu Glu
            35                  40                  45

Trp Leu Ala Leu Ile Tyr Trp Asn Asp Asp Lys Arg Tyr Ser Pro Ser
         50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Arg Ile His Leu Trp Ser Tyr Phe Tyr Tyr Gly Met Asp
                100                 105                 110

Val Trp Gly Gln Gly Thr Thr Val Thr Val Ser Ser
            115                 120

<210> SEQ ID NO 165
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Gln Val Gln Leu Val Gln Ser Gly Pro Glu Val Lys Asn Pro Gly Ala
 1               5                  10                  15

Ser Val Lys Val Ser Cys Lys Ala Ser Gly Tyr Thr Phe Thr Thr Tyr
                20                  25                  30

Gly Ile Ser Trp Val Arg Gln Ala Pro Gly Gln Gly Leu Glu Trp Met
            35                  40                  45

Gly Trp Ile Ser Gly Tyr Asn Gly Lys Thr Asn Asp Ala Gln Lys Phe
         50                  55                  60

Gln Asp Arg Val Ala Met Thr Thr Asp Thr Ser Thr Ser Thr Ala Tyr
 65                  70                  75                  80

Met Glu Leu Arg Ser Leu Arg Ser Asp Asp Thr Ala Ile Tyr Tyr Cys
                 85                  90                  95
```

```
Ser Arg Asp Arg Leu Val Val Pro Pro Ala Leu Asn Tyr Ser Tyr Tyr
            100                 105                 110

Val Met Asp Val Trp Gly Gln Gly Thr Thr Val Thr Val Ser Ser
            115                 120                 125

<210> SEQ ID NO 166
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Gln Val Gln Leu Val Gln Ser Gly Pro Glu Val Lys Asn Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Asn Tyr Ser Tyr Tyr
            100                 105                 110

Val Met Asp Val Trp Gly Gln Gly Thr Thr Val Thr Val Ser Ser
            115                 120                 125

<210> SEQ ID NO 167
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Asp Arg Leu Val Val Pro Pro Ala Leu Asn Tyr Ser Tyr Tyr
            100                 105                 110

Val Met Asp Val Trp Gly Gln Gly Thr Thr Val Thr Val Ser Ser
            115                 120                 125

<210> SEQ ID NO 168
```

<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 168

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asp Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Thr Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Gly Ser Ser Arg Leu Phe Asp Tyr Trp Gly Gln Gly Thr
            100                 105                 110

Leu Val Thr Val Ser Ser
        115

<210> SEQ ID NO 169
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 169

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asp Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Thr Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Gly Ser Ser Arg Leu Phe Asp Tyr Trp Gly Gln Gly Thr
            100                 105                 110

Leu Val Thr Val Ser Ser
        115

<210> SEQ ID NO 170
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 170

-continued

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ser Ser Arg Leu Phe Asp Tyr Trp Gly Gln Gly Thr
            100                 105                 110

Leu Val Thr Val Ser Ser
            115

<210> SEQ ID NO 171
<211> LENGTH: 128
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 171

Gln Val His Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Ile
        35                  40                  45

Ser Tyr Ile Ser Asn Asp Gly Gly Thr Lys Tyr Tyr Val Asp Ser Val
    50                  55                  60

Glu Gly Arg Phe Ile Ile Ser Arg Asp Asn Ala Lys Asn Ser Leu Tyr
65                  70                  75                  80

Leu His Met Asn Ser Leu Arg Ala Asp Asp Thr Ala Val Tyr Tyr Cys
                85                  90                  95

Ala Arg Asp Gln Gly Tyr Ile Gly Tyr Asp Ser Tyr Tyr Tyr Tyr Ser
            100                 105                 110

Tyr Gly Met Asp Val Trp Gly Gln Gly Thr Thr Val Thr Val Ala Ser
        115                 120                 125

<210> SEQ ID NO 172
<211> LENGTH: 128
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 172

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Ile
        35                  40                  45

Ser Tyr Ile Ser Asn Asp Gly Gly Thr Lys Tyr Tyr Val Asp Ser Val
        50                  55                  60

Glu Gly Arg Phe Ile Ile Ser Arg Asp Asn Ala Lys Asn Ser Leu Tyr
65                  70                  75                  80

Leu His Met Asn Ser Leu Arg Ala Asp Thr Ala Val Tyr Tyr Cys
                85                  90                  95

Ala Arg Asp Gln Gly Tyr Ile Gly Tyr Asp Ser Tyr Tyr Tyr Tyr Ser
                100                 105                 110

Tyr Gly Met Asp Val Trp Gly Gln Gly Thr Thr Val Thr Val Ser Ser
            115                 120                 125

<210> SEQ ID NO 173
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
                20                  25                  30

Tyr Met Ser Trp Ile Arg Gln Ala Pro Gly Lys Gly Leu Glu Trp Val
            35                  40                  45

Ser Tyr Ile Ser Asn Asp Gly Gly Thr Lys Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Tyr Ile Gly Tyr Asp Ser Tyr Tyr Tyr Tyr Ser
                100                 105                 110

Tyr Gly Met Asp Val Trp Gly Gln Gly Thr Thr Val Thr Val Ser Ser
            115                 120                 125

<210> SEQ ID NO 174
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Glu Val Gln Lys Val Glu Ser Gly Gly Gly Leu Val Lys Pro Gly Gly
1               5                   10                  15

Ser Leu Arg Leu Ser Cys Thr Ala Ser Gly Phe Thr Phe Ser Thr Tyr
                20                  25                  30

Asn Met Asn Trp Val Arg Gln Ala Pro Gly Lys Gly Leu Glu Trp Val
            35                  40                  45

Ser Ser Ile Arg Ser Ser Ser Asn Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120

<210> SEQ ID NO 175
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120

<210> SEQ ID NO 176
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120

<210> SEQ ID NO 177
<211> LENGTH: 120

-continued

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120

<210> SEQ ID NO 178
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120

<210> SEQ ID NO 179
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Glu Val Gln Leu Val Glu Ser Gly Gly Gly Leu Val Lys Pro Gly Gly
```

```
1               5                   10                  15
Ser Leu Arg Leu Ser Cys Ala Ala Ser Gly Phe Thr Phe Ser Thr Tyr
            20                  25                  30

Asn Met Asn Trp Val Arg Gln Ala Pro Gly Lys Gly Leu Glu Trp Val
            35                  40                  45

Ser Ser Ile Arg Ser Ser Asn Tyr Ile Tyr Tyr Ala Asp Ser Val
            50                  55                  60

Lys Gly Arg Phe Thr Ile Ser Arg Asp Asn Ala Lys Asn Ser Leu Tyr
65                      70                  75                  80

Leu Gln Met Asn Ser Leu Arg Ala Glu Asp Thr Ala Val Tyr Tyr Cys
            85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
            115                 120

<210> SEQ ID NO 180
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
            35                  40                  45

Ser Ser Ile Arg Ser Ser Asn Tyr Ile Tyr Tyr Ala Asp Ser Val
            50                  55                  60

Lys Gly Arg Phe Thr Ile Ser Arg Asp Asn Ala Lys Ser Ser Leu Tyr
65                      70                  75                  80

Leu Gln Met Asn Ser Leu Arg Ala Glu Asp Thr Ala Val Tyr Tyr Cys
            85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
            115                 120

<210> SEQ ID NO 181
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
            35                  40                  45

Ser Ser Ile Arg Ser Ser Asn Tyr Ile Tyr Tyr Ala Asp Ser Val
```

```
                50                  55                  60
Lys Gly Arg Phe Thr Ile Ser Arg Asp Asn Ala Lys Ser Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ser Ser Trp Tyr Asp Tyr Ser Asp Tyr Trp Gly Gln
                100                 105                 110

Gly Thr Leu Val Thr Val Ser Ser
            115                 120

<210> SEQ ID NO 182
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
                20                  25                  30

Asn Met Asn Trp Val Arg Gln Ala Pro Gly Lys Gly Leu Glu Trp Val
            35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ser Ser Trp Tyr Asp Tyr Ser Asp Tyr Trp Gly Gln
                100                 105                 110

Gly Thr Leu Val Thr Val Ser Ser
            115                 120

<210> SEQ ID NO 183
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Glu Val Gln Leu Val Glu Ser Gly Gly Gly Leu Val Lys Pro Gly Gly
 1               5                  10                  15

Ser Leu Arg Leu Ser Cys Thr Ala Ser Gly Phe Thr Phe Ser Thr Tyr
                20                  25                  30

Asn Met Asn Trp Val Arg Gln Ala Pro Gly Lys Gly Leu Glu Trp Val
            35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Asp Gly Ser Ser Trp Tyr Asp Tyr Ser Asp Tyr Trp Gly Gln
```

```
                 100                 105                 110

Gly Thr Leu Val Thr Val Ser Ser
            115                 120

<210> SEQ ID NO 184
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
            115                 120

<210> SEQ ID NO 185
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
            115                 120

<210> SEQ ID NO 186
<211> LENGTH: 118
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 186

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Gly Asp Tyr
            20                  25                  30

Asp Met His Trp Val Arg Gln Ala Thr Gly Arg Gly Leu Glu Trp Val
        35                  40                  45

Ser Gly Ile Ala Pro Ala Gly Asp Thr Ser Tyr Thr Gly Ser Val Lys
    50                  55                  60

Gly Arg Phe Thr Ile Ser Arg Glu Asn Ala Lys Asn Ser Leu His Leu
65                  70                  75                  80

Gln Met Asn Ser Leu Thr Thr Gly Asp Thr Ala Ile Tyr Tyr Cys Ala
                85                  90                  95

Arg Glu Asp Ile Ala Val Pro Gly Phe Asp Tyr Trp Gly Gln Gly Thr
            100                 105                 110

Leu Val Thr Val Ser Ser
        115

<210> SEQ ID NO 187
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Gly Asp Tyr
            20                  25                  30

Asp Met His Trp Val Arg Gln Ala Thr Gly Arg Gly Leu Glu Trp Val
        35                  40                  45

Ser Gly Ile Ala Pro Ala Gly Asp Thr Ser Tyr Thr Gly Ser Val Lys
    50                  55                  60

Gly Arg Phe Thr Ile Ser Arg Glu Asn Ala Lys Asn Ser Leu His Leu
65                  70                  75                  80

Gln Met Asn Ser Leu Thr Thr Gly Asp Thr Ala Ile Tyr Tyr Cys Ala
                85                  90                  95

Arg Glu Asp Ile Ala Val Pro Gly Phe Asp Tyr Trp Gly Gln Gly Thr
            100                 105                 110

Leu Val Thr Val Ser Ser
        115

<210> SEQ ID NO 188
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Glu Val Gln Leu Val Glu Ser Gly Gly Gly Leu Val Gln Pro Gly Gly
1               5                   10                  15
```

-continued

Ser Leu Arg Leu Ser Cys Ala Ala Ser Gly Phe Thr Phe Gly Asp Tyr
            20                  25                  30

Asp Met His Trp Val Arg Gln Ala Thr Gly Lys Gly Leu Glu Trp Val
        35                  40                  45

Ser Ala Ile Ala Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Asp Ile Ala Val Pro Gly Phe Asp Tyr Trp Gly Gln Gly Thr
            100                 105                 110

Leu Val Thr Val Ser Ser
        115

<210> SEQ ID NO 189
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gln Ile Leu Leu Val Gln Ser Gly Pro Glu Val Lys Glu Pro Gly Ala
1               5                   10                  15

Ser Val Lys Val Ser Cys Lys Ala Ser Gly Tyr Thr Phe Thr Asn Tyr
            20                  25                  30

Ala Ile Ser Trp Val Arg Gln Val Pro Gly Gln Gly Leu Glu Trp Met
        35                  40                  45

Gly Trp Val Ser Ala Tyr Asn Gly His Thr Asn Tyr Ala His Glu Val
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Met Tyr Tyr Cys
                85                  90                  95

Ala Arg Gly Gly Val Val Val Pro Val Ala Pro His Phe Tyr Asn Gly
            100                 105                 110

Met Asp Val Trp Gly Gln Gly Thr Thr Val Thr Val Ser Ser
        115                 120                 125

<210> SEQ ID NO 190
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gln Val Gln Leu Val Gln Ser Gly Pro Glu Val Lys Glu Pro Gly Ala
1               5                   10                  15

Ser Val Lys Val Ser Cys Lys Ala Ser Gly Tyr Thr Phe Thr Asn Tyr
            20                  25                  30

Ala Ile Ser Trp Val Arg Gln Val Pro Gly Gln Gly Leu Glu Trp Met
        35                  40                  45

Gly Trp Val Ser Ala Tyr Asn Gly His Thr Asn Tyr Ala His Glu Val
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Met Tyr Tyr Cys
                85                  90                  95

Ala Arg Gly Gly Val Val Val Pro Val Ala Pro His Phe Tyr Asn Gly
            100                 105                 110

Met Asp Val Trp Gly Gln Gly Thr Thr Val Thr Val Ser Ser
        115                 120                 125

<210> SEQ ID NO 191
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ala Ile Ser Trp Val Arg Gln Ala Pro Gly Gln Gly Leu Glu Trp Met
        35                  40                  45

Gly Trp Val Ser Ala Tyr Asn Gly His Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Val Val Val Pro Val Ala Pro His Phe Tyr Asn Gly
            100                 105                 110

Met Asp Val Trp Gly Gln Gly Thr Thr Val Thr Val Ser Ser
        115                 120                 125

<210> SEQ ID NO 192
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Thr Gly Ser Val Met
    50                  55                  60

Gly Arg Phe Thr Ile Ser Arg Asp Ala Ala Lys Asn Ser Phe Tyr Leu
65                  70                  75                  80

Glu Met Asn Ser Leu Arg Val Gly Asp Thr Ala Val Tyr Tyr Cys Ala
                85                  90                  95

Arg Glu Gly Ile Arg Thr Pro Tyr Asp Tyr Trp Gly Gln Gly Ala Arg
            100                 105                 110

Val Thr Val Ser Ser
        115

<210> SEQ ID NO 193
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Thr Gly Ser Val Met
    50                  55                  60

Gly Arg Phe Thr Ile Ser Arg Asp Ala Ala Lys Asn Ser Phe Tyr Leu
65                  70                  75                  80

Glu Met Asn Ser Leu Arg Val Gly Asp Thr Ala Val Tyr Tyr Cys Ala
                85                  90                  95

Arg Glu Gly Ile Arg Thr Pro Tyr Asp Tyr Trp Gly Gln Gly Thr Leu
            100                 105                 110

Val Thr Val Ser Ser
        115

<210> SEQ ID NO 194
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Ile Arg Thr Pro Tyr Asp Tyr Trp Gly Gln Gly Thr Leu
            100                 105                 110

Val Thr Val Ser Ser
        115

<210> SEQ ID NO 195
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Thr Gly Ser Val Met
    50                  55                  60

Gly Arg Phe Thr Ile Ser Arg Asp Ala Ala Lys Asn Ser Phe Tyr Leu
65                  70                  75                  80

Glu Met Asn Ser Leu Arg Val Gly Asp Thr Ala Val Tyr Tyr Cys Ala
                85                  90                  95

Arg Glu Gly Ile Arg Thr Pro Tyr Asp Tyr Trp Gly Gln Gly Ala Arg
            100                 105                 110

Val Thr Val Ser Ser
        115

<210> SEQ ID NO 196
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Thr Gly Ser Val Met
    50                  55                  60

Gly Arg Phe Thr Ile Ser Arg Asp Ala Ala Lys Asn Ser Phe Tyr Leu
65                  70                  75                  80

Glu Met Asn Ser Leu Arg Val Gly Asp Thr Ala Val Tyr Tyr Cys Ala
                85                  90                  95

Arg Glu Gly Ile Arg Thr Pro Tyr Asp Tyr Trp Gly Gln Gly Thr Leu
            100                 105                 110

Val Thr Val Ser Ser
        115

<210> SEQ ID NO 197
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Ile Arg Thr Pro Tyr Asp Tyr Trp Gly Gln Gly Thr Leu
            100                 105                 110

Val Thr Val Ser Ser
        115

<210> SEQ ID NO 198
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Asn Ser Gly Ser Ile Gly Tyr Ala Asp Ser Val
    50                  55                  60

Lys Gly Arg Phe Thr Ile Ser Arg Asp Asn Ala Lys His Ser Leu Tyr
65                  70                  75                  80

Leu Gln Met Asn Ser Leu Arg Pro Glu Asp Thr Ala Leu Tyr Tyr Cys
                85                  90                  95

Val Lys Glu Val Thr Thr Gly Tyr Tyr Tyr Gly Met Asp Val Trp Gly
            100                 105                 110

Gln Gly Thr Thr Val Thr Val Ser Ser
        115                 120

<210> SEQ ID NO 199
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Asn Ser Gly Ser Ile Gly Tyr Ala Asp Ser Val
    50                  55                  60
```

```
Lys Gly Arg Phe Thr Ile Ser Arg Asp Asn Ala Lys His Ser Leu Tyr
 65                  70                  75                  80

Leu Gln Met Asn Ser Leu Arg Pro Glu Asp Thr Ala Leu Tyr Tyr Cys
                 85                  90                  95

Val Lys Glu Val Thr Thr Gly Tyr Tyr Tyr Gly Met Asp Val Trp Gly
            100                 105                 110

Gln Gly Thr Thr Val Thr Val Ser Ser
            115                 120

<210> SEQ ID NO 200
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Val Lys Glu Val Thr Thr Gly Tyr Tyr Tyr Gly Met Asp Val Trp Gly
            100                 105                 110

Gln Gly Thr Thr Val Thr Val Ser Ser
            115                 120

<210> SEQ ID NO 201
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Asp Trp Val
        35                  40                  45

Ser Gly Ile Ser Gly Asn Gly Gly Ser Thr Tyr Tyr Ala Asp Ser Val
    50                  55                  60

Lys Gly Arg Phe Thr Ile Ser Arg Asp Ile Ser Lys Asn Thr Leu Tyr
 65                  70                  75                  80

Val Gln Met His Ser Leu Arg Val Glu Asp Thr Ala Val Tyr Tyr Cys
                 85                  90                  95

Ala Lys Ala Arg Tyr Tyr Asp Phe Trp Gly Gly Asn Phe Asp Leu Trp
            100                 105                 110
```

Gly Arg Gly Thr Gln Val Thr Val Ser Ser
            115                 120

<210> SEQ ID NO 202
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Asp Trp Val
        35                  40                  45

Ser Gly Ile Ser Gly Asn Gly Gly Ser Thr Tyr Tyr Ala Asp Ser Val
    50                  55                  60

Lys Gly Arg Phe Thr Ile Ser Arg Asp Ile Ser Lys Asn Thr Leu Tyr
65                  70                  75                  80

Val Gln Met His Ser Leu Arg Val Glu Asp Thr Ala Val Tyr Tyr Cys
                85                  90                  95

Ala Lys Ala Arg Tyr Tyr Asp Phe Trp Gly Asn Phe Asp Leu Trp
            100                 105                 110

Gly Arg Gly Thr Leu Val Thr Val Ser Ser
            115                 120

<210> SEQ ID NO 203
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Arg Tyr Tyr Asp Phe Trp Gly Asn Phe Asp Leu Trp
            100                 105                 110

Gly Arg Gly Thr Leu Val Thr Val Ser Ser
            115                 120

<210> SEQ ID NO 204
<211> LENGTH: 127
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 204

Gln Val Gln Leu Val Gln Ser Gly Pro Glu Val Lys Asn Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Tyr Tyr Ser Tyr Tyr
            100                 105                 110

Val Met Asp Val Trp Gly Gln Gly Thr Thr Val Thr Val Ser Ser
        115                 120                 125

<210> SEQ ID NO 205
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Gln Val Gln Leu Val Gln Ser Gly Pro Glu Val Lys Asn Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Tyr Tyr Ser Tyr Tyr
            100                 105                 110

Val Met Asp Val Trp Gly Gln Gly Thr Thr Val Thr Val Ser Ser
        115                 120                 125

<210> SEQ ID NO 206
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr

```
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Asp Arg Leu Val Val Pro Pro Ala Leu Tyr Tyr Ser Tyr Tyr
               100                 105                 110

Val Met Asp Val Trp Gly Gln Gly Thr Thr Val Thr Val Ser Ser
           115                 120                 125
```

<210> SEQ ID NO 207
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

```
Gln Val Gln Leu Val Gln Ser Gly Pro Glu Val Lys Asn Pro Gly Ala
1               5                  10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Asn Tyr Tyr Tyr Tyr
               100                 105                 110

Val Met Asp Val Trp Gly Gln Gly Thr Thr Val Thr Val Ser Ser
           115                 120                 125
```

<210> SEQ ID NO 208
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

```
Gln Val Gln Leu Val Gln Ser Gly Pro Glu Val Lys Asn Pro Gly Ala
1               5                  10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
```

```
                 65                  70                  75                  80
Met Glu Leu Arg Ser Leu Arg Ser Asp Asp Thr Ala Ile Tyr Tyr Cys
                 85                  90                  95

Ser Arg Asp Arg Leu Val Val Pro Pro Ala Leu Asn Tyr Tyr Tyr Tyr
            100                 105                 110

Val Met Asp Val Trp Gly Gln Gly Thr Thr Val Thr Val Ser Ser
            115                 120                 125

<210> SEQ ID NO 209
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Gly Ile Ser Trp Val Arg Gln Ala Pro Gly Gln Gly Leu Glu Trp Met
            35                  40                  45

Gly Trp Ile Ser Gly Tyr Asn Gly Lys Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Asp Arg Leu Val Val Pro Pro Ala Leu Asn Tyr Tyr Tyr Tyr
            100                 105                 110

Val Met Asp Val Trp Gly Gln Gly Thr Thr Val Thr Val Ser Ser
            115                 120                 125

<210> SEQ ID NO 210
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Gln Val Gln Leu Val Gln Ser Gly Pro Glu Val Lys Asn Pro Gly Ala
1               5                   10                  15

Ser Val Lys Val Ser Cys Lys Ala Ser Gly Tyr Thr Phe Thr Thr Tyr
                20                  25                  30

Gly Ile Ser Trp Val Arg Gln Ala Pro Gly Gln Gly Leu Glu Trp Met
            35                  40                  45

Gly Trp Ile Ser Gly Tyr Asn Gly Lys Thr Asn Asp Ala Gln Lys Phe
        50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Tyr Tyr Tyr Tyr Tyr
            100                 105                 110

Val Met Asp Val Trp Gly Gln Gly Thr Thr Val Thr Val Ser Ser
```

```
                115           120           125
```

<210> SEQ ID NO 211
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

```
Gln Val Gln Leu Val Gln Ser Gly Pro Glu Val Lys Asn Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Tyr Tyr Tyr Tyr Tyr
            100                 105                 110

Val Met Asp Val Trp Gly Gln Gly Thr Thr Val Thr Val Ser Ser
        115                 120                 125
```

<210> SEQ ID NO 212
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Asp Arg Leu Val Val Pro Pro Ala Leu Tyr Tyr Tyr Tyr Tyr
            100                 105                 110

Val Met Asp Val Trp Gly Gln Gly Thr Thr Val Thr Val Ser Ser
        115                 120                 125
```

<210> SEQ ID NO 213
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 213

Gln Val His Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Ile
        35                  40                  45

Ser Tyr Ile Ser Asn Asp Gly Gly Thr Lys Tyr Tyr Val Asp Ser Val
    50                  55                  60

Glu Gly Arg Phe Ile Ile Ser Arg Asp Asn Ala Lys Asn Ser Leu Tyr
65                  70                  75                  80

Leu His Met Asn Ser Leu Arg Ala Asp Asp Thr Ala Val Tyr Tyr Cys
                85                  90                  95

Ala Arg Asp Gln Gly Tyr Ile Gly Tyr Asp Ser Tyr Tyr Tyr Tyr Ser
            100                 105                 110

Tyr Gly Met Asp Val Trp Gly Gln Gly Thr Thr Val Thr Val Ala Ser
        115                 120                 125

<210> SEQ ID NO 214
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Ile
        35                  40                  45

Ser Tyr Ile Ser Asn Asp Gly Gly Thr Lys Tyr Tyr Val Asp Ser Val
    50                  55                  60

Glu Gly Arg Phe Ile Ile Ser Arg Asp Asn Ala Lys Asn Ser Leu Tyr
65                  70                  75                  80

Leu His Met Asn Ser Leu Arg Ala Asp Asp Thr Ala Val Tyr Tyr Cys
                85                  90                  95

Ala Arg Asp Gln Gly Tyr Ile Gly Tyr Asp Ser Tyr Tyr Tyr Tyr Ser
            100                 105                 110

Tyr Gly Met Asp Val Trp Gly Gln Gly Thr Thr Val Thr Val Ser Ser
        115                 120                 125

<210> SEQ ID NO 215
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Val
            35                  40                  45

Ser Tyr Ile Ser Asn Asp Gly Thr Lys Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Tyr Ile Gly Tyr Asp Ser Tyr Tyr Tyr Tyr Ser
            100                 105                 110

Tyr Gly Met Asp Val Trp Gly Gln Gly Thr Thr Val Thr Val Ser Ser
            115                 120                 125

<210> SEQ ID NO 216
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Gln Ile Leu Leu Val Gln Ser Gly Pro Glu Val Lys Glu Pro Gly Ala
1               5                   10                  15

Ser Val Lys Val Ser Cys Lys Ala Ser Gly Tyr Thr Phe Thr Asn Tyr
                20                  25                  30

Ala Ile Ser Trp Val Arg Gln Val Pro Gly Gln Gly Leu Glu Trp Met
            35                  40                  45

Gly Trp Val Ser Ala Tyr Asn Gly His Thr Asn Tyr Ala His Glu Val
50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Met Tyr Tyr Cys
                85                  90                  95

Ala Arg Gly Gly Val Val Val Pro Val Ala Pro His Phe Tyr Asn Gly
            100                 105                 110

Met Asp Val Trp Gly Gln Gly Thr Thr Val Thr Val Ser Ser
            115                 120                 125

<210> SEQ ID NO 217
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Gln Val Gln Leu Val Gln Ser Gly Pro Glu Val Lys Glu Pro Gly Ala
1               5                   10                  15

Ser Val Lys Val Ser Cys Lys Ala Ser Gly Tyr Thr Phe Thr Asn Tyr
                20                  25                  30

Ala Ile Ser Trp Val Arg Gln Val Pro Gly Gln Gly Leu Glu Trp Met
            35                  40                  45

Gly Trp Val Ser Ala Tyr Asn Gly His Thr Asn Tyr Ala His Glu Val
50                  55                  60

Gln Gly Arg Val Thr Met Thr Thr Asp Thr Ser Thr Thr Thr Ala Tyr
65                  70                  75                  80

```
Met Glu Leu Arg Ser Leu Arg Ser Asp Asp Thr Ala Met Tyr Tyr Cys
                85                  90                  95

Ala Arg Gly Gly Val Val Val Pro Val Ala Pro His Phe Tyr Asn Gly
            100                 105                 110

Met Asp Val Trp Gly Gln Gly Thr Thr Val Thr Val Ser Ser
            115                 120                 125

<210> SEQ ID NO 218
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ala Ile Ser Trp Val Arg Gln Ala Pro Gly Gln Gly Leu Glu Trp Met
        35                  40                  45

Gly Trp Val Ser Ala Tyr Asn Gly His Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Val Val Val Pro Val Ala Pro His Phe Tyr Asn Gly
            100                 105                 110

Met Asp Val Trp Gly Gln Gly Thr Thr Val Thr Val Ser Ser
            115                 120                 125

<210> SEQ ID NO 219
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe His Thr
            20                  25                  30

Ser Asn Asn Lys Asn Tyr Leu Val Trp Tyr Gln Gln Lys Pro Gly Gln
        35                  40                  45

Pro Pro Lys Leu Leu Leu Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Asn Tyr Tyr Cys His Gln
                85                  90                  95

Tyr Tyr Ser Ile Pro Trp Thr Phe Gly Gln Gly Thr Lys Val Glu Ile
            100                 105                 110

Lys
```

<210> SEQ ID NO 220
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys

<210> SEQ ID NO 221
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Asp Ile Gln Met Thr Gln Ser Pro Ser Phe Leu Ser Ala Ser Val Gly
1               5                   10                  15

Asp Arg Val Thr Ile Thr Cys Trp Ala Ser Gln Asp Ile Ser Ser Tyr
            20                  25                  30

Leu Ala Trp Tyr Gln Gln Lys Pro Gly Ile Ala Pro Lys Leu Leu Ile
        35                  40                  45

Tyr Ala Ala Ser Thr Leu Gln Ser Gly Val Pro Ser Arg Phe Gly Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Arg
                85                  90                  95

Thr Phe Gly Gln Gly Thr Lys Val Glu Ile Lys
            100                 105

<210> SEQ ID NO 222
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Asp Ile Val Met Thr Gln Ser Pro Leu Ser Leu Pro Val Thr Pro Gly
1               5                   10                  15

```
Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100                 105                 110
```

<210> SEQ ID NO 223
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

```
Asp Ile Gln Met Thr Gln Ser Pro Ala Thr Leu Ser Val Ser Pro Gly
1               5                   10                  15

Glu Arg Ala Ala Leu Ser Cys Arg Ala Ser Gln Ser Val Ser Ser Asn
            20                  25                  30

Leu Ala Trp Tyr His Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ile Gly Ser Gly Thr Glu Phe Thr Leu Ile Ile Ser Ser Leu Gln Ser
65                  70                  75                  80

Glu Asp Phe Ala Phe Tyr Phe Cys Gln Gln Tyr Asn Asn Trp Pro Pro
                85                  90                  95

Phe Thr Phe Gly Pro Gly Thr Lys Val Glu Ile Lys Arg
            100                 105
```

<210> SEQ ID NO 224
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

```
Glu Ile Val Met Thr Gln Ser Pro Ala Thr Leu Ser Val Ser Pro Gly
1               5                   10                  15

Glu Arg Ala Ala Leu Ser Cys Arg Ala Ser Gln Ser Val Ser Ser Asn
            20                  25                  30

Leu Ala Trp Tyr His Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ile Gly Ser Gly Thr Glu Phe Thr Leu Ile Ile Ser Ser Leu Gln Ser
65                  70                  75                  80

Glu Asp Phe Ala Phe Tyr Phe Cys Gln Gln Tyr Asn Asn Trp Pro Pro
                85                  90                  95
```

```
Phe Thr Phe Gly Pro Gly Thr Lys Val Asp Ile Lys
            100                 105
```

<210> SEQ ID NO 225
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
            100                 105
```

<210> SEQ ID NO 226
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

```
Ala Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Tyr Thr
                85                  90                  95

Phe Gly Gln Gly Thr Lys Val Glu Ile Lys Arg
            100                 105
```

<210> SEQ ID NO 227
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Tyr Thr
                85                  90                  95

Phe Gly Gln Gly Thr Lys Leu Glu Ile Lys
            100                 105

<210> SEQ ID NO 228
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Tyr Thr
                85                  90                  95

Phe Gly Gln Gly Thr Lys Leu Glu Ile Lys
            100                 105

<210> SEQ ID NO 229
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Ala Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Phe His Thr
            20                  25                  30

Ser Asn Asn Lys Asn Tyr Leu Val Trp Tyr Gln Gln Lys Pro Gly Gln
        35                  40                  45

Pro Pro Lys Leu Leu Leu Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80
```

-continued

Ile Ser Ser Leu Gln Ala Glu Asp Val Ala Asn Tyr Tyr Cys His Gln
                85                  90                  95

Tyr Tyr Ser Ile Pro Trp Thr Phe Gly Gln Gly Thr Lys Val Glu Ile
            100                 105                 110

Lys Arg

<210> SEQ ID NO 230
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe His Thr
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Ile Pro Trp Thr Phe Gly Gln Gly Thr Lys Val Glu Ile
            100                 105                 110

Lys

<210> SEQ ID NO 231
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Val Glu Ile
            100                 105                 110

Lys Arg

<210> SEQ ID NO 232
<211> LENGTH: 113

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Arg Asn Phe Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys

<210> SEQ ID NO 233
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys Arg
            100                 105

<210> SEQ ID NO 234
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30
```

```
Leu Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Trp
                 85                  90                  95

Thr Phe Gly Gln Gly Thr Lys Val Glu Ile Lys
                100                 105
```

<210> SEQ ID NO 235
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

```
Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
             20                  25                  30

Leu Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Trp
                 85                  90                  95

Thr Phe Gly Gln Gly Thr Lys Val Glu Ile Lys
                100                 105
```

<210> SEQ ID NO 236
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

```
Asp Ile Gln Met Thr Gln Ser Pro Ser Phe Leu Ser Ala Ser Val Gly
 1               5                  10                  15

Asp Arg Val Thr Ile Thr Cys Trp Ala Ser Gln Asp Ile Ser Ser Tyr
             20                  25                  30

Leu Ala Trp Tyr Gln Gln Lys Pro Gly Ile Ala Pro Lys Leu Leu Ile
            35                  40                  45

Tyr Ala Ala Ser Thr Leu Gln Ser Gly Val Pro Ser Arg Phe Gly Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Arg
                 85                  90                  95

Thr Phe Gly Gln Gly Thr Lys Val Glu Ile Lys Arg
                100                 105
```

<210> SEQ ID NO 237
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Arg
                85                  90                  95

Thr Phe Gly Gln Gly Thr Lys Val Glu Ile Lys
            100                 105

<210> SEQ ID NO 238
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Ala Ile Gln Met Thr Gln Ser Pro Leu Ser Leu Ser Val Thr Leu Gly
1               5                   10                  15

Gln Pro Ala Ser Ile Ser Cys Arg Ser Ser Gln Ser Leu Val Tyr Ser
            20                  25                  30

Asp Gly Asp Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Ala Phe Thr Leu Lys Ile
65                  70                  75                  80

Ser Gly Val Glu Ala Glu Asp Val Gly Val Tyr Tyr Cys Met Gln Ala
                85                  90                  95

Thr His Trp Pro Arg Thr Phe Gly Gln Gly Thr Lys Val Glu Ile Lys
            100                 105                 110

Arg

<210> SEQ ID NO 239
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Asp Val Val Met Thr Gln Ser Pro Leu Ser Leu Ser Val Thr Leu Gly

```
                1               5                  10                 15
Gln Pro Ala Ser Ile Ser Cys Arg Ser Ser Gln Ser Leu Val Tyr Ser
                20                 25                 30

Asp Gly Asp Thr Tyr Leu Asn Trp Phe Gln Gln Arg Pro Gly Gln Ser
            35                 40                 45

Pro Arg Arg Leu Ile Tyr Lys Val Ser Asn Arg Asp Ser Gly Val Pro
    50                 55                 60

Asp Arg Phe Ser Gly Ser Gly Ser Gly Thr Ala Phe Thr Leu Lys Ile
65                 70                 75                 80

Ser Gly Val Glu Ala Glu Asp Val Gly Val Tyr Tyr Cys Met Gln Ala
                85                 90                 95

Thr His Trp Pro Arg Thr Phe Gly Gln Gly Thr Lys Val Glu Ile Lys
            100                105                110

<210> SEQ ID NO 240
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Asp Val Val Met Thr Gln Ser Pro Leu Ser Leu Pro Val Thr Leu Gly
1               5                  10                 15

Gln Pro Ala Ser Ile Ser Cys Arg Ser Ser Gln Ser Leu Val Tyr Ser
                20                 25                 30

Asp Gly Asp Thr Tyr Leu Asn Trp Phe Gln Gln Arg Pro Gly Gln Ser
            35                 40                 45

Pro Arg Arg Leu Ile Tyr Lys Val Ser Asn Arg Asp Ser Gly Val Pro
    50                 55                 60

Asp Arg Phe Ser Gly Ser Gly Ser Gly Thr Asp Phe Thr Leu Lys Ile
65                 70                 75                 80

Ser Arg Val Glu Ala Glu Asp Val Gly Val Tyr Tyr Cys Met Gln Ala
                85                 90                 95

Thr His Trp Pro Arg Thr Phe Gly Gln Gly Thr Lys Val Glu Ile Lys
            100                105                110

<210> SEQ ID NO 241
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Asp Ile Gln Met Thr Gln Ser Pro Leu Ser Leu Pro Val Thr Pro Gly
1               5                  10                 15

Glu Pro Ala Ser Ile Ser Cys Arg Ser Ser Gln Ser Leu Leu His Ser
                20                 25                 30

His Gly Tyr Asp Tyr Leu Asp Trp Tyr Leu Gln Lys Pro Gly Gln Ser
            35                 40                 45

Pro Gln Leu Leu Ile Tyr Leu Gly Ser Asn Arg Ala Ser Gly Val Pro
    50                 55                 60

Asp Arg Phe Ser Gly Ser Gly Ser Gly Thr Asp Phe Thr Leu Lys Ile
65                 70                 75                 80

Ser Arg Val Glu Ala Glu Asp Val Gly Val Tyr Tyr Cys Met Gln Ala
```

```
                    85                  90                  95

Leu Gln Thr Pro Leu Thr Phe Gly Gly Gly Thr Lys Val Glu Ile Lys
            100                 105                 110

Arg

<210> SEQ ID NO 242
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

His Gly Tyr Asp Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 243
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

His Gly Tyr Asp Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 244
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 244

Asp Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

His Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Leu Thr Phe Gly Gly Gly Thr Lys Val Glu Ile Lys
            100                 105                 110

Arg

<210> SEQ ID NO 245
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

His Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 246
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

His Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro

```
                    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                     85                  90                  95

Leu Gln Thr Pro Leu Thr Phe Gly Gly Gly Thr Lys Val Glu Ile Lys
                100                 105                 110

<210> SEQ ID NO 247
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Asp Ile Val Met Thr Gln Ser Pro Leu Ser Leu Pro Val Thr Pro Gly
 1                   5                  10                  15

Glu Pro Ala Ser Ile Ser Cys Arg Ser Ser Gln Ser Leu Leu His Ser
                    20                  25                  30

Asn Gly Asn Asn Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Thr
                     85                  90                  95

Leu Gln Thr Pro Leu Thr Phe Gly Gly Gly Thr Lys Val Glu Ile Lys
                100                 105                 110

<210> SEQ ID NO 248
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Asp Ile Val Met Thr Gln Ser Pro Leu Ser Leu Pro Val Thr Pro Gly
 1                   5                  10                  15

Glu Pro Ala Ser Ile Ser Cys Arg Ser Ser Gln Ser Leu Leu His Ser
                    20                  25                  30

Asn Gly Asn Asn Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Thr
                     85                  90                  95

Leu Gln Thr Pro Leu Thr Phe Gly Gly Gly Thr Lys Val Glu Ile Lys
                100                 105                 110

<210> SEQ ID NO 249
<211> LENGTH: 112
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 249

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Arg
            100                 105                 110

<210> SEQ ID NO 250
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 251
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45
```

Pro Gln Leu Leu Ile Tyr Leu Gly Phe Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 252
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Phe Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Arg
            100                 105                 110

<210> SEQ ID NO 253
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Phe Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 254

```
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 255
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Leu Leu His Ser
            20                  25                  30

Asn Gly Tyr Asn Tyr Phe Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Leu Thr Phe Gly Gly Gly Thr Lys Val Glu Ile Arg
            100                 105                 110

<210> SEQ ID NO 256
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Leu Leu His Ser
            20                  25                  30
```

Asn Gly Tyr Asn Tyr Phe Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 257
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 258
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Ser Gln Gln Arg Pro Gly Gln Ser
            35                  40                  45

Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 259
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Ser Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 260
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 261
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp

```
            20                  25                  30

Leu Ala Trp Tyr Gln Gln Arg Pro Gly Lys Ala Pro Lys Leu Leu Ile
            35                  40                  45

Tyr Lys Ala Ser Ser Leu Glu Gly Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Trp Tyr
                 85                  90                  95

Thr Phe Gly Gln Gly Thr Lys Leu Glu Ile Lys
            100                 105

<210> SEQ ID NO 262
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Arg Pro Gly Lys Ala Pro Lys Leu Leu Ile
            35                  40                  45

Tyr Lys Ala Ser Ser Leu Glu Gly Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Trp Tyr
                 85                  90                  95

Thr Phe Gly Gln Gly Thr Lys Leu Glu Ile Lys
            100                 105

<210> SEQ ID NO 263
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Trp Tyr
                 85                  90                  95

Thr Phe Gly Gln Gly Thr Lys Leu Glu Ile Lys
```

-continued

```
                100                 105

<210> SEQ ID NO 264
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Lys Ile Val Leu Thr Gln Ser Pro Gly Thr Leu Pro Leu Phe Pro Gly
1               5                   10                  15

Glu Arg Ala Thr Leu Ser Cys Arg Ala Ser Gln Ser Val Asn Asn Lys
            20                  25                  30

Phe Leu Ala Trp Tyr Gln Gln Lys Ser Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Gly Leu Glu
65                  70                  75                  80

Pro Glu Asp Phe Glu Val Tyr Tyr Cys Gln Val Tyr Gly Asn Ser Leu
                85                  90                  95

Thr Leu Gly Gly Gly Thr Lys Val Glu Ile Lys
            100                 105

<210> SEQ ID NO 265
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Glu Ile Val Leu Thr Gln Ser Pro Gly Thr Leu Pro Leu Phe Pro Gly
1               5                   10                  15

Glu Arg Ala Thr Leu Ser Cys Arg Ala Ser Gln Ser Val Asn Asn Lys
            20                  25                  30

Phe Leu Ala Trp Tyr Gln Gln Lys Ser Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Gly Leu Glu
65                  70                  75                  80

Pro Glu Asp Phe Glu Val Tyr Tyr Cys Gln Val Tyr Gly Asn Ser Leu
                85                  90                  95

Thr Leu Gly Gly Gly Thr Lys Val Glu Ile Lys
            100                 105

<210> SEQ ID NO 266
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Glu Ile Val Leu Thr Gln Ser Pro Gly Thr Leu Ser Leu Ser Pro Gly
1               5                   10                  15
```

Glu Arg Ala Thr Leu Ser Cys Arg Ala Ser Gln Ser Val Asn Asn Lys
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Val Tyr Gly Asn Ser Leu
                85                  90                  95

Thr Phe Gly Gly Gly Thr Lys Val Glu Ile Lys
            100                 105

<210> SEQ ID NO 267
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Asn Gly Val Pro Ser Arg Phe Ser Gly
 50                  55                  60

Ser Gly Ser Gly Thr Glu Phe Thr Leu Ile Ile Ser Ser Leu Gln Pro
 65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105

<210> SEQ ID NO 268
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Asn Gly Val Pro Ser Arg Phe Ser Gly
 50                  55                  60

Ser Gly Ser Gly Thr Glu Phe Thr Leu Ile Ile Ser Ser Leu Gln Pro
 65                  70                  75                  80

Asp Asp Phe Ala Thr Tyr Tyr Cys Gln Gln Tyr Ile Ser Tyr Ser Arg
                85                  90                  95

```
Thr Phe Gly Gln Gly Thr Lys Val Glu Ile Lys
            100                 105
```

<210> SEQ ID NO 269
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105
```

<210> SEQ ID NO 270
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Asn Gly Val Pro Ser Arg Phe Ser Gly
50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105
```

<210> SEQ ID NO 271
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Asn Gly Val Pro Ser Arg Phe Ser Gly
50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105
```

<210> SEQ ID NO 272
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 272

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105
```

<210> SEQ ID NO 273
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 273

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Val Pro Gly Lys Ala Pro Lys Leu Leu Ile
        35                  40                  45

Tyr Lys Ala Ser Ser Leu Glu Asn Gly Val Pro Ser Arg Phe Ser Gly
50                  55                  60

Ser Gly Ser Gly Thr Glu Phe Thr Leu Ile Ile Ser Ser Leu Gln Pro
65                  70                  75                  80
```

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105

<210> SEQ ID NO 274
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Val Pro Gly Lys Ala Pro Lys Leu Leu Ile
        35                  40                  45

Tyr Lys Ala Ser Ser Leu Glu Asn Gly Val Pro Ser Arg Phe Ser Gly
    50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105

<210> SEQ ID NO 275
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105

<210> SEQ ID NO 276
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Asn Gly Val Pro Ser Arg Phe Ser Gly
50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105

<210> SEQ ID NO 277
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Asn Gly Val Pro Ser Arg Phe Ser Gly
50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105

<210> SEQ ID NO 278
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro

```
            65                  70                  75                  80
Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105
```

<210> SEQ ID NO 279
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

```
Glu Ile Val Met Thr Gln Ser Pro Ala Thr Leu Ser Val Ser Pro Gly
1               5                   10                  15

Glu Arg Gly Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Phe Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Pro
                85                  90                  95

Phe Thr Phe Gly Pro Gly Thr Lys Val Asp Phe Lys
            100                 105
```

<210> SEQ ID NO 280
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

```
Glu Ile Val Met Thr Gln Ser Pro Ala Thr Leu Ser Val Ser Pro Gly
1               5                   10                  15

Glu Arg Gly Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Phe Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Pro
                85                  90                  95

Phe Thr Phe Gly Pro Gly Thr Lys Val Asp Ile Lys
            100                 105
```

<210> SEQ ID NO 281
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 281

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Pro
                85                  90                  95

Phe Thr Phe Gly Pro Gly Thr Lys Val Asp Ile Lys
            100                 105

<210> SEQ ID NO 282
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Asp Ile Val Met Thr Gln Phe Pro Leu Ser Leu Pro Val Thr Pro Gly
1               5                   10                  15

Glu Pro Ala Ser Ile Ser Cys Arg Ser Ser Gln Ser Leu Leu His Ile
            20                  25                  30

Asn Glu Tyr Asn Tyr Leu Asp Trp Tyr Leu Lys Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Leu Gly Gln Gly Thr Lys Val Glu Ile Lys
            100                 105                 110

<210> SEQ ID NO 283
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ile
            20                  25                  30

Asn Glu Tyr Asn Tyr Leu Asp Trp Tyr Leu Lys Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Leu Gly Gln Gly Thr Lys Val Glu Ile Lys
            100                 105                 110

<210> SEQ ID NO 284
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ile
                20                  25                  30

Asn Glu Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 285
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Val Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
            100                 105

<210> SEQ ID NO 286
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 286

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Val Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
            100                 105

<210> SEQ ID NO 287
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 287

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
            100                 105

<210> SEQ ID NO 288
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 288

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Val Ala Trp Tyr Gln Gln Lys Pro Gly Gln Ala Pro Arg Leu Leu Ile
        35                  40                  45

```
Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
                100                 105
```

<210> SEQ ID NO 289
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Val Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
                100                 105
```

<210> SEQ ID NO 290
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
                100                 105
```

<210> SEQ ID NO 291
<211> LENGTH: 107

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Lys Lys Pro Gly Lys Ala Pro Asn Leu Leu Ile
        35                  40                  45

Tyr Asp Ala Ser Thr Leu Gln Ser Gly Val Pro Ser Arg Phe Ser Gly
50                  55                  60

Ser Gly Ser Gly Thr Glu Phe Thr Leu Thr Leu Ser Ser Leu Gln Pro
65                  70                  75                  80

Glu Asp Phe Ala Thr Tyr Tyr Cys Gln Gln Leu Asn Ile Tyr Pro Phe
                85                  90                  95

Thr Phe Gly Pro Gly Thr Lys Val Asp Ile Lys
            100                 105

<210> SEQ ID NO 292
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Lys Lys Pro Gly Lys Ala Pro Asn Leu Leu Ile
        35                  40                  45

Tyr Asp Ala Ser Thr Leu Gln Ser Gly Val Pro Ser Arg Phe Ser Gly
50                  55                  60

Ser Gly Ser Gly Thr Glu Phe Thr Leu Thr Leu Ser Ser Leu Gln Pro
65                  70                  75                  80

Glu Asp Phe Ala Thr Tyr Tyr Cys Gln Gln Leu Asn Ile Tyr Pro Phe
                85                  90                  95

Thr Phe Gly Pro Gly Thr Lys Val Asp Ile Lys
            100                 105

<210> SEQ ID NO 293
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
```

```
                    35                  40                  45
Tyr Asp Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ile Tyr Pro Phe
                 85                  90                  95

Thr Phe Gly Pro Gly Thr Lys Val Asp Ile Lys
                100                 105

<210> SEQ ID NO 294
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ile Arg
                20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Val Ser Val Ser Gly Thr Asp Phe Thr Leu Thr Ile Thr Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys
             100                 105

<210> SEQ ID NO 295
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ile Arg
                20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Val Ser Val Ser Gly Thr Asp Phe Thr Leu Thr Ile Thr Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys
             100                 105
```

```
<210> SEQ ID NO 296
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ile Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 297
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 298
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30
```

```
Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Tyr Thr Phe Gly Gln Gly Thr Lys Leu Glu Ile Lys
            100                 105                 110

<210> SEQ ID NO 299
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
                 20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Tyr Thr Phe Gly Gln Gly Thr Lys Leu Glu Ile Lys
            100                 105                 110

<210> SEQ ID NO 300
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
                 20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Tyr Thr Phe Gly Gln Gly Thr Lys Leu Glu Ile Lys
            100                 105                 110
```

<210> SEQ ID NO 301
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 302
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 303
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
                100                 105                 110

<210> SEQ ID NO 304
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
                100                 105                 110

<210> SEQ ID NO 305
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

```
Thr His Trp Pro Tyr Thr Phe Gly Gln Gly Thr Lys Leu Glu Ile Lys
            100                 105                 110
```

<210> SEQ ID NO 306
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

```
Lys Ile Val Leu Thr Gln Ser Pro Gly Thr Leu Pro Leu Phe Pro Gly
1               5                   10                  15

Glu Arg Ala Thr Leu Ser Cys Arg Ala Ser Gln Ser Val Asn Asn Lys
            20                  25                  30

Phe Leu Ala Trp Tyr Gln Gln Lys Ser Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Gly Leu Glu
65                  70                  75                  80

Pro Glu Asp Phe Glu Val Tyr Tyr Cys Gln Val Tyr Gly Asn Ser Leu
                85                  90                  95

Thr Phe Gly Gly Gly Thr Lys Val Glu Ile Lys
            100                 105
```

<210> SEQ ID NO 307
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

```
Glu Ile Val Leu Thr Gln Ser Pro Gly Thr Leu Pro Leu Phe Pro Gly
1               5                   10                  15

Glu Arg Ala Thr Leu Ser Cys Arg Ala Ser Gln Ser Val Asn Asn Lys
            20                  25                  30

Phe Leu Ala Trp Tyr Gln Gln Lys Ser Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Gly Leu Glu
65                  70                  75                  80

Pro Glu Asp Phe Glu Val Tyr Tyr Cys Gln Val Tyr Gly Asn Ser Leu
                85                  90                  95

Thr Phe Gly Gly Gly Thr Lys Val Glu Ile Lys
            100                 105
```

<210> SEQ ID NO 308
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

```
Glu Ile Val Leu Thr Gln Ser Pro Gly Thr Leu Ser Leu Ser Pro Gly
```

```
            1               5                  10                 15
        Glu Arg Ala Thr Leu Ser Cys Arg Ala Ser Gln Ser Val Asn Asn Lys
                        20                  25                  30

Phe Leu Ala Trp Tyr Gln Gln Lys Pro Gly Gln Ala Pro Arg Leu Leu
                        35                  40                  45

Ile Tyr Gly Ala Ser Ser Arg Ala Thr Gly Ile Pro Asp Arg Phe Ser
                    50                  55                  60

Gly Ser Gly Ser Gly Thr Asp Phe Thr Leu Thr Ile Ser Arg Leu Glu
        65                  70                  75                  80

Pro Glu Asp Phe Ala Val Tyr Tyr Cys Gln Val Tyr Gly Asn Ser Leu
                        85                  90                  95

Thr Phe Gly Gly Gly Thr Lys Val Glu Ile Lys
                        100                 105

<210> SEQ ID NO 309
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Asp Ile Val Met Thr Gln Phe Pro Leu Ser Leu Pro Val Thr Pro Gly
        1               5                   10                  15

Glu Pro Ala Ser Ile Ser Cys Arg Ser Ser Gln Ser Leu Leu His Ile
                        20                  25                  30

Asn Glu Tyr Asn Tyr Leu Asp Trp Tyr Leu Lys Lys Pro Gly Gln Ser
                        35                  40                  45

Pro Gln Leu Leu Ile Tyr Leu Gly Phe Asn Arg Ala Ser Gly Val Pro
                    50                  55                  60

Asp Arg Phe Ser Gly Ser Gly Ser Gly Thr Asp Phe Thr Leu Lys Ile
        65                  70                  75                  80

Ser Arg Val Glu Ala Glu Asp Val Gly Val Tyr Tyr Cys Met Gln Ala
                        85                  90                  95

Leu Gln Thr Pro Trp Thr Phe Gly Gln Gly Thr Lys Val Glu Ile Lys
                        100                 105                 110

<210> SEQ ID NO 310
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Asp Ile Val Met Thr Gln Ser Pro Leu Ser Leu Pro Val Thr Pro Gly
        1               5                   10                  15

Glu Pro Ala Ser Ile Ser Cys Arg Ser Ser Gln Ser Leu Leu His Ile
                        20                  25                  30

Asn Glu Tyr Asn Tyr Leu Asp Trp Tyr Leu Lys Lys Pro Gly Gln Ser
                        35                  40                  45

Pro Gln Leu Leu Ile Tyr Leu Gly Phe Asn Arg Ala Ser Gly Val Pro
                    50                  55                  60

Asp Arg Phe Ser Gly Ser Gly Ser Gly Thr Asp Phe Thr Leu Lys Ile
        65                  70                  75                  80

Ser Arg Val Glu Ala Glu Asp Val Gly Val Tyr Tyr Cys Met Gln Ala
```

Leu Gln Thr Pro Trp Thr Phe Gly Gln Gly Thr Lys Val Glu Ile Lys
            100                 105                 110

<210> SEQ ID NO 311
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ile
            20                  25                  30

Asn Glu Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 312
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Tyr
            20                  25                  30

Ala Ile His Trp Val Arg Gln Ala Pro Gly Lys Gly Leu Glu Trp Val
        35                  40                  45

Gly Arg Ile Ser Pro Ala Asn Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120

<210> SEQ ID NO 313
<211> LENGTH: 121
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 313

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Tyr
            20                  25                  30

Ala Ile His Trp Val Arg Gln Ala Pro Gly Lys Gly Leu Glu Trp Val
        35                  40                  45

Gly Arg Ile Ser Pro Ala Asn Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120

<210> SEQ ID NO 314
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Tyr
            20                  25                  30

Ala Ile His Trp Val Arg Gln Ala Pro Gly Lys Gly Leu Glu Trp Val
        35                  40                  45

Gly Arg Ile Ser Pro Ala Asn Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120

<210> SEQ ID NO 315
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Arg His
            20                  25                  30

Thr Ile His Trp Val Arg Gln Ala Pro Gly Lys Gly Leu Glu Trp Val
            35                  40                  45

Gly Arg Ile Ser Pro Ala Asn Gly Asn Thr Asn Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120

<210> SEQ ID NO 316
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Thr
            20                  25                  30

Ala Ile His Trp Val Arg Gln Ala Pro Gly Lys Gly Leu Glu Trp Val
            35                  40                  45

Gly Arg Ile Ser Pro Ala Asn Gly Asn Thr Asn Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120

<210> SEQ ID NO 317
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Tyr
            20                  25                  30

Ala Ile His Trp Val Arg Gln Ala Pro Gly Lys Gly Leu Glu Trp Val
            35                  40                  45

Gly Arg Ile Ser Pro Ala Asn Gly Asn Thr Asn Tyr Ala Asp Ser Val
        50                  55                  60

Lys Gly Arg Phe Thr Ile Ser Ala Asp Thr Ser Lys Asn Thr Ala Tyr
65                  70                  75                  80

```
Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120

<210> SEQ ID NO 318
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 319
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Ala Pro Ala
                85                  90                  95

Thr Phe Gly Gln Gly Thr Lys Val Glu Ile Lys Arg
            100                 105

<210> SEQ ID NO 320
<211> LENGTH: 108
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 320

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Pro Pro Ala
                85                  90                  95

Thr Phe Gly Gln Gly Thr Lys Val Glu Ile Lys Arg
            100                 105

<210> SEQ ID NO 321
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Ile Gln Pro
                85                  90                  95

Thr Phe Gly Gln Gly Thr Lys Val Glu Ile Lys Arg
            100                 105

<210> SEQ ID NO 322
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45
```

```
Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Ala Leu His
                85                  90                  95

Thr Phe Gly Gln Gly Thr Lys Val Glu Ile Lys Arg
                100                 105
```

<210> SEQ ID NO 323
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Ala
                20                  25                  30

Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Ala Pro Ser
                85                  90                  95

Thr Phe Gly Gln Gly Thr Lys Val Glu Ile Lys Arg
                100                 105
```

<210> SEQ ID NO 324
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

```
Glu Val Gln Leu Val Glu Ser Gly Gly Leu Val Lys Pro Gly Gly
1               5                   10                  15

Ser Leu Arg Leu Ser Cys Ala Ala Ser Gly Phe Pro Phe Ser Lys Leu
                20                  25                  30

Gly Met Val Trp Val Arg Gln Ala Pro Gly Lys Gly Leu Glu Trp Val
            35                  40                  45

Ser Thr Ile Ser Ser Gly Gly Gly Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Ser Phe Gln Gly Gly Thr Tyr Thr Tyr Val Met
                100                 105                 110

Asp Tyr Trp Gly Gln Gly Thr Leu Val Thr Val Ser Ser
            115                 120                 125
```

```
<210> SEQ ID NO 325
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Arg
            20                  25                  30

Asn Gly Ile Thr Tyr Ser Tyr Trp Tyr Leu Gln Lys Pro Gly Gln Ser
        35                  40                  45

Pro Gln Leu Leu Ile Tyr Gln Leu Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Tyr Gln Asn
                85                  90                  95

Leu Glu Leu Pro Leu Thr Phe Gly Gln Gly Thr Lys Val Glu Ile Lys
            100                 105                 110

<210> SEQ ID NO 326
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Lys Pro Leu Phe Asp Ile Trp Gly Gln Gly
            100                 105                 110

Thr Leu Val Thr Val Ser Ser
        115

<210> SEQ ID NO 327
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Asp Ile Val Met Thr Gln Ser Pro Asp Ser Leu Ala Val Ser Leu Gly
```

```
                1               5                   10                  15
        Glu Arg Ala Thr Ile Asn Cys Arg Ser Ser Gln Ser Val Leu Tyr Ser
                        20                  25                  30

Ser Asn Asn Lys Asn Tyr Leu Ala Trp Tyr Gln Gln Lys Pro Gly Gln
                35                  40                  45

Pro Pro Lys Leu Leu Ile Tyr Trp Ala Ser Thr Arg Glu Ser Gly Val
                50                  55                  60

Pro Asp Arg Phe Ser Gly Ser Gly Ser Gly Thr Asp Phe Thr Leu Thr
        65                  70                  75                  80

Ile Ser Ser Leu Gln Ala Glu Asp Val Ala Val Tyr Tyr Cys Gln Gln
                        85                  90                  95

Tyr Ser Ser Phe Pro Ile Thr Phe Gly Gln Gly Thr Lys Val Glu Ile
                    100                 105                 110

Lys Arg

<210> SEQ ID NO 328
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Asn or Asp
<220> FEATURE:
<221> NAME/KEY: MOD_RES
<222> LOCATION: (8)..(8)
<223> OTHER INFORMATION: Trp or Tyr
<220> FEATURE:
<221> NAME/KEY: MOD_RES
<222> LOCATION: (10)..(10)
<223> OTHER INFORMATION: Ser, Thr or Ala

<400> SEQUENCE: 328

Gly Tyr Ser Phe Thr Xaa Tyr Xaa Ile Xaa
1               5                   10

<210> SEQ ID NO 329
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ile, Arg, Trp, Leu or Met
<220> FEATURE:
<221> NAME/KEY: MOD_RES
<222> LOCATION: (11)..(11)
<223> OTHER INFORMATION: Tyr or Asp
<220> FEATURE:
<221> NAME/KEY: MOD_RES
<222> LOCATION: (13)..(13)
<223> OTHER INFORMATION: Asn, Arg, His, Ser, Lys or Gln
<220> FEATURE:
<221> NAME/KEY: MOD_RES
<222> LOCATION: (15)..(15)
<223> OTHER INFORMATION: Ser or Asn
<220> FEATURE:
<221> NAME/KEY: MOD_RES
<222> LOCATION: (16)..(16)
<223> OTHER INFORMATION: Pro, Gln or His
<220> FEATURE:
<221> NAME/KEY: MOD_RES
<222> LOCATION: (17)..(17)
```

<223> OTHER INFORMATION: Ser, Lys, Asn or Arg

<400> SEQUENCE: 329

Trp Met Gly Xaa Ile Tyr Pro Gly Asp Ser Xaa Thr Xaa Tyr Xaa Xaa
1               5                   10                  15

Xaa Phe Gln Gly
            20

<210> SEQ ID NO 330
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr, Arg or His
<220> FEATURE:
<221> NAME/KEY: MOD_RES
<222> LOCATION: (3)..(3)
<223> OTHER INFORMATION: Trp, Tyr, Gly, Ala or Phe
<220> FEATURE:
<221> NAME/KEY: MOD_RES
<222> LOCATION: (4)..(4)
<223> OTHER INFORMATION: Tyr or Ser
<220> FEATURE:
<221> NAME/KEY: MOD_RES
<222> LOCATION: (5)..(5)
<223> OTHER INFORMATION: Lys, Arg, Thr, Gly, Ser, Asp, Glu, His or Asn
<220> FEATURE:
<221> NAME/KEY: MOD_RES
<222> LOCATION: (6)..(6)
<223> OTHER INFORMATION: Pro, Ser, Gly, Asp, Ala, His, Arg or Tyr
<220> FEATURE:
<221> NAME/KEY: MOD_RES
<222> LOCATION: (7)..(7)
<223> OTHER INFORMATION: Leu, Tyr, Phe, Ala, Asp, His, Pro or Ser
<220> FEATURE:
<221> NAME/KEY: MOD_RES
<222> LOCATION: (8)..(8)
<223> OTHER INFORMATION: Phe or Ser
<220> FEATURE:
<221> NAME/KEY: MOD_RES
<222> LOCATION: (10)..(10)
<223> OTHER INFORMATION: Ile, Val, Tyr, Phe or Asn

<400> SEQUENCE: 330

Asp Xaa Xaa Xaa Xaa Xaa Xaa Xaa Asp Xaa
1               5                   10

<210> SEQ ID NO 331
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ile or Arg
<220> FEATURE:
<221> NAME/KEY: MOD_RES
<222> LOCATION: (13)..(13)
<223> OTHER INFORMATION: Asn, Arg, His or Ser
<220> FEATURE:
<221> NAME/KEY: MOD_RES
<222> LOCATION: (16)..(16)
<223> OTHER INFORMATION: Pro or Gln

<400> SEQUENCE: 331

```
Trp Met Gly Xaa Ile Tyr Pro Gly Asp Ser Tyr Thr Xaa Tyr Ser Xaa
1               5                   10                  15

Ser Phe Gln Gly
            20
```

<210> SEQ ID NO 332
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys, Gly, Arg, Ser, Asp, Glu, His, Asn or Gln
<220> FEATURE:
<221> NAME/KEY: MOD_RES
<222> LOCATION: (6)..(6)
<223> OTHER INFORMATION: Pro, Gly, Asp, Ser, Ala, His, Arg or Tyr
<220> FEATURE:
<221> NAME/KEY: MOD_RES
<222> LOCATION: (7)..(7)
<223> OTHER INFORMATION: Leu, Ala, Tyr, Asp, Phe, His, Pro, Ser or Val
<220> FEATURE:
<221> NAME/KEY: MOD_RES
<222> LOCATION: (10)..(10)
<223> OTHER INFORMATION: Ile, Tyr, Phe or Asn

<400> SEQUENCE: 332

```
Asp Tyr Trp Tyr Xaa Xaa Xaa Phe Asp Xaa
1               5                   10
```

<210> SEQ ID NO 333
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, Lys, His, Asn, Gln or Ser
<220> FEATURE:
<221> NAME/KEY: MOD_RES
<222> LOCATION: (7)..(7)
<223> OTHER INFORMATION: Leu or Phe
<220> FEATURE:
<221> NAME/KEY: MOD_RES
<222> LOCATION: (8)..(8)
<223> OTHER INFORMATION: Tyr or His
<220> FEATURE:
<221> NAME/KEY: MOD_RES
<222> LOCATION: (10)..(10)
<223> OTHER INFORMATION: Ser, Arg or Gly
<220> FEATURE:
<221> NAME/KEY: MOD_RES
<222> LOCATION: (11)..(11)
<223> OTHER INFORMATION: Asn or Thr
<220> FEATURE:
<221> NAME/KEY: MOD_RES
<222> LOCATION: (12)..(12)
<223> OTHER INFORMATION: Asn, Arg, His or Ser
<220> FEATURE:
<221> NAME/KEY: MOD_RES
<222> LOCATION: (15)..(15)
<223> OTHER INFORMATION: Tyr or Phe
<220> FEATURE:
<221> NAME/KEY: MOD_RES
<222> LOCATION: (17)..(17)
<223> OTHER INFORMATION: Ala or Thr

<400> SEQUENCE: 333

```
Xaa Ser Ser Gln Ser Val Xaa Xaa Ser Xaa Xaa Xaa Lys Asn Xaa Leu
1               5                   10                  15

Xaa

<210> SEQ ID NO 334
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Trp, Phe or Leu
<220> FEATURE:
<221> NAME/KEY: MOD_RES
<222> LOCATION: (6)..(6)
<223> OTHER INFORMATION: Ala or Thr
<220> FEATURE:
<221> NAME/KEY: MOD_RES
<222> LOCATION: (8)..(8)
<223> OTHER INFORMATION: Thr, Ile, Ala or Val
<220> FEATURE:
<221> NAME/KEY: MOD_RES
<222> LOCATION: (10)..(10)
<223> OTHER INFORMATION: Glu, Ala or Lys
<220> FEATURE:
<221> NAME/KEY: MOD_RES
<222> LOCATION: (11)..(11)
<223> OTHER INFORMATION: Ser or Thr

<400> SEQUENCE: 334

Leu Leu Ile Tyr Xaa Xaa Ser Xaa Arg Xaa Xaa
1               5                   10

<210> SEQ ID NO 335
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Tyr
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Phe, Tyr, Leu, Thr, His, Ile, Asn, Pro or Ser
<220> FEATURE:
<221> NAME/KEY: MOD_RES
<222> LOCATION: (8)..(8)
<223> OTHER INFORMATION: Ile, Arg, Val, Tyr, Asp, Phe, Gly, His, Leu,
      Asn or Ser

<400> SEQUENCE: 335

Gln Gln Tyr Xaa Xaa Xaa Pro Xaa
1               5

<210> SEQ ID NO 336
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (15)..(15)
<223> OTHER INFORMATION: Tyr or Phe
<220> FEATURE:
<221> NAME/KEY: MOD_RES
<222> LOCATION: (17)..(17)
<223> OTHER INFORMATION: Ala or Thr

<400> SEQUENCE: 336

Arg Ser Ser Gln Ser Val Leu Tyr Ser Ser Asn Asn Lys Asn Xaa Leu
1               5                   10                  15

Xaa

<210> SEQ ID NO 337
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Trp, Phe or Leu
<220> FEATURE:
<221> NAME/KEY: MOD_RES
<222> LOCATION: (10)..(10)
<223> OTHER INFORMATION: Glu or Lys
<220> FEATURE:
<221> NAME/KEY: MOD_RES
<222> LOCATION: (11)..(11)
<223> OTHER INFORMATION: Ser or Thr

<400> SEQUENCE: 337

Leu Leu Ile Tyr Xaa Ala Ser Thr Arg Xaa Xaa
1               5                   10

<210> SEQ ID NO 338
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phe, Tyr, Thr, Ile, Asn or Ser
<220> FEATURE:
<221> NAME/KEY: MOD_RES
<222> LOCATION: (8)..(8)
<223> OTHER INFORMATION: Ile, Tyr, Arg, Phe, His, Leu, Asn or Ser

<400> SEQUENCE: 338

Gln Gln Tyr Ser Ser Xaa Pro Xaa
1               5

<210> SEQ ID NO 339
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Asn or Asp
<220> FEATURE:
<221> NAME/KEY: MOD_RES
<222> LOCATION: (33)..(33)
<223> OTHER INFORMATION: Trp or Tyr
```

```
<220> FEATURE:
<221> NAME/KEY: MOD_RES
<222> LOCATION: (35)..(35)
<223> OTHER INFORMATION: Ser, Thr or Ala
<220> FEATURE:
<221> NAME/KEY: MOD_RES
<222> LOCATION: (50)..(50)
<223> OTHER INFORMATION: Ile, Arg, Trp, Leu or Met
<220> FEATURE:
<221> NAME/KEY: MOD_RES
<222> LOCATION: (57)..(57)
<223> OTHER INFORMATION: Tyr or Asp
<220> FEATURE:
<221> NAME/KEY: MOD_RES
<222> LOCATION: (59)..(59)
<223> OTHER INFORMATION: Asn, Arg, His, Ser, Lys or Gln
<220> FEATURE:
<221> NAME/KEY: MOD_RES
<222> LOCATION: (61)..(61)
<223> OTHER INFORMATION: Ser or Asn
<220> FEATURE:
<221> NAME/KEY: MOD_RES
<222> LOCATION: (62)..(62)
<223> OTHER INFORMATION: Pro, Gln or His
<220> FEATURE:
<221> NAME/KEY: MOD_RES
<222> LOCATION: (63)..(63)
<223> OTHER INFORMATION: Ser, Lys, Asn or Arg
<220> FEATURE:
<221> NAME/KEY: MOD_RES
<222> LOCATION: (100)..(100)
<223> OTHER INFORMATION: Tyr, Arg or His
<220> FEATURE:
<221> NAME/KEY: MOD_RES
<222> LOCATION: (101)..(101)
<223> OTHER INFORMATION: Trp, Tyr or Gly
<220> FEATURE:
<221> NAME/KEY: MOD_RES
<222> LOCATION: (102)..(102)
<223> OTHER INFORMATION: Tyr or Ser
<220> FEATURE:
<221> NAME/KEY: MOD_RES
<222> LOCATION: (103)..(103)
<223> OTHER INFORMATION: Lys, Arg, Thr, Gly, Ser, Asp, Glu, His, Asn or
      Gln
<220> FEATURE:
<221> NAME/KEY: MOD_RES
<222> LOCATION: (104)..(104)
<223> OTHER INFORMATION: Pro, Ser, Gly, Asp, Ala, His, Arg or Tyr
<220> FEATURE:
<221> NAME/KEY: MOD_RES
<222> LOCATION: (105)..(105)
<223> OTHER INFORMATION: Leu, Tyr, Phe, Ala, Asp, His, Pro, Ser or Val
<220> FEATURE:
<221> NAME/KEY: MOD_RES
<222> LOCATION: (106)..(106)
<223> OTHER INFORMATION: Phe or Ser
<220> FEATURE:
<221> NAME/KEY: MOD_RES
<222> LOCATION: (108)..(108)
<223> OTHER INFORMATION: Ile, Val, Tyr, Phe or Asn

<400> SEQUENCE: 339

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Xaa Tyr
            20                  25                  30

Xaa Ile Xaa Trp Val Arg Gln Met Pro Gly Lys Gly Leu Glu Trp Met
        35                  40                  45

Gly Xaa Ile Tyr Pro Gly Asp Ser Xaa Thr Xaa Tyr Xaa Xaa Xaa Phe
    50                  55                  60

Gln Gly Gln Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg Asp Xaa Xaa Xaa Xaa Xaa Xaa Asp Xaa Trp Gly Gln Gly
            100                 105                 110

Thr Leu Val Thr Val Ser Ser
        115

<210> SEQ ID NO 340
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Asn or Asp
<220> FEATURE:
<221> NAME/KEY: MOD_RES
<222> LOCATION: (33)..(33)
<223> OTHER INFORMATION: Trp or Tyr
<220> FEATURE:
<221> NAME/KEY: MOD_RES
<222> LOCATION: (35)..(35)
<223> OTHER INFORMATION: Ser, Thr or Ala
<220> FEATURE:
<221> NAME/KEY: MOD_RES
<222> LOCATION: (50)..(50)
<223> OTHER INFORMATION: Ile or Arg
<220> FEATURE:
<221> NAME/KEY: MOD_RES
<222> LOCATION: (59)..(59)
<223> OTHER INFORMATION: Asn, Arg, His, Ser, Lys or Gln
<220> FEATURE:
<221> NAME/KEY: MOD_RES
<222> LOCATION: (62)..(62)
<223> OTHER INFORMATION: Pro or Gln
<220> FEATURE:
<221> NAME/KEY: MOD_RES
<222> LOCATION: (103)..(103)
<223> OTHER INFORMATION: Lys, Gly, Arg, Ser, Asp, Glu, His, Asn or Gln
<220> FEATURE:
<221> NAME/KEY: MOD_RES
<222> LOCATION: (104)..(104)
<223> OTHER INFORMATION: Pro, Gly, Asp, Ser, Ala, His, Arg or Tyr
<220> FEATURE:
<221> NAME/KEY: MOD_RES
<222> LOCATION: (105)..(105)
<223> OTHER INFORMATION: Leu, Ala, Tyr, Asp, Phe, His, Pro, Ser or Val
<220> FEATURE:
<221> NAME/KEY: MOD_RES
<222> LOCATION: (108)..(108)
<223> OTHER INFORMATION: Ile, Tyr, Phe or Asn

<400> SEQUENCE: 340

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Xaa Tyr
                20                  25                  30

Xaa Ile Xaa Trp Val Arg Gln Met Pro Gly Lys Gly Leu Glu Trp Met
            35                  40                  45

Gly Xaa Ile Tyr Pro Gly Asp Ser Tyr Thr Xaa Tyr Ser Xaa Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Trp Tyr Trp Xaa Xaa Xaa Phe Asp Xaa Trp Gly Gln Gly
```

100                 105                 110
Thr Leu Val Thr Val Ser Ser
        115

<210> SEQ ID NO 341
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Arg, Lys, His, Asn, Gln or Ser
<220> FEATURE:
<221> NAME/KEY: MOD_RES
<222> LOCATION: (30)..(30)
<223> OTHER INFORMATION: Leu or Phe
<220> FEATURE:
<221> NAME/KEY: MOD_RES
<222> LOCATION: (31)..(31)
<223> OTHER INFORMATION: Tyr or His
<220> FEATURE:
<221> NAME/KEY: MOD_RES
<222> LOCATION: (33)..(33)
<223> OTHER INFORMATION: Ser, Arg or Gly
<220> FEATURE:
<221> NAME/KEY: MOD_RES
<222> LOCATION: (34)..(34)
<223> OTHER INFORMATION: Asn or Thr
<220> FEATURE:
<221> NAME/KEY: MOD_RES
<222> LOCATION: (35)..(35)
<223> OTHER INFORMATION: Asn, Arg, His or Ser
<220> FEATURE:
<221> NAME/KEY: MOD_RES
<222> LOCATION: (38)..(38)
<223> OTHER INFORMATION: Tyr or Phe
<220> FEATURE:
<221> NAME/KEY: MOD_RES
<222> LOCATION: (40)..(40)
<223> OTHER INFORMATION: Ala or Thr
<220> FEATURE:
<221> NAME/KEY: MOD_RES
<222> LOCATION: (56)..(56)
<223> OTHER INFORMATION: Trp, Phe or Leu
<220> FEATURE:
<221> NAME/KEY: MOD_RES
<222> LOCATION: (57)..(57)
<223> OTHER INFORMATION: Ala or Thr
<220> FEATURE:
<221> NAME/KEY: MOD_RES
<222> LOCATION: (59)..(59)
<223> OTHER INFORMATION: Thr, Ile, Ala or Val
<220> FEATURE:
<221> NAME/KEY: MOD_RES
<222> LOCATION: (61)..(61)
<223> OTHER INFORMATION: Glu, Ala or Lys
<220> FEATURE:
<221> NAME/KEY: MOD_RES
<222> LOCATION: (62)..(62)
<223> OTHER INFORMATION: Ser or Thr
<220> FEATURE:
<221> NAME/KEY: MOD_RES
<222> LOCATION: (98)..(98)
<223> OTHER INFORMATION: Ser or Tyr
<220> FEATURE:
<221> NAME/KEY: MOD_RES
<222> LOCATION: (99)..(99)
<223> OTHER INFORMATION: Ser or Thr
<220> FEATURE:
<221> NAME/KEY: MOD_RES
<222> LOCATION: (100)..(100)
<223> OTHER INFORMATION: Phe, Tyr, Leu, Thr, His, Ile, Asn, Pro or Ser
<220> FEATURE:
<221> NAME/KEY: MOD_RES

```
<222> LOCATION: (102)..(102)
<223> OTHER INFORMATION: Ile, Arg, Val, Tyr, Asp, Phe, Gly, His, Leu,
      Asn or Ser

<400> SEQUENCE: 341

Asp Ile Val Met Thr Gln Ser Pro Asp Ser Leu Ala Val Ser Leu Gly
1               5                   10                  15

Glu Arg Ala Thr Ile Asn Cys Xaa Ser Ser Gln Ser Val Xaa Xaa Ser
            20                  25                  30

Xaa Xaa Xaa Lys Asn Xaa Leu Xaa Trp Tyr Gln Gln Lys Pro Gly Gln
        35                  40                  45

Pro Pro Lys Leu Leu Ile Tyr Xaa Xaa Ser Xaa Arg Xaa Xaa Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Xaa Xaa Xaa Pro Xaa Thr Phe Gly Gln Gly Thr Lys Val Glu Ile
            100                 105                 110

Lys Arg

<210> SEQ ID NO 342
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Tyr or Phe
<220> FEATURE:
<221> NAME/KEY: MOD_RES
<222> LOCATION: (40)..(40)
<223> OTHER INFORMATION: Ala or Thr
<220> FEATURE:
<221> NAME/KEY: MOD_RES
<222> LOCATION: (56)..(56)
<223> OTHER INFORMATION: Trp, Phe or Leu
<220> FEATURE:
<221> NAME/KEY: MOD_RES
<222> LOCATION: (61)..(61)
<223> OTHER INFORMATION: Glu or Lys
<220> FEATURE:
<221> NAME/KEY: MOD_RES
<222> LOCATION: (62)..(62)
<223> OTHER INFORMATION: Ser or Thr
<220> FEATURE:
<221> NAME/KEY: MOD_RES
<222> LOCATION: (100)..(100)
<223> OTHER INFORMATION: Phe, Tyr, Thr, Ile, Asn or Ser
<220> FEATURE:
<221> NAME/KEY: MOD_RES
<222> LOCATION: (102)..(102)
<223> OTHER INFORMATION: Ile, Tyr, Arg, Phe, His, Leu, Asn or Ser

<400> SEQUENCE: 342

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Asn Asn Lys Asn Xaa Leu Xaa Trp Tyr Gln Gln Lys Pro Gly Gln
        35                  40                  45

Pro Pro Lys Leu Leu Ile Tyr Xaa Ala Ser Thr Arg Xaa Xaa Gly Val
    50                  55                  60
```

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Ser Xaa Pro Xaa Thr Phe Gly Gln Gly Thr Lys Val Glu Ile
            100                 105                 110

Lys Arg

<210> SEQ ID NO 343
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr Arg Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Tyr Ser Arg Pro Phe Ser Asp Ile Trp Gly Gln Gly
            100                 105                 110

Thr Leu Val Thr Val Ser Ser
        115

<210> SEQ ID NO 344
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr Arg Tyr Asn Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Tyr Ser Arg Pro Tyr Ser Asp Val Trp Gly Gln Gly
            100                 105                 110

Thr Leu Val Thr Val Ser Ser
        115

<210> SEQ ID NO 345
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
                20                  25                  30

Tyr Ile Ser Trp Val Arg Gln Met Pro Gly Lys Gly Leu Glu Trp Met
            35                  40                  45

Gly Leu Ile Tyr Pro Gly Asp Ser Tyr Thr Arg Tyr Ser Pro Asn Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Gly Tyr Arg Pro Tyr Ser Asp Ile Trp Gly Gln Gly
                100                 105                 110

Thr Leu Val Thr Val Ser Ser
        115

<210> SEQ ID NO 346
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Tyr Ile Ser Trp Val Arg Gln Met Pro Gly Lys Gly Leu Glu Trp Met
            35                  40                  45

Gly Leu Ile Tyr Pro Gly Asp Ser Tyr Thr Asn Tyr Asn Pro Asn Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Tyr Ser Thr Pro Phe Phe Asp Val Trp Gly Gln Gly
                100                 105                 110

Thr Leu Val Thr Val Ser Ser
        115

<210> SEQ ID NO 347
<211> LENGTH: 119
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 347

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr Arg Tyr Asn Arg Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Tyr Ser Arg Pro Leu Ser Asp Val Trp Gly Gln Gly
            100                 105                 110

Thr Leu Val Thr Val Ser Ser
        115

<210> SEQ ID NO 348
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr Arg Tyr Ser Pro Arg Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Gly Tyr Lys Pro Tyr Ser Asp Ile Trp Gly Gln Gly
            100                 105                 110

Thr Leu Val Thr Val Ser Ser
        115

<210> SEQ ID NO 349
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr

```
                    20                  25                  30

Tyr Ile Ser Trp Val Arg Gln Met Pro Gly Lys Gly Leu Glu Trp Met
            35                  40                  45

Gly Leu Ile Tyr Pro Gly Asp Ser Tyr Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Tyr Ser Lys Pro Leu Phe Asp Val Trp Gly Gln Gly
            100                 105                 110

Thr Leu Val Thr Val Ser Ser
        115

<210> SEQ ID NO 350
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Ile Ile Tyr Pro Gly Asp Ser Tyr Ile His Tyr Asn Gln Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Tyr Ser Arg Pro Phe Ser Asp Ile Trp Gly Gln Gly
            100                 105                 110

Thr Leu Val Thr Val Ser Ser
        115

<210> SEQ ID NO 351
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

Gln Val Lys Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ala Trp Val Arg Gln Met Pro Gly Lys Gly Leu Glu Trp Met
        35                  40                  45

Gly Ile Ile Tyr Pro Gly Asp Ser Tyr Thr His Tyr Asn Pro Lys Phe
    50                  55                  60

Gln Gly Gln Val Thr Ile Ser Ala Asp Lys Ser Ile Ser Thr Ala Tyr
```

```
                65                  70                  75                  80
Leu Gln Trp Ser Ser Leu Lys Ala Ser Asp Thr Ala Met Tyr Tyr Cys
                    85                  90                  95

Ala Arg Asp His Gly Tyr Lys Pro Phe Ser Asp Ile Trp Gly Gln Gly
                100                 105                 110

Thr Leu Val Thr Val Ser Ser
        115

<210> SEQ ID NO 352
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Tyr Ile Ala Trp Val Arg Gln Met Pro Gly Lys Gly Leu Glu Trp Met
            35                  40                  45

Gly Val Ile Tyr Pro Gly Asp Ser Tyr Thr Arg Tyr Asn Pro Lys Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                    85                  90                  95

Ala Arg Asp Tyr Trp Ser Arg Pro Tyr Phe Asp Ile Trp Gly Gln Gly
                100                 105                 110

Thr Leu Val Thr Val Ser Ser
        115

<210> SEQ ID NO 353
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Tyr Ile Ala Trp Val Arg Gln Met Pro Gly Lys Gly Leu Glu Trp Met
            35                  40                  45

Gly Ile Ile Tyr Pro Gly Asp Ser Tyr Thr His Tyr Asn Pro Lys Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                    85                  90                  95

Ala Arg Asp His Trp Ser Arg Pro Phe Ser Asp Val Trp Gly Gln Gly
                100                 105                 110

Thr Leu Val Thr Val Ser Ser
```

115

<210> SEQ ID NO 354
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Ile Ile Tyr Pro Gly Asp Ser Tyr Thr Arg Tyr Asn Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Lys Pro Leu Ser Asp Val Trp Gly Gln Gly
            100                 105                 110

Thr Leu Val Thr Val Ser Ser
        115

<210> SEQ ID NO 355
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr His Tyr Asn Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Lys Pro Tyr Phe Asp Val Trp Gly Gln Gly
            100                 105                 110

Thr Leu Val Thr Val Ser Ser
        115

<210> SEQ ID NO 356
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 356

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Tyr Ile Thr Trp Val Arg Gln Met Pro Gly Arg Gly Leu Glu Trp Met
            35                  40                  45

Gly Ile Ile Tyr Pro Gly Asp Ser Tyr Thr Arg Tyr Asn Pro Lys Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Lys Pro Phe Ser Asp Val Trp Gly Gln Gly
            100                 105                 110

Thr Leu Val Thr Val Ser Ser
        115

<210> SEQ ID NO 357
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Tyr Ile Thr Trp Val Arg Gln Met Pro Gly Lys Gly Leu Glu Trp Met
            35                  40                  45

Gly Leu Ile Tyr Pro Gly Asp Ser Tyr Thr Arg Tyr Ser Pro Arg Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Arg Pro Tyr Ser Asp Val Trp Gly Gln Gly
            100                 105                 110

Thr Leu Val Thr Val Ser Ser
        115

<210> SEQ ID NO 358
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
                20                  25                  30

```
Tyr Ile Ala Trp Val Arg Gln Met Pro Gly Lys Gly Leu Glu Trp Met
            35                  40                  45

Gly Ile Ile Tyr Pro Gly Asp Ser Tyr Thr Arg Tyr Asn Pro Lys Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Arg Pro Phe Ser Asp Val Trp Gly Gln Gly
                100                 105                 110

Thr Leu Val Thr Val Ser Ser
        115

<210> SEQ ID NO 359
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
            35                  40                  45

Gly Leu Ile Tyr Pro Gly Asp Ser Tyr Thr His Tyr Asn Pro Asn Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Lys Pro Leu Phe Asp Val Trp Gly Gln Gly
                100                 105                 110

Thr Leu Val Thr Val Ser Ser
        115

<210> SEQ ID NO 360
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ala Trp Val Arg Gln Met Pro Gly Lys Gly Leu Glu Trp Met
            35                  40                  45

Gly Ile Ile Tyr Pro Gly Asp Ser Tyr Thr Arg Tyr Asn Pro Arg Phe
50                  55                  60

Gln Gly Gln Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg Asp Tyr Trp Ser Lys Pro Leu Ser Asp Ile Trp Gly Gln Gly
            100                 105                 110

Thr Leu Val Thr Val Ser Ser
        115
```

<210> SEQ ID NO 361
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

```
Gln Val Lys Leu Val Gln Ser Gly Ala Glu Val Lys Pro Gly Glu
1               5                   10                  15

Ser Leu Lys Ile Ser Cys Lys Gly Ser Gly Tyr Ser Phe Thr Asp Tyr
                20                  25                  30

Tyr Ile Ser Trp Val Arg Gln Met Pro Gly Lys Gly Leu Glu Trp Met
            35                  40                  45

Gly Ile Ile Tyr Pro Gly Asp Ser Tyr Thr His Tyr Asn Pro Lys Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Arg Trp Ser Lys Pro Leu Phe Asp Val Trp Gly Gln Gly
            100                 105                 110

Thr Leu Val Thr Val Ser Ser
        115
```

<210> SEQ ID NO 362
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
                20                  25                  30

Tyr Ile Ser Trp Val Arg Gln Met Pro Gly Lys Gly Leu Glu Trp Met
            35                  40                  45

Gly Leu Ile Tyr Pro Gly Asp Ser Tyr Thr Arg Tyr Asn Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Lys Pro Leu Ser Asp Ile Trp Gly Gln Gly
            100                 105                 110

Thr Leu Val Thr Val Ser Ser
        115
```

<210> SEQ ID NO 363
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
                20                  25                  30

Tyr Ile Ser Trp Val Arg Gln Met Pro Gly Lys Gly Leu Glu Trp Met
            35                  40                  45

Gly Ser Ile Tyr Pro Gly Asp Ser Tyr Thr His Tyr Ser His Lys Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Arg Asp His Trp Ser Arg Pro Phe Phe Asp Val Trp Gly Gln Gly
            100                 105                 110

Thr Leu Val Thr Val Ser Ser
        115

<210> SEQ ID NO 364
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
                20                  25                  30

Tyr Ile Ala Trp Val Arg Gln Met Pro Gly Lys Gly Leu Glu Trp Met
            35                  40                  45

Gly Leu Ile Tyr Pro Gly Asp Ser Tyr Thr Ser Tyr Asn Pro Arg Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Thr Pro Tyr Phe Asp Ile Trp Gly Gln Gly
            100                 105                 110

Thr Leu Val Thr Val Ser Ser
        115

<210> SEQ ID NO 365
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Ile Ile Tyr Pro Gly Asp Ser Tyr Thr Ser Tyr Ser Pro Arg Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Arg Pro Leu Phe Asp Val Trp Gly Gln Gly
                100                 105                 110

Thr Leu Val Thr Val Ser Ser
        115

<210> SEQ ID NO 366
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr His Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Tyr Lys Pro Phe Ser Asp Ile Trp Gly Gln Gly
                100                 105                 110

Thr Leu Val Thr Val Ser Ser
        115

<210> SEQ ID NO 367
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 367

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
            35                  40                  45

Gly Ile Ile Tyr Pro Gly Asp Ser Tyr Thr Asn Tyr Asn Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Arg Pro Phe Ser Asp Ile Trp Gly Gln Gly
            100                 105                 110

Thr Leu Val Thr Val Ser Ser
            115

<210> SEQ ID NO 368
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 368

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
            35                  40                  45

Gly Ile Ile Tyr Pro Gly Asp Ser Tyr Thr His Tyr Ser Pro Asn Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Thr Pro Phe Phe Asp Val Trp Gly Gln Gly
            100                 105                 110

Thr Leu Val Thr Val Ser Ser
            115

<210> SEQ ID NO 369
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
            35                  40                  45

Gly Leu Ile Tyr Pro Gly Asp Ser Tyr Thr Asn Tyr Ser Pro Lys Phe
        50                  55                  60

Gln Gly Gln Val Thr Ile Ser Ala Asp Lys Ser Ile Ser Thr Ala Tyr
65                  70                  75                  80

```
Leu Gln Trp Ser Ser Leu Lys Ala Ser Asp Thr Ala Met Tyr Tyr Cys
                85                  90                  95

Ala Arg Asp His Trp Ser Lys Pro Leu Ser Asp Val Trp Gly Gln Gly
            100                 105                 110

Thr Leu Val Thr Val Ser Ser
        115

<210> SEQ ID NO 370
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 370

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr His Tyr Ser Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Lys Pro Tyr Phe Asp Val Trp Gly Gln Gly
            100                 105                 110

Thr Leu Val Thr Val Ser Ser
        115

<210> SEQ ID NO 371
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 371

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr Ser Tyr Asn Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Lys Pro Tyr Phe Asp Ile Trp Gly Gln Gly
            100                 105                 110

Thr Leu Val Thr Val Ser Ser
        115
```

<210> SEQ ID NO 372
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 372

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr Asn Tyr Asn Gln Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Arg Pro Tyr Ser Asp Ile Trp Gly Gln Gly
            100                 105                 110

Thr Leu Val Thr Val Ser Ser
        115

<210> SEQ ID NO 373
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr His Tyr Ser Gln Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Arg Pro Phe Phe Asp Val Trp Gly Gln Gly
            100                 105                 110

Thr Leu Val Thr Val Ser Ser
        115

<210> SEQ ID NO 374
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 374

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Ser Ser Ser Leu Lys Ala Ser Asp Thr Ala Met Tyr Tyr Cys
                85                  90                  95

Ala Arg Asp Tyr Trp Tyr Lys Pro Phe Ser Asp Val Trp Gly Gln Gly
            100                 105                 110

Thr Leu Val Thr Val Ser Ser
        115

<210> SEQ ID NO 375
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr Ser Tyr Asn Pro Asn Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Lys Pro Phe Phe Asp Ile Trp Gly Gln Gly
            100                 105                 110

Thr Leu Val Thr Val Ser Ser
        115

<210> SEQ ID NO 376
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Thr Trp Val Arg Gln Met Pro Gly Lys Gly Leu Glu Trp Met

```
                35                  40                  45
Gly Met Ile Tyr Pro Gly Asp Ser Tyr Thr Arg Tyr Ser Pro Lys Phe
 50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Asp His Trp Ser Lys Pro Leu Ser Asp Val Trp Gly Gln Gly
                100                 105                 110
Thr Leu Val Thr Val Ser Ser
            115

<210> SEQ ID NO 377
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Gln Val Gln Leu Val Gln Ser Gly Ala Glu Val Lys Lys Pro Gly Glu
 1               5                  10                  15
Ser Leu Lys Ile Ser Cys Lys Gly Ser Gly Tyr Ser Phe Thr Asn Tyr
                20                  25                  30
Tyr Ile Ser Trp Val Arg Gln Met Pro Gly Lys Gly Leu Glu Trp Met
                35                  40                  45
Gly Met Ile Tyr Pro Gly Asp Ser Tyr Thr Arg Tyr Ser Pro Lys Phe
 50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Asp His Trp Tyr Arg Pro Tyr Ser Asp Ile Trp Gly Gln Gly
                100                 105                 110
Thr Leu Val Thr Val Ser Ser
            115

<210> SEQ ID NO 378
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378

Gln Val Gln Leu Val Gln Ser Gly Ala Glu Val Lys Lys Pro Gly Glu
 1               5                  10                  15
Ser Leu Lys Ile Ser Cys Lys Gly Ser Gly Tyr Ser Phe Thr Asn Tyr
                20                  25                  30
Tyr Ile Thr Trp Val Arg Gln Met Pro Gly Lys Gly Leu Glu Trp Met
            35                  40                  45
Gly Met Ile Tyr Pro Gly Asp Ser Tyr Thr His Tyr Ser Gln Arg Phe
 50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Ile Tyr Tyr Cys
```

Ala Arg Asp His Trp Ser Arg Pro Leu Phe Asp Val Trp Gly Gln Gly
            100                 105                 110

Thr Leu Val Thr Val Ser Ser
        115

<210> SEQ ID NO 379
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr Arg Tyr Ser Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Tyr Arg Pro Tyr Ser Asp Ile Trp Gly Gln Gly
            100                 105                 110

Thr Leu Val Thr Val Ser Ser
        115

<210> SEQ ID NO 380
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Trp Ile Tyr Pro Gly Asp Ser Tyr Thr His Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Lys Pro Tyr Phe Asp Val Trp Gly Gln Gly
            100                 105                 110

Thr Leu Val Thr Val Ser Ser
        115

```
<210> SEQ ID NO 381
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 381
```

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Thr Trp Val Arg Gln Met Pro Gly Lys Gly Leu Glu Trp Met
        35                  40                  45

Gly Met Ile Tyr Pro Gly Asp Ser Tyr Thr His Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Tyr Lys Pro Leu Phe Asp Ile Trp Gly Gln Gly
            100                 105                 110

Thr Leu Val Thr Val Ser Ser
        115

```
<210> SEQ ID NO 382
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 382
```

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Asn Trp Val Arg Gln Met Pro Gly Lys Gly Leu Glu Trp Met
        35                  40                  45

Gly Met Ile Tyr Pro Gly Asp Ser Tyr Thr Asn Tyr Asn Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Arg Asp His Trp Ser Arg Pro Phe Ser Asp Val Trp Gly Gln Gly
            100                 105                 110

Thr Leu Val Thr Val Ser Ser
        115

```
<210> SEQ ID NO 383
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 383
```

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Trp Ile Tyr Pro Gly Asp Ser Tyr Thr Ser Tyr Asn Gln Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Lys Pro Tyr Ser Asp Val Trp Gly Gln Gly
                100                 105                 110

Thr Leu Val Thr Val Ser Ser
            115

<210> SEQ ID NO 384
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 384

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Thr Trp Val Arg Gln Met Pro Gly Lys Gly Leu Glu Trp Met
        35                  40                  45

Gly Met Ile Tyr Pro Gly Asp Ser Tyr Thr Asn Tyr Arg His Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Arg Pro Tyr Phe Asp Ile Trp Gly Gln Gly
                100                 105                 110

Thr Leu Val Thr Val Ser Ser
            115

<210> SEQ ID NO 385
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 385

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Trp Ile Tyr Pro Gly Asp Ser Tyr Thr His Tyr Ser His Asn Phe
            50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Asp His Trp Ser Arg Pro Phe Ser Asp Val Trp Gly Gln Gly
                100                 105                 110

Thr Leu Val Thr Val Ser Ser
        115

<210> SEQ ID NO 386
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 386

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
                20                  25                  30

Tyr Ile Ser Trp Val Arg Gln Met Pro Gly Lys Gly Leu Glu Trp Met
            35                  40                  45

Gly Met Ile Tyr Pro Gly Asp Ser Tyr Thr Ser Tyr Ser Pro Arg Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Arg Pro Phe Ser Asp Ile Trp Gly Gln Gly
                100                 105                 110

Thr Leu Val Thr Val Ser Ser
        115

<210> SEQ ID NO 387
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 387

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
                20                  25                  30

Tyr Ile Thr Trp Val Arg Gln Met Pro Gly Lys Gly Leu Glu Trp Met
            35                  40                  45

Gly Met Ile Tyr Pro Gly Asp Ser Tyr Thr Arg Tyr Ser Pro Lys Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Lys Pro Phe Phe Asp Val Trp Gly Gln Gly
            100                 105                 110

Thr Leu Val Thr Val Ser Ser
        115

<210> SEQ ID NO 388
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 388

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr His Tyr Ser Gln Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Tyr Arg Pro Leu Phe Asp Ile Trp Gly Gln Gly
            100                 105                 110

Thr Leu Val Thr Val Ser Ser
        115

<210> SEQ ID NO 389
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 389

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ala Trp Val Arg Gln Met Pro Gly Lys Gly Leu Glu Trp Met
        35                  40                  45

Gly Met Ile Tyr Pro Gly Asp Ser Tyr Thr Ser Tyr Ser His Arg Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Tyr Arg Pro Tyr Phe Asp Ile Trp Gly Gln Gly
            100                 105                 110

Thr Leu Val Thr Val Ser Ser
        115

<210> SEQ ID NO 390

<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 390

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Trp Ile Tyr Pro Gly Asp Ser Tyr Thr His Tyr Asn Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Arg Trp Ser Thr Pro Tyr Phe Asp Val Trp Gly Gln Gly
            100                 105                 110

Thr Leu Val Thr Val Ser Ser
        115

<210> SEQ ID NO 391
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 391

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr His Tyr Ser Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Lys Pro Tyr Phe Asp Val Trp Gly Gln Gly
            100                 105                 110

Thr Leu Val Thr Val Ser Ser
        115

<210> SEQ ID NO 392
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 392

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Pro Glu Trp Met
        35                  40                  45

Gly Met Ile Tyr Pro Gly Asp Ser Tyr Thr Arg Tyr Ser Gln Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Arg Asp His Trp Ser Arg Pro Leu Ser Asp Ile Trp Gly Gln Gly
                100                 105                 110

Thr Leu Val Thr Val Ser Ser
            115

<210> SEQ ID NO 393
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 393

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Trp Ile Tyr Pro Gly Asp Ser Tyr Thr His Tyr Asn Pro Met Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Arg Trp Ser Arg Pro Tyr Phe Asp Ile Trp Gly Gln Gly
                100                 105                 110

Thr Leu Val Thr Val Ser Ser
            115

<210> SEQ ID NO 394
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 394

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

```
Gly Met Ile Tyr Pro Gly Asp Ser Tyr Thr Arg Tyr Ser Pro Asn Phe
            50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Asp His Trp Tyr Arg Pro Leu Ser Asp Ile Trp Gly Gln Gly
            100                 105                 110

Thr Leu Val Thr Val Ser Ser
        115
```

<210> SEQ ID NO 395
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 395

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
                 20                  25                  30

Trp Ile Ser Trp Val Arg Gln Met Pro Gly Lys Gly Leu Glu Trp Met
             35                  40                  45

Gly Ile Ile Tyr Pro Gly Asp Ser Tyr Thr Lys Tyr Ser Pro Ser Phe
            50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Asp Tyr Trp Tyr Lys Pro Leu Phe Asp Ile Trp Gly Gln Gly
            100                 105                 110

Thr Leu Val Thr Val Ser Ser
        115
```

<210> SEQ ID NO 396
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
                 20                  25                  30

Trp Ile Ser Trp Val Arg Gln Met Pro Gly Lys Gly Leu Glu Trp Met
             35                  40                  45

Gly Ile Ile Tyr Pro Gly Asp Ser Tyr Thr Gln Tyr Ser Pro Ser Phe
            50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95
```

Ala Arg Asp Tyr Trp Tyr Lys Pro Leu Phe Asp Ile Trp Gly Gln Gly
            100                 105                 110

Thr Leu Val Thr Val Ser Ser
        115

<210> SEQ ID NO 397
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Lys Pro Leu Phe Asp Ile Trp Gly Gln Gly
            100                 105                 110

Thr Leu Val Thr Val Ser Ser
        115

<210> SEQ ID NO 398
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 398

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Ala Tyr Lys Pro Leu Phe Asp Ile Trp Gly Gln Gly
            100                 105                 110

Thr Leu Val Thr Val Ser Ser
        115

<210> SEQ ID NO 399
<211> LENGTH: 119

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 399

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Phe Tyr Lys Pro Leu Phe Asp Ile Trp Gly Gln Gly
            100                 105                 110

Thr Leu Val Thr Val Ser Ser
        115

<210> SEQ ID NO 400
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 400

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Tyr Tyr Lys Pro Leu Phe Asp Ile Trp Gly Gln Gly
            100                 105                 110

Thr Leu Val Thr Val Ser Ser
        115

<210> SEQ ID NO 401
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Gly Gly Gly Gly Gly Gly Gly Gly Gly Gly Gly Cys Gly Gly
```

```
<210> SEQ ID NO 402
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Gly Gly Gly Gly Gly Gly Gly Gly Gly Gly Gly Gly Cys Gly
1               5                   10

<210> SEQ ID NO 403
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Gly Gly Gly Gly Ser Gly Gly Gly Gly Ser
1               5                   10

<210> SEQ ID NO 404
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 404

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
        35                  40                  45

Ser Thr Ile Ser Gly Ser Gly Gly Thr Thr Asn Tyr Ala Asp Ser Val
    50                  55                  60

Lys Gly Arg Phe Ile Ile Ser Arg Asp Ser Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Leu Val Thr Val Ser Ser
        115

<210> SEQ ID NO 405
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 405

Asp Ile Val Met Thr Gln Ser Pro Asp Ser Leu Ala Val Ser Leu Gly
1               5                   10                  15
```

```
Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys
```

<210> SEQ ID NO 406
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 406

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Ser Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Phe Cys
                85                  90                  95

Ala Arg Asp Tyr Asp Phe Trp Ser Ala Tyr Tyr Asp Ala Phe Asp Val
            100                 105                 110

Trp Gly Gln Gly Thr Met Val Thr Val Ser Ser
        115                 120
```

<210> SEQ ID NO 407
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

```
Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Ser Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
```

```
                65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
                100                 105                 110

<210> SEQ ID NO 408
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Glu Met Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
                20                  25                  30

Trp Met Lys Trp Val Arg Gln Ala Pro Gly Lys Gly Leu Glu Trp Val
            35                  40                  45

Ala Asn Ile Asn Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Ile Val Leu Met Val Tyr Asp Met Asp Tyr Tyr Tyr Tyr
                100                 105                 110

Gly Met Asp Val Trp Gly Gln Gly Thr Thr Val Thr Val Ser Ser
            115                 120                 125

<210> SEQ ID NO 409
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Asn Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
                100                 105                 110

<210> SEQ ID NO 410
<211> LENGTH: 131
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 410

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser His
            20                  25                  30

Ala Ile Ser Trp Val Arg Gln Ala Pro Gly Gln Gly Leu Glu Trp Met
        35                  40                  45

Gly Gly Ile Asn Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Tyr Glu Ile Gln Ile Gly Arg Tyr Gly Met Asn Val Tyr
            100                 105                 110

Tyr Leu Met Tyr Arg Phe Ala Ser Trp Gly Gln Gly Thr Leu Val Thr
        115                 120                 125

Val Ser Ser
    130

<210> SEQ ID NO 411
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 411

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Asn Trp Tyr Gln Gln Lys Pro Gly Lys Ala Pro Lys Leu Leu Ile
        35                  40                  45

Tyr Asn Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Phe Asp Gly Asp Pro Thr
                85                  90                  95

Phe Gly Gln Gly Thr Lys Val Glu Ile Lys
            100                 105

<210> SEQ ID NO 412
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Gln Val Gln Leu Val Gln Ser Gly Ala Glu Val Lys Lys Pro Gly Glu
1               5                   10                  15
```

```
Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
            35                  40                  45

Gly Ile Ile Tyr Pro Gly Asp Ser Tyr Thr Asn Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Lys Pro Leu Phe Asp Ile Trp Gly Gln Gly
            100                 105                 110

Thr Leu Val Thr Val Ser Ser
            115

<210> SEQ ID NO 413
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Ser Phe Pro Ile Thr Phe Gly Gln Gly Thr Lys Val Glu Ile
            100                 105                 110

Lys

<210> SEQ ID NO 414
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 414

Gln Val Asn Leu Arg Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Glu Gly Leu Glu Trp Val
        35                  40                  45

Ser Ala Ile Ser Gly Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Arg Phe Gly Glu Phe Ala Phe Asp Ile Trp Gly Arg Gly Thr
            100                 105                 110

Thr Val Thr Val Ser Ser
            115

<210> SEQ ID NO 415
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Ala Ile Arg Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys
            100                 105

<210> SEQ ID NO 416
<211> LENGTH: 228
<212> TYPE: PRT
<213> ORGANISM: Homo sapiens

<400> SEQUENCE: 416

Glu Ser Lys Tyr Gly Pro Pro Cys Pro Pro Cys Pro Ala Pro Glu Ala
  1               5                  10                  15

Ala Gly Gly Pro Ser Val Phe Leu Phe Pro Pro Lys Pro Lys Asp Thr
                 20                  25                  30

Leu Met Ile Ser Arg Thr Pro Glu Val Thr Cys Val Val Val Asp Val
             35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140
```

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 417
<211> LENGTH: 99
<212> TYPE: PRT
<213> ORGANISM: Homo sapiens

<400> SEQUENCE: 417

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp

<210> SEQ ID NO 418
<211> LENGTH: 90
<212> TYPE: PRT
<213> ORGANISM: Homo sapiens

<400> SEQUENCE: 418

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln
                85                  90

<210> SEQ ID NO 419
<211> LENGTH: 266
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 419

His Gly Glu Gly Thr Phe Thr Ser Asp Leu Ser Lys Gln Met Glu Glu
1               5                   10                  15

Glu Cys Ala Arg Leu Phe Ile Glu Trp Leu Lys Asn Gly Gly Pro Ser
            20                  25                  30

Ser Gly Ala Pro Pro Gly Cys Gly Gly Gly Gly Ser Gly Gly
        35                  40                  45

Gly Gly Ser Ala Asp Ile Gln Met Thr Gln Ser Pro Ser Ser Leu Ser
    50                  55                  60

Ala Ser Val Gly Asp Arg Val Thr Ile Thr Cys Gln Ala Ser Gln Asp
65                  70                  75                  80

Val Lys Thr Ala Val Ala Trp Tyr Gln Gln Lys Pro Gly Lys Ala Pro
                85                  90                  95

Lys Leu Leu Ile Tyr Ser Ala Ser Tyr Arg Tyr Thr Gly Val Pro Ser
            100                 105                 110

Arg Phe Ser Gly Ser Gly Ser Gly Thr Asp Phe Thr Phe Thr Ile Ser
        115                 120                 125

Ser Leu Gln Pro Glu Asp Ile Ala Thr Tyr Tyr Cys Gln Gln Arg Tyr
    130                 135                 140

Ser Leu Trp Arg Thr Phe Gly Gln Gly Thr Lys Leu Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265

<210> SEQ ID NO 420
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

His Gly Glu Gly Thr Phe Thr Ser Asp Leu Ser Lys Gln Met Glu Glu
1               5                   10                  15

Glu Cys Ala Arg Leu Phe Ile Glu Trp Leu Lys Asn Gly Gly Pro Ser
            20                  25                  30

Ser Gly Ala Pro Pro Gly Cys Gly Gly Gly Gly Ser Ala Asp
        35                  40                  45

Ile Gln Met Thr Gln Ser Pro Ser Ser Leu Ser Ala Ser Val Gly Asp
    50                  55                  60

Arg Val Thr Ile Thr Cys Gln Ala Ser Gln Asp Val Lys Thr Ala Val

```
                65                  70                  75                  80
Ala Trp Tyr Gln Gln Lys Pro Gly Lys Ala Pro Lys Leu Leu Ile Tyr
                    85                  90                  95

Ser Ala Ser Tyr Arg Tyr Thr Gly Val Pro Ser Arg Phe Ser Gly Ser
                100                 105                 110

Gly Ser Gly Thr Asp Phe Thr Phe Thr Ile Ser Ser Leu Gln Pro Glu
                115                 120                 125

Asp Ile Ala Thr Tyr Tyr Cys Gln Gln Arg Tyr Ser Leu Trp Arg Thr
            130                 135                 140

Phe Gly Gln Gly Thr Lys Leu Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
                180                 185                 190

Val Gln Trp Lys Val Asp Asn Ala Leu Gln Ser Gly Asn Ser Gln Glu
            195                 200                 205

Ser Val Thr Glu Gln Asp Ser Lys Asp Ser Thr Tyr Ser Leu Ser Ser
        210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 421
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

His Gly Glu Gly Thr Phe Thr Ser Asp Leu Ser Lys Gln Met Glu Glu
1               5                   10                  15

Glu Cys Ala Arg Leu Phe Ile Glu Trp Leu Lys Asn Gly Gly Pro Ser
                20                  25                  30

Ser Gly Ala Pro Pro Pro Gly Cys Gly Ala Asp Ile Gln Met Thr Gln
            35                  40                  45

Ser Pro Ser Ser Leu Ser Ala Ser Val Gly Asp Arg Val Thr Ile Thr
        50                  55                  60

Cys Gln Ala Ser Gln Asp Val Lys Thr Ala Val Ala Trp Tyr Gln Gln
65                  70                  75                  80

Lys Pro Gly Lys Ala Pro Lys Leu Leu Ile Tyr Ser Ala Ser Tyr Arg
                85                  90                  95

Tyr Thr Gly Val Pro Ser Arg Phe Ser Gly Ser Gly Ser Gly Thr Asp
                100                 105                 110

Phe Thr Phe Thr Ile Ser Ser Leu Gln Pro Glu Asp Ile Ala Thr Tyr
            115                 120                 125

Tyr Cys Gln Gln Arg Tyr Ser Leu Trp Arg Thr Phe Gly Gln Gly Thr
        130                 135                 140

Lys Leu Glu Ile Lys Arg Thr Val Ala Ala Pro Ser Val Phe Ile Phe
145                 150                 155                 160
```

```
Pro Pro Ser Asp Glu Gln Leu Lys Ser Gly Thr Ala Ser Val Val Cys
            165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
            195                 200                 205

Asp Ser Lys Asp Ser Thr Tyr Ser Leu Ser Ser Thr Leu Thr Leu Ser
        210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
            245                 250                 255
```

<210> SEQ ID NO 422
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Ser Ile Ser Ser Ser Gly Asp Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Leu Val Thr Ser Met Val Ala Phe Asp Tyr Trp Gly Gln
            100                 105                 110

Gly Thr Leu Val Thr Val Ser Ser
            115                 120
```

<210> SEQ ID NO 423
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Tyr Val
            20                  25                  30

Phe Trp Tyr Gln Gln Lys Ser Gly Gln Ala Pro Val Leu Val Ile Tyr
            35                  40                  45

Glu Asp Ser Lys Arg Pro Ser Gly Ile Pro Glu Arg Phe Ser Gly Ser
        50                  55                  60

Ser Ser Gly Thr Met Ala Thr Leu Thr Ile Ser Gly Ala Gln Val Glu
65                  70                  75                  80
```

Asp Glu Ala Asp Tyr Tyr Cys Tyr Ser Thr Asp Arg Ser Gly Asn His
                85                  90                  95

Arg Val Phe Gly Gly Gly Thr Lys Leu Thr Val Leu
            100                 105

<210> SEQ ID NO 424
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Lys Pro Ser Gly Gly Ser Thr Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
        115

<210> SEQ ID NO 425
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 425

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Tyr Thr Ala
            20                  25                  30

Val Ala Trp Tyr Gln Gln Lys Pro Gly Lys Ala Pro Lys Leu Leu Ile
        35                  40                  45

Tyr Tyr Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 426
<211> LENGTH: 118
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 426

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Lys Pro Ser Gly Gly Ser Thr Ser Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
        115

<210> SEQ ID NO 427
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Tyr Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 428
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met

```
                35                  40                  45
Gly Glu Ile Lys Pro Ser Gly Gly Ser Thr Ser Tyr Asn Gln Lys Phe
         50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Glu Arg Pro Leu Tyr Ala Ser Asp Leu Trp Gly Gln Gly Thr
            100                 105                 110
Thr Val Thr Val Ser Ser
            115

<210> SEQ ID NO 429
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 429

Asp Ile Gln Met Thr Gln Ser Pro Ser Ser Leu Ser Ala Ser Val Gly
 1               5                  10                  15
Asp Arg Val Thr Ile Thr Cys Gln Ala Ser Gln Asp Val Lys Thr Ala
             20                  25                  30
Val Ala Trp Tyr Gln Gln Lys Pro Gly Lys Ala Pro Lys Leu Leu Ile
         35                  40                  45
Tyr Tyr Ala Ser Tyr Arg Tyr Thr Gly Val Pro Ser Arg Phe Ser Gly
     50                  55                  60
Ser Gly Ser Gly Thr Asp Phe Thr Phe Thr Ile Ser Ser Leu Gln Pro
 65                  70                  75                  80
Glu Asp Ile Ala Thr Tyr Tyr Cys Gln Gln Arg Tyr Ser Leu Trp Arg
                 85                  90                  95
Thr Phe Gly Gln Gly Thr Lys Leu Glu Ile Lys
            100                 105

<210> SEQ ID NO 430
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 430

Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Ser Tyr
             20                  25                  30
Tyr Met His Trp Val Arg Gln Ala Pro Gly Gln Gly Leu Glu Trp Met
         35                  40                  45
Gly Glu Ile Lys Pro Ser Gly Gly Ser Thr Ser Tyr Asn Gln Lys Phe
     50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Glu Arg Pro Leu Tyr Ala Ser Asp Leu Trp Gly Gln Gly Thr
```

<210> SEQ ID NO 431
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 431

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Lys Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 432
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 432

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Lys Pro Ser Gly Gly Ser Thr Ser Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
        115

<210> SEQ ID NO 433
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 433

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 434
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 434

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Ser Pro Ser Gly Ser Thr Ser Tyr Asn Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
        115

<210> SEQ ID NO 435
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 435

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Tyr Thr Ala
            20                  25                  30

Val Ala Trp Tyr Gln Gln Lys Pro Gly Lys Ala Pro Lys Leu Leu Ile
        35                  40                  45

Tyr Tyr Ala Ser Tyr Arg Tyr Thr Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                    85                  90                  95

Thr Phe Gly Gln Gly Thr Lys Leu Glu Ile Lys
            100                 105

<210> SEQ ID NO 436
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 436

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Glu Ile Ser Pro Ser Gly Gly Ser Thr Ser Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
        115

<210> SEQ ID NO 437
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 437

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Tyr Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 438
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 438

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Ser Pro Ser Gly Gly Ser Thr Ser Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
        115

<210> SEQ ID NO 439
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 439

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Lys Thr Ala
            20                  25                  30

Val Ala Trp Tyr Gln Gln Lys Pro Gly Lys Ala Pro Lys Leu Leu Ile
        35                  40                  45

Tyr Tyr Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 440
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 440

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Ser Pro Ser Gly Gly Ser Thr Ser Tyr Asn Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
            115

<210> SEQ ID NO 441
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 441

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Lys Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 442
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 442

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Ser Pro Ser Gly Gly Ser Thr Ser Tyr Asn Gln Lys Phe
50                  55                  60

```
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Arg Pro Leu Tyr Ala Ser Asp Leu Trp Gly Gln Gly Thr
            100                 105                 110

Thr Val Thr Val Ser Ser
        115
```

```
<210> SEQ ID NO 443
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105
```

```
<210> SEQ ID NO 444
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

His Tyr Glu Gly Thr Phe Thr Ser Asp Leu Ser Lys Gln Met Glu Glu
1               5                   10                  15

Glu Cys Val Arg Leu Phe Ile Glu Trp Leu Lys Asn Gly Gly Pro Ser
            20                  25                  30

Ser Gly Ala Pro Pro Pro Gly Cys Gly Gly Gly Gly Ser Gly Gly
        35                  40                  45

Gly Gly Ser Gly Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125
```

```
Thr Phe Thr Ile Ser Ser Leu Gln Pro Glu Asp Ile Ala Thr Tyr Tyr
            130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 445
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 445

His Val Glu Gly Thr Phe Thr Ser Asp Leu Ser Lys Gln Met Glu Glu
1               5                   10                  15

Glu Cys Val Arg Leu Phe Ile Glu Trp Leu Lys Asn Gly Gly Pro Ser
                20                  25                  30

Ser Gly Ala Pro Pro Gly Cys Gly Gly Gly Gly Ser Gly Gly
            35                  40                  45

Gly Gly Ser Gly Gly Gly Gly Ser Ala Asp Ile Gln Met Thr Gln Ser
50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
                100                 105                 110

Thr Gly Val Pro Ser Arg Phe Ser Gly Ser Gly Ser Gly Thr Asp Phe
            115                 120                 125

Thr Phe Thr Ile Ser Ser Leu Gln Pro Glu Asp Ile Ala Thr Tyr Tyr
            130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 446
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

His Thr Glu Gly Thr Phe Thr Ser Asp Leu Ser Lys Gln Met Glu Glu
1               5                   10                  15

Glu Cys Val Arg Leu Phe Ile Glu Trp Leu Lys Asn Gly Gly Pro Ser
                20                  25                  30

Ser Gly Ala Pro Pro Gly Cys Gly Gly Gly Gly Ser Gly Gly
            35                  40                  45

Gly Gly Ser Gly Gly Gly Gly Ser Ala Asp Ile Gln Met Thr Gln Ser
50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95
```

```
Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 447
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

His Gln Glu Gly Thr Phe Thr Ser Asp Leu Ser Lys Gln Met Glu Glu
1               5                   10                  15

Glu Cys Val Arg Leu Phe Ile Glu Trp Leu Lys Asn Gly Gly Pro Ser
            20                  25                  30

Ser Gly Ala Pro Pro Gly Cys Gly Gly Gly Gly Ser Gly Gly
        35                  40                  45

Gly Gly Ser Gly Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 448
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

His Asn Glu Gly Thr Phe Thr Ser Asp Leu Ser Lys Gln Met Glu Glu
1               5                   10                  15

Glu Cys Val Arg Leu Phe Ile Glu Trp Leu Lys Asn Gly Gly Pro Ser
            20                  25                  30

Ser Gly Ala Pro Pro Gly Cys Gly Gly Gly Gly Ser Gly Gly
        35                  40                  45

Gly Gly Ser Gly Gly Gly Gly Ser Ala Asp Ile Gln Met Thr Gln Ser
```

```
                    50                  55                  60
Pro Ser Ser Leu Ser Ala Ser Val Gly Asp Arg Val Thr Ile Thr Cys
 65                  70                  75                  80

Gln Ala Ser Gln Asp Val Lys Thr Ala Val Ala Trp Tyr Gln Gln Lys
                 85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
        130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 449
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

His Ile Glu Gly Thr Phe Thr Ser Asp Leu Ser Lys Gln Met Glu Glu
  1               5                  10                  15

Glu Cys Val Arg Leu Phe Ile Glu Trp Leu Lys Asn Gly Gly Pro Ser
                 20                  25                  30

Ser Gly Ala Pro Pro Pro Gly Cys Gly Gly Gly Gly Ser Gly Gly
             35                  40                  45

Gly Gly Ser Gly Gly Gly Gly Ser Ala Asp Ile Gln Met Thr Gln Ser
         50                  55                  60

Pro Ser Ser Leu Ser Ala Ser Val Gly Asp Arg Val Thr Ile Thr Cys
 65                  70                  75                  80

Gln Ala Ser Gln Asp Val Lys Thr Ala Val Ala Trp Tyr Gln Gln Lys
                 85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
        130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 450
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

His Phe Glu Gly Thr Phe Thr Ser Asp Leu Ser Lys Gln Met Glu Glu
  1               5                  10                  15
```

```
Glu Cys Val Arg Leu Phe Ile Glu Trp Leu Lys Asn Gly Gly Pro Ser
             20                  25                  30

Ser Gly Ala Pro Pro Gly Cys Gly Gly Gly Gly Ser Gly Gly
         35                  40                  45

Gly Gly Ser Gly Gly Gly Ser Ala Asp Ile Gln Met Thr Gln Ser
     50                  55                  60

Pro Ser Ser Leu Ser Ala Ser Val Gly Asp Arg Val Thr Ile Thr Cys
 65                  70                  75                  80

Gln Ala Ser Gln Asp Val Lys Thr Ala Val Ala Trp Tyr Gln Gln Lys
                 85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
            115                 120                 125

Thr Phe Thr Ile Ser Ser Leu Gln Pro Glu Asp Ile Ala Thr Tyr Tyr
130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 451
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

His Gly Glu Gly Thr Phe Thr Ser Asp Leu Ser Lys Gln Met Gly Glu
 1               5                  10                  15

Glu Cys Val Arg Leu Phe Ile Glu Trp Leu Lys Asn Gly Gly Pro Ser
             20                  25                  30

Ser Gly Ala Pro Pro Gly Cys Gly Gly Gly Gly Ser Gly Gly
         35                  40                  45

Gly Gly Ser Gly Gly Gly Ser Ala Asp Ile Gln Met Thr Gln Ser
     50                  55                  60

Pro Ser Ser Leu Ser Ala Ser Val Gly Asp Arg Val Thr Ile Thr Cys
 65                  70                  75                  80

Gln Ala Ser Gln Asp Val Lys Thr Ala Val Ala Trp Tyr Gln Gln Lys
                 85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
            115                 120                 125

Thr Phe Thr Ile Ser Ser Leu Gln Pro Glu Asp Ile Ala Thr Tyr Tyr
130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 452
<211> LENGTH: 164
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 452

His Gly Glu Gly Thr Phe Thr Ser Asp Leu Ser Lys Gln Met Ala Glu
1               5                   10                  15

Glu Cys Val Arg Leu Phe Ile Glu Trp Leu Lys Asn Gly Gly Pro Ser
            20                  25                  30

Ser Gly Ala Pro Pro Gly Cys Gly Gly Gly Gly Ser Gly Gly
        35                  40                  45

Gly Gly Ser Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Lys
                85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 453
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

His Gly Glu Gly Thr Phe Thr Ser Asp Leu Ser Lys Gln Met Glu Glu
1               5                   10                  15

Glu Cys Thr Arg Leu Phe Ile Glu Trp Leu Lys Asn Gly Gly Pro Ser
            20                  25                  30

Ser Gly Ala Pro Pro Gly Cys Gly Gly Gly Gly Ser Gly Gly
        35                  40                  45

Gly Gly Ser Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 454
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

His Gly Glu Gly Thr Phe Thr Ser Asp Leu Ser Lys Gln Met Glu Glu
1               5                   10                  15

Glu Cys Ser Arg Leu Phe Ile Glu Trp Leu Lys Asn Gly Gly Pro Ser
                20                  25                  30

Ser Gly Ala Pro Pro Gly Cys Gly Gly Gly Gly Ser Gly Gly
        35                  40                  45

Gly Gly Ser Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
                100                 105                 110

Thr Gly Val Pro Ser Arg Phe Ser Gly Ser Gly Ser Gly Thr Asp Phe
                115                 120                 125

Thr Phe Thr Ile Ser Ser Leu Gln Pro Glu Asp Ile Ala Thr Tyr Tyr
            130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 455
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

His Gly Glu Gly Thr Phe Thr Ser Asp Leu Ser Lys Gln Met Glu Glu
1               5                   10                  15

Glu Cys Gly Arg Leu Phe Ile Glu Trp Leu Lys Asn Gly Gly Pro Ser
                20                  25                  30

Ser Gly Ala Pro Pro Gly Cys Gly Gly Gly Gly Ser Gly Gly
        35                  40                  45

Gly Gly Ser Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
                100                 105                 110

Thr Gly Val Pro Ser Arg Phe Ser Gly Ser Gly Ser Gly Thr Asp Phe
                115                 120                 125

Thr Phe Thr Ile Ser Ser Leu Gln Pro Glu Asp Ile Ala Thr Tyr Tyr

```
                130               135               140
Cys Gln Gln Arg Tyr Ser Leu Trp Arg Thr Phe Gly Gln Gly Thr Lys
145                 150               155               160

Leu Glu Ile Lys

<210> SEQ ID NO 456
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

His Gly Glu Gly Thr Phe Thr Ser Asp Leu Ser Lys Gln Met Glu Glu
1               5                   10                  15

Glu Cys Ala Arg Leu Phe Ile Glu Trp Leu Lys Asn Gly Gly Pro Ser
                20                  25                  30

Ser Gly Ala Pro Pro Pro Gly Cys Gly Gly Gly Gly Ser Gly Gly
            35                  40                  45

Gly Gly Ser Gly Gly Gly Gly Ser Ala Asp Ile Gln Met Thr Gln Ser
        50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155               160

Leu Glu Ile Lys

<210> SEQ ID NO 457
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 457

His Gly Glu Gly Thr Phe Thr Ser Asp Leu Ser Lys Gln Met Glu Glu
1               5                   10                  15

Glu Cys Val Arg Leu Phe Thr Glu Trp Leu Lys Asn Gly Gly Pro Ser
                20                  25                  30

Ser Gly Ala Pro Pro Pro Gly Cys Gly Gly Gly Gly Ser Gly Gly
            35                  40                  45

Gly Gly Ser Gly Gly Gly Gly Ser Ala Asp Ile Gln Met Thr Gln Ser
        50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95
```

```
Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 458
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

His Gly Glu Gly Thr Phe Thr Ser Asp Leu Ser Lys Gln Met Glu Glu
1               5                   10                  15

Glu Cys Val Arg Leu Phe Ser Glu Trp Leu Lys Asn Gly Gly Pro Ser
            20                  25                  30

Ser Gly Ala Pro Pro Pro Gly Cys Gly Gly Gly Gly Ser Gly Gly
        35                  40                  45

Gly Gly Ser Gly Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 459
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

His Gly Glu Gly Thr Phe Thr Ser Asp Leu Ser Lys Gln Met Glu Glu
1               5                   10                  15

Glu Cys Val Arg Leu Phe Gly Glu Trp Leu Lys Asn Gly Gly Pro Ser
            20                  25                  30

Ser Gly Ala Pro Pro Pro Gly Cys Gly Gly Gly Gly Ser Gly Gly
        35                  40                  45

Gly Gly Ser Gly Gly Gly Gly Ser Ala Asp Ile Gln Met Thr Gln Ser
    50                  55                  60
```

```
Pro Ser Ser Leu Ser Ala Ser Val Gly Asp Arg Val Thr Ile Thr Cys
 65                  70                  75                  80

Gln Ala Ser Gln Asp Val Lys Thr Ala Val Ala Trp Tyr Gln Gln Lys
                 85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 460
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 460

His Gly Glu Gly Thr Phe Thr Ser Asp Leu Ser Lys Gln Met Glu Glu
1               5                  10                  15

Glu Cys Val Arg Leu Phe Ala Glu Trp Leu Lys Asn Gly Gly Pro Ser
            20                  25                  30

Ser Gly Ala Pro Pro Gly Cys Gly Gly Gly Gly Ser Gly Gly
        35                  40                  45

Gly Gly Ser Gly Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
 65                  70                  75                  80

Gln Ala Ser Gln Asp Val Lys Thr Ala Val Ala Trp Tyr Gln Gln Lys
                 85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 461
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 461

His Gly Glu Gly Thr Phe Thr Ser Asp Leu Ser Lys Gln Met Glu Glu
1               5                  10                  15

Glu Cys Val Arg Leu Phe Ile Glu Trp Thr Lys Asn Gly Gly Pro Ser
```

```
                20                  25                  30
Ser Gly Ala Pro Pro Gly Cys Gly Gly Gly Gly Ser Gly Gly
        35                  40                  45

Gly Gly Ser Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 462
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462

His Gly Glu Gly Thr Phe Thr Ser Asp Leu Ser Lys Gln Met Glu Glu
1               5                   10                  15

Glu Cys Val Arg Leu Phe Ile Glu Trp Ser Lys Asn Gly Gly Pro Ser
                20                  25                  30

Ser Gly Ala Pro Pro Gly Cys Gly Gly Gly Gly Ser Gly Gly
        35                  40                  45

Gly Gly Ser Gly Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 463
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 463

His Gly Glu Gly Thr Phe Thr Ser Asp Leu Ser Lys Gln Met Glu Glu
1               5                   10                  15

Glu Cys Val Arg Leu Phe Ile Glu Trp Pro Lys Asn Gly Gly Pro Ser
            20                  25                  30

Ser Gly Ala Pro Pro Pro Gly Cys Gly Gly Gly Gly Ser Gly Gly
        35                  40                  45

Gly Gly Ser Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Lys
                85                  90                  95

Pro Gly Lys Ala Pro Lys Leu Leu Ile Tyr Ser Ala Ser Tyr Arg Tyr
                100                 105                 110

Thr Gly Val Pro Ser Arg Phe Ser Gly Ser Gly Ser Gly Thr Asp Phe
            115                 120                 125

Thr Phe Thr Ile Ser Ser Leu Gln Pro Glu Asp Ile Ala Thr Tyr Tyr
        130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 464
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 464

His Gly Glu Gly Thr Phe Thr Ser Asp Leu Ser Lys Gln Met Glu Glu
1               5                   10                  15

Glu Cys Val Arg Leu Phe Ile Glu Trp Asn Lys Asn Gly Gly Pro Ser
            20                  25                  30

Ser Gly Ala Pro Pro Pro Gly Cys Gly Gly Gly Gly Ser Gly Gly
        35                  40                  45

Gly Gly Ser Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
                100                 105                 110

Thr Gly Val Pro Ser Arg Phe Ser Gly Ser Gly Ser Gly Thr Asp Phe
            115                 120                 125

Thr Phe Thr Ile Ser Ser Leu Gln Pro Glu Asp Ile Ala Thr Tyr Tyr
        130                 135                 140

Cys Gln Gln Arg Tyr Ser Leu Trp Arg Thr Phe Gly Gln Gly Thr Lys
145                 150                 155                 160

Leu Glu Ile Lys

```
<210> SEQ ID NO 465
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 465

His Gly Glu Gly Thr Phe Thr Ser Asp Leu Ser Lys Gln Met Glu Glu
1               5                   10                  15

Glu Cys Val Arg Leu Phe Ile Glu Trp Gln Lys Asn Gly Gly Pro Ser
            20                  25                  30

Ser Gly Ala Pro Pro Pro Gly Cys Gly Gly Gly Gly Ser Gly Gly
        35                  40                  45

Gly Gly Ser Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 466
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 466

His Gly Glu Gly Thr Phe Thr Ser Asp Leu Ser Lys Gln Met Glu Glu
1               5                   10                  15

Glu Cys Val Arg Leu Phe Ile Glu Trp Met Lys Asn Gly Gly Pro Ser
            20                  25                  30

Ser Gly Ala Pro Pro Pro Gly Cys Gly Gly Gly Gly Ser Gly Gly
        35                  40                  45

Gly Gly Ser Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140
```

Cys Gln Gln Arg Tyr Ser Leu Trp Arg Thr Phe Gly Gln Gly Thr Lys
145                 150                 155                 160

Leu Glu Ile Lys

<210> SEQ ID NO 467
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 467

His Gly Glu Gly Thr Phe Thr Ser Asp Leu Ser Lys Gln Met Glu Glu
1               5                   10                  15

Glu Cys Val Arg Leu Phe Ile Glu Trp Ile Lys Asn Gly Gly Pro Ser
                20                  25                  30

Ser Gly Ala Pro Pro Gly Cys Gly Gly Gly Gly Ser Gly Gly
        35                  40                  45

Gly Gly Ser Gly Gly Gly Ser Ala Asp Ile Gln Met Thr Gln Ser
        50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 468
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 468

His Gly Glu Gly Thr Phe Thr Ser Asp Leu Ser Lys Gln Met Glu Glu
1               5                   10                  15

Glu Cys Val Arg Leu Phe Ile Glu Trp His Lys Asn Gly Gly Pro Ser
                20                  25                  30

Ser Gly Ala Pro Pro Gly Cys Gly Gly Gly Gly Ser Gly Gly
        35                  40                  45

Gly Gly Ser Gly Gly Gly Ser Ala Asp Ile Gln Met Thr Gln Ser
        50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr

```
                100                 105                 110
Thr Gly Val Pro Ser Arg Phe Ser Gly Ser Gly Ser Gly Thr Asp Phe
            115                 120                 125

Thr Phe Thr Ile Ser Ser Leu Gln Pro Glu Asp Ile Ala Thr Tyr Tyr
        130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 469
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 469

His Gly Glu Gly Thr Phe Thr Ser Asp Leu Ser Lys Gln Met Glu Glu
1               5                   10                  15

Glu Cys Val Arg Leu Phe Ile Glu Trp Gly Lys Asn Gly Gly Pro Ser
            20                  25                  30

Ser Gly Ala Pro Pro Gly Cys Gly Gly Gly Gly Ser Gly Gly
        35                  40                  45

Gly Gly Ser Gly Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 470
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 470

His Gly Glu Gly Thr Phe Thr Ser Asp Leu Ser Lys Gln Met Glu Glu
1               5                   10                  15

Glu Cys Val Arg Leu Phe Ile Glu Trp Glu Lys Asn Gly Gly Pro Ser
            20                  25                  30

Ser Gly Ala Pro Pro Gly Cys Gly Gly Gly Gly Ser Gly Gly
        35                  40                  45

Gly Gly Ser Gly Gly Gly Gly Ser Ala Asp Ile Gln Met Thr Gln Ser
    50                  55                  60
```

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 471
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 471

His Gly Glu Gly Thr Phe Thr Ser Asp Leu Ser Lys Gln Met Glu Glu
1               5                   10                  15

Glu Cys Val Arg Leu Phe Ile Glu Trp Asp Lys Asn Gly Gly Pro Ser
            20                  25                  30

Ser Gly Ala Pro Pro Pro Gly Cys Gly Gly Gly Ser Gly Gly
        35                  40                  45

Gly Gly Ser Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Gln Lys
                85                  90                  95

Pro Gly Lys Ala Pro Lys Leu Leu Ile Tyr Ser Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 472
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 472

His Gly Glu Gly Thr Phe Thr Ser Asp Leu Ser Lys Gln Met Glu Glu
1               5                   10                  15

Glu Cys Val Arg Leu Phe Ile Glu Trp Leu Lys Asn Gly Gly Pro Ser
            20                  25                  30

```
Ser Gly Ala Pro Pro Gly Cys Gly Gly Gly Gly Ser Gly Gly
        35                  40                  45

Gly Gly Ser Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Gln Ala Ser Gln Asp Val Lys Thr Ala Val Ala Trp Tyr Gln Lys
                85                  90                  95

Pro Gly Lys Ala Pro Lys Leu Leu Ile Tyr Ser Ala Ser Tyr Arg Tyr
                100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
    130                 135                 140

Cys Gln Gln Arg Tyr Ser Leu Trp Arg Thr Phe Gly Gln Gly Thr Lys
145                 150                 155                 160

Leu Glu Ile Lys
```

<210> SEQ ID NO 473
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 473

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30
```

<210> SEQ ID NO 474
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

```
His Gly Glu Gly Thr Phe Thr Ser Asp Val Ser Ser Tyr Leu Glu Glu
1               5                   10                  15

Gln Asn Ala Ser Glu Phe Ile Ala Trp Leu Val Lys Gly Gly
            20                  25                  30
```

<210> SEQ ID NO 475
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 475

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Asn Gly Ser
            20                  25                  30
```

```
<210> SEQ ID NO 476
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Asn Gly
            20                  25                  30

<210> SEQ ID NO 477
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 477

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Asn
            20                  25                  30

<210> SEQ ID NO 478
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 478

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30

<210> SEQ ID NO 479
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 479

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30

<210> SEQ ID NO 480
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 480

His Gly Glu Gly Thr Phe Thr Ser Asp Val Ser Ser Tyr Leu Glu Glu
```

```
                1               5                  10                  15
Gln Ala Ala Lys Glu Phe Ile Ala Asn Leu Ser Lys Gly Gly
            20                  25                  30
```

<210> SEQ ID NO 481
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 481

```
His Gly Glu Gly Thr Phe Thr Ser Asp Val Ser Ser Tyr Leu Glu Glu
1               5                   10                  15
Gln Ala Ala Lys Glu Phe Ile Ala Asn Leu Thr Lys Gly Gly
            20                  25                  30
```

<210> SEQ ID NO 482
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

```
Gly Gly Gly Gly Gly Ser Gly Gly Gly Gly Ser Gly Gly Gly Gly Ser
1               5                   10                  15
Ala
```

<210> SEQ ID NO 483
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

```
Ser Gly Gly Gly Gly Ser Gly Gly Gly Gly Ser Gly Gly Gly Gly Ser
1               5                   10                  15
Ala
```

<210> SEQ ID NO 484
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

```
Gly Ser Gly Gly Gly Ser Gly Gly Gly Gly Ser Gly Gly Gly Gly Ser
1               5                   10                  15
Ala
```

<210> SEQ ID NO 485
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Asn Gly Ser Gly Gly Ser Gly Gly Gly Ser Gly Gly Gly Ser
1               5                   10                  15

Ala

<210> SEQ ID NO 486
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Gly Asn Gly Ser Gly Ser Gly Gly Gly Ser Gly Gly Gly Ser
1               5                   10                  15

Ala

<210> SEQ ID NO 487
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 487

His Gly Glu Gly Thr Phe Thr Ser Cys Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Gly Gly Gly Gly Gly Gly Gly Gly
            35                  40                  45

Gly Gly Cys Gly Gly Gly Gly Gly Ser Gly Gly Gly Ser Gly
        50                  55                  60

Gly Gly Ser Ala Asp Ile Gln Met Thr Gln Ser Pro Ser Ser Leu
65                  70                  75                  80

Ser Ala Ser Val Gly Asp Arg Val Thr Ile Thr Cys Lys Ala Ser Gln
                85                  90                  95

Asp Val His Thr Ala Val Ala Trp Tyr Gln Gln Lys Pro Gly Lys Ala
            100                 105                 110

Pro Lys Leu Leu Ile Tyr His Ala Ser Tyr Arg Tyr Thr Gly Val Pro
        115                 120                 125

Ser Arg Phe Ser Gly Ser Gly Ser Gly Thr Asp Phe Thr Phe Thr Ile
130                 135                 140

Ser Ser Leu Gln Pro Glu Asp Ile Ala Thr Tyr Tyr Cys Gln Gln Arg
145                 150                 155                 160

Tyr Ser Leu Trp Arg Thr Phe Gly Gln Gly Thr Lys Leu Glu Ile Lys
                165                 170                 175

<210> SEQ ID NO 488
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 488

His Gly Glu Gly Thr Phe Thr Ser Asp Leu Ser Lys Gln Met Glu Glu

```
                1               5                   10                  15
        Glu Cys Val Arg Leu Phe Ile Glu Trp Leu Lys Asn Gly Gly Pro Ser
                        20                  25                  30
        Ser Gly Ala Pro Pro Gly Cys Gly Gly Gly Ser Gly Gly Gly Gly
                        35                  40                  45
        Ser Gly Gly Gly Gly Ser Ala Asp Ile Gln Met Thr Gln Ser Pro Ser
                50                  55                  60
        Ser Leu Ser Ala Ser Val Gly Asp Arg Val Thr Ile Thr Cys Lys Ala
        65                  70                  75                  80
        Ser Gln Asp Val His Thr Ala Val Ala Trp Tyr Gln Gln Lys Pro Gly
                        85                  90                  95
        Lys Ala Pro Lys Leu Leu Ile Tyr His Ala Ser Tyr Arg Tyr Thr Gly
                        100                 105                 110
        Val Pro Ser Arg Phe Ser Gly Ser Gly Thr Asp Phe Thr Phe
                        115                 120                 125
        Thr Ile Ser Ser Leu Gln Pro Glu Asp Ile Ala Thr Tyr Tyr Cys Gln
        130                 135                 140
        Gln Arg Tyr Ser Leu Trp Arg Thr Phe Gly Gln Gly Thr Lys Leu Glu
        145                 150                 155                 160
        Ile Lys

<210> SEQ ID NO 489
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 489

His Gly Glu Gly Thr Phe Thr Ser Asp Val Ser Ser Tyr Leu Glu Glu
        1               5                   10                  15
        Gln Ala Ala Lys Glu Phe Ile Ala Asn Leu Ser Lys Gly Gly Gly Gly
                        20                  25                  30
        Gly Gly Gly Ser Gly Gly Gly Gly Ser Gly Gly Gly Gly Ser Ala Asp
                        35                  40                  45
        Ile Gln Met Thr Gln Ser Pro Ser Ser Leu Ser Ala Ser Val Gly Asp
                50                  55                  60
        Arg Val Thr Ile Thr Cys Lys Ala Ser Gln Asp Val His Thr Ala Val
        65                  70                  75                  80
        Ala Trp Tyr Gln Gln Lys Pro Gly Lys Ala Pro Lys Leu Leu Ile Tyr
                        85                  90                  95
        His Ala Ser Tyr Arg Tyr Thr Gly Val Pro Ser Arg Phe Ser Gly Ser
                        100                 105                 110
        Gly Ser Gly Thr Asp Phe Thr Phe Thr Ile Ser Ser Leu Gln Pro Glu
                        115                 120                 125
        Asp Ile Ala Thr Tyr Tyr Cys Gln Gln Arg Tyr Ser Leu Trp Arg Thr
                        130                 135                 140
        Phe Gly Gln Gly Thr Lys Leu Glu Ile Lys
        145                 150

<210> SEQ ID NO 490
<211> LENGTH: 164
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 490

His Gly Glu Gly Thr Phe Thr Ser Asp Leu Ser Lys Gln Met Glu Glu
1               5                   10                  15

Glu Cys Val Arg Leu Phe Ile Glu Trp Leu Lys Asn Gly Gly Pro Ser
            20                  25                  30

Ser Gly Ala Pro Pro Gly Cys Gly Gly Gly Gly Ser Gly Gly
        35                  40                  45

Gly Gly Ser Gly Gly Gly Ser Ala Asp Ile Gln Met Thr Gln Ser
    50                  55                  60

Pro Ser Ser Leu Ser Ala Ser Val Gly Asp Arg Val Thr Ile Thr Cys
65                  70                  75                  80

Lys Ala Ser Gln Asp Val His Thr Ala Val Ala Trp Tyr Gln Gln Lys
                85                  90                  95

Pro Gly Lys Ala Pro Lys Leu Leu Ile Tyr His Ala Ser Tyr Arg Tyr
            100                 105                 110

Thr Gly Val Pro Ser Arg Phe Ser Gly Ser Gly Ser Gly Thr Asp Phe
        115                 120                 125

Thr Phe Thr Ile Ser Ser Leu Gln Pro Glu Asp Ile Ala Thr Tyr Tyr
130                 135                 140

Cys Gln Gln Arg Tyr Ser Leu Trp Arg Thr Phe Gly Gln Gly Thr Lys
145                 150                 155                 160

Leu Glu Ile Lys

<210> SEQ ID NO 491
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 491

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Pro Phe Ser Lys Leu
            20                  25                  30

Gly Met Val Trp Val Arg Gln Ala Pro Gly Lys Gly Leu Glu Trp Val
        35                  40                  45

Ser Thr Ile Ser Ser Gly Gly Gly Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Ser Phe Gln Gly Gly Tyr Thr Tyr Val Met
            100                 105                 110

Asp Tyr Trp Gly Gln Gly Thr Leu Val Thr Val Ser Ser
        115                 120                 125

<210> SEQ ID NO 492
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 492

Asp Ile Val Met Thr Gln Ser Pro Leu Ser Leu Pro Val Thr Pro Gly
1               5                  10                  15

Glu Pro Ala Ser Ile Ser Cys Arg Ser Ser Lys Ser Leu Leu His Arg
            20                  25                  30

Asn Gly Ile Thr Tyr Ser Tyr Trp Tyr Leu Gln Lys Pro Gly Gln Ser
        35                  40                  45

Pro Gln Leu Leu Ile Tyr Gln Leu Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Tyr Gln Asn
                85                  90                  95

Leu Glu Leu Pro Leu Thr Phe Gly Gln Gly Thr Lys Val Glu Ile Lys
            100                 105                 110

<210> SEQ ID NO 493
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Gly Phe Pro Phe Ser Lys Leu Gly Met Val
1               5                   10

<210> SEQ ID NO 494
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Thr Ile Ser Ser Gly Gly Gly Tyr Thr Tyr Tyr Pro Asp Ser Val Lys
1               5                   10                  15

<210> SEQ ID NO 495
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Glu Gly Ile Ser Phe Gln Gly Gly Thr Tyr Thr Tyr Val Met Asp Tyr
1               5                   10                  15

<210> SEQ ID NO 496
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Arg Ser Ser Lys Ser Leu Leu His Arg Asn Gly Ile Thr Tyr Ser Tyr
1               5                   10                  15

-continued

<210> SEQ ID NO 497
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Gln Leu Ser Asn Leu Ala Ser
1               5

<210> SEQ ID NO 498
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Tyr Gln Asn Leu Glu Leu Pro Leu Thr
1               5

<210> SEQ ID NO 499
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 499

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Glu Ile His Pro Ser Gly Gly Arg Thr Asn Tyr Asn Glu Lys Phe
        50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 500
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 500

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val His Thr Ala
                20                  25                  30

Val Ala Trp Tyr Gln Gln Lys Pro Gly Lys Ala Pro Lys Leu Leu Ile
            35                  40                  45

Tyr His Ala Ser Tyr Arg Tyr Thr Gly Val Pro Ser Arg Phe Ser Gly
            50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln
                85                  90

<210> SEQ ID NO 501
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 501

His Gly Glu Gly Thr Phe Thr Ser Asp Val Ser Ser Tyr Leu Glu Glu
 1               5                  10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Gly Ser Ala
            35                  40                  45

<210> SEQ ID NO 502
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 502

His Gly Glu Gly Thr Phe Thr Ser Asp Val Ser Ser Tyr Leu Glu Glu
 1               5                  10                  15

Gln Asn Ala Ser Glu Phe Ile Ala Trp Leu Val Lys Gly Gly Gly Gly
                20                  25                  30

Gly Gly Gly Ser Gly Gly Gly Gly Ser Gly Gly Gly Gly Ser Ala
            35                  40                  45

<210> SEQ ID NO 503
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 503

His Gly Glu Gly Thr Phe Thr Ser Asp Val Ser Ser Tyr Leu Glu Glu
 1               5                  10                  15

Gln Ala Ala Lys Glu Phe Ile Ala Trp Leu Val Asn Gly Ser Gly Gly
                20                  25                  30

Gly Gly Gly Ser Gly Gly Gly Ser Gly Gly Gly Ser Ala
            35                  40                  45

<210> SEQ ID NO 504
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 504

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Asn Gly Ser Gly
            20                  25                  30

Gly Gly Gly Ser Gly Gly Gly Ser Gly Gly Gly Ser Ala
        35                  40                  45

<210> SEQ ID NO 505
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 505

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Asn Gly Ser
            20                  25                  30

Gly Gly Gly Ser Gly Gly Gly Ser Gly Gly Gly Ser Ala
        35                  40                  45

<210> SEQ ID NO 506
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 506

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Asn Gly
            20                  25                  30

Ser Gly Gly Ser Gly Gly Gly Ser Gly Gly Gly Ser Ala
        35                  40                  45

<210> SEQ ID NO 507
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 507

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Asn
            20                  25                  30

Gly Ser Gly Ser Gly Gly Gly Ser Gly Gly Gly Ser Ala
        35                  40                  45

<210> SEQ ID NO 508
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 508

His Gly Glu Gly Thr Phe Thr Ser Asp Val Ser Ser Tyr Leu Glu Glu
1               5                   10                  15

Gln Ala Ala Lys Glu Phe Ile Ala Asn Leu Ser Lys Gly Gly Gly Gly
            20                  25                  30

Gly Gly Gly Ser Gly Gly Gly Gly Ser Gly Gly Gly Gly Ser Ala
        35                  40                  45

<210> SEQ ID NO 509
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 509

His Gly Glu Gly Thr Phe Thr Ser Asp Val Ser Ser Tyr Leu Glu Glu
1               5                   10                  15

Gln Ala Ala Lys Glu Phe Ile Ala Asn Leu Thr Lys Gly Gly Gly Gly
            20                  25                  30

Gly Gly Gly Ser Gly Gly Gly Gly Ser Gly Gly Gly Gly Ser Ala
        35                  40                  45

<210> SEQ ID NO 510
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Gly Gly Gly Gly Ser Gly Gly Gly Gly Ser Gly Gly Gly Gly Ser
1               5                   10                  15
```

ANTI-PCSK9-GLP-1 FUSIONS AND METHODS FOR USE

CROSS-REFERENCE TO RELATED APPLICATIONS

This application is a U.S. National Stage application of International Application No. PCT/US2015/016911, filed on Feb. 20, 2015, said International Application No. PCT/US2015/016911 claims benefit under 35 U.S.C. § 119(e) of the U.S. Provisional Application Nos. 61/943,300, filed Feb. 21, 2014 and 61/944,550, filed Feb. 25, 2014. Each of the above listed applications is incorporated by reference herein in its entirety for all purposes.

REFERENCE TO THE SEQUENCE LISTING

This application incorporates by reference a Sequence Listing submitted with this application as text file entitled PCSK-100WO1_SL created on Feb. 2, 2016, and having a size of 534 kilobytes.

FIELD

Anti-PCSK9-GLP-1 Fusions and Methods for Use

BACKGROUND

Diabetes is associated with higher cardiovascular morbidity and mortality. Hypertension, hyperlipidemia, and diabetes are independently associated with increased risk of cardiovascular disease. Subjects with Type 2 diabetes are at two- to four-fold increased risk of cardiovascular disease compared to those without diabetes.

Glucagon-like peptide-1 (GLP-1) is known as a pleiotropic peptide with metabolic and cardiovascular benefits. It is derived from pre-proglucagon, a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. GLP-1 is produced as a 37-amino acid peptide that corresponds to amino acids 72 through 108 of proglucagon (92 to 128 of preproglucagon). The predominant biologically active form is a 30-amino acid peptide hormone (GLP-1(7-37) acid) that is produced in the gut following a meal and rapidly degraded by an abundant endogenous protease-DPP4. Baggio, L. and Drucker, D., Gasteroenterology, 132:2131-2157 (2007).

GLP-1 and GLP-1 analogs, acting as agonists at the GLP-1 receptor, have been shown to be effective hypoglycemic control, e.g., type-2 diabetes. Certain GLP-1 analogs are being sold or are in development for treatment of type-2 diabetes including, e.g., liraglutide (Victoza® from Novo Nordisk), dulaglutide (Eli Lilly), Bydureon (AZ/BMS), Aliblutide (GSK) and Exenatide (Byetta® from Eli Lilly/Amylin).

One of the primary side effects following the initiation of GLP-1 therapy is gastrointestinal side effects, particularly nausea. This side effect is transient, resolves over time and can be mitigated by dose escalation. However, therapy is limited to patients that can tolerate the gastrointestinal side effects.

PCSK9 is a nonenzymatic target for LDL cholesterol reduction and PCSK9 mutations correlate with reductions in LDL cholesterol and coronary heart disease. Cohen J C, N Engl J Med, 354:1264 (2006). PCSK9 antibodies have been shown to reduce LDL cholesterol in statin-treated patients and multiple candidates are undergoing clinical review.

While there are a plurality of individual treatments for diabetes and cardiovascular diseases, there is a need for a single pharmaceutical composition to address both disease states (and the relationship between diabetes and cardiovascular disease). Providing a single pharmaceutical compound that has dual activities will reduce side effects, difficulties with patient compliance, and will increase beneficial outcomes to individual patients and will decrease costs incurred by the health care system.

SUMMARY

In accordance with the description, disclosed is a dual active fusion molecule for the treatment of diabetes comprising an anti-PCSK9 antibody stably fused to a GLP-1 peptide, wherein the anti-PCSK9 antibody binds a PCSK9 polypeptide and the GLP-1 peptide binds a GLP-1 receptor.

In one aspect, wherein the GLP-1 peptide is fused to the PCSK9 antibody via a linker peptide.

In a further mode, the linker peptide is fused to the C-terminus of the GLP-1 peptide.

In one embodiment, the GLP-1 peptide comprises the amino acid sequence of SEQ ID NO: 36.

In one embodiment, the GLP-1 peptide comprises the amino acid sequence of SEQ ID NO: 3.

In one mode, wherein the Cys18 of the GLP-1 molecule forms a disulfide bridge with the linker peptide or with the GLP-1 peptide itself.

In one aspect, the fusion molecule controls glucose and/or reduces LDL in an animal. The animal may be human.

Disclosed also is a dual active fusion molecule for the treatment of diabetes comprising an anti-PCSK9 antibody stably fused to a GLP-1 peptide comprising the amino acid sequence of SEQ ID NO: 3, wherein C-terminus of the GLP-1 peptide is fused via a peptide linker to the light chain of the anti-PCSK9 antibody, and wherein the anti-PCSK9 antibody binds a PCSK9 polypeptide and the GLP-1 peptide binds a GLP-1 receptor.

Another embodiment disclosed is a method of treating Type 2 Diabetes comprising administering to a subject in need thereof, a fusion molecule described herein.

A further aspect comprises administering to a subject in need thereof, a fusion molecule described herein.

In one mode, a method of reducing low density lipoprotein (LDL) in a subject comprises administering to a subject in need thereof, a fusion molecule described herein.

Another aspect encompasses a method of controlling glucose and reducing LDL in a subject comprising administering to a subject in need thereof, a fusion molecule described herein.

Another aspect encompasses a method of promoting weight loss and reducing LDL in a subject comprising administering to a subject in need thereof, a fusion molecule described herein.

In one embodiment, the subject has Type 2 diabetes.

In another embodiment, the subject has metabolic syndrome.

An additional aspect is a dual active fusion molecule comprising an antibody stably fused to a GLP-1 peptide comprising the amino acid sequence of SEQ ID NO: 3, wherein C-terminus of the GLP-1 peptide is fused via a peptide linker to the light chain of the antibody, and wherein the antibody binds a target polypeptide and the GLP-1 peptide binds a GLP-1 receptor.

A further aspect is a dual active fusion molecule comprising an antibody stably fused to a GLP-1 peptide comprising the amino acid sequence of SEQ ID NO: 36, wherein C-terminus of the GLP-1 peptide is fused via a peptide linker to the light chain of the antibody, and wherein the antibody binds a target polypeptide and the GLP-1 peptide binds a GLP-1 receptor.

In some aspects, the GLP-1 molecule comprises the amino acid sequence of SEQ ID NO: 36. In some aspects, the antibody is an anti-PCSK9 antibody.

In certain modes, the light chain of the anti-PCSK9 antibody is at least 90% identical to the amino acid sequence of SEQ ID NO: 2. In other modes, the light chain of the anti-PCSK9 antibody comprises the amino acid sequence of SEQ ID NO: 2. In yet further modes, the heavy chain of the anti-PCSK9 antibody is at least 90% identical to the amino acid sequence of SEQ ID NO: 1. In some aspects, the heavy chain of the anti-PCSK9 antibody comprises the amino acid sequence of SEQ ID NO: 1.

In some embodiments, the peptide linker comprises the amino acid sequence of SEQ ID NO: 4. In some embodiments of the dual active fusion molecule, the Cys18 of the GLP-1 molecule forms a disulfide bridge with the C terminus of the GLP-1 peptide.

In some embodiments, the dual active fusion molecule is for the treatment of diabetes. In some embodiments, the dual active fusion molecule controls glucose and/or reduces LDL in an animal.

In some modes, the animal is a human.

Some embodiments include a dual active fusion molecule for the treatment of diabetes comprising an anti-PCSK9 antibody stably fused to a GLP-1 peptide that has reduced potency at the human GLP-1 receptor compared to a GLP-1 peptide comprising the amino acid sequence of SEQ ID NO: 29, wherein the C-terminus of the GLP-1 peptide is fused via a peptide linker to the anti-PCSK9 antibody, and wherein the anti-PCSK9 antibody binds a PCSK9 polypeptide and the GLP-1 peptide binds a GLP-1 receptor. In some embodiments, the GLP-1 peptide comprising the amino acid sequence of SEQ ID NO: 28 or SEQ ID NO: 29 is fused using a linker comprising SEQ ID NO:4 to the amino acid sequence comprising SEQ ID NO: 416. In further embodiments, the dual active fusion molecule of claim 25 or 26, wherein the potency at the human GLP-1 receptor is reduced by 30 to 60 fold compared to a GLP-1 peptide comprising the amino acid sequence of SEQ ID NO: 28 or SEQ ID NO: 29.

Some embodiments include an isolated polynucleotide encoding the fusion molecule described herein.

In certain modes, encompassed is a vector comprising the polynucleotide described herein. In other modes, a host cell comprises the polynucleotide or vector described herein.

In some embodiments, a method of making the fusion molecule comprises culturing the host cell under conditions allowing expression of the fusion molecule, and recovering the fusion molecule.

In some modes, a pharmaceutical composition comprises the fusion molecule described herein and a carrier. In some modes, a kit comprises the composition described herein.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIGS. 1B-D show various schematics of certain embodiments of antibody-peptide fusion molecules.

FIG. 1E shows alignment using numerical numbering of PC9#2 variable heavy chain with germline sequence 1-46 (DP-7). Discrepancies are shown in white with a black background.

FIG. 1F shows alignment using numerical numbering of PC9#2 variable light chain with germline sequence VK1 O18 O8 (DPK1). Discrepancies are shown in white with a black background.

FIGS. 2A-G show inhibition of human PCSK9 binding to anti-PCSK9 mAbs by anti-PCSK9 antibody/GLP-1 peptide fusions at the heavy chain N-terminus.

FIGS. 3A-G show inhibition of human PCSK9 binding to anti-PCSK9 mAbs by anti-PCSK9 antibody/GLP-1 peptide fusions at the light chain N-terminus.

FIGS. 4A-B show activation of human GLP1-Receptor by anti-PCSK9 antibody/GLP-1 peptide N-terminus fusions at the antibody heavy chain (A) and light chain (B).

FIG. 5B demonstrates stability in rat for an Exendin-4 GLP-1 analogue in light chain fusion with the anti-PCSK9 antibody PC9#2.

FIG. 7A provides peptide and linker amino acid sequences for eight compounds with an incorporated N-glycosylation consensus motif.

FIG. 7B provides peptide amino acid sequence for three compounds incorporating a disulphide bridge.

FIG. 8 shows a visual representation of the PC9#2_GLP1 molecule and the anti-PC9#2 antibody and GLP-1Fc(G4) used as a benchmark control.

FIG. 11 shows stability in mice of PC9#2_DSB#3, Exendin-4 analogue DSB#3 in light chain fusion with the anti-PCSK9 antibody PC9#2.

FIG. 14A shows stability in mice for benchmark compound GLP-1-Fc fusion Open squares: concentration of test molecule in serum over time; open diamonds concentration of "active" test molecule (as measured by GLP-1 activity) over time for the same samples.

FIG. 17 shows the amino acid sequence of additional Exendin-4 variant peptides incorporating a cysteine bridge. Cysteine residues are shown in black, other mutated residues are shown as underline and additional glycine residues at the C-terminus cap are shown in grey.

FIGS. 29A-D show specificity of the fusion molecule HS9_DSB7_V19 for GLP-1 receptor determined by cAMP assay.

FIGS. 47A-B shows blood glucose levels in a diet-induced obesity mouse model.

FIGS. 48A-B shows body weight (grams) (A) and % change in body weight (B) in a diet-induced obesity mouse model.

FIGS. 50A-B show the effect of the GLP-1 component of HS9_DSB7_V19A on glycemic control in a weekly dosing setting, measuring fed glucose (A) and terminal fasting glucose (B).

DESCRIPTION OF THE SEQUENCES

Figure 1A:
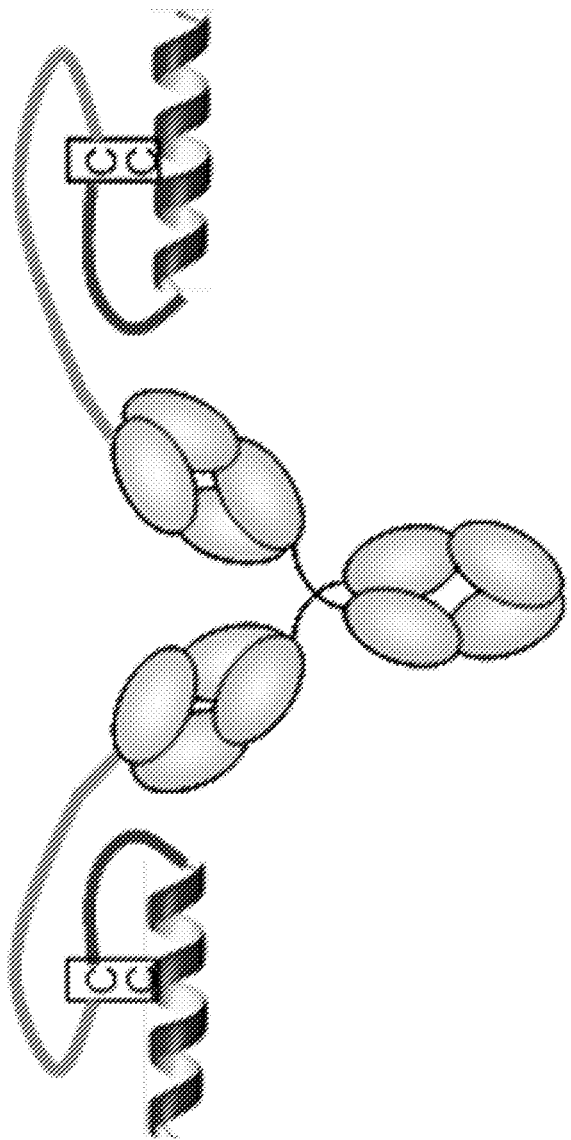
FIG. 1A is a schematic for a dual action fusion molecule as described herein.
Figure 2G:
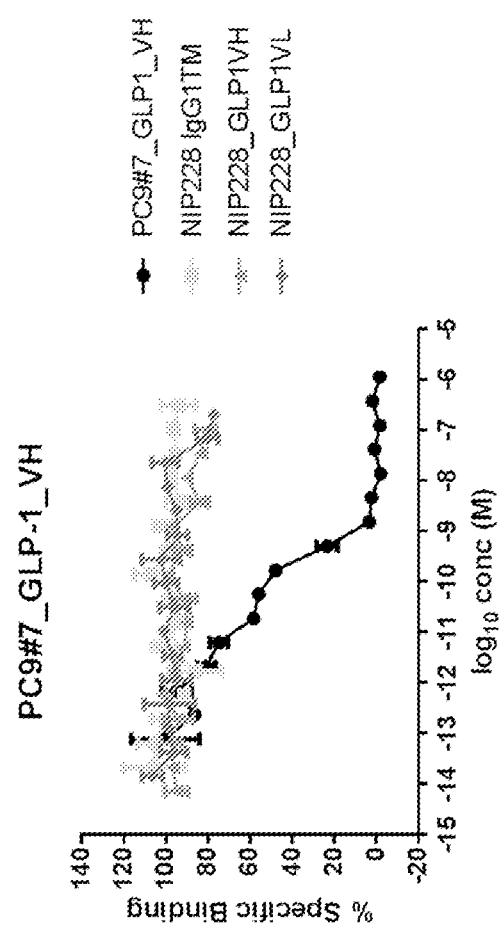
Figure 3G:
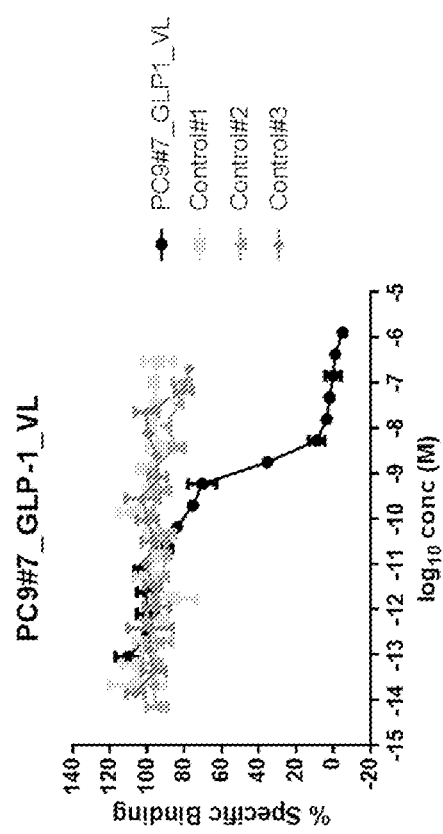

Table 1 provides a listing of certain sequences referenced in present embodiments.

TABLE 1

| Description | Sequence | SEQ ID NO |
|---|---|---|
| | GROUP A | |
| anti-PCSK9 antibody heavy chain (HS9_VH) | QVQLVQSGAEVKKPGASVKVSCKASGYTFTSYYMHWVRQAPGQGLEWMGEISPSGGSTSYNQKFQGRVTMTRDT STSTVYMELSSLRSEDTAVYYCARERPLYASDLWGQGTTVTVSS | 1. |
| anti-PCSK9 antibody light chain (HS9_Vk) | DIQMTQSPSSLSASVGDRVTITCQASQDVKTAVAWYQQKPGKAPKLLIYSASYRYTGVPSRFSGSGSGTDFTFT ISSLQPEDIATYYCQQRYSLWRTFGQGTKLEIK | 2. |
| GLP-1 moiety with cysteine bridge and double mutation |                           *^                        #<br>HGEGTFTSDLSKQMEEECARLFIEWLKNGGPSSGAPPPGCG<br>With the * designating a cysteine bridge to the linker,<br>the ^ designating a point mutation to reduce potency and match CDTP<br>(maximum efficacy without nausea side effect), and<br>the # designating a point mutation to optimize disulfide bonding and<br>reduce aggregation | 3. |
| Linker | GGGGSGGGGSGGGGSA | 4. |
| pH dependent version of anti-PCSK9 antibody heavy chain (PC9#2_FG_VH) | QVQLVQSGAEVKKPGASVKVSCKASGYTFTSYYMHWVRQAPGQGLEWMGEIHPSGGSTSYNQKFQGRVTMTRDT STSTVYMELSSLRSEDTAVYYCARERPLYASDLWGQGTTVTVSS | 5. |
| pH dependent version of anti-PCSK9 antibody light chain (PC9#2_FG_Vk) | DIQMTQSPSSLSASVGDRVTITCQASQDVHTAVAWYQQKPGKAPKLLIYHASYRYTGVPSRFSGSGSGTDFTFT ISSLQPEDIATYYCQQRYSLWRTFGQGTKLEIK | 6. |
| GLP-1 moiety with cysteine mutation to create disulfide bridge to linker |                        *<br>HGEGTFTSDLSKQMEEECVRLFIEWLKNGGPSSGAPPPSCG | 7. |
| Antibody A pH dependent heavy chain (PC9_2_VH) | QVQLVQSGAEVKKPGASVKVSCKASGYTFTSYYMHWVRQAPGQGLEWMGEIHPSGGRTNYNEKFKSRVTMTRDT STSTVYMELSSLRSEDTAVYYCARERPLYASDLWGQGTTVTVSS | 8. |
| Antibody A pH dependent light chain (PC9_2_Vk) | DIQMTQSPSSLSASVGDRVTITCKASQDVHTAVAWYQQKPGKAPKLLIYHASYRYTGVPSRFSGSGSGTDFTFT ISSLQPEDIATYYCQQRYSLWRTFGQGTKLEIK | 9. |
| Antibody B non pH dependent heavy chain (PC9_1_VH) | QVQLVQSGAEVKKPGASVKVSCKASGYTFTSYYMHWVRQAPGQGLEWMGEISPFGGRTNYNEKFKSRVTMTRDT STSTVYMELSSLRSEDTAVYYCARERPLYASDLWGQGTTVTVSS | 10. |

TABLE 1-continued

| Description | Sequence | SEQ ID NO |
|---|---|---|
| Antibody B non pH dependent light chain (PC9_1_Vk) | DIQMTQSPSSLSASVGDRVTITCRASQGISSALAWYQQKPGKAPKLLIYSASYRYTGVPSRFSGSGSGTDFTFTISSLQPEDIATYYCQQRYSLWRTFGQGTKLEIK | 11. |
| GLP-1 moiety (exenatide (Exe4)) | HGEGTFTSDLSKQMEEEAVRLFIEWLKNGGPSSGAPPPS | 12. |
| GLP-1 moiety DSB#7 with linker (PC9_HS9_DSB#7) | HGEGTFTSDLSKQMEEECVRLFIEWLKNGGPSSGAPPPGCGGGGGSGGGGSGGGGSA | 13. |
| anti-PCSK9 antibody heavy chain CDR1 (PC9_2_HS9) | SYYMH | 14. |
| anti-PCSK9 antibody heavy chain CDR2 (PC9_2_HS9_VH) | EISPSGGSTSYNQKFQG | 15. |
| anti-PCSK9 antibody heavy chain CDR2 (PC9#2_FG_VH) | EIHPSGGSTSYNQKFQG | 16. |
| anti-PCSK9 antibody heavy chain CDR2 (PC9_2_VH) | EIHPSGGRTNYNEKFKS | 17. |
| anti-PCSK9 antibody heavy chain CDR2 (PC9_1_VH) | EISPFGGRTNYNEKFKS | 18. |
| anti-PCSK9 antibody heavy chain CDR3 | ERPLYASDL | 19. |
| anti-PCSK9 antibody light chain CDR1 (PC9_2_HS9_Vk) | QASQDVKTAVA | 20. |
| anti-PCSK9 antibody light chain CDR1 (PC9#2_FG_Vk) | QASQDVHTAVA | 21. |
| anti-PCSK9 antibody light chain CDR1 (PC9_2_Vk) | KASQDVHTAVA | 22. |

TABLE 1-continued

| Description | Sequence | SEQ ID NO |
|---|---|---|
| anti-PCSK9 antibody light chain CDR1 (PC9_1_Vk) | RASQGISSALA | 23. |
| anti-PCSK9 antibody light chain CDR2 (PC9_2_HS9_Vk) (PC9_1_Vk) | SASYRYT | 24. |
| anti-PCSK9 antibody light chain CDR2 (PC9#2_FG_Vk) (PC9_2_Vk) | HASYRYT | 25. |
| anti-PCSK9 antibody light chain CDR3 | QQRYSLWRT | 26. |
| linker repeat | GGGGS | 27. |
| GLP-1 moiety from dulaglitude (GLP-1 L) | HGEGTFTSDVSSYLEEQAAKEFIAWLVKGGG | 28. |
| Human GLP-1 (7-37) | HAEGTFTSDVSSYLEGQAAKEFIAWLVKGRG | 29. |
| GLP-1 with disulfide Bridge (DSB) #1 DSB#1 | HGEGTFTSCLSKQMEEEAVRLFIEWLKNGGPSSGAPPPSGGGGGGGGGGCGG | 30. |
| GLP-1 with DSB#2 | HGECTFTSDLSKQMEEEAVRLFIEWLKNGGPSSGAPPPSGGGGGGGGGGCG | 31. |
| GLP-1 with DSB#3 | HGEGTFTSDLSKQMEEECVRLFIEWLKNGGPSSGAPPGC | 32. |
| GLP-1 with DSB#4 | HGEGTFTSDLSKQMEEEAVRCFIEWLKNGGPSSGAGGCS | 33. |
| GLP-1 with DSB#5 | HGEGTFTSCLSKQMEEEAVRLFIEWLKNGGPSSGAPPPSGGGGGGGGCGG | 34. |
| GLP-1 with DSB#6 | HGEGTFTSCLSKQMEEEAVRLFIEWLKNGGPSSGAPPPSGGGGGGGGGCGGG | 35. |
| GLP-1 with DSB#7 | HGEGTFTSDLSKQMEEECVRLFIEWLKNGGPSSGAPPPGCG | 36. |
| GLP-1 with DSB#8 | HGEGTFTSDLSKQMEEECVRLFIEWLKNGGPSSGAPPGGCG | 37. |
| GLP-1 with DSB#9 | HGEGTFTSDLSKQMEEEAVRCFIEWLKNGGPSSGAPPCGG | 38. |
| GLP-1 with DSB#10 | HGEGTFTSDLSKQMEEEAVRCFIEWLKNGGPSSGAPPGCG | 39. |
| GLP-1 with DSB#11 | HGEGTFTSDLSKQMEEEAVRLFIECLKNGGPSSGACGGS | 40. |
| GLP-1 with DSB#12 | HGEGTFTSDLSKQMEEEAVRLFIECLKNGGPSSGAPCPS | 41. |

TABLE 1-continued

| Description | Sequence | SEQ ID NO |
|---|---|---|
| GLP-1 with DSB#13 | HGEGTFTSDLSKQMEEEAVRLFIECLKNGGPSSGAPPCS | 42. |
| PC9#2_GLP1 VL with the linker of SEQ ID NO: 4 underlined (also referenced as PC9_2_GLP1) | HGEGTFTSDVSSYLEEQAAKEFIAWLVKGGGGGGGSGGGGSGGGGSADIQMTQSPSSLSASVGDRVTITCKASQDVHTAVAWYQQKPGKAPKLLIYHASYRYTGVPSRFSGSGSGTDFTFTISSLQPEDIATYYCQQRYSLWRTFGQGTKLEIKR | 43. |
| DSB#7 Variant G2V | HVEGTFTSDLSKQMEEECVRLFIEWLKNGGPSSGAPPPGCG | 44. |
| DSB#7 Variant E15A | HGEGTFTSDLSKQMAEECVRLFIEWLKNGGPSSGAPPPGCG | 45. |
| DSB#7 Variant L26I | HGEGTFTSDLSKQMEEECVRLFIEWIKNGGPSSGAPPPGCG | 46. |
| HS9_DSB7_V19A VL | *HGEGTFTSDLSKQMEEECARLFIEWLKNGGPSSGAPPPGCG*GGGGSGGGGSGGGGSADIQMTQSPSSLSASVGDRVTITCQASQDVKTAVAWYQQKPGKAPKLLIYSASYRYTGVPSRFSGSGSGTDFTFTISSLQPEDIATYYCQQRYSLWRTFGQGTKLEIK | 47. |
| PC9_2_DSB#1 VL | *HGEGTFTSCLSKQMEEEAVRLFIEWLKNGGPSSGAPPSGGGGGGGGGGCGG*GGGGSGGGGSGGGGSADIQMTQSPSSLSASVGDRVTITCKASQDVHTAVAWYQQKPGKAPKLLIYHASYRYTGVPSRFSGSGSGTDFTFTISSLQPEDIATYYCQQRYSLWRTFGQGTKLEIKR | 48. |
| PC9_2_DSB#3 VL | *HGEGTFTSDLSKQMEEECVRLFIEWLKNGGPSSGAPPGC*GGGGSGGGGSGGGGSADIQMTQSPSSLSASVGDRVTITCKASQDVHTAVAWYQQKPGKAPKLLIYHASYRYTGVPSRFSGSGSGTDFTFTISSLQPEDIATYYCQQRYSLWRTFGQGTKLEIKR | 49. |
| PC9_2_NGS#7 VL | *HGEGTFTSDVSSYLEEQAAKEFIANLSKGGG*GGGGSGGGGSGGGGSADIQMTQSPSSLSASVGDRVTITCKASQDVHTAVAWYQQKPGKAPKLLIYHASYRYTGVPSRFSGSGSGTDFTFTISSLQPEDIATYYCQQRYSLWRTFGQGTKLEIKR | 50. |
| PC9_2_DSB#7 VL | *HGEGTFTSDLSKQMEEECVRLFIEWLKNGGPSSGAPPPGCG*GGGGSGGGGSGGGGSADIQMTQSPSSLSASVGDRVTITCKASQDVHTAVAWYQQKPGKAPKLLIYHASYRYTGVPSRFSGSGSGTDFTFTISSLQPEDIATYYCQQRYSLWRTFGQGTKLEIKR | 51. |
| HS9_DSB#7 VL | *HGEGTFTSDLSKQMEEECVRLFIEWLKNGGPSSGAPPPGCG*GGGGSGGGGSGGGGSADIQMTQSPSSLSASVGDRVTITCQASQDVKTAVAWYQQKPGKAPKLLIYSASYRYTGVPSRFSGSGSGTDFTFTISSLQPEDIATYYCQQRYSLWRTFGQGTKLEIK | 52. |
| GROUP B ||| 
| VH AB1 (pH-Dep) | QVQLVQSGAEVKKPGASVKVSCKASGYTFTSYYMHWVRQAPGQGLEWMGEIHPSGGRTNYNEKFKSRVTMTRDTSTSTVYMELSSLRSEDTAVYYCARERPLYASDLWGQGTTVTVSS | 53. |
| VL AB1 (pH-Dep) | DIQMTQSPSSLSASVGDRVTITCKASQDVHTAVAWYQQKPGKAPKLLIYHASYRYTGVPSRFSGSGSGTDFTFTISSLQPEDIATYYCQQRYSLWRTFGQGTKLEIK | 54. |
| VH AB2 L1L3 | QVQLVQSGAEVKKPGASVKVSCKASGYTFTSYYMHWVRQAPGQGLEWMGEISPFGGRTNYNEKFKSRVTMTRDTSTSTVYMELSSLRSEDTAVYYCARERPLYASDLWGQGTTVTVSS | 55. |
| VL AB2 L1L3 | DIQMTQSPSSLSASVGDRVTITCRASQGISSALAWYQQKPGKAPKLLIYSASYRYTGVPSRFSGSGSGTDFTFTISSLQPEDIATYYCQQRYSLWRTFGQGTKLEIK | 56. |
| VH AB3 4A5 | EVQLQQSGPELVKPGASVKISCKASGYTFTDYYMNWVKQSHGKSLEWIGDINPNNGGTTYNQKFKGKATLTVDKSYSTAYMELRSLTSEDSAVYYCARWLLFAYWGQGTLVTVSA | 57. |
| VL AB3 4A5 | DIVMTQSQKFMSTSVGDRVSVTCKASQNVGTNVAWYQQKPGQSPKALIYSASYRYSGVPDRFTGSGSGTDFTLTISNVLSEDLAEYFCQQFYSYPYTFGGGTKLEIKR | 58. |
| VH AB4 5A10 | QVQLQQPGAELVKPGASVKLSCKASGYTFTSYWMHWVKQRPGQGLEWIGEINPSNGRTNYNEKFKSKATLTVDKSSSTAYMQLSSLTSEDSAVYYCARERPLYAMDYWGQGTSVTVSS | 59. |
| VL AB4 5A10 | DIVMTQSHKFMSTSVGDRVSITCKASQDVSTAVAWYQQKPGQSPKLLIYSASYRYTGVPDRFTGSGSGTDFTFTISSVQAEDLAVYYCQQRYSTPRTFGGGTKLEIKR | 60. |
| VH AB4 6F6 | EVQLQQSGPELVKPGASVKISCKASGYTFTDYYMNWVKQSHGKSLEWIGDINPNNGGTSYNQKFKGKATLTVDKSSSTAYMELRSLTSEDSAVYYCAGGGIYYRYDRNYFDYWGQGTTLTVSS | 61. |

TABLE 1-continued

| Description | Sequence | SEQ ID NO |
|---|---|---|
| VL AB4 6F6 | DIQMTQTTSSLSASLGDRVTISCSASQGISNYLNWYQQKPDGTVKLLIYYTSSLHSGVPSRFSGSGSGTDYSLT ISNLEPEDIATYYCQQYSKLPFTFGSGTKLEIK | 62. |
| VH AB4 7D4 | EVKLVESEGGGLVQPGSSMKLSCTASGFTFSDYYMAWVRQVPEKGLEWVANINYDGSNTSYLDSLKSRFIISRDN AKNILYLQMSSLKSEDTATYYCAREKFAAMDYWGQGTSVTVSS | 63. |
| VL AB4 7D4 | DIVMTQSHKFMSTSFGDRVSITCKASQDVSNALAWYQQKPGHSPKLLIFSASYRYTGVPDRFTGSGSGTDFTFT ISSVQAEDLAVYYCQQHYSTPWTFGGGTKLEIKR | 64. |
| GROUP C | | |
| VH A74 30A4 | QVQLVESGGGVVQPGRSLRLSCAASGFTFSSYGMHWVRQAPGKGLKWVAVIWYDGSDKYYADSVKGRFTISRDN SKNTLYLQMNSLRAEDTAVYYCARETGLPKLYYYGMDVWGQGTTVTVSS | 65. |
| VH A85 3C4 | QVQLQESGPGLVKPSQTLSLTCTVSGGSISSSDYYWSWIRQHPGKGLEWIGYIYYSGSTYYNPSLKSRITISVD TSKNLFSLKLSSVTAADTAVYYCARGGVTTYYYAMDVWGQGTTVTVSS | 66. |
| VH A71 23B5 | EVQLLESGGGLVQPGGSLRLSCAASGFTFSSYAMNWVRQAPGKGLEWVSTISGSGDNTYYADSVKGRFTISRDN SKNTLYLQMNSLRAEDTAVYYCAKKFVLMVYAMLDYWGQGTLVTVSS | 67. |
| VH A72 25G4 | EVQLLESGGGLVQPGGSLRLSCAASGFTFSSYAMNWVRQAPGKGLEWVSTISGSGGNTYYADSVKGRFTISRDN SKNTLYLQMNSLRAEDTAVYYCAKKFVLMVYAMLDYWGQGTLVTVSS | 68. |
| VH A67 31H4 | EVQLVESGGGLVKPGGSLRLSCAASGFTFSSYSMNWVRQAPGKGLEWVSSISSSSSYISYADSVKGRFTISRD NAKNSLYLQMNSLRAEDTAVYFCARDYDFWSAYYDAFDVWGQGTMVTVSS | 69. |
| VH A87 27B2 | QVQLQESGPGLVKPSQTLSLTCTVSGGSISSGGYYWSWIRQHPGKGLEWIGYIYNSGSTYYNPSLKSRVTISVD TSKNQFSLKLSSVTAADTAVYYCAREDTAMVPYFDYWGQGTLVTVSS | 70. |
| VH A58 25A7 | QVQLVQSGAEVKKPGASVKVSCKASGYTFPSYGISWVRQAPGQGLEWMGWISAYNGNTNYAEKLQGRVTMTTDT STSTAYMEVRSLRSDDTAVFYCARGYVMDVWGQGTTVTVSS | 71. |
| VH A52 27H5 | QVQLVQSGAEVKRPGASVKVSCKASGYTLTSYGISWVRQAPGQGLEWMGWISVYNGNTNYAQKVQGRVTMTTDT STSTVYMELRSLSSDDTAVYYCARGYGMDVWGQGTTVTVSS | 72. |
| VH A51 26H5 | QVQLVQSGAEVKKPGASVKVSCKASGYTLTSYGISWVRQAPGQGLEWMGWISFYNGNTNYAQKVQGRVTMTTDT STSTVYMELRSLRSDDTAVYYCARGYGMDVWGQGTTVTVSS | 73. |
| VH A53 31D1 | QIQLVQSGAEVKKPGASVKVSCKASGYTLTSYGISWVRQAPGQGLEWMGWISFYNGNTNYAQKVQGRVTMTTDT STSTVYMELRSLRSDDTAVYFCARGYGMDVWGQGTTVTVSS | 74. |
| VH A48 20D10 | QIQLVQSGAEVKKPGASVKVSCKASGYPLTSYGISWVRQAPGQGLEWMGWISAYNGNTNYAQKVQGSVTMTTDT STSTVYMELRSLRSDDTAVYYCARGYGMDVWGQGTTVTVSS | 75. |
| VH A54 27E7 | QVQLVQSGAEVKKPGASLKVSCKASGYSLTSYGISWVRQAPGQGLEWMGWISAYNGNTNYAQKVQGRVTMTTDT STSTVYMEVRSLRSDDTAVYYCARGYGMDVWGQGTTVTVSS | 76. |
| VH A55 30B9 | QVQLVQSGAEVKKPGASVKVSCKASGYPLTSYGISWVRQAPGQGLEWMGWISAYNGNTNYAQKVQGRVTMTTD STSTVYMELRSLRSDDTAVYYCARGYGMDVWGQGTTVTVSS | 77. |
| VH A56 19H9 | QVQLVQSGAEVKKPGASVKVSCKASGYALTSYGISWVRQAPGQGLEWMGWISAYNGNTNYAQKVQGRVTMTTDT STSTVYMELRSLRSDDTAVYYCARGYGMDVWGQGTTVTVSS | 78. |
| VH A49 21B12 | QVQLVQSGAEVKKPGASVKVSCKASGYTLTSYGISWVRQAPGQGLEWMGWVSFYNGNTNYAQKLQGRGTMTTDP STSTAYMELRSLRSDDTAVYYCARGYGMDVWGQGTTVTVSS | 79. |
| VH A57 17C2 | QVQLVQSGAEVKKPGASVKVSCKASGYSFTSYGISWVRQAPGQGLEWMGWVSAYNGNTNYAQKFQGRVTMTTDT STSTAYMELRSLRSDDTAVYYCARGYVMDVWGQGTTVTVSS | 80. |
| VH A50 23G1 | QVQLVQSGAEVKKPGASVKVSCKASGYTLTSYGISWVRQAPGQGLEWMGWVSFYNGNTNYAQKLQGRGTMTTDP STSTAYMELRSLRSDDTAVYYCARGYGMDVWGQGTTVTVSS | 81. |
| VH A91 13H1 | QVQLQQSGPGLVKPSQTLSLTCAISGDSVSSNSAAMNWIRQSPSRGLEWLGRTYYRSKWYKNYSVSVKSRITIN PDTSKNQFSLQLNSVTPGDTAVYYCARGGPTAAFDYWGQGTLVTVSS | 82. |
| VH A64 9C9 | EVQLVESGGGLVQPGGSLRLSCVVSGFTFSSYWMSWVRQAPGKGLEWVANIKQDGSEKYYVDSVKGRFTISRDN AKNSLYLQMNSLRAEDTAVYYCARESNWGFAFDIWGQGTMVTVSS | 83. |
| VH A62 9H6 | EVQLVESGGGLVQPGGSLRLSCAASGFTFSRYWMSWVRQAPGKGLEWVANIKHDGSEKYYVDSVKGRFTISRDN AKNSLYLQMNSLRAEDTAVYYCARESNWGFAFDVWGHGTMVTVSS | 84. |
| VH A89 31A4 | QVQLQQWGAGLLKPSETLSLTCAVYGGSFSAYYWNWIRQPPGKGLEWIGEINHSGRTDYNPSLKSRVTISVDTS KKQFSLKLNSVTAADTAVYYCARGQLVPFDYWGQGTLVTVSS | 85. |
| VH A65 1A12 | EVQLVESGGGLVQPGGSLRLSCAASGLTFSNFWMSWVRQAPGKGLEWVANIKQDGSEKYYVDSVKGRFTISRDN AKNSLYLQMNSLRAEDTAVYSCTRESNWGFAFDIWGQGTMVTVSS | 86. |

TABLE 1-continued

| Description | Sequence | SEQ ID NO |
|---|---|---|
| VH A79 16F12 | QVHLVESGGGVVQPGRSLRLSCAASGFTFNSFGMHWVRQAPGKGLEWVALIWSDGSDEYYADSVKGRFTISRDN SKNTLYLQMNSLRAEDTAVYYCARAIAALYYYYGMDVWGQGTTVTVSS | 87. |
| VH A80 22E2 | QVQLVESCCGVVQPGRSLRLSCAASGFTFSSFGMHWVRQAPGKCLEWVALIWNDGSNKYYADSVKGRFTISRDN SKNTLYLQMNSLRAEDTAVYYCARAIAALYYYYGMDVWGQGTTVTVSS | 88. |
| VH A76 27A6 | QVHLVESGGGVVQPGRSLRLSCAASGFTFNSFGMHWVRQAPGKGLEWVALIWSDGSDKYYADSVKGRFTISRDN SKNTLYLQMNSLRAEDTAVYYCARAIAALYYYYGMDVWGQGTTVTVSS | 89. |
| VH A77 28B12 | QVQLVESGGGVVQPGRSLRLSCAASGFTFSSFGMHWVRQAPGKGLEWVALIWNDGSNKYYADSVKGRFTISRDN SKNTLYLQMNSLRAEDTAVYYCARAIAALYYYYGMDVWGHGTTVTVSS | 90. |
| VH A78 28D6 | QVQLVESGGGVVQPGRSLRLSCAASGFTFSSFGMHWVRQAPGKGLEWVALIWNDGSNKYYADSVKGRFTISRDN SKNTLYLQMNSLRAEDTAVYYCARAIAALYYYYGMDVWGQGTTVTVSS | 91. |
| VH A83 31G11 | QVQLVESGGGVVQPGRSLRLSCAASGFTFRSYGMHKVRQAPGKGLEWVALIWHDGSNTYYVDSVKGRFTISRDN SKNTLYLQMNSLRAEDTAVYYCARGIAVAYYYYGMDVWGQGTTVTVSS | 92. |
| VH A69 13B5 | EVQLLESGGGLVQPGGSLRLSCAASGFTFSSYAMSWVRQAPGKGLEWVSTISGSGGRTYYADSVKGRFTISRDN SKNTLYLQMNSLRAEDTAVYYCAKEVGSPFDYWGQGTLVTVSS | 93. |
| VH A81 31B12 | QVQLVESGGGVVQPGRSLRLSCAASGFTFSSYGMHWVRQAPGKGLEWVAIIWYDGSNKYYADSVKGRFTISRDN SKNTLYLQMNSLRAEDTAVYYCARRGGLAARPGGMDVWGQGTTVTVSS | 94. |
| VH A60 3B6 | QVQLVQSGAEVKKPGASVKVSCKASGYTFTSYGISWVRQAPGQGLEWMGWISTYNGNTNYAQKVQGRVTMTTDT STSTAYMELRSLRSDDTAVYYCARGYTRDYWGQGTLVTVSS | 95. |
| VL 5 30A4 | DIVMTQSPLSLSVTPGEPPSISCRSSQSLLHSNGYNFLNWYLQKPGQSPQLLIYLGSHRASGVPDRFSGSGSGT DFTLEISRVEAEDVGVYYCMQVLQTPFTFGPGTKVDIK | 96. |
| VL 73C4 | DIQMTQSPSSLSASVGDRVTITCRASQRISNYLSWYLQKPGIAPKLLIYAASSLQSGVPSRFSGSGSGTDFTLT ISSLQSEDFATYYCQQSYSTPLIFGGGTKVEIK | 97. |
| VL 9 23B5 | DILMTQSPSSLSASVGDRVTITCRASQSISSYLNWYQQKPGKAPKVLIYAASSLQSGVPSRFSGSGSGTDFTLT INSLQPEDFATYYCQQSYSSPITFGQGTRLEIK | 98. |
| VL 10 25G4 | DIQMTQSPSSLSASVGDRVTITCRASQSISIYLNWYQQKPGKAPYLLIYAAASLQSGVPSRFSGSGSGTDFTLT ISSLQPEDFATYYCQQSYSAPITFGQGTRLEIK | 99. |
| VL 12 31H4 | QSVLTQPPSVSGAPGQRVTISCTGSSSNIGAGYDVHWYQQLPGTAPKLLISGNSNRPSGVPDRFSGSKSGTSAS LAITGLQAEDEADYYCQSYDSSLSGSVFGGGTKLTVL | 100. |
| VL 13 27B2 | QSVLTQPPSVSGAPGQRVTISCTGSSSNIGAHYDVHWYQQVPGTAPKLLIYGNTYRPSGVPDRFSGSKSGTSAS LAITGLQAEDEADYYCQSYDNSLSGVVFGGGTKLTVL | 101. |
| VL 15 25A7 | QSALTQPASVSGSPGQSITISCTGTSSDVGRYNSVSWYQHHPGKAPKVMIYEVSNRPSGVSTRFSGSKSGNTAS LTISGLQAEDEADYYCSSYTSSSVVFGGGTKLTVL | 102. |
| VL 16 27H5 | QSALTQPASVSGSPGQSITISCTGTSSDVGGYNSVSWYQQHPGKPPKLMIYEVSNRPSGVSIRFSGSKSGNTAS LTISGLQAEDEADYFCSSYTSTSMVFGGGTKLTVL | 103. |
| VL 17 26H5 | QSALTQPASVSGSPGQSITISCTGTSSDVGGYNSVSWYQQHPGKPPKLMIYEVSNRPSGVSIRFSGSKSGNTAS LTISGLQAEDEADYFCSSYTSTSMVFGGGTKLTVL | 104. |
| VL 18 31D1 | QSALTQPASVSGSPGQSITISCTGTSSDVGGYNSVSWYQQHPGKPPKLMIYEVSNRPSGVSNRFSGSKSGNTAS LTISGLQAEDEADYFCSSYTSTSMVFGGGTKLTVL | 105. |
| VL 19 20D10 | QSALTQPASVSGSPGQSITISCTGTSSDVGGYNSVSWYQQYPGKPPKLKIYEVSNRPSGVSNRFSGSKSGNTAS LTISGLQAEDEADYFCSSYTSTSMVFGGGTKLTVL | 106. |
| VL 20 27K7 | QSALTQPASVSGSPGQSITISCTGTSSDVGGYNSVSWYQQHPGKPPKLMIYEVSNRPSGVSNRFSGSKSGNTAS LTISGLQAEDEADYFCSSYTSTSMVFGGGTKLTVL | 107. |
| VL 21 30B9 | QSALTQPASVSGSPGQSITISCTGTSSDVGGYNSVSWYQQHPGKPPKLMIYEVSNRPSGVSNRFSGSKSGNTAS LTISGLQAEDEADYFCSSYTSTSMVFGGGTKLTVL | 108. |
| VL 22 19H9 | QSALTQPASVSGSPGQSITISCTGTNSDVGGYNSVSWYQQHPGKPPKLMIYEVSNRPSGISNRFSGSKSGNTAS LTISGLQAEDEADYFCSSYTSTSMVFGGGTKLTVL | 109. |
| VL 23 21B12 | QSALTQPASVSGSPGQSITISCTGTSSDVGGYNSVSWYQQHPGKAPKLMIYEVSNRPSGVSXRFSGSKSGNTAS LTISGLQAEDEADYYCNSYTSTSMVFGGGTKLTVL | 110. |
| VL 24 17C2 | QSALTQPASVSGSPGQSITISCTGTSSDVGAYNSVSWYQQHPGKAPKRMIYEVSNRPSGVSNRFSGSKSGNTAS LTISGLQAEDEADYYCSSYTSTNMVFGGGTKLTVL | 111. |

TABLE 1-continued

| Description | Sequence | SEQ ID NO |
|---|---|---|
| VL 26 23G1 | QSALTQPASVSGSPGQSITISCTGTSSDVGGYNSVSWYQQHPGKAPKRMIYEVTNRPSGVSNRFSGSKSGNTAS LTISGLQAEDEADYYCNSYTSTNMVFGGGTKLTVL | 112. |
| VL 28 13HT | LSALTQPASVSGSPGQSITISCTGTSSDVGNYNLVSWYQQYSGKAPKLMIYEVSKRPSGVSNRFSGSKSGNTAS LTISGLQAEDEADYYCCSYAGSSTLVFGGGTKLTVL | 113. |
| VL 30 9C9 | QSVLTQPPSASGTPGQRVTISCSGSSSNIGSKTVNWYQQVPGTAPKLLIYRNNQRPLGVPDRFSGSKSGTSASL AISGLQSEDEADYYCAAWDDSLNWVFGGGTKLTVL | 114. |
| VL 31 9H6 | QSVLTQPPSASGPPGQRVTISCSGSSSNIGSNTVNWYQQLPGTAPKLLIYSNNRRPSGVPDRFSGSKSGTSASL AISGLQSEDEADYYCAAWDDSLNWVFGGGTKLTVL | 115. |
| VL 32 31A4 | QSVLTQPPSASGTPGQRVTISCSGSSSNIGSNTVNWYQQLPGTAPKLLIYSNNQRPSGVPDRFSGSKSGTSASL AISGLQSEDEADYYCAVWDDSLNGWVFGGGTKLTVL | 116. |
| VL 33 1A12 | QSVLTQPPSASGTPGQRVTISCSGSSSNIGSKTVNWYQQFPGTAPKLLIYSNNRRPSGVPDRFSGSKSGTSASL AISGLQSEDEADYYCAAWDDSLNWVFGAGTKLTVL | 117. |
| VL 35 16F12 | QSVLTQPPSVSAAPGQKVTISCSGSSSNIGNNFVSWYQQLPGTAPKLLIYDYNKRPSGIPDRFSGSKSGTSATL GITGLQTGDEADYYCGTWDSSLSAYVFGTGTRVTVL | 118. |
| VL 36 22E2 | QSVLTQPPSVSAAPGQKVTISCSGSSSNIGNNFVSWYQQLPGTAPKLLIYDYNKRPSGIPDRFSGSKSGTSATL GITGLQTGDEADYYCGTWDSSLSGYVFGTGTRVTVL | 119. |
| VL 37 27A6 | QSVLTQPPSVSAAPGQKVTISCSGSSSNIGNNFVSWYQQFPGTAPKLLIYDYNKRPSGIPDRFSGSKSGTSATL GITGLQTGDEADYYCGTWDSSLSSYVFGTGTRVTVL | 120. |
| VL 38 28B12 | QSVLTQPPSVSAAPGQKVTISCSGSSSNIGNNFVSWYQQLPGTAPKLLIYDYNKRPSGIPDRFSGSKSGTSATL GITGLQTGDEADYYCGTWDSSLSSYVFGTGTRVTVL | 121. |
| VL 39 28D6 | QSVLTQPPTVSAAPGQKVTISCSGSSSNIGNNFVSWYQQLPGTAPKLLIYDYNKRPSGIPDRFSGSKSGTSATL GITGLQTGDEADYYCGTWDSSLSGYVFGTGTRVTVL | 122. |
| VL 40 31G11 | QSVLTQPPSVSAAPGQKVTISCSGSSSNIGNNFVSWYQQLPGTAPKLLIYDSNKRPSGIPDRFSGSKSGTSATL DITGLQTGDEADYYCGTWDSSLSAYVFGTGTKVTVL | 123. |
| VL 42 13B5 | QSVLTQPPSVSAAPGQKVTISCSGSNSNIGNNYVSWYQQLPGTAPKLLIYDNNKRPSGIPDRFSGSNSGTSATL GITGLQTGDEADYYCGTWDSSLSAVVFGGGTKLTVL | 124. |
| VL 44 31B12 | SYELTQPPSVSVSPGQTARITCSGDKLGDKYACWYQQKPGQSPVLVIYQNTKWPLGIPERFSGSKSGNTVTLTI SGTQAMDEADYYCQAWDSSTVVFGGGTKLTVL | 125. |
| VL 46 3B6 | QPVLTQPLFASASLGASVTLTCTLSSGYSSYEVDWYQQRPGKGPRFVMRVDTGGIVGSKGEGIPDRFSVLGSGL NRYLTIKNIQEEDESDYHCGADHGSGTNFVVVFGGGTKLTVL | 126. |
| GROUP D | | |
| VH 66 | QVQLVESGGGVVQPGRSLRLSCAASGFTFSSYGMHWVRQAPGKGLEWVAFIGFDGSNIYYGDSVRGRIIISRDN SENTLYLEMNSLRAEDTAVYYCAREKGLDWGQGTLVTVSS | 127. |
| VH 90 H1H316P | EVQLVESGGGLVQPGGSLRLSCAASGFTFNNYAMNWVRQAPGKGLDWVSTISGSGGTTNYADSVKGRFIISRDS SKHTLYLQMNSLRAEDTAVYYCAKDSNWGNFDLWGRGTLVTVSS | 128. |
| VH 138 | QVQLQESGPGLVKPSETLSLTCTVSGDSINTYYWSWFRQPPGKGLEWIGYIYYSGTTNYNPSLKSRVTISIDTP RNQFSLKLISVTAADTAVYYCARERITMIRGVTLYYYSYGMDVWGQGTTVTVSS | 129. |
| VH 218 H1M300N | EMQLVESGGGLVQPGGSLRLSCAASGFTFSSHWMKWVRQAPGKGLEWVANINQDGSEKYYVDSVKGRFTISRDN AKNSLFLQMNSLRAEDTAVYYCARDIVLMVYDMDYYYYGMDVWGQTTVTVSS | 130. |
| VH 2 | QVQLVQSGGGLVQPGGSLRLSCAASGFTLSSYDMHWVRQSTGKGLEWVSAIGSTGDTYYPGSVKGRFTITREKA KNSVYLQMNSLRAGDTAVYYCVREGWEVPFDYWGQGTLVTVSS | 131. |
| VH 18 | EVQLVESGGGLVQPGGSLRLSCAASGFTLSSYDMHWVRQSTGKGLEWVSAIGSTGDTYYPGSVKGRFTITREKA KNSVYLQMNSLRAGDTAVYYCVREGWEVPFDYWGQGTLVTVSS | 132. |
| VH 22 | EVQLVESGGGLVQPGGSLRLSCAASGFTLSSYDMHWVRQATGKGLEWVSAIGSTGDTYYPGSVKGRFTISRENA KNSLYLQMNSLRAGDTAVYYCVREGWEVPFDYWGQGTLVTVSS | 133. |
| VH 26 | QVQLVQSGGGVVQPGRSLRLSCAASGFTLSSYGMHWVRQAPGKGLEWVAFIGSDGSNIHYGDSVKGRIIISRDN SENTLYLEMNSLRAEDTAMYYCAREKGLDWGQGTTVTVSS | 134. |
| VH 42 | QVQLVESGGGVVQPGRSLRLSCAASGFTFSSYGMHWVRQAPGKGLEWVAFIGFDGSNIHYGDSVKGRIIISRDN SENTLYLEMNSLRAEDTAMYYCAREKGLDWGQGTLVTVSS | 135. |
| VH 46 | QVQLVESGGGVVQPGRSLRLSCAASGFTFSSYGMHWVRQAPGKGLEWVAVIGFDGSNIYYADSVKGRFTISRDN SKNTLYLQMNSLRAEDTAVYYCAREKGLDWGQGTLVTVSS | 136. |

TABLE 1-continued

| Description | Sequence | SEQ ID NO |
|---|---|---|
| VH 50 | QVQLQESGGGVVQPGRSLRLSCAASGFTFSSYGMHWVRQAPGKGLEWVAFIGFDGSNIYYGDSVRGRIIISRDN SENTLYLEMNSLRAEDTAVYYCAREKGLDKGQGTLVTVSS | 137. |
| VH 70 | QVQLVESGGGVVQPGRSLRLSCAASGFTFSSYGMHWVRQAPGKGLEWVAVIGFDGSNIYYADSVKGRFTISRDN SKNTLYLQMNSLRAEDTAVYYCAREKGLDWGQGTLVTVSS | 138. |
| VH 94 | EVQLVESGGGLVQPGGSLRLSCAASGFTFNNYAMSWVRQAPGKGLEWVSAISGSGGTTYYADSVKGRFTISRDN SKNTLYLQMNSLRAEDTAVYYCAKDSNWGNFDLWGRGTLVTVSS | 139. |
| VH 98 | QVQLVESGGGLVQPGGSLRLSCAVSGFTLSSYDMHWVRQPTGKGLEWVSAIGSTGDTYYPGSVKGRFTISRENA KNSLYLQMNSLRAGDTAVYYCAREGWDVPFDFWGQGTLVTVSS | 140. |
| VH 114 | EVQLVESGGGLVQPGGSLRLSCAVSGFTLSSYDMHWVRQPTGKGLEWVSAIGSTGDTYYPGSVKGRFTISRENA KNSLYLQMNSLRAGDTAVYYCAREGWDVPFDFWGQGTLVTVSS | 141. |
| VH 118 | EVQLVESGGGLVQPGGSLRLSCAASGFTLSSYDMHWVRQATGKGLEWVSAIGSTGDTYYPGSVKGRFTISRENA KNSLYLQMNSLRAGDTAVYYCAREGWDVPFDFWGQGTLVTVSS | 142. |
| VH 122 | QVQLQESGPGLVKPSETLSLTCTVSGDSINTYYWSWIRQPPGKGLEWIGYIYYSGTTNYNPSLKSRVTISVDTS KNQFSLKLSSVTAADTAVYYCARERITMIRGVTLYYYSGMDVWGQGTTVTVSS | 143. |
| VH 142 | QVQLQESGPGLVKPSETLSLTCTVSGDSINTYYWSWIRQPPGKGLEWIGYIYYSGTTNYNPSLKSRVTISVDTS KNQFSLKLSSVTAADTAVYYCARERITMIRGVTLYYYSGMDVWGQGTTVTVSS | 144. |
| VH 146 | QVQLVQSGAEVKKPGASVKVSCKASGYTFTNYGTSWVRQAPGQGLELMGWISGYNGNTNYAQELQARVTMTTDT STSTAYMELRNLRSDDTAVYYCARDRVVAAANYYFYSMDVWGQGTTVTVSS | 145. |
| VH 162 | QVQLVQSGAEVKKPGASVKVSCKASGYTFTNYGTSWVRQAPGQGLELMGWISGYNGNTNYAQELQARVTMTTDT STSTAYMELRNLRSDDTAVYYCARDRVVAAANYYFYSMDVWGQGTTVTVSS | 146. |
| VH 166 | QVQLVQSGAEVKKPGASVKVSCKAHGYTFTNYGISWVRQAPGQGLEWMGWISGYNGNTNYAQKLQGRVTMTTDT STSTAYMELRSLRSDDTAVYYCARDRVVAAANYYFYSMDVWGQGTTVTVSS | 147. |
| VH 170 | QVHLKESGPTLVKPTQTLTLTCTFSGFSLITSGVGVGWIRQPPGKALEWLALIYWMGDKRYSPSLKSRLTITKD TSKNQVVLTMTNMDPVDTATYYCAHRITETSYYFYYGMDVWGQGTTVTVSS | 148. |
| VH 186 | QITLKESGPTLVKPTQTLTLTCTFSGFSLITSGVGVGWIRQPPGKALEWLALIYWNGDKRYSPSLKSRLTITKD TSKNQVVLTMTNMDPVDTATYYCAHRITETSYYFYYGMDVWGQGTTVTVSS | 149. |
| VH 190 | QITLKESGPTLVKPTQTLTLTCTFSGFSLITSGVGVGWIRQPPGKALEWLALIYWNGDKRYSPSLKSRLTITKD TSKNQVVLTMTNMDPVDTATYYCAHRITETSYYFYYGMDVWGQGTTVTVSS | 150. |
| VH 194 | QITLKESGPTLVKPTQTLTLTCTFSGFSLSTSGVGVGWIRQPPGKALEWLALIYWNSDKRYSPSLKSRLTITKD TSKNQVVLTMTNMDPVDTATYYCAHRHDSSYYFYYGMDVWGQGITVTVSS | 151. |
| VH 210 | QITLKESGPTLVKPSQTLTLTCTFSGFSLSTSGVGVGWIRQPPGKALEWLALIYWNSDKRYSPSLKSRLTITKD TSKNQVVLTMTNMDPVDTATYYCAHRHDSSYYFYYGMDVWGQGTTVTVSS | 152. |
| VH 214 | QITLKESGPTLVKPTQTLTLTCTFSGFSLSTSGVGVGWIRQPPGKALEWLALIYWNSDKRYSPSLKSRLTITKD TSKNQVVLTMTNMDPVDTATYYCAHRHDSSYYFYYGMDVWGQGTTVTVSS | 153. |
| VH 234 | EVQLVESGGGLVQPGGSLRLSCAASGFTFSSHWMKWVRQAPGKGLEWVANINQDGSEKYYVDSVKGRFTISRDN AKNSLFLQMNSLRAEDTAVYYCARDIVLMVYDMDYYYGMDVWGQGTTVTVSS | 154. |
| VH 238 | EVQLVESGGGLVQPGGSLRLSCAASGFTFSSHWMSWVRQAPGKGLEWVANINQDGSEKYYVDSVKGRFTISRDN AKNSLYLQMNSLRAEDTAVYYCARDIVLMVYDMDYYYGMDVWGQGTTVTVSS | 155. |
| VH 242 | QVQLVESGGGVVQPGRSLRLSCAVSGFTFSSYGMHWVRQAPGKGLEWVAAISYDGSNKYYVDSVKGRFTISRDN SKKTLYLQMNSLRAEDTAVYNCAKNIVLVMYDIDYHYYGMDVWGQGTTVTVSS | 156. |
| VH 258 | QVQLVESGGGVVQPGRSLRLSCAASGFTFSSYGMHWVRQAPGKGLEWVAAISYDGSNKYYVDSVKGRFTISRDN SKKTLYLQMNSLRAEDTAVYNCAKNIVLVMYDIDYHYYGMDVWGQGTTVTVSS | 157. |
| VH 262 | QVQLVESGGGVVQPGRSLRLSCAASGFTFSSYGMHWVRQAPGKGLEWVAVISYDGSNKYYADSVKGRFTISRDN SKNTLYLQMNSLRAEDTAVYYCAKNIVLVMYDIDYHYYGMDVWGQGTTVTVSS | 158. |
| VH 266 | QVQLVESGGGVVQPGRSLRLSCAASGFTFSSYGMHWVRQAPGKGLEWVAAISYDGSNKYYVDSVKGRFTISRDN SKKTLYLQMNSLRAEDTAVYNCAKNIVLVMYDIDYHYYGMDVWGQGTTVTVSS | 159. |
| VH 282 | QVQLVESGGGVVQPGRSLRLSCAVSGFTFSSYGMHWVRQAPGKGLEWVAAISYDGSNKYYVDSVKGRFTISRDN SKKTLYLQMNSLRAEDTAVYNCAKNIVLVMYDIDYHYYGMDVWGQGTTVTVSS | 160. |
| VH 286 | QVQLVESGGGVVQPGRSLRLSCAVSGFTFSSYGMHWVRQAPGKGLEWVAVISYDGSNKYYADSVKGRFTISRDN SKNTLYLQMNSLRAEDTAVYYCAKNIVLVMYDIDYHYYGMDVWGQGTTVTVSS | 161. |

TABLE 1-continued

| Description | Sequence | SEQ ID NO |
|---|---|---|
| VH 290 | QITLKESGPTLVKPTQTLTLTCTFSGFSLSASGVGVGWFRQPPGKALEWLALIYWNDDKRYSPSLKNSLTITKDTSKNQVVLTMTNMDPVDTATYYCAHRIHLWSYFYYGMDVWGQGTTVTVSS | 162. |
| VH 306 | QITLKESGPTLVKPTQTLTLTCTFSGFSLSASGVGVGWFRQPPGKALEWLALIYWNDDKRYSPSLKNSLTITKDTSKNQVVLTMTNMDPVDTATYYCAHRIHLWSYFYYGMDVWGQGTTVTVSS | 163. |
| VH 310 | QITLKESGPTLVKPTQTLTLTCTFSGFSLSASGVGVGWIRQPPGKALEWLALIYWNDDKRYSPRLKNSLTITKDTSKNQVVLTMTNMDPVDTATYYCAHRIHLWSYFYYGMDVWGQGTTVTVSS | 164. |
| VH 314 | QVQLVQSGPEVKNPGASVKVSCKASGYTFTTYGISWVRQAPGQGLEWMGWISGYHGKTNDAQKFQDRVAMTTDTSTSTAYMELRSLRSDDTAIYYCSRDRLVVPPALNYSYYVMDVWGQGTTVTVSS | 165. |
| VH 330 | QVQLVQSGPEVKMPGASVKVSCKASGYTFTTYGISWVRQAPGQGLEWMGWISGYHGKTNDAQKFQDRVAMTTDTSTSTAYMELRSLRSDDTAIYYCSRDRLVVPPALNYSYYVMDVWGQGTTVTVSS | 166. |
| VH 334 | QVQLVQSGPEVKMPGASVKVSCKASGYTFTTYGISWVRQAPGQGLEWMGWISGYHGKTNYAQKFQGRVTMTTDTSTSTAYMELRSLRSDDTAVYYCSRDRLVVPPALNYSYYVMDVWGQGTTVTVSS | 167. |
| VH 338 | EVQLVESGGGLVKPGGSLRLSCAASGFTFSSYSMDWVRQAPGKGLEWVSSISSSSSYIYYADSVKGRFTISRDTAKNSLYLQMNSLRDEDTAVYYCAREGSSRLFDYWGQGTLVTVSS | 168. |
| VH 354 | EVQLVESGGGLVKPGGSLRLSCAASGFTFSSYSMDWVRQAPGKGLEWVSSISSSSSYIYYADSVKGRFTISRDTAKNSLYLQMNSLRDEDTAVYYCAREGSSRLFDYWGQGTLVTVSS | 169. |
| VH 358 | EVQLVESGGGLVKPGGSLRLSCAASGFTFSSYSMNWVRQAPGKGLEWVSSISSSSSYIYYADSVKGRFTISRDNAKNSLYLQMNSLRAEDTAVYYCAREGSSRLFDYWGQGTLVTVSS | 170. |
| VH 362 | QVHLVESGGGLVKPGGSLRLSCAASGFTFSDHYMSWIRQAPGKGLEWISYISNDGGTKYYVDSVEGRFIISRDNAKNSLYLHMNSLRADDTAVYYCARDQGYIGYDSYYYSYGMDVWGQGTTVTVAS | 171. |
| VH 378 | QVQLVESGGGLVKPGGSLRLSCAASGFTFSDHYMSWIRQAPGKGLEWISYISNDGGTKYYVDSVEGRFIISRDNAKNSLYLHMNSLRADDTAVYYCARDQGYIGYDSYYYSYGMDVWGQGTTVTVSS | 172. |
| VH 382 | QVQLVESGGGLVKPGGSLRLSCAASGFTFSDHYMSWIRQAPGKGLEWVSYISNDGGTKYYADSVKGRFTISRDNAKNSLYLQMNSLRAEDTAVYYCARDQGYIGYDSYYYSYGMDVWGQGTTVTVSS | 173. |
| VH 386 | EVQKVESGGGLVKPGGSLRLSCTASGFTFSTYNMNWVRQAPGKGLEWVSSIRSSSNYIYYADSVKGRFTISRDNAKNSLYLQMNSLRADDTAVYYCARDGSSWYDYSDYWGQGTLVTVSS | 174. |
| VH 402 | EVQLVESGGGLVKPGGSLRLSCGASGFTFSTYNMNWVRQAPGKGLEWVSSIRSSSNYIYYADSVKGRFTISRDNAKNSLYLQMNSLRADDTAVYYCARDGSSWYDYSDYWGQGTLVTVSS | 175. |
| VH 406 | EVQLVESGGGLVKPGGSLRLSCAASGFTFSTYNMNWVRQAPGKGLEWVSSIRSSSNYIYYADSVKGRFTISRDNAKNSLYLQMNSLRAEDTAVYYCARDGSSWYDYSDYWGQGTLVTVSS | 176. |
| VH 410 | EVQLVESGGGLVKPGGSLRLSCTASGFTFSTYNMNWVRQAPGKGLEWVSSIRSSSNYIYYADSVKGRFTISRDNAKNSLYLQMNSLRADDTAVYYCARDGSSWYDYSDYWGQGTLVTVSS | 177. |
| VH 426 | EVQLVESGGGLVKPGGSLRLSCTASGFTFSTYNMNWVRQAPGKGLEWVSSIRSSSNYIYYADSVKGRFTISRDNAKNSLYLQMNSLRADDTAVYYCARDGSSWYDYSDYWGQGTLVTVSS | 178. |
| VH 430 | EVQLVESGGGLVKPGGSLRLSCAASGFTFSTYNMNWVRQAPGKGLEWVSSIRSSSNYIYYADSVKGRFTISRDNAKNSLYLQMNSLRAEDTAVYYCARDGSSWYDYSDYWGQGTLVTVSS | 179. |
| VH 434 | EVQLVESGGGLVKPGGSLRLSCTASGFTFSTYNMNWVRQAPGKGLEWVSSIRSSSNYIYYADSVKGRFTISRDNAKSSLYLQMNSLRAEDTAVYYCARDGSSWYDYSDYWGQGTLVTVSS | 180. |
| VH 450 | EVQLVESGGGLVKPGGSLRLSCTASGFTFSTYNMNWVRQAPGKGLEWVSSIRSSSNYIYYADSVKGRFTISRDNAKSSLYLQMNSLRAEDTAVYYCARDGSSWYDYSDYWGQGTLVTVSS | 181. |
| VH 454 | EVQLVESGGGLVKPGGSLRLSCAASGFTFSTYNMNWVRQAPGKGLEWVSSIRSSSNYIYYADSVKGRFTISRDNAKNSLYLQMNSLRAEDTAVYYCARDGSSWYDYSDYWGQGTLVTVSS | 182. |
| VH 458 | EVQLVESGGGLVKPGGSLRLSCTASGFTFSTYNMNWVRQAPGKGLEWVSSIRSSSNYIYYADSVKGRFTISRDNAKNSLYLQMNSLRADDTAVYYCARDGSSWYDYSDYWGQGTLVTVSS | 183. |
| VH 474 | EVQLVESGGGLVKPGGSLRLSCTASGFTFSTYNMNWVRQAPGKGLEWVSSIRSSSNYIYYADSVKGRFTISRDNAKNSLYLQMNSLRADDTAVYYCARDGSSWYDYSDYWGQGTLVTVSS | 184. |
| VH 478 | EVQLVESGGGLVKPGGSLRLSCAASGFTFSTYNMNWVRQAPGKGLEWVSSIRSSSNYIYYADSVKGRFTISRDNAKNSLYLQMNSLRAEDTAVYYCARDGSSWYDYSDYWGQGTLVTVSS | 185. |
| VH 482 | EVQLVESGGGLVQPGGSLRLSCVVSGFTFGDYDMHWVRQATGRGLEWVSGIAPAGDTSYTGSVKGRFTISRENAKNSLHLQMNSLTTGDTAIYYCAREDIAVPGFDYWGQGTLVTVSS | 186. |

TABLE 1-continued

| Description | Sequence | SEQ ID NO |
|---|---|---|
| VH 498 | EVQLVESGGGLVQPGGSLRLSCVVSGFTFGDYDMHWVRQATGRGLEWVSGIAPAGDTSYTGSVKGRFTISRENA KNSLHLQMNSLTTGDTAIYYCAREDIAVPGFDYWGQGTLVTVSS | 187. |
| VH 502 | EVQLVESGGGLVQPGGSLRLSCAASGFTFGDYDMHWVRQATGKGLEWYSAIAPAGDTYYPGSVKGRFTISRENA KNSLYLQMNSLRAGDTAVYYCAREDIAVPGFDYWGQGTLVTVSS | 188. |
| VH 506 | QILLVQSGPEVKEPGASVKVSCKASGYTFTNYAISWVRQVPGQGLEWMGWVSAYNGHTNYAHEVQGRVTMTTDT STTTAYMELRSLRSDDTAMYYCARGGVVVPVAPHFYNGMDVWGQGTTVTVSS | 189. |
| VH 522 | QVQLVQSGPEVKEPGASVKVSCKASGYTFTNYAISWVRQVPGQGLEWMGWVSAYNGHTNYAHEVQGRVTMTTDT STTTAYMELRSLRSDDTAMYYCARGGVVVPVAPHFYNGMDVWGQGTTVTVSS | 190. |
| VH 526 | QVQLVQSGAEVKKPGASVKVSCKASGYTFTNYAISWVRQAPGQGLEWMGWVSAYNGHTNYAQKLQGRVTMTTDT STSTAYMELRSLRSDDTAVYYCARGGVVVPVAPHFYNGMDVWGQGTTVTVSS | 191. |
| VH 530 | EVQLVESGGGLVQPGGSLRLSCAASGFTLSSYDMHWVRQATGKGLEWVSAIGSTGDTYYTGSVMGRFTISRDAA KNSFYLEMNSLRVGDTAVYYCAREGIRTPYDYWGQGARVTVSS | 192. |
| VH 546 | EVQLVESGGGLVQPGGSLRLSCAASGFTLSSYDMHWVRQATGKGLEWVSAIGSTGDTYYTGSVMGRFTISRDAA KNSFYLEMNSLRVGDTAVYYCAREGIRTPYDYWGQGTLVTVSS | 193. |
| VH 550 | EVQLVESGGGLVQPGGSLRLSCAASGFTLSSYDMHWVRQATGKGLEWVSAIGSTGDTYYPGSVKGRFTISRENA KNSLYLQMNSLRAGDTAVYYCAREGIRTPYDYWGQGTLVTVSS | 194. |
| VH 554 | EVQLVESGGGLVQPGGSLRLSCAASGFTLSSYDMHWVRQATGKGLEWVSAIGSTGDTYYTGSVMGRFTISRDAA KNSFYLEMNSLRVGDTAVYYCAREGIRTPYDYWGQGARVTVSS | 195. |
| VH 570 | EVQLVESGGGLVQPGGSLRLSCAASGFTLSSYDMHWVRQATGKGLEWVSAIGSTGDTYYTGSVMGRFTISRDAA KNSFYLEMNSLRVGDTAVYYCAREGIRTPYDYWGQGTLVTVSS | 196. |
| VH 574 | EVQLVESGGGLVQPGGSLRLSCAASGFTLSSYDMHWVRQATGKGLEWVSAIGSTGDTYYPGSVKGRFTISRENA KNSLYLQMNSLRAGDTAVYYCAREGIRTPYDYWGQGTLVTVSS | 197. |
| VH 578 | EVQLVESGGGLVQPGRSLRLSCAASGFTFDDYAMHWVRQAPGKGLEWVSGINWNSGSIGYADSVKGRFTISRDN AKHSLYLQMNSLRPEDTALYYCVKEVTTGYYYGMDVWGQGTTVTVSS | 198. |
| VH 594 | EVQLVESGGGLVQPGRSLRLSCAASGFTFDDYAMHWVRQAPGKGLEWVSGINWNSGSIGYADSVKGRFTISRDN AKHSLYLQMNSLRPEDTALYYCVKEVTTGYYYGMDVWGQGTTVTVSS | 199. |
| VH 598 | EVQLVESGGGLVQPGRSLRLSCAASGFTFDDYAMHWVRQAPGKGLEWVSGINWNSGSIGYADSVKGRFTISRDN AKHSLYLQMNSLRPEDTALYYCVKEVTTGYYYGMDVWGQGTTVTVSS | 200. |
| VH 602 | EVQLLESGGGLVQPGGLSRLSCAASGFTFSSYAMNWVRQAPGKGLDWVSGISGNGGSTYYADSVKGRFTISRDI SKNTLYVQMHSLRVEDTAVYYCAKARYYDFWGGNFDLWGRTQVTVSS | 201. |
| VH 618 | EVQLLESGGGLVQPGGLSRLSCAASGFTFSSYAMNWVRQAPGKGLDWVSGISGNGGSTYYADSVKGRFTISRDI SKNTLYVQMHSLRVEDTAVYYCAKARYYDFWGGNFDLWGRGTQVTVSS | 202. |
| VH 622 | EVQLLESGGGLVQPGGSLRLSCAASGFTFSSYAMSWVRQAPGKGLEWVSAISGNGGSTYYADSVKGRFTISRDN SKNTLYLQMNSLRAEDTAVYYCAKARYYDFWGGNFDLWGRGTLVTVSS | 203. |
| VH 626 | QVQLVQSGPEVKNPGASVKVSCKASGYTFTTYGISWVRQAPGQGLEWMGWISGYNGKTNDAQKFQDRVAMTTDT STSTAYMELRSLRSDDTAIYYCSRDRLVVPPALYYSYYVMDVWGQGTTVTVSS | 204. |
| VH 642 | QVQLVQSGPEVKNPGASVKVSCKASGYTFTTYGISWVRQAPGQGLEWMGWISGYNGKTNDAQKFQDRVAMTTDT STSTAYMELRSLRSDDTAIYYCSRDRLVVPPALYYSYYVMDVWGQGTTVTVSS | 205. |
| VH 646 | QVQLVQSGAEVKKPGASVKVSCKASGYTFTTYGISWVRQAPGQGLEWMGWISGYNGKTNYAQKLQDRVTMTTDT STSTAYMELRSLRSDDTAVYYCSRDRLVVPPALYYSYYVMDVWGQGTTVTVSS | 206. |
| VH 650 | QVQLVQSGPEVKNPGASVKVSCKASGYTFTTYGISWVRQAPGQGLEWMGWISGYNGKTNDAQKFQDRVAMTTDT STSTAYMELRSLRSDDTAIYYCSRDRLVVPPALYYSYYVMDVWGQGTTVTVSS | 207. |
| VH 666 | QVQLVQSGPEVKNPGASVKVSCKASGYTFTTYGISWVRQAPGQGLEWMGWISGYNGKTNDAQKFQDRVAMTTDT STSTAYMELRSLRSDDTAIYYCSRDRLVVPPALYYSYYVMDVWGQGTTVTVSS | 208. |
| VH 670 | QVQLVQSGAEVKKPGASVKVSCKASGYTFTTYGISWVRQAPGQGLEWMGWISGYNGKTNYAQKLQGRVTMTTDT STSTAYMELRSLRSDDTAVYYCSRDRLVVPPALNYYYYVMDVWGQGTTVTVSS | 209. |
| VH 674 | QVQLVQSGPEVKNPGASVKVSCKASGYTFTTYGISWVRQAPGQGLEWMGWISGYNGKTNDAQKFQDRVAMTTDT STSTAYMELRSLRSDDTAIYYCSRDRLVVPPALYYYYYVMDVWGQGTTVTVSS | 210. |
| VH 690 | QVQLVQSGPEVKNPGASVKVSCKASGYTFTTYGTSWVRQAPGQGLEWMGWISGYNGKTNDAQKFQDRVAMTTDT STSTAYMELRSLRSDDTAIYYCSRDRLVVPPALYYYYYVMDVWGQGTTVTVSS | 211. |

TABLE 1-continued

| Description | Sequence | SEQ ID NO |
|---|---|---|
| VH 694 | QVQLVQSGAEVKKPGASVKVSCKASGYTFTTYGISWVRQAPGQGLEWMGWISGYNGKTNYAQKLQGRVTMTTDT STSTAYMELRSLRSDDTAVYYCSRDRLVVPPALYYYYYVMDVWGQGTTVTVSS | 212. |
| VH 698 | QVHLVESGGGLVKPGGSLRLSCAASGFTFSDHYMSWIRQAPGKGLEWISYISNDGGTKYYVDSVEGRFIISRDN AKNSLYLHMNSLRADDTAVYYCARDQGYIGYDSYYYYSYGMDVWGQGTTVTVAS | 213. |
| VH 714 | QVQLVESGGGLVKPGGSLRLSCAASGFTFSDHYMSWIRQAPGKGLEWISYISNDGGTKYYVDSVEGRFIISRDN AKNSLYLHMNSLRADDTAVYYCARDQGYIGYDSYYYYSYGMDVWGQGTTVTVSS | 214. |
| VH 718 | QVQLVESGGGLVKPGGSLRLSCAASGFTFSDHYMSWIRQAPGKGLEWVSYISNDGGTKYYADSVKGRFTISRDN AKNSLYLQMNSLRAEDTAVYYCARDQGYIGYDSYYYYSYGMDVWGQGTTVTVSS | 215. |
| VH 722 | QILLVQSGPEVKEPGASVKVSCKASGYTFTNYAISWVRQVPGQGLEWMGWVSAYNGHTNYAHEVQGRVTMTTDT STTTAYMELRSLRSDDTAMYYCARGGVVVPVAPHFYNGMDVWGQGTTVTVSS | 216. |
| VH 738 | QVQLVQSGPEVKEPGASVKVSCKASGYTFTNYAISWVRQVPGQGLEWMGWVSAYNGHTNYAHEVQGRVTMTTDT STTTAYMELRSLRSDDTAMYYCARGGVVVPVAPHFYNGMDVWGQGTTVTVSS | 217. |
| VH 742 | QVQLVQSGAEVKKPGASVKVSCKASGYTFTNYAISWVRQAPGQGLEWMGWVSAYNGHTNYAQKLQGRVTMTTDT STSTAYMELRSLRSDDTAVYYCARGGVVVPVAPHFYNGMDVWGQGTTVTVSS | 218. |
| VL 68 | DIVMTQSPDSLAVSLGERATINCKSSQSVFHTSNNKNYLVWYQQKPGQPPKLLLYMASTRESGVPDRFSGSGS GTDFTLTISSLQAEDVANYYCHQYYSIPWTFGQGTKVEIK | 219. |
| VL 92 H1H316P | DIVMTQSPDSLAVSLGERATINCKSSQSVLYRSNNRNFLGWYQQKPGQPPNLLIYWASTRESGVPDRFSGSGS GTDFTLTISSLQAEDVAVYYCQQYYTTPYTFGQGTKLEIK | 220. |
| VL 140 | DIQMTQSPSFLSASVGDRVTITCWASQDISSYLAWYQQKPGIAPKLLIYAASTLQSGVPSRFGGSGSGTEFTLT ISSLQPEDFATYYCQQLNSYPRTFGQGTKVEIK | 221. |
| VL 226 H1M300N | DIVMTQSPLSLPVTGEPASISCRSSQSLLHSNGNNYLDWYLQKPGQSPQLLIYLGSNRASGVPDRFSGSGSGT DFTLKISRVEAEDVGVYYCMQTLQTPLTFGGGTKVEIK | 222. |
| VL 10 | DIQMTQSPATLSVSPGERAALSCRASQSVSSNLAWYHQKPGQAPRLLIYGASTRATGIPARFSGIGSGTEFTLI ISSLQSEDFAFYFCQQYNNWPPFTFGPGTKVEIKR | 223. |
| VL 20 | EIVMTQSPATLSVSPGERAALSCRASQSVSSNLAWYHQKPGQAPRLLIYGASTRATGIPARFSGIGSGTEFTLI ISSLQSEDFAFYFCQQYNNWPPFTFGPGTKVDIK | 224. |
| VL 24 | EIVMTQSPATLSVSPGERATLSCRASQSVSSNLAWYHQKPGQAPRLLIYGASTRATGIPARFSGSGSGTEFTLI ISSLQSEDFAVYYCQQYNNWPPFTFGPGTKVDIK | 225. |
| VL 34 | AIQMTQSPSTLSASVGDRVTITCRASQSISSWLAWYQQKPGKAPKLLIYKASSLESGVPSRFSGSGSGTEFTLT ISSLQPDDFATYYCQQYNSYYTFGQGTKVEIKR | 226. |
| VL 44 | DIQMTQSPSTLSASVGDRVTITCRASQSISSWLAWYQQKPGKAPKLLIYKASSLESGVPSRFSGSGSGTEFTLT ISSLQPDDFATYYCQQYNSYYTFGQGTKLEIK | 227. |
| VL 48 | DIQMTQSPSTLSASVGDRVTITCRASQSISSWLAWYQQKPGKAPKLLIYKASSLESGVPSRFSGSGSGTEFTLT ISSLQPDDFATYYCQQYNSYYTFGQGTKLEIK | 228. |
| VL 58 | AIQMTQSPDSLAVSLGERATINCKSSQSVFHTSNNKNYLVWYQQKPGQPPKLLLYWASTRESGVPDRFSGSGS GTDFTLTISSLQAEDVANYYCHQYYSIPWTFGQGTKVEIKR | 229. |
| VL 72 | DIVMTQSPDSLAVSLGERATINCKSSQSVFHTSNNKNYLAWYQQKPGQPPKLLIYWASTRESGVPDRFSGSGS GTDFTLTISSLQAEDVAVYYCHQYYSIPWTFGQGTKVEIK | 230. |
| VL 82 | DIQMTQSPDSLAVSLGERATINCKSSQSVLYRSNNRNFLGWYQQKPGQPPNLLIYWASTRESGVPDRFSGSGS GTDFTLTISSLQAEDVAVYYCQQYYTTPYTFGQGTKVEIKR | 231. |
| VL 96 | DIVMTQSPDSLAVSLGERATINCKSSQSVLYRSNNRNFLAWYQQKPGQPPNLLIYWASTRESGVPDRFSGSGS GTDFTLTISSLQAEDVAVYYCQQYYTTPYTFGQGTKVEIK | 232. |
| VL 106 | AIQLTQSPSSLSASVGDRVTITCRASQDIRNDLGWYQQKPGKAPKLLIYAASSLQSGVPSRFSGSGSGTDFTLT ISSLQPEDFATYYCLQDYNYPWTFGQGTKVEIKR | 233. |
| VL 116 | AIQMTQSPSSLSASVGDRVTITCRASQDIRNDLGWYQQKPGKAPKLLIYAASSLQSGVPSRFSGSGSGTDFTLT TSSLQPEDFATYYCLQDYNYPWTFGQGTKVEIK | 234. |
| VL 120 | AIQMTQSPSSLSASVGDRVTITCRASQDIRNDLGWYQQKPGKAPKLLIYAASSLQSGVPSRFSGSGSGTDFTLT ISSLQPEDFATYYCLQDYNYPWTFGQGTKVEIK | 235. |
| VL 130 | DIQMTQSPSFLSASVGDRVTITCWASQDISSYLAWYQQKPGIAPKLLIYAASTLQSGVPSRFGGSGSGTEFTLT ISSLQPEDFATYYCQQLNSYPRTFGQGTKVEIKR | 236. |

TABLE 1-continued

| Description | Sequence | SEQ ID NO |
|---|---|---|
| VL 144 | DIQMTQSPSSLSASVGDRVTITCRASQDISSYLGWYQQKPGKAPKRLIYAASSLQSGVPSRFSGSGSGTEFTLT ISSLQPEDFATYYCQQLNSYPRTFGQGTKVEIK | 237. |
| VL 154 | AIQMTQSPLSLSVTLGQPASISCRSSQSLVYSDGDTYLNWFQQRPGQSPRRLIYKVSNRDSGVPDRFSGSGSGT AFTLKISGVEAEDVGVYYCMQATHWPRTFGQGTKVEIKR | 238. |
| VL 164 | DVVMTQSPLSLSVTLGQPASISCRSSQSLVYSDGDTYLNWFQQRPGQSPRRLIYKVSNRDSGVPDRFSGSGSGT AFTLKISGVEAEDVGVYYCMQATHWPRTFGQGTKVEIK | 239. |
| VL 168 | DVVMTQSPLSLPVTLGQPASISCRSSQSLVYSDGDTYLNWFQQRPGQSPRRLIYKVSNRDSGVPDRFSGSGSGT DFTLKISRVEAEDVGVYYCMQATHWPRTFGQGTKVEIK | 240. |
| VL 178 | DIQMTQSPLSLPVTPGEPASISCRSSQSLLHSHGYDYLDWYLQKPGQSPQLLIYLGSNRASGVPDRFSGSGSGT DFTLKISRVEAEDVGVYYCMQALQTPLTFGGGTKVEIKR | 241. |
| VL 188 | DIVMTQSPLSLPVTPGEPASISCRSSQSLLHSHGYDYLDWYLQKPGQSPQLLIYLGSNRASGVPDRFSGSGSGT DFTLKISRVEAEDVGVYYCMQALQTPLTFGGGTKVEIK | 242. |
| VL 192 | DIVMTQSPLSLPVTPGEPASISCRSSQSLLHSHGYDYLDWYLQKPGQSPQLLIYLGSNRASGVPDRFSGSGSGT DFTLKISRVEAEDVGVYYCMQALQTPLTFGGGTKVKIK | 243. |
| VL 202 | DIQMTQSPLSLPVTPGEPASISCRSSQSLLHSHGYNYLDWYLQKPGQSPQLLIYLGSNRASGVPDRFSGGGSGT DFTLKISRVEAEDVGIYYCMQALQTPLTFGGGTKVKIKR | 244. |
| VL 212 | DIVMTQSPLSLPVTPGEPASISCRSSQSLLHSHGYDYLDWYLQKPGQSPQLLIYLGSNRASGVPDRFSGSGSGT DFTLKISRVEAEDVGIYYCMQALQTPLTFGGGTKVKIK | 245. |
| VL 216 | DIVMTQSPLSLPVTPGEPASISCRSSQSLLHSHGYNYLDWYLQKPGQSPQLLIYLGSNRASGVPDRFSGSGSGT DFTLKISRVEAEDVGVYYCMQALQTPLTFGGGTKVKIK | 246. |
| VL 236 | DIVMTQSPLSLPVTPGEPASISCRSSQSLLHSNGNNYLDWYLQKPGQSPQLLIYLGSNRASGVPDRFSGSGSGT DFTLKISRVEAEDVGVYYCMQTLQTPLTFGGGTKVEIK | 247. |
| VL 2-10 | DIVMTQSPLSLPVTPGEPASISCRSSQSLLHSNGNNYLDWYLQKPGQSPQLLIYLGSNRASGVPDRFSGSGSGT DFTLKISRVEAEDVGVYYCMQTLQTPLTFGGGTKVEIK | 248. |
| VL 250 | DIVMTQSPLSLPVTPGEPASISCRSSQSLLHSNGYNYLDWYLQKPGQSPQLLIYLGFNRASGVPDRFSGSGSGT DFTLKISRVEAEDVGVYYCMQALQTPLTFGGGTKVEIR | 249. |
| VL 260 | DIVMTQSPLSLPVTPGEPASISCRSSQSLLHSNGYNYLDWYLQKPGQSPQLLIYLGFNRASGVPDRFSGSGSGT DFTLKISRVEAEDVGVYYCMQALQTPLTFGGGTKVEIK | 250. |
| VL 264 | DIVMTQSPLSLPVTPGEPASISCRSSQSLLHSNGYNYLDWYLQKPGQSPQLLIYLGFNRASGVPDRFSGSGSGT DFTLKISRVEAEDVGVYYCMQALQTPLTFGGGTKVEIK | 251. |
| VL 274 | DIVMTQSPLSLPVTPGEPASISCRSSQSLLHSNGYNYLDWYLQKPGQSPQLLIYLGFNRASGVPDRFSGSGSGT DFTLKISRVEAEDVGVYYCMQALQTPLTFGGGTKVEIR | 252. |
| VL 284 | DIVMTQSPLSLPVTPGEPASISCRSSQSLLHSNGYNYLDWYLQKPGQSPQLLIYLGFNRASGVPDRFSGSGSGT DFTLKISRVEAEDVGVYYCMQALQTPLTFGGGTKVEIK | 253. |
| VL 288 | DIVMTQSPLSLPVTPGEPASISCRSSQSLLHSNGYNYLDWYLQKPGQSPQLLIYLGFNRASGVPDRFSGSGSGT DFTLKISRVEAEDVGVYYCMQALQTPLTFGGGTKVEIK | 254. |
| VL 298 | DIVMTQSPLSLPVTPGEPASISCRSSQTLLHSNGYNYFDWYLQKPGQSPQLLIYLGSNRASGVPDRFSGSGSGT DFTLKISRVEAEDVGIYYCMQALQTPLTFGGGTKVEIR | 255. |
| VL 308 | DIVMTQSPLSLPVTPGEPASISCRSSQTLLHSHGYNYFDWYLQKPGQSPQLLIYLGSNRASGVPDRFSGSGSGT DFTLKISRVEAEDVGIYYCMQALQTPLTFGGGTKVEIK | 256. |
| VL 312 | DIVMTQSPLSLPVTPGEPASISCRSSQTLLHSNGYNYLDWYLQKPGQSPQLLIYLGSNRASGVPDRFSGSGSGT DFTLKISRVEAEDVGVYYCMQALQTPLTFGGGTKVEIK | 257. |
| VL 322 | DVVMTQSPLSLPVTLGQPASISCRSSQSLVYSDGNTYLNWSQQRPGQSPRRLIYKVSNRDSGVPDRFSGSGSGT DFTLKISRVEAEDVGVYYCMQGTHWPYTFGQGTKLEIK | 258. |
| VL 332 | DVVMTQSPLSLPVTLGQPASISCRSSQSLVYSDGNTYLNWSQQRPGQSPRRLIYKVSNRDSGVPDRFSGSGSGT DFTLKISRVEAEDVGVYYCMQGTHWPYTFGQGTKLEIK | 259. |
| VL 336 | DVVMTQSPLSLPVTLGQPASISCRSSQSLVYSDGNTYLHWFQQRPGQSPRRLIYKVSNRDSGVPDRFSGSGSGT DFTLKISRVEAEDVGVYYCMQGTHWPYTFGQGTKLEIK | 260. |
| VL 346 | DIQMTQSPSTLSASVGDRVTITCRASQSISSWLAWYQQRPGKAPKLLIYKASSLEGGVPSRFSGSGSGTEFTLT ISSLQPEDFATYYCQQYNSYWYTFGQGTKLEIK | 261. |

TABLE 1-continued

| Description | Sequence | SEQ ID NO |
|---|---|---|
| VL 356 | DIQMTQSPSTLSASVGDRVTITCRASQSISSWLAWYQQRPGKAPKLLIYKASSLEGGVPSRFSGSGSGTEFTLT ISSLQPEDFATYYCQQYNSYWYTFGQGTKLEIK | 262. |
| VL 360 | DIQMTQSPSTLSASVGDRVTITCRASQSISSWLAWYQQKPGKAPKLLIYKASSLESGVPSRFSGSGSGTEFTLT ISSLQPDDFATYYCQQYNSYWYTFGQGTKLEIK | 263. |
| VL 370 | KIVLTQSPGTLPLFPGERATLSCRASQSVNNKFLAWYQQKSGQAPRLLIYGASSRATGIPDRFSGSGSGTDFTL TISGLEPEDFEVYYCQVYGNSLTLGGGTKVEIK | 264. |
| VL 380 | EIVLTQSPGTLPLFPGERATLSCRASQSVNNKFLAWYQQKSGQAPRLLIYGASSRATGIPDRFSGSGSGTDFTL TISGLEPEDFEVYYCQVYGNSLTLGGGTKVEIK | 265. |
| VL 384 | EIVLTQSPGTLSLSPGERATLSCRASQSVNNKFLAWYQQKPGQAPRLLIYGASSRATGIPDRFSGSGSGTDFTL TISRLEPEDFAVYYCQVYGNSLTFGGGTKVEIK | 266. |
| VL 394 | DIQMTQSPSTLSASVGDRVTITCRASQSISSWLAWYQQIPGKAPKLLIYKASSLENGVPSRFSGSGSGTEFTLI ISSLQPDDFATYYCQQYISYSRTFGQGTKVEIK | 267. |
| VL 404 | DIQMTQSPSTLSASVGDRVTITCRASQSISSWLAWYQQIPGKAPKLLIYKASSLENGVPSRFSGSGSGTEFTLI ISSLQPDDFATYYCQQYISYSRTFGQGTKVEIK | 268. |
| VL 408 | DIQMTQSPSTLSASVGDRVTITCRASQSISSWLAWYQQKPGKAPKLLIYKASSLESGVPSRFSGSGSGTEFTLT ISSLQPDDFATYYCQQYISYSRTFGQGTKVEIK | 269. |
| VL 418 | DIQMTQSPSTLSASVGDRVTITCRASQSISSWLAWYQQIPGKAPKLLIYKASSLENGVPSRFSGSGSGTEFTLI ISSLQPDDFATYYCQQYISYSRTFGQGTKVEIK | 270. |
| VL 428 | DIQMTQSPSTLSASVGDRVTITCRASQSISSWLAWYQQIPGKAPKLLIYKASSLENGVPSRFSGSGSGTEFTLI ISSLQPDDFATYYCQQYISYSRTFGQGTKVEIK | 271. |
| VL 432 | DIQMTQSPSTLSASVGDRVTITCRASQSISSWLAWYQQKPGKAPKLLIYKASSLESGVPSRFSGSGSGTEFTLT ISSLQPDDFATYYCQQYISYSRTFGQGTKVEIK | 272. |
| VL 442 | DIQMTQSPSTLSASVGDRVTITCRASQSISSWLAWYQQVPGKAPKLLIYKASSLENGVPSRFSGSGSGTEFTLI ISSLQPDDFATYYCQQYISYSRTFGQGTKVEIK | 273. |
| VL 452 | DIQMTQSPSTLSASVGDRVTITCRASQSISSWLAWYQQVPGKAPKLLIYKASSLENGVPSRFSGSGSGTEFTLI ISSLQPDDFATYYCQQYISYSRTFGQGTKVEIK | 274. |
| VL 456 | DIQMTQSPSTLSASVGDRVTITCRASQSISSWLAWYQQKPGKAPKLLIYKASSLESGVPSRFSGSGSGTEFTLI ISSLQPDDFATYYCQQYISYSRTFGQGTKVEIK | 275. |
| VL 466 | DIQMTQSPSTLSASVGDRVTITCRASQSISSWLAWYQQIPGKAPKLLIYKASSLENGVPSRFSGSGSGTEFTLI ISSLQPDDFATYYCQQYISYSRTFGQGTKVEIK | 276. |
| VL 476 | DIQMTQSPSTLSASVGDRVTITCRASQSISSWLAWYQQIPGKAPKLLIYKASSLENGVPSRFSGSGSGTEFTLI ISSLQPDDFATYYCQQYISYSRTFGQGTKVEIK | 277. |
| VL 480 | DIQMTQSPSTLSASVGDRVTITCRASQSISSWLAWYQQKPGKAPKLLIYKASSLESGVPSRFSGSGSGTEFTLT ISSLQPDDFATYYCQQYISYSRTFGQGTKVEIK | 278. |
| VL 490 | EIVMTQSPATLSVSPGERGTLSCRASQSVSSNLAWYQQKPGQAPRLLIYGASTRATGFPARFSGSGSGTEFTLT ISSLQSEDFAVYYCQQYNKWPPFTFGPGTKVDFK | 279. |
| VL 500 | EIVMTQSPATLSVSPGERGTLSCRASQSVSSNLAWYQQKPGQAPRLLIYGASTRATGFPARFSGSGSGTEFTLT ISSLQSEDFAVYYCQQYNKWPPFTFGPGTKVDIK | 280. |
| VL 504 | EIVMTQSPATLSVSPGERATLSCRASQSVSSNLAWYQQKPGQAPRLLIYGASTRATGIPARFSGSGSGTEFTLT ISSLQSEDFAVYYCQQYNKWPPFTFGPGTKVDIK | 281. |
| VL 514 | DIVMTQFPLSLPVTPGEPASISCRSSQSLLHINEYNYLDWYLKKPGOSPOLLIYLGFNRASGVPDRFSGSGSGT DFTLKISRVEAEDVGVYYCMQALQTPWTLGQGTKVEIK | 282. |
| VL 524 | DIVMTQSPLSLPVTPGEPASISCRSSQSLLHINEYNYLDWYLKKPGQSPQLLIYLGFNRASGVPDRFSGSGSGT DFTLKISRVEAEDVGVYYCMQALQTPWTLGQGTKVEIK | 283. |
| VL 528 | DIVMTQSPLSLPVTPGEPASISCRSSQSLLHINEYNYLDWYLQKPGQSPQLLIYLGSNRASGVPDRFSGSGSGT DFTLKISRVEAEDVGVYYCMQALQTPWTFGQGTKVEIK | 284. |
| VL 538 | EIVMTQSPATLSVSPGERATLSCRASQSVSSNVAWYQQKPGQAPRLLIYGASTRATGIPARFSGSGSGTEFTLT ISSLQSEDFAVYYCQQYNNWPPFTFGPGTKVDIK | 285. |
| VL 548 | EIVMTQSPATLSVSPGERATLSCRASQSVSSNVAWYQQKPGQAPRLLIYGASTRATGIPARFSGSGSGTEFTLT ISSLQSEDFAVYYCQQYNNWPPFTFGPGTKVDIK | 286. |

TABLE 1-continued

| Description | Sequence | SEQ ID NO |
|---|---|---|
| VL 552 | EIVMTQSPATLSVSPGERATLSCRASQSVSSNLAWYQQKPGQAPRLLIYGASTRATGIPARFSGSGSGTEFTLTISSLQSEDFAVYYCQQYNNWPPFTFGPGTKVDIK | 287. |
| VL 562 | EIVMTQSPATLSVSPGERATLSCRASQSVSSNVAWYQQKPGQAPRLLIYGASTRATGIPARFSGSGSGTEFTLTISSLQSEDFAVYYCQQYNNWPPFTFGPGTKVDIK | 288. |
| VL 572 | EIVMTQSPATLSVSPGERATLSCRASQSVSSNVAWYQQKPGQAPRLLIYGASTRATGIPARFSGSGSGTEFTLTISSLQSEDFAVYYCQQYNNWPPFTFGPGTKVDIK | 289. |
| VL 576 | EIVMTQSPATLSVSPGERATLSCHAYQSVSSNLAWYQQKPGQAPRLLIYGASTRATGIPARFSGSGSGTEFTLTISSLQSEDFAVYYCQQYNNWPPFTFGPGTKVDIK | 290. |
| VL 586 | DIQLTQSPSFLSASVGDRVTITCWASQGISSYLAWYQKKPGKAPNLLIYDASTLQSGVPSRFSGSGSGTEFTLTLSSLQPEDFATYYCQQLNIYPFTFGPGTKVDIK | 291. |
| VL 596 | DIQLTQSPSFLSASVGDRVTITCWASQGISSYLAWYQKKPGKAPNLLIYDASTLQSGVPSRFSGSGSGTEFTLTLSSLQPEDFATYYCQQLNIYPFTFGPGTKVDIK | 292. |
| VL 600 | DIQLTQSPSFLSASVGDRVTITCRASQGISSYLAWYQKKPGKAPKLLIYDASTLQSGVPSRFSGSGSGTEFTLTISSLQPEDFATYYCQQLNIYPFTFGPGTKVDIK | 293. |
| VL 610 | EIVLTQSPGTLSLSPGERATLSCRASQSVSIRYLAWYQQKPGQAPRLLIYGASSRATGIPDRFSVSVSGTDFTLTITRLEPEDFAVYYCQQYGSSPLTFGGGTKVEIK | 294. |
| VL 620 | EIVLTQSPGTLSLSPGERATLSCRASQSVSIRYLAWYQQKPGQAPRLLIYGASSRATGIPDRFSVSVSGTDFTLTITRLEPEDFAVYYCQQYGSSPLTFGGGTKVEIK | 295. |
| VL 624 | EIVLTQSPGTLSLSPGERATLSCRASQSVSIRYLAWYQQKPGQAPRLLIYGASSRATGIPDRFSGSGSGTDFTLTISRLEPEDFAVYYCQQYGSSPLTFGGGTKVEIK | 296. |
| VL 634 | DVVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWPYTFGQGTKLEIK | 297. |
| VL 644 | DVVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWPYTFGQGTKLEIK | 298. |
| VL 648 | DVVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWPYTFGQGTKLEIK | 299. |
| VL 658 | DVVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWPYTFGQGTKLEIK | 300. |
| VL 668 | DVVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWPYTFGQGTKLEIK | 301. |
| VL 672 | DVVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWPYTFGQGTKLEIK | 302. |
| VL 682 | DVVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWPYTFGQGTKLEIK | 303. |
| VL 692 | DVVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWPYTFGQGTKLEIK | 304. |
| VL 696 | DVVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWPYTFGQGTKLEIK | 305. |
| VL 706 | KIVLTQSPGTLPLFPGERATLSCRASQSVNNKFLAWYQQKSGQAPRLLIYGASSRATGIPDRFSGSGSGTDFTLTISGLEPEDFEVYYCQVYGNSLTFGGGTKVEIK | 306. |
| VL 716 | EIVLTQSPGTLPLFPGERATLSCRASQSVNNKFLAWYQQKSGQAPRLLIYOQVYGNSLTFGGGTKVEIK TISGLEPEDFEVYY | 307. |
| VL 720 | EIVLTQSPGTLSLSPGERATLSCRASQSVNNKFLAWYQQKPGQAPRLLIYGASSRATGIPDRFSGSGSGTDFTLTISRLEPEDFAVYYCQVYGNSLTFGGGTKVEIK | 308. |
| VL 730 | DIVMTQFPLSLPVTPGEPASISCRSSQSLLHINEYNYLDWYLKKPGQSPQLLIYLGFNRASGVPDRFSGSGSGTDFTLKISRVEAEDVGVYYCMQALQTPWTFGQGTKVEIK | 309. |
| VL 740 | DIVMTQSPLSLPVTPGEPASISCRSSQSLLHINEYNYLDWYLKKPGQSPQLLIYLGFNRASGVPDRFSGSGSGTDFTLKISRVEAEDVGVYYCMQALQTPWTFGQGTKVEIK | 310. |
| VL 744 | DIVMTQSPLSLPVTPGEPASISCRSSQSLLHINEYNYLDWYLQKPGQSPQLLIYLGSNRASGVPDRFSGSGSGTDFTLKISRVEAEDVGVYYCMQALQTPWTFGQGTKVEIK | 311. |

TABLE 1-continued

| Description | Sequence | SEQ ID NO |
|---|---|---|
| GROUP E | | |
| VH 508.20 | EVQLVESGGGLVQPGGSLRLSCAASGFTFTGYAIHWVRQAPGKGLEWVGRISPANGNTNYADSVKGRFTISADT SKNTAYLQMNSLRAEDTAVYYCARWIGSRELYIMDYWGQGTLVTVSS | 312. |
| VH 508.04 | EVQLVESGGGLVQPGGSLRLSCAASGFTFTGYAIHWVRQAPGKGLEWVGRISPAHGNTNYADSVKGRFTISADT SKNTAYLQMNSLRAEDTAVYYCARWIGSRELYIMDYWGQGTLVTVSS | 313. |
| VH 508.06 | EVQLVESGGGLVQPGGSLRLSCAASGFTFTGYAIHWVRQAPGKGLEWVGRISPANGNTNYADSVKGRFTISADT SKNTAYLQMNSLRAEDTAVYYCARWIGSRELYIMDYWGQGTLVTVSS | 314. |
| VH 508.28 | EVQLVESGGGLVQPGGSLRLSCAASGFTFTRHTIHWVRQAPGKGLEWVGRISPANGNTNYADSVKGRFTISADT SKNTAYLQMNSLRAEDTAVYYCARWIGSRELYIMDYKGQGTLVTVSS | 315. |
| VH 508.33 | EVQLVESGGGLVQPGGSLRLSCAASGFTFSSTAIHWVRQAPGKGLEWVGRISPANGNTNYADSVKGRFTISADT SKNTAYLQMNSLRAEDTAVYYCARWIGSRELYIMDYWGQGTLVTVSS | 316. |
| VH 508.84 | EVQLVESGGGLVQPGGSLRLSCAASGFTFTGYAIHWVRQAPGKGLEWVGRISPANGNTNYADSVKGRFTISADT SKNTAYLQMNSLRAEDTAVYYCARWIGSRELYIMDYWGQGTLVTVSS | 317. |
| VL 508.20 | DIQMTQSPSSLSASVGDRVTITCRASQDVSSAVAWYQQKPGKAPKLLIYSASSLYSGVPSRFSGSRSGTDFTLT ISSLQPEDFATYYCQQSYTTPPTFGQGTKVEIKR | 318. |
| VL 508.04 | DIQMTQSPSSLSASVGDRVTITCRASQDVSSAVAWYQQKPGKAPKLLIYSASSLYSGVPSRFSGSRSGTDFTLT ISSLQPEDFATYYCQQSYPAPATFGQGTKVEIKR | 319. |
| VL 508.06 | DIQMTQSPSSLSASVGDRVTITCRASQDVSSAVAWYQQKPGKAPKLLIYSASSLYSGVPSRFSGSRSGTDFTLT ISSLQPEDFATYYCQQSYPSPATFGQGTKVEIKR | 320. |
| VL 508.28 | DIQMTQSPSSLSASVGDRVTITCRASQDVSSAVAWYQQKPGKAPKLLIYSASSLYSGVPSRFSGSRSGTDFTLT ISSLQPEDFATYYCQQSYRIQPTFGQGTKVEIKR | 321. |
| VL 508.33 | DIQMTQSPSSLSASVGDRVTITCRASQDVSSAVAWYQQKPGKAPKLLIYSASSLYSGVPSRFSGSRSGTDFTLT ISSLQPEDFATYYCQQSYRIQPTFGQGTKVEIKR | 322. |
| VL 508.84 | DIQMTQSPSSLSASVGDRVTITCRASQDVSSAVAWYQQKPGKAPKLLIYSASSLYSGVPSRFSGSRSGTDFTLT ISSLQPEDFATYYCQQSYPAPSTFGQGTKVEIKR | 323. |
| GROUP F | | |
| VH | EVQLVESGGGLVKPGGSLRLSCAASGFPFSKLGMVWVRQAPGKGLEWVSTISSGGGYTYYPDSVKGRFTISRDN AKNSLYLQMNSLRAEDTAVYYCAREGISFQGGTYTYVMDYWGQGTLVTVSS | 324. |
| VL | DIVMTQSPLSLPVTPGEPASISCRSSKSLLHRNGITYSYWYLQKPGQSPQLLIYQLSNLASGVPDRFSGSGSGT DFTLKISRVEAEDVGVYYCYQNLELPLTFGQGTKVEIK | 325. |
| GROUP G | | |
| VH IB20 | QVQLVQSGAEVKKPGESLKISCKGSGYSFTNYWISWVRQMPGKGLEWMGIIYPGDSYTNYSPSFQGQVTISADK SISTAYLQWSSLKASDTAMYYCARDYWYKPLFDIWGQGTLVTVSS | 326. |
| VL IB20 | DIVMTQSPDSLAVSLGERATINCRSSQSVLYSSNNKNYLAWYQQKPGQPPKLLIYWASTRESGVPDRFSGSGSG TDFTLTISSLQAEDVAVYYCQQYSSFPITFGQGTKVEIKR | 327. |
| IB20 Variant HC CDR1 | GYSFTX$_1$YX$_2$IX$_3$<br>X$_1$ = N or D<br>X$_2$ = W or Y | 328. |
| IB20 Variant HC CDR2 | WMGX$_1$IYPGDSX$_2$TX$_3$YX$_4$X$_5$X$_6$FQG<br>X$_1$ = I, R, W, L, or M<br>X$_2$ = Y or D<br>X$_3$ = N, R, H, S, K, Q<br>X$_4$ = S or N<br>X$_5$ = P, Q, H<br>X$_6$ = S, K, N, or R | 329. |
| IB20 Variant HC CDR3 | DX$_1$X$_2$X$_3$X$_4$X$_5$X$_6$X$_7$DX$_8$<br>X$_1$ = Y, R, or H<br>X$_2$ = W, Y, G, A, or F<br>X$_3$ = Y or S<br>X$_4$ = K, R, T, G, S, D, E, H, or N<br>X$_5$ = P, S, G, D, A, H, or Y<br>X$_6$ = L, Y, F, A, D, H, P, or S<br>X$_7$ = F or S<br>X$_8$ = I, V, Y, F, or N | 330. |

TABLE 1-continued

| Description | Sequence | SEQ ID NO |
|---|---|---|
| IB30 Variant VH CDR2 | WMGX$_1$IYPGDSYTX$_2$YSX$_3$SFQG<br>X$_1$ = I or R<br>X$_2$ = N, R, H, or S<br>X$_3$ = P or Q | 331. |
| IB30 Variant VH CDR3 | DYWYX$_1$X$_2$X$_3$FDX$_4$<br>X$_1$ = K, G, R, S, D, E, H,N, or Q<br>X$_2$ = P, G, D, S, A, H, R, or Y<br>X$_3$ = L, A, Y, D, F, H, P, S, or V<br>X$_4$ = I, Y, F, or N | 332. |
| IB20 Variant LC CDR1 | X$_1$ Ser Ser Gln Ser Val X$_2$ X$_3$ Ser X$_4$ X$_5$ X$_6$ Lys Asn X$_7$ Leu X$_8$<br>X$_1$ = Arg, Lys, His, Asn, Gln or Ser<br>X$_2$ = Leu or Phe<br>X$_3$ = Tyr or His<br>X$_4$ = Ser, Arg or Gly<br>X$_5$ = Asn or Thr<br>X$_6$ = Asn, Arg, His or Ser<br>X$_7$ = Tyr or Phe<br>X$_5$ = Ala or Thr | 333. |
| IB20 Variant LC CDR2 | LLIYX$_1$X$_2$SX$_3$RX$_4$X$_5$<br>X$_1$ = Trp, Phe or Leu<br>X$_2$ = Ala or Thr<br>X$_3$ = Thr, Ile, Ala or val<br>X$_4$ = Glu, Ala or Lys<br>X$_5$ = Ser or Thr | 334. |
| IB20 Variant LC CDR3 | QQYX$_1$X$_2$X$_3$PX$_4$<br>X$_1$ = Ser or Tyr<br>X$_2$ = Ser or Thr<br>X$_3$ = Phe, Tyr, Leu, Thr, His, Ile, Asn, Pro or Ser<br>X$_4$ = Ile, Arg, Val, Tyr, Asp, Phe, Gly, His, Leu, Asn or Ser | 335. |
| 1B20 Antibody Variant VL CDR1 Sequence | RSSQSVLYSSNNKNX$_1$LX$_2$<br>X$_1$ = Tyr or Phe<br>X$_2$ = Ala or Thr | 336. |
| 1B20 Antibody Variant VL CDR2 Sequence | LLIYX$_1$ASTRX$_2$X$_3$<br>X$_1$ = Trp, Phe or Leu<br>X$_2$ = Glu or Lys<br>X$_3$ = Ser or Thr | 337. |
| 1B20 Antibody Variant VL CDR3 Sequence | QQYSSX$_1$PX$_2$<br>X$_1$ = Phe, Tyr, Thr, Ile, Asn or Ser<br>X$_2$ = Ile, Tyr, Arg, Phe, His, Leu, Asn or Ser | 338. |
| VH; 1B20 VARIANT SEQUENCE | QVQLVQSGAEVKKPGESLKISCKGSGYSFTX$_1$YX$_2$IX$_3$WVRQMPGKGLEWMGX$_4$IYPGDSX$_5$TX$_6$YX$_7$X$_8$X$_9$F QGQVTISADKSISTAYLQWSSLKASDTAMYYCARDX$_{10}$X$_{11}$X$_{12}$X$_{13}$X$_{14}$X$_{15}$X$_{16}$DX$_{17}$WGQGTLVTVSS<br>X$_1$ = Asn or Asp<br>X$_2$ = Trp or Tyr<br>X$_3$ = Ser, Thr or Ala<br>X$_4$ = Ile, Arg, Trp, Leu or Met<br>X$_5$ = Tyr or Asp<br>X$_6$ = Asn, Arg, His, Ser, Lys or Gln<br>X$_7$ = Ser or Asn<br>X$_8$ = Pro, Gln or His<br>X$_9$ = Ser, Lys, Asn or Arg<br>X$_{10}$ = Tyr, Arg or His<br>X$_{11}$ = Trp, Tyr or Gly<br>X$_{12}$ = Tyr or Ser<br>X$_{13}$ = Lys, Arg, Thr, Gly, Ser, Asp, Glu, His, Asn or Gln<br>X$_{14}$ = Pro, Ser, Gly, Asp, Ala, His, Arg or Tyr<br>X$_{15}$ = Leu, Tyr, Phe, Ala, Asp, His, Pro, Ser or Val<br>X$_{15}$ = Phe or Ser<br>X$_{17}$ = Ile, Val, Tyr, Phe or Asn | 339. |
| VH; 1B20 VARIANT SEQUENCE | QVQLVQSGAEVKKPGESLKISCKGSGYSFTX$_1$YX$_2$IX$_3$WVRQMPGKGLEWMGX$_4$IYPGDSYTX$_5$YSX$_6$SFQGQ VTISADKSISTAYLQWSSLKASDTAMYYCARDWYWX$_7$X$_8$X$_9$FDX$_{10}$WGQGTLVTVSS<br>X$_1$ = Asn or Asp<br>X$_2$ = Trp or Tyr<br>X$_3$ = Ser, Thr or Ala<br>X$_4$ = Ile or Arg<br>X$_5$ = Asn, Arg, His, Ser, Lys or Gln<br>X$_6$ = Pro or Gln<br>X$_7$ = Lys, Gly, Arg, Ser, Asp, Glu, His, Asn or Gln | 340. |

TABLE 1-continued

| Description | Sequence | SEQ ID NO |
|---|---|---|
| | $X_8$ = Pro, Gly, Asp, Ser, Ala, His, Arg or Tyr<br>$X_9$ = Leu, Ala, Tyr, Asp, Phe, His, Pro, Ser or Val<br>$X_{10}$ = Ile, Tyr, Phe or Asn | |
| VL; 1B20 Variant Sequence | DIVMTQSPDSLAVSLGERATINCX$_1$SSQSVX$_2$X$_3$SX$_4$X$_5$X$_6$KNX$_7$LX$_8$WYQQKPGQPPKLLIYX$_9$X$_{10}$SX$_{11}$RX$_{12}$X$_{13}$GVPDRFSGSGSGTDFTLTISSLQAEDVAVYYCQQYX$_{14}$X$_{15}$X$_{16}$PX$_{17}$TFGQGTKVEIKR<br>$X_1$ = Arg, Lys, His, Asn, Gln or Ser<br>$X_2$ = Leu or Phe<br>$X_3$ = Tyr or His<br>$X_4$ = Ser, Arg or Gly<br>$X_5$ = Asn or Thr<br>$X_6$ = Asn, Arg, His or Ser<br>$X_7$ = Tyr or Phe<br>$X_8$ = Ala or Thr<br>$X_9$ = Trp, Phe or Leu<br>$X_{10}$ = Ala or Thr<br>$X_{11}$ = Thr, Ile, Ala or Val<br>$X_{12}$ = Glu, Ala or Lys<br>$X_{13}$ = Ser or Thr<br>$X_{14}$ = Ser or Tyr<br>$X_{15}$ = Ser or Thr<br>$X_{16}$ = Phe, Tyr, Leu, Thr, His, Ile, Asn, Pro or Ser<br>$X_{17}$ = Ile, Arg, Val, Tyr, Asp, Phe, Gly, His, Leu, Asn or Ser | 341. |
| VL; 1B20 VARIANT SEQUENCE | DIVMTQSPDSLAVSLGERATINCRSSQSVLYSSNNKNX$_1$LX$_2$WYQQKPGQPPKLLIYX$_3$ASTRX$_4$X$_5$GVPDRFSGSGSGTDFTLTISSLQAEDVAVYYCQQYSSX$_6$PX$_7$TFGQGTKVEIKR<br>$X_1$ = Y or F<br>$X_2$ = A or T<br>$X_3$ = W, F, or L<br>$X_4$ = E or K<br>$X_5$ = S or T<br>$X_6$ = F, Y, T, I, N, or S<br>$X_7$ = I, Y, R, F, H, L, N, or S | 342. |
| VH; 1B20 Variant Sequence F120 | QVQLVQSGAEVKKPGESLKISCKGSGYSFTNYYISWVRQMPGKGLEWMGLIYPGDSYTRYNPSFQGQVTISADKSISTAYLQWSSLKASDTAMYYCARDYYSRPFSDIWGQGTLVTVSS | 343. |
| VH; 1B20 Variant Sequence F116 | QVQLVQSGAEVKKPGESLKISCKGSGYSFTNYYISWVRQMPGKGLEWMGLIYPGDSYTRYNPKFQGQVTISADKSISTAYLQWSSLKASDTAMYYCARDYYSRPYSDVWGQGTLVTVSS | 344. |
| VH; 1B20 Variant Sequence F119 | QVQLVQSGAEVKKPGESLKTSCKGSGYSFTDYYISWVRQMPGKGLEWMGLIYPGDSYTRYSPNFQGQVTISADKSISTAYLQWSSLKASDTAMYYCARDHGYRPYSDIWGQGTLVTVSS | 345. |
| VH; 1B20 Variant Sequence F113 | QVQLVQSGAEVKKPGESLKISCKGSGYSFTNYYISWVRQMPGKGLEWMGLIYPGDSYTNYNPNFQGQVTISADKSISTAYLQWSSLKASDTAMYYCARDHYSTPFFDVWGQGTLVTVSS | 346. |
| VH; 1B20 Variant Sequence E2 | QVQLVQSGAEVKKPGESLKISCKGSGYSFTNYYISWVRQMPGKGLEWMGLIYPGDSYTRYNRKFQGQVTISADKSISTAYLQWSSLKASDTAMYYCARDYYSRPLSDVWGQGTLVTVSS | 347. |
| VH; 1B20 Variant Sequence G4 | QVQLVQSGAEVKKPGESLKISCKGSGYSFTNYYISWVRQMPGKGLEWMGLIYPGDSYTRYSPRFQGQVTISADKSISTAYLQWSSLKASDTAMYYCARDHGYKPYSDIWGQGTLVTVSS | 348. |
| VH; 1B20 Variant Sequence F4 | QVQLVQSGAEVKKPGESLKISCKGSGYSFTDYYISWVRQMPGKGLEWMGLIYPGDSYTRYSPSFQGQVTISADKSISTAYLQWSSLKASDTAMYYCARDYYSKPLFDVWGQGTLVTVSS | 349. |
| VH; 1B20 Variant Sequence B9 | QVQLVQSGAEVKKPGESLKISCKGSGYSFTNYYISWVRQMPGKGLEWMGIIYPGDSYIHYNQNFQGQVTISADKSISTAYLQWSSLKASDTAMYYCARDYYSRPFSDIWGQGTLVTVSS | 350. |
| VH; 1B20 Variant Sequence C3 | QVKLVQSGAEVKKPGESLKISCKGSGYSFTNYYIAWVRQMPGKGLEWMGIIYPGDSYTHYNPKFQGQVTISADKSISTAYLQWSSLKASDTAMYYCARDHGYKPFSDIWGQGTLVTVSS | 351. |
| VH; 1B20 Variant Sequence F2 | QVQLVQSGAEVKKPGESLKISCKGSGYSFTNYYIAWVRQMPGKGLEWMGVIYPGDSYTRYNPKFQGQVTISADKSISTAYLQWSSLKASDTAMYYCARDYWSRPYFDIWGQGTLVTVSS | 352. |
| VH; 1B20 Variant Sequence F7 | QVQLVQSGAEVKKPGESLKISCKGSGYSFTNYYIAWVRQMPGKGLEWMGIIYPGDSYTHYNPKFQGQVTISADKSISTAYLQWSSLKASDTAMYYCARDHWSRPFSDIWGQGTLVTVSS | 353. |

TABLE 1-continued

| Description | Sequence | SEQ ID NO |
|---|---|---|
| VH; 1B20 Variant Sequence A7 | QVQLVQSGAEVKKPGESLKISCKGSGYSFTNYYISWVRQMPGKGLEWMGIIYPGDSYTRYNPNFQGQVTISADKSISTAYLQWSSLKASDTAMYYCARDYWSKPLSDVWGQGTLVTVSS | 354. |
| VH; 1B20 Variant Sequence G8 | QVQLVQSGAEVKKPGESLKISCKGSGYSFTDYYISWVRQMPGKGLEWMGLIYPGDSYTHYNPNFQGQVTISADKSISTAYLQWSSLKASDTAMYYCARDHWSKPYFDVWGQGTLVTVSS | 355. |
| VH; 1B20 Variant Sequence H4 | QVQLVQSGAEVKKPGESLKISCKGSGYSFTNYYITWVRQMPGRGLEWMGIIYPGDSYTRYNPKFQGQVTISADKSISTAYLQWSSLKASDTAMYYCARDHWSKPFSDVWGQGTLVTVSS | 356. |
| VH; 1B20 Variant Sequence D5 | QVQLVQSGAEVKKPGESLKISCKGSGYSFTNYYITWVRQMPGKGLEWMGIIYPGDSYTRYSPRFQGQVTISADKSISTAYLQWSSLKASDTAMYYCARDHWSRPYSDVWGQGTLVTVSS | 357. |
| VH; 1B20 Variant Sequence D4 | QVQLVQSGAEVKKPGESLKISCKGSGYSFTDYYIAWVRQMPGKGLEWMGIIYPGDSYTRYNPKFQGQVTISADKSISTAYLQWSSLKASDTAMYYCARDHWSRPFSDVWGQGTLVTVSS | 358. |
| VH; 1B20 Variant Sequence B4 | QVQLVQSGAEVKKPGESLKISCKGSGYSFTDYYISWVRQMPGKGLEWMGLIYPGDSYTHYNPNFQGQVTISADKSISTAYLQWSSLKASDTAMYYCARDYWSKPLFDVWGQGTLVTVSS | 359. |
| VH; 1B20 Variant Sequence H1 | QVQLVQSGAEVKKPGESLKISCKGSGYSFTDYYIAWVRQMPGKGLEWMGIIYPGDSYTRYNPRFQGQVTISADKSISTAYLQWSSLKASDTAMYYCARDYWSKPLSDIWGQGTLVTVSS | 360. |
| VH; 1B20 Variant Sequence G2 | QVKLVQSGAEVKKPGESLKISCKGSGYSFTDYYISWVRQMPGKGLEWMGIIYPGDSYTHYNPKFQCQVTISADKSISTAYLQWSSLKASDTAMYYCARDRWSKPLFDVWCQCTLVTVSS | 361. |
| VH; 1B20 Variant Sequence A1 | QVQLVQSGAEVKKPGESLKISCKGSGYSFTDYYISWVRQMPGKGLEWMGLIYPGDSYTRYNPSFQGQVTISADKSISTAYLQWSSLKASDTAMYYCARDYWSKPLSDIWGQGTLVTVSS | 362. |
| VH; 1B20 Variant Sequence A4 | QVQLVQSGAEVKKPGESLKISCKGSGYSFTDYYISWVRQMPGKGLEWMGSIYPGDSYTHYSHKFQGQVTISADKSISTAYLQWSSLKASDTAIYYCARDHWSRPFFDVWGQGTLVTVSS | 363. |
| VH; 1B20 Variant Sequence C2 | QVQLVQSGAEVKKPGESLKISCKGSGYSFTDYYIAWVRQMPGKGLEWMGLIYPGDSYTSYNPRFQGQVTISADKSISTAYLQWSSLKASDTAMYYCARDYWSTPYFDIWGQGTLVTVSS | 364. |
| VH; 1B20 Variant Sequence H5 | QVQLVQSGAEVKKPGESLKISCKGSGYSFTDYYISWVRQMPGKGLEWMGIIYPGDSYTSYSPRFQGQVTISADKSISTAYLQWSSLKASDTAMYYCARDYWSRPLFDIWGQGTLVTVSS | 365. |
| VH; 1B20 Variant Sequence F6 | QVQLVQSGAEVKKPGESLKISCKGSGYSFTDYYISWVRQMPGKGLEWMGLIYPGDSYTHYNPSFQGQVTISADKSISTAYLQWSSLKASDTAMYYCARDHWYKPFSDIWGQGTLVTVSS | 366. |
| VH; 1B20 Variant Sequence B6 | QVQLVQSGAEVKKPGESLKISCKGSGYSFTDYYISWVRQMPGKGLEWMGIIYPGDSYTNYNPSFQGQVTISADKSISTAYLQWSSLKASDTAMYYCARDYWYRPFSDIWGQGTLVTVSS | 367. |
| VH; 1B20 Variant Sequence B1 | QVQLVQSGAEVKKPGESLKISCKGSGYSFTDYYISWVRQMPGKGLEWMGIIYPGDSYTHYSPNFQGQVTISADKSISTAYLQWSSLKASDTAMYYCARDYWYTPFFDVWGQGTLVTVSS | 368. |
| VH; 1B20 Variant Sequence F1 | QVQLVQSGAEVKKPGESLKISCKGSGYSFTDYYISWVRQMPGKGLEWMGLIYPGDSYTNYSPKFQGQVTISADKSISTAYLQWSSLKASDTAMYYCARDYWSKPLSDVWGQGTLVTVSS | 369. |
| VH; 1B20 Variant Sequence A8 | QVQLVQSGAEVKKPGESLKISCKGSGYSFTNYYISWVRQMPGKGLEWMGMIYPGDSYTHYSPNFQGQVTISADKSISTAYLQWSSLKASDTAMYYCARDYWSKPYFDVWGQGTLVTVSS | 370. |
| VH; 1B20 Variant Sequence B3 | QVQLVQSGAEVKKPGESLKISCKGSGYSFTNYYISWVRQMPGKGLEWMGMIYPGDSYTSYNPKFQGQVTISADKSISTAYLQWSSLKASDTAMYYCARDHWSKPYFDIWGQGTLVTVSS | 371. |
| VH; 1B20 Variant Sequence F8 | QVQLVQSGAEVKKPGESLKISCKGSGYSFTNYYISWVRQMPGKGLEWMGMIYPGDSYTNYNQKFQGQVTISADKSISTAYLQWSSLKASDTAMYYCARDYWSRPYSDIWGQGTLVTVSS | 372. |

TABLE 1-continued

| Description | Sequence | SEQ ID NO |
|---|---|---|
| VH; 1B20 Variant Sequence H8 | QVQLVQSGAEVKKPGESLKISCKGSGYSFTDYYISWVRQMPGKGLEWMGMIYPGDSYTHY SQNFQGQVTTSADKSTSTAYLQWSSLKASDTAMYYCARDHWSRPFFDVWGQGTLVTVSS | 373. |
| VH; 1B20 Variant Sequence B5 | QVQLVQSGAEVKKPGESLKISCKGSGYSFTDYYISWVRQMPGKGLEWMGMIYPGDSYTRY SPSFQGQVTISADKSISTAYLQSSSLKASDTAMYYCARDYWYKPFSDVWGQGTLVTVSS | 374. |
| VH; 1B20 Variant Sequence E1 | QVQLVQSGAEVKKPGESLKISCKGSGYSFTNYYISWVRQMPGKGLEWMGMIYPGDSYTSY NPNFQGQVTISADKSISTAYLQWSSLKASDTAMYYCARDHWSKPFFDIWGQGTLVTVSS | 375. |
| VH; 1B20 Variant Sequence E8 | QVQLVQSGAEVKKPGESLKISCKGSGYSFTNYYITWVRQMPGKGLEWMGMIYPGDSYTRY SPKFQGQVTISADKSISTAYLQWSSLKASDTAMYYCARDHWSKPLSDVWGQGTLVTVSS | 376. |
| VH; 1B20 Variant Sequence C1 | QVQLVQSGAEVKKPGESLKISCKGSGYSFTNYYISWVRQMPGKGLEWMGMIYPGDSYTRY SPKFQGQVTISADKSISTAYLQWSSLKASDTAMYYCARDHWYRPYSDIWGQGTLVTVSS | 377. |
| VH; 1B20 Variant Sequence H3 | QVQLVQSGAEVKKPGESLKISCKGSGYSFTNYYITWVRQMPGKGLEWMGMIYPGDSYTHY SQRFQGQVTISADKSISTAYLQWSSLKASDTAIYYCARDHWSRPLFDVWGQGTLVTVSS | 378. |
| VH; 1B20 Variant Sequence A9 | QVQLVQSGAEVKKPGESLKISCKGSGYSFTNYYISWVRQMPGKGLEWMGMIYPGDSYTRY SPKFQGQVTISADKSISTAYLQWSSLKASDTAMYYCARDHWYRPYSDIWGQGTLVTVSS | 379. |
| VH; 1B20 Variant Sequence G7 | QVQLVQSGAEVKKPGESLKISCKGSGYSFTDYYISWVRQMPGKGLEWMGWIYPGDSYTHY SPSFQGQVTISADKSISTAYLQWSSLKASDTAMYYCARDHWSKPYFDVWGQGTLVTVSS | 380. |
| VH; 1B20 Variant Sequence C6 | QVQLVQSGAEVKKPGESLKISCKGSGYSFTNYYITWVRQMPGKGLEWMGMIYPGDSYTHY NPSFQCQVTISADKSISTAYLQWSSLKASDTAMYYCARDHWYKPLFDIWCQCTLVTVSS | 381. |
| VH; 1B20 Variant Sequence G6 | QVQLVQSGAEVKKPGESLKISCKGSGYSFTDYYINWVRQMPGKGLEWMGMIYPGDSYTNY NPKFQGQVTISADKSISTAYLQWSSLKASDTAIYYCARDHWSRPFSDVWGQGTLVTVSS | 382. |
| VH; 1B20 Variant Sequence E4 | QVQLVQSGAEVKKPGESLKISCKGSGYSFTNYYISWVRQMPGKGLEWMGWIYPGDSYTSY NQKFQGQVTISADKSISTAYLQWSSLKASDTAMYYCARDYWSKPYSDVWGQGTLVTVSS | 383. |
| VH; 1B20 Variant Sequence F5 | QVQLVQSGAEVKKPGESLKISCKGSGYSFTDYYITWVRQMPGKGLEWMGMIYPGDSYTNY RHNFQGQVTISADKSISTAYLQWSSLKASDTAMYYCARDYWSRPYFDIWGQGTLVTVSS | 384. |
| VH; 1B20 Variant Sequence C7 | QVQLVQSGAEVKKPGESLKISCKGSGYSFTDYYISWVRQMPGKGLEWMGMIYPGDSYTHY SHNFQGQVTISADKSISTAYLQWSSLKASDTAMYYCARDHWSRPFSDVWGQGTLVTVSS | 385. |
| VH; 1B20 Variant Sequence E3 | QVQLVQSGAEVKKPGESLKISCKGSGYSFTDYYISWVRQXPGKGLEWMGMIYPCOSYTSY SPRFQGQVTISADKSISTAYLQWSSLKASDTAMYYCARDYWYRPFSDIWGQGTLVTVSS | 386. |
| VH; 1B20 Variant Sequence D3 | QVQLVQSGAEVKKPGESLKISCKGSGYSFTDYYITWVRQMPGKGLEWMGMIYPGDSYTRY SPKFQGQVTISADKSISTAYLQWSSLKASDTAMYYCARDYWSKPFFDVWGQGTLVTVSS | 387. |
| VH; 1B20 Variant Sequence D8 | QVQLVQSGAEVKKPGESLKISCKGSGYSFTDYYISWVRQMPGKGLEWMGMIYPGDSYTHY SQSFQGQVTISADKSISTAYLQWSSLKASDTAMYYCARDHWYRPLFDIWGQGTLVTVSS | 388. |
| VH; 1B20 Variant Sequence C8 | QVQLVQSGAEVKKPGESLKISCKGSGYSFTDYYIAWVRQMPGKGLEWMGMIYPGDSYTSY SHRFQGQVTISADKSISTAYLQWSSLKASDTAMYYCARDHWYRPYFDIWGQGTLVTVSS | 389. |
| VH; 1B20 Variant Sequence E5 | QVQLVQSGAEVKKPGESLKISCKGSGYSFTDYYISWVRQMPGKGLEWMGMIYPGDSYTHY NPNFQGQVTISADKSISTAYLQWSSLKASDTAMYYCARDRWSTPYFDVWGQGTLVTVSS | 390. |
| VH; 1B20 Variant Sequence B8 | QVQLVQSGAEVKKPGESLKISCKGSGYSFTNYYISWVRQMPGKGLEWMGMIYPGDSYTHY SPNFQCQVTISADKSISTAYLQWSSLKASDTAMYYCARDYWSKPYFDVWCQCTLVTVSS | 391. |

TABLE 1-continued

| Description | Sequence | SEQ ID NO |
|---|---|---|
| VH; 1B20 Variant Sequence H7 | QVQLVQSGAEVKKPGESLKISCKGSGYSFTDYYISWVRQMPGKGPEWMGMIYPGDSYTRY SQKFQGQVTISADKSISTAYLQWSSLKASDTAIYYCARDHWSRPLSDIWGQGTLVTVSS | 392. |
| VH; 1B20 Variant Sequence A5 | QVQLVQSGAEVKKPGESLKISCKGSGYSFTDYYISWVRQMPGKGLEWMGWIYPGDSYTHY NPMFQGQVTISADKSISTAYLQWSSLKASDTAMYYCARDRWSRPYFDIWGQGTLVTVSS | 393. |
| VH; 1B20 Variant Sequence A3 | QVQLVQSGAEVKKPGESLKISCKGSGYSFTDYYISWVRQMPGKGLEWMGMIYPGDSYTRY SPNFQGQVTISADKSISTAYLQWSSLKASDTAMYYCARDHWYRPLSDIWGQGTLVTVSS | 394. |
| 1B20 Antibody Variant VH Sequence N59K | QVQLVQSGAEVKKPGESLKISCKGSGYSFTNYWISWVRQMPGKGLEWMGIIYPGDSYTKY SPSFQGQVTISADKSISTAYLQWSSLKASDTAMYYCARDYWYKPLFDIWGQGTLVTVSS | 395. |
| 1B20 Antibody Variant VH Sequence N59Q | QVQLVQSGAEVKKPGESLKISCKGSGYSFTNYWISWVRQYPGKCLEWMGIIYPGDSYTQY SPSFQGQVTISADKSISTAYLQWSSLKASDTAMYYCARDYWYKPLFDIWGQGTLVTVSS | 396. |
| 1B20 Antibody Variant VH Sequence N59R | QVQLVQSGAEVKKPGESLKISCKGSGYSFTNYWISWVRQMPGKGLEWMGIIYPGDSYTRY SPSFQGQVTISADKSISTAYLQWSSLKASDTAMYYCARDYWYKPLFDIWGQGTLVTVSS | 397. |
| 1B20 Antibody Variant VH Sequence W101A | QVQLVQSGAEVKKPGESLKISCKGSGYSFTNYWISWVRQMPGKGLEWMGIIYPGDSYTNY SPSFQGQVTISADKSISTAYLQWSSLKASDTAMYYCARDYAYKPLFDIWGQGTLVTVSS | 398. |
| 1B20 Antibody Variant VH Sequence W101F | QVQLVQSGAEVKKPGESLKISCKGSGYSFTNYWISWVRQMPGKGLEWMGIIYPGDSYTNY SPSFQGQVTISADKSISTAYLQWSSLKASDTAMYYCARDYFYKPLFDIWGQGTLVTVSS | 399. |
| 1B20 Antibody Variant VH Sequence W101Y | QVQLVQSGAEVKKPGESLKISCKGSGYSFTNYWISWVRQMPGKGLEWMGIIYPGDSYTNY SPSFQGQVTISADKSISTAYLQWSSLKASDTAMYYCARDYYYKPLFDIWGQGTLVTVSS | 400. |
| GROUP H | | |
| Linker Sequence (used in DSB#1) | GGGGGGGGGGGCGG | 401. |
| Linker Seqeunce (used in DSB#2) | GGGGGGGGGGGGCG | 402. |
| Linker | GGGGSGGGGS | 403. |
| Group I | | |
| PC9#3 variable heavy chain | EVQLVESGGGLVQPGGSLRLSCAASGFTFNNYAMNWVRQAPGKGLDWVSTISGSGGTTNYADSVKGRFIISRDS SKHTLYLQMNSLRAEDTAVYYCAKDSNWGNFDLWGRGTLVTVSS | 404. |
| PC9#3 variable light chain | DIVMTQSPDSLAVSLGERATINCKSSQSVLYRSNNRNFLGWYQQKPGQPPNLLIYWASTRESGVPDRFSGSGSG TDFTLTISSLQAEDVAVYYCQQYYTTPYTFGQGTKLEIK | 405. |
| PC9#4 variable heavy chain | EVQLVESGGGLVKPGGSLRLSCAASGFTFSSYSMNWVRQAPGKGLEWVSSISSSSSYISYADSVKGRFTISRDN AKNSLYLQMNSLRAEDTAVYFCARDYDFWSAYYDAFDVWGQGTMVTVSS | 406. |
| PC9#4 variable light chain | QSVLTQPPSVSGAPGQRVTISCTGSSSNIGAGYDVHWYQQLPGTAPKLLISGNSNRPSGVPDRFSGSKSGTSAS LAITGLQAEDEADYYCQSYDSSLSGSVFGGGTKLTVL | 407. |
| PC9#5 variable heavy chain | EMQLVESCCCLVQPCCSLRLSCAASCFTFSSHWMKWVRQAPCKCLEWVANINQDCSEKYYVDSVKCRFTISRDN AKNSLFLQMNSLRAEDTAVYYCARDIVLMVYDMDYYYGMDVWGQGTTVTVSS | 408. |

TABLE 1-continued

| Description | Sequence | SEQ ID NO |
|---|---|---|
| PC9#5 variable light chain | DIVMTQSPLSLPVTPGEPASISCRSSQSLLHSNGNNYLDWYLQKPGQSPQLLIYLGSNRASGVPDRFSGSGSGT DFTLKISRVEAEDVGVYYCMQTLQTPLTFGGGTKVEIK | 409. |
| PC9#6 variable heavy chain | QVQLVQSGAEVKKPGSSVKVSCKASGGTFNSHAISWVRQAPGQGLEWMGGINPILGIANYAQKFQGRVTITADE STSTAYMELSSLRSEDTAVYYCARHYEIQTGRYGMNVYYLMYRFASWGQGTLVTSS | 410. |
| PC9#6 variable light chain | DIQMTQSPSSLSASVGDRVTITCRASQGIRSALNWYQQKPGKAPKLLIYNGSTLQSGVPSRFSGSGSGTDFTLT ISSLQPEDFAVYYCQQFDGDPTFGQGTKVEIK | 411. |
| PC9#7 variable heavy chain | QVQLVQSGAEVKKPGESLKISCKGSGYSFTNYWISWVRQMPGKGLEWMGIIYPGDSYTNYSPSFQGQVTISADK SISTAYLQWSSLKASDTAMYYCARDYWYKPLFDIWGQGTLVTVSS | 412. |
| PC9#7 variable light chain | DIVMTQSPDSLAVSLGERATINCRSSQSVLYSSNNKNYLAWYQQKPGQPPKLLIYWASTRESGVPDRFSGSGSG TDFTLTISSLQAEDVAVYYCQQYSSFPITFGQGTKVEIK | 413. |
| NIP228 variable heavy chain | QVNLRESGGGVVQPGRSLRLSCAASGFTFSSYGMHWVRQAPGEGLEWVSAISGSGGSTYYADSVKGRFTISRDN SKNTLYLQMXSLRAEDTVYYCAKRFGEFAFDIGRGTTVTVSS | 414. |
| NIP228 variable light chain | AIRMTQSPSSLSASVGDRVTITCRASQSISSYLNWYQQKPGKAPKLLIYAASSLQSGVPSRFSGSGSGTDFTLT ISSLQPEDFATYYCQQSYSTPLTFGGGTKVEIK | 415. |
| Human IgG4 Fc fragment | ESKYGPPCPPCPAPEAAGGPSVFLFPPKPKDTLMISRTPEVTCVVVDVSQEDPEVQFNWYVDGVEVHNAKTKPR EEQFNSTYRVVSVLTVLHQDWLNGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQEGNVFSCSVMHEALHNHYTQKS LSLSLG | 416. |
| Human germline 1-46 (DP-7) | QVQLVQSGAEVKKPGASVfCVSCKASGYTFTSYYMHWVRQAPGQGLEWMGIINPSGGSTSYAQKFQGRVTMTRDT STSTVYMELSSLRSEDTAVYYCARD | 417. |
| Human germline VK1 O18 O8 (DPK1) | DIQMTQSPSSLSASVGDRVTITCQASQDISNYLNWYQQKPGKAPKLLIYDASNLETGVPSRFSGSGSGTDFTFT ISSLQPEDIATYYCQQ | 418. |
| HS9_DSB7_ V19A_L2 | HGEGTFTSDLSKQMEEECARLFIEWLKNGGPSSGAPPPGCGGGGGSGGGGSADIQMTQSPSSLSASVGDRVTIT CQASQDVKTAVAWYQQKPGKAPKLLIYSASYRYTGVPSRFSGSGSGTDFTFTISSLQPEDIATYYCQQRYSLWR TFGQGTKLEIKRTVAAPSVFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC | 419. |
| HS9_DSB7_ V19A_L1 | HGEGTFTSDLSKQMEEECARLFIEWLKNGGPSSGAPPPGCGGGGGSADIQMTQSPSSLSASVGDRVTITCQASQ DVKTAVAWYQQKPGKAPKLLIYSASYRYTGVPSRFSGSGSGTDFTFTISSLQPEDIATYYCQQRYSLWRTFGQG TKLEIKRTVAAPSVFIFPPSDEQLKSGTASVVCLLNNFYPREAKVQWKVDNALQSGNSQESVTEQDSKDSTYSL SSTLTLSKADYEKHKVYACEVTHQGLSSPVTKSFNRGEC | 420. |
| HS9_DSB7_ V19A_L0 | HGEGTFTSDLSKQMEEECARLFIEWLKNGGPSSGAPPPGCGADIQMTQSPSSLSASVGDRVTITCQASQDVKTA VAWYQQKPGKAPKLLIYSASYRYTGVPSRFSGSGSGTDFTFTISSLQPEDIATYYCQQRYSLWRTFGQGTKLEI KRTVAAPSVFIFPPSDEQLKSGTASVVCLLNNFYPREAKVQWKVDNALQSGNSQESVTEQDSKDSTYSLSSTLT LSKADYEKHKVYACEVTHQGLSSPVTKSFNRGEC | 421. |
| 2.7A4_VH | EVQLVESGGGLVKPGGSLRLSCAASGFTFSTYSMNWVRQAPGKGLEWVSSISSSGDYIYYADSVKGRFTISRDN AKNSLYLQMNSLRAEDTAVYYCARDLVTSMVAFDYWGQGTLVTVSS | 422. |
| 2.7A4_VL | SYELTQPPSVSVSPGQTARITCSGDALPQKYVFWYQQKSGQAPVLVIYEDSKRPSGIPERFSGSSSGTMATLTI SGAQVEDEADYYCYSTDRSGNHRVFGGGTKLTVL | 423. |

| GROUP J | | |
|---|---|---|
| HS1_VH | QVQLVQSGAEVKKPGASVKVSCKASGYTFT<u>SYYMH</u>WVRQAPGQGLEWMG<u>EIKPSGGSTSYNQKFQG</u>RVTMTRDTSTST VYMELSSLRSEDTAVYYCAR<u>ERPLYASDL</u>WGQGTTVTVSS | 424. |
| HS1_VL | DIQMTQSPSSLSASVGDRVTITC<u>QASQDYTAVAW</u>YQQKPGKAPKLLIY<u>YASYRYT</u>GVPSRFSGSGSGTDFTFTISSL QPEDIATYYC<u>QQRYSLWRT</u>FGQGTKLEIK | 425. |
| HS2_VH | QVQLVQSGAEVKKPGASVKVSCKASGYTFT<u>SYYMH</u>WVRQAPGQGLEWMG<u>EIKPSGGSTSYNQKFQG</u>RVTMTRDTSTST VYMELSSLRSEDTAVYYCAR<u>ERPLYASDL</u>WGQGTTVTVSS | 426. |
| HS2_VL | DIQMTQSPSSLSASVGDRVTITC<u>QASQDYTAVAW</u>YQQKPGKAPKLLIY<u>SASYRYT</u>GVPSRFSGSGSGTDFTFTISSL QPEDIATYYC<u>QQRYSLWRT</u>FGQGTKLEIK | 427. |

TABLE 1-continued

| Description | Sequence | SEQ ID NO |
|---|---|---|
| HS3_VH | QVQLVQSGAEVKKPGASVKVSCKASGYTFT<u>SYYMH</u>WVRQAPGQGLEWMGE<u>IKPSGGSTSYNQKFQG</u>RVTMTRDTSTST VYMELSSLRSEDTAVYYCAR<u>ERPLYASD</u>LWGQGTTVTSS | 428. |
| HS3_VL | DIQMTQSPSSLSASVGDRVTITC<u>QASQDVKTAVA</u>WYQQKPGKAPKLLIY<u>YASYRYT</u>GVPSRFSGSGSGTDFTFTISSL QPEDIATYYC<u>QQRYSLWRT</u>FGQGTKLEIK | 429. |
| HS4_VH | QVQLVQSGAEVKKPGASVKVSCKASGYTFT<u>SYYMH</u>WVRQAPGQGLEWMGE<u>IKPSGGSTSYNQKFQG</u>RVTMTRDTSTST VYMELSSLRSEDTAVYYCAR<u>ERPLYASD</u>LWGQGTTVTSS | 430. |
| HS4_VL | DIQMTQSPSSLSASVGDRVTITC<u>QASQDVKTAVA</u>WYQQKPGKAPKLLIY<u>SASYRYT</u>GVPSRFSGSGSGTDFTFTISSL QPEDIATYYC<u>QQRYSLWRT</u>FGQGTKLEIK | 431. |
| HS5_VH | QVQLVQSGAKVKKPGASVKVSCKASGYTFT<u>SYYMH</u>WVRQAPGQGLEWMGE<u>IKPSGGSTSYNQKFQG</u>RVTMTRDTSTST VYMELSSLRSEDTAVYYCAR<u>ERPLYASD</u>LWGQGTTVTSS | 432. |
| HS5_VL | DIQMTQSPSSLSASVGDRVTITC<u>QASQDVSTAVA</u>WYQQKPGKAPKLLIY<u>SASYRYT</u>GVPSRFSGSGSGTDFTFTISSL QPEDIATYYC<u>QQRYSLWRT</u>FGQGTKLEIK | 433. |
| HS6_VH | QVQLVQSGAEVKKPGASVKVSCKASGYTFT<u>SYYMH</u>WVRQAPGQGLEWMGE<u>ISPSGGSTSYNQKFQG</u>RVTMTRDTSTST VYMELSSLRSEDTAVYYCAR<u>ERPLYASD</u>LWGQGTTVTSS | 434. |
| HS6_VL | DIQMTQSPSSLSASVGDRVTITC<u>QASQDVYTAVA</u>WYQQKPGKAPKLLIY<u>YASYRYT</u>GVPSRFSGSGSGTDFTFTISSL QPEDIATYYC<u>QQRYSLWRT</u>FGQGTKLEIK | 435. |
| HS7_VH | QVQLVQSGAEVKKPGASVKVSCKASGYTFT<u>SYYMH</u>WVRQAPGQGLEWMGE<u>ISPSGGSTSYNQKFQG</u>RVTMTRDTSTST VYMELSSLRSEDTAVYYCAR<u>ERPLYASD</u>LWGQGTTVTSS | 436. |
| HS7_VL | DIQMTQSPSSLSASVGDRVTITC<u>QASQDVYTAVA</u>WYQQKPGKAPKLLIY<u>SASYRYT</u>GVPSRFSGSGSGTDFTFTISSL QPEDIATYYC<u>QQRYSLWRT</u>FGQGTKLEIK | 437. |
| HS8_VH | QVQLVQSGAEVKKPGASVKVSCKASGYTFT<u>SYYMH</u>WVRQAPGQGLEWMGE<u>ISPSGGSTSYNQKFQG</u>RVTMTRDTSTST VYMELSSLRSEDTAVYYCAR<u>ERPLYASD</u>LWGQGTTVTSS | 438. |
| HS8_VL | DIQMTQSPSSLSASVGDRVTITC<u>QASQDVKTAVA</u>WYQQKPGKAPKLLIY<u>YASYRYT</u>GVPSRFSGSGSGTDFTFTISSL QPEDIATYYC<u>QQRYSLWRT</u>FGQGTKLEIK | 439. |
| HS9_VH | QVQLVQSGAEVKKPGASVKVSCKASGYTFT<u>SYYMH</u>WVRQAPGQGLEWMGE<u>ISPSGGSTSYNQKFQG</u>RVTMTRDTSTST VYMELSSLRSEDTAVYYCAR<u>ERPLYASD</u>LWGQGTTVTSS | 440. |
| HS9_VL | DIQMTQSPSSLSASVGDRVTITC<u>QASQDVKTAVA</u>WYQQKPGKAPKLLIY<u>SASYRYT</u>GVPSRFSGSGSGTDFTFTISSL QPEDIATYYC<u>QQRYSLWRT</u>FGQGTKLEIK | 441. |
| HS10_VH | QVQLVQSGAEVKKPGASVKVSCKASGYTFT<u>SYYMH</u>WVRQAPGQGLEWMGE<u>ISPSGGSTSYNQKFQG</u>RVTMTRDTSTST VYMELSSLRSEDTAVYYCARERPLYASDLWGQGTTVTSS | 442. |
| HS10_VL | DIQMTQSPSSLSASVGDRVTITC<u>QASQDVSTAVA</u>WYQQKPGKAPKLLIY<u>SASYRYT</u>GVPSRFSGSGSGTDFTFTISSL QPEDIATYYC<u>QQRYSLWRT</u>FGQGTKLEIK | 443. |
| HS9_DS B7_G2Y | HYEGTFTSDLSKQMEEECVRLFIEWLKNGGPSSGAPPPGCGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 444. |
| HS9_DS B7_G2V | HVEGTFTSDLSKQMEEECVRLFIEWLKNGGPSSGAPPPGCGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 445. |
| HS9_DS B7_G2T | HTEGTFTSDLSKQMEEECVRLFIEWLKNGGPSSGAPPPGCGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 446. |
| HS9_DS B7_G2Q | HQEGTFTSDLSKQMEEECVRLFIEWLKNGGPSSGAPPPGCGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 447. |
| HS9_DS B7_G2N | HNEGTFTSDLSKQMEEECVRLFISWLKNGGPSSGAPPLGCGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 448. |
| HS9_DS B7_G2I | HIEGTFTSDLSKQMEEECVRLFIEWLKNGGPSSGAPPPGCGGGGSGGGGSGGGGSADIQMTQSPSSLSASVGDRVT ITCQASQDVKTAVAWYQQKPGKAPKLLTYSASYRYTGVPSRFSGSGSGTDFTFTISSLQPEDIATYYCQQRYSLWRT FGQGTKLEIK | 449. |
| HS9_DS B7_G2F | HFEGTFTSDLSKQMEEECVRLF1EWLKNGGPSSGAPPPGCGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDTATYYCQQRYSLWRT FGQGTKLEIK | 450. |

TABLE 1-continued

| Description | Sequence | SEQ ID NO |
|---|---|---|
| HS9_DS B7_E15G | HGEGTFTSDLSKQMGEECVRLFIEWLKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 451. |
| HS9_DS B7_E15A | HGEGTFTSDLSKQMAEECVRLFIEWLKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 452. |
| HS9_DS B7_V19T | HGEGTFTSDLSKQMEEECTRLFIEWLKNGGPSSGAPPPGCGGGGGSGGGGSGGGGSADTQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 453. |
| HS9_DS B7_V19S | HGEGTFTSDLSKQMEEECSRLFIEWLKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 454. |
| HS9_DS B7_V19G | HGEGTFTPTSDLSKQMEEECGRLFIEWLKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT | 455. |
| HS9_DS B7_V19A | HGEGTFTSDLSKQMEFECARLFIEKLKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 456. |
| HS9.DS B7J23T | HGEGTFTSDLSKQMEEECVRLFTEWLKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 457. |
| HS9_DS B7_I23S | HGEGTFTSDLSKQMEEECVRLFSEWLKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 458. |
| HS9_DS B7_L23G | HGEGTFTSDLSKQMEEECVRLFGEWLKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 459. |
| HS9_DS B7_L23A | HGEGTFTSDLSKQMEEECVRLFAEWLKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 460. |
| HS9_DS B7_L26T | HGEGTFTSDLSKQMEEECVRLFIEWTKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 461. |
| HS9_DS B7_L26S | HGEGTFTSDLSKQMEEECVRLFIEWSKNGGPSSGAPPPGCGGGGGSGGGGSGGGGSADIQMTQSPSSLSA5VGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 462. |
| HS9_DS B7_L26P | HGEGTFTSDLSKQMEEECVRLFIEWPKNGGPSSGAPPPGCGGGGGSGGGGSGGGGSADIQMTQ3PSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 463. |
| HS9_DS B7_L26N | HGEGTFTSDLSKQMEEECVRLFIEWNKNGGPSSGAPPPGCGGGGGSGGGGSGGGGSADIQMTQSPSSLSASVGDRVT ITCQASQDVKTAVAWYQQKPGKAPKLLIYSA5YRYTGVP5RFSGSGSGTDFTFTISSLQPEDIATYYCQQRYSLWRT FGQGTKLEIK | 464. |
| HS9_DS B7_L26Q | HGEGTFTSDLSKQMEEECVRLFTEWQKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 465. |
| HS9_DS B7_L26M | HGEGTFTSDLSKQMEEECVRLFIEWMKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 466. |
| HS9_DS B7_L26I | HGEGTFTSDLSKQMEEECVRLFIEWIKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 467. |
| HS9JDS B7_L26H | HGEGTFTSDLSKQMEEECVRLFIEWHKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 468. |
| HS9_DS B7_L26G | HGEGTFTSDLSKQMEEECVRLFIEWGKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 469. |

TABLE 1-continued

| Description | Sequence | SEQ ID NO |
|---|---|---|
| HS9_DS B7_L26B | HGEGTFTSDLSKQMEEECVRLFIEWEKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTTSSLQPEDIATYYCQQRYSLWRT FGQGTKLEIK | 470. |
| HS9_DS B7_L26D | HGEGTFTSDLSKQMEEECVRLFIEMDKNGGPSSGAPPPGCGGGGGSGGGGSGGGGSADIQMTQSPSSLSASVGDRVT ITCQASQDVKTAVAWYQQKPGKAPKLLIYSASYRYTGVPSRFSGSGSGTDFTFTISSLQPEDIATYYCQQRYSLWRT FGQGTKLEIK | 471. |
| HS9_DS B7 | HGEGTFTSDLSKQMEEECVRLFIEWLKNGGPSSGAPPPGCGGGGGSGGGGSGGGGSADIQMTQSPSSLSASVGDRVT ITCQASQDVKTAVAWYQQKPGKAPKLLIYSASYTYTGVPSRFSGSGSGTDFTFTISSLQPEDIATYYCQQRYSLWRT FGQGTKLEIK | 472. |
| GLP-1 analogue | HGEGTFTSDVSSYLEEQAAKEFIAWLVKGG | 473. |
| NGS#1 | HGEGTFTSDVSSYLEEQNASEFIAWLVKGG | 474. |
| NGS#2 | HGEGTFTSDVSSYLEEQAAKEFIAWLVNGS | 475. |
| NGS#3 | HGEGTFTSDVSSYLEEQAAKEFIAWLVKNG | 476. |
| NGS#4 | HGEGTFTSDVSSYLEEQAAKEFIAWLVKGN | 477. |
| NGS#5 | HGEGTFTSDVSSYLEEQAAKEFIAWLVKGG | 478. |
| NGS#6 | HGEGTFTSDVSSYLEEQAAKEFIAWLVKGG | 479. |
| NGS#7 | HGEGTFTSDVSSYLEEQAAKEFIANLSKGG | 480. |
| NGS#8 | HGEGTFTSDVSSYLEEQAAKEFIANLTKGG | 481. |
| Linker | GGGGGSGGGGSGGGGSA | 482. |
| Linker | SGGGGSGGGGSGGGGSA | 483. |
| Linker | GSGGGGSGGGGSGGGGSA | 484. |
| Linker | NGSGGGGSGGGGSGGGGSA | 485. |
| Linker | GNGSGSGGGGSGGGGSA | 486. |
| PC9_2_DSB#1 VL (Version B) (with K at end of variable light chain) | *HGEGTFTSCLSKQMEEEAVRLFIEWLKNGGPSSGAPPPSGGGGGGGGGGGCGG*GGGG SGGGGSGGGGSADIQMTQSPSSLSASVGDRVTITCKASQDVHTAVAWYQQKPGKAPKLLIYHASYRYTGVPSRFSGSG SGTDFTFTISSLQPEDIATYYCQQRYSLWRTFGQGTKLEIK | 487. |
| PC9_2_DSB#3 VL (Version B) (with K at end of variable light chain) | *HGEGTFTSDLSKQMEEECVRLFIEWLKGGPSSGAPPGC*GGGGSGGGGSGGGGSADIQMTQSP SSLSASVGDRVTITCKASQDVHTAVAWYQQKPGKAPKLLIYHASYRYTGVPSRFSGSGSGTDFTFTISSLQPEDIAT YYCQQRYSLWRTFGQGTKLEIK | 488. |
| PC9_2_NGS#7 VL (Version B) (with K at end of variable light chain) | *HGEGTFTSDVSSYLEEQAAKEFIANLSKGGG*GGGGSGGGGSGGGGSADIQMTQSPSSLSASVGDRV TITCKASQDVHTAVAWYQQKPGKAPKLLIYHASYRYTGVPSRFSGSGSGTDFTFTISSLQPEDIATYYCQQRYSLWR TFGQGTKLEIK | 489. |
| PC9_2_DSB#7 VL (Version B) (with K at end of variable light chain) | *HGEGTFTSDLSKQMEEECVRLFIEWLKNGGPSSGAPPPGCG*GGGSGGGGSGGGGSADIQM TQSPSSLSASVGDRVTITCKASQDVHTAVAWYQQKPGKAPKLLIYHASYRYTGVPSRFSGSGSGTDFTFTISSLQPE DIATYYCQQRYSLWRTFGQGTKLEIK | 490. |
| Engineered PCSK9 antibody VH | EVQLVESGGGLVKPGGSLRLSCAASGFPFSKLGMWVRQAPGKGLEWVSTISSGGGYTYYPDSVKGRFTISRDNAKN SLY LQMNSLRAEDTAVYYCAREGISFQGGTYTYVMDYWGQGTLVTVSS | 491. |

TABLE 1-continued

| Description | Sequence | SEQ ID NO |
|---|---|---|
| Engineered PCSK9 antibody VL | DIVMTQSPLSLPVTPGEPASISCRSSKSLLHRNGITYSYWYLQKPGQSPQLLIYQLSNLASGVPDRFSGSGSGTDFT LKI SRVEAEDVGVYYCYQNLELPLTFGQGTKVEIK | 492. |
| Engineered PCSK9 antibody VH CDR1 | GFPFSKLGMV | 493. |
| Engineered PCSK9 antibody VH CDR2 | TISSGGGYTYYPDSVK | 494. |
| Engineered PCSK9 antibody VH CDR3 | EGISFQGGTYTYVMDY | 495. |
| Engineered PCSK9 antibody VL CDR1 | RSSKSLLHRNGITYSY | 496. |
| Engineered PCSK9 antibody VL CDR2 | QLSNLAS | 497. |
| Engineered PCSK9 antibody VL CDR3 | YQNLELPLT | 498. |

DESCRIPTION OF THE EMBODIMENTS

I. Anti-PCSK9~GLP-1 Fusion Molecules

The present disclosure is directed to fusions of antibodies (e.g., anti-PCSK9 antibodies or antigen-binding fragments thereof) with a GLP-1 moiety.

In one embodiment the fusion is constructed as:
GLP-1 moiety—Linker—Antibody Light Chain.
or
GLP-1 moiety-Linker-Antibody Heavy Chain The fusion protein can be constructed as a genetic fusion. Alternatively, the fusion protein may be constructed as a chemical conjugate, such as through a cysteine:cysteine disulfide bond.

Other arrangements of the GLP-1 moiety and antibody portion are also within the scope herein.

A. Antibodies and Antigen-Binding Fragments Thereof

1. Anti-PCSK9 Portion

The antibody portion may be an anti-PCSK9 antibody or an antigen-binding fragment thereof. In one embodiment, the anti-PCSK9 portion provides an LDLc (bad cholesterol) lowering effect.

In one embodiment, the anti-PCSK9 VL portion may be SEQ ID NO: 2 (PC9_2_HS9). In another embodiment, the anti-PCSK9 VL portion may be an antigen binding portion of SEQ ID NO: 2. In one embodiment, the anti-PCSK9 VL portion may comprise all six CDRs of SEQ ID NO: 2. In one embodiment, the anti-PCSK9 VH portion may be a pH dependent version of the antibody, as shown in SEQ ID NO: 5.

In one embodiment, the antibody or antigen-binding fragment thereof may be pH dependent, such that the antibody binding to the antigen is pH dependent. This can be used to modify half-life of the antibody and/or antigen. By modifying the antibody half-life, in one embodiment, we mean lengthening the half-life. By modifying the antibody half-life, in one embodiment, we mean shortening the half-life. In one embodiment, the antibody half-life may be modified (lengthened or shortened) to maximize the stability of it fusion partner (i.e., GLP-1). By modifying the antigen half-life we may also mean that the antigen-antibody complex can change the antigen's half-life, such as through antibody-mediated degradation (shortening the half-life) or by protecting the antigen from the typical degradation process (lengthening the half-life). In one instance, antibodies may have a higher affinity for the antigen at pH 7.4 as compared to endosomal pH (i.e., pH 5.5-6.0), such that the $K_D$ ratio at pH 5/5/pH 7.4 or at pH 6.0/pH 7.2 is 2 or more. Methods of engineering pH dependent antibodies are described in US 2011/0229489 and 2014/0044730, which are incorporated by reference herein.

In one embodiment the anti-PCSK9 portion provides sustained suppression of free PCSK9. In one embodiment, is provides at least 70%, 75%, 80%, 85%, 90%, 95%, or 99% suppression.

In one embodiment, an anti-PCSK9 antibody or antigen binding fragment thereof capable of specifically binding PCSK9 comprises:
a. a heavy chain variable region comprising a sequence which is at least 70%, 75%, 80%, 85%, 90%, 95%, 96%, 97%, 98%, or 99% A identical to SEQ ID NO: 1, 5, 8, or 10; and
b. a light chain variable region comprising a sequence which is at least 70%, 75%, 80%, 85%, 90%, 95%, 96%, 97%, 98%, or 99% A identical to SEQ ID NO: 2, 6, 9 or 11.

In one embodiment, an anti-PCSK9 antibody or antigen binding fragment thereof capable of specifically binding PCSK9 comprises:

a. a heavy chain variable region CDR1 sequence comprising a sequence which has one mutation compared to SEQ ID NO: 14;
b. a heavy chain variable region CDR2 sequence comprising a sequence which has one or two mutations compared to SEQ ID NO: 15, 16, 17, or 18;
c. a heavy chain variable region CDR3 sequence comprising a sequence which is one mutation compared to SEQ ID NO: 19.
d. a light chain variable region CDR1 sequence comprising a sequence which has one or two mutations compared to SEQ ID NO: 20, 21, 22, or 23;
e. a light chain variable region CDR2 sequence comprising a sequence which has one mutation compared to SEQ ID NO: 24 or 25; and
f. a light chain variable region CDR3 sequence comprising a sequence which has one mutation compared to SEQ ID NO: 26.

In one embodiment, an anti-PCSK9 antibody or antigen binding fragment thereof capable of specifically binding PCSK9 comprises:
a. a heavy chain variable region CDR1 sequence comprising SEQ ID NO: 14;
b. a heavy chain variable region CDR2 sequence comprising SEQ ID NO: 15, 16, 17, or 18;
c. a heavy chain variable region CDR3 sequence comprising SEQ ID NO: 19.
d. a light chain variable region CDR1 sequence comprising SEQ ID NO: 20, 21, 22, or 23;
e. a light chain variable region CDR2 sequence comprising SEQ ID NO: 24 or 25; and
f. a light chain variable region CDR3 sequence comprising SEQ ID NO: 26.

In another embodiment, the anti-PCSK9 portion may comprise an anti-PCSK9 antibody or antigen-binding fragment as described in any of U.S. Pat. No. 8,030,457, U.S. Pat. No. 8,062,640, U.S. Pat. No. 8,357,371, U.S. Pat. No. 8,168,762, U.S. Pat. No. 8,563,698, U.S. Pat. No. 8,829,165, U.S. Pat. No. 8,859,741, U.S. Pat. No. 8,188,233, WO 2012/088313, US 2012/0195910, U.S. Pat. No. 8,530,414, US 2013/0189278, U.S. Pat. No. 8,344,144, US 2011/0033465, U.S. Pat. No. 8,188,234, U.S. Pat. No. 8,080,243, US 2011/0229489, US 2010/0233177, US 2013/315927 and US 2013/0071405. Each of these references is incorporated reference for the sequence and description of anti-PSCK9 antibodies and antigen-binding fragments thereof.

In one embodiment, the anti-PCSK9 portion may comprise a heavy and light chain variable region chosen from the sequences in Group B of Table 1 above. Alternatively, the anti-PCSK9 portion may comprise a heavy and light chain variable region with CDRs identical to a heavy and light chain variable region from Group B of Table 1 above. Additionally, the anti-PCSK9 portion may comprise a heavy chain variable region chosen from SEQ ID NOS: 53, 55, 57, 59, 61, or 63 and a light chain variable region chosen from SEQ ID NOS: 54, 56, 58, 60, 62, or 64, Alternatively, the anti-PCSK9 portion may comprise heavy chain CDR1, CDR2, and CDR3 from any one of SEQ ID NOS: 53, 55, 57, 59, 61, or 63 and light chain CDR1, CDR2, and CDR3 from any one of SEQ ID NOS: 54, 56, 58, 60, 62, or 64.

In one embodiment, the anti-PCSK9 portion may comprise a heavy and light chain variable region chosen from the sequences in Group C of Table 1 above. Alternatively, the anti-PCSK9 portion may comprise a heavy and light chain variable region with CDRs identical to a heavy and light chain variable region from Group C of Table 1 above. Additionally, the anti-PCSK9 portion may comprise a heavy chain variable region chosen from SEQ ID NOS: 65-95 and a light chain variable region chosen from SEQ ID NOS: 96-126. Alternatively, the anti-PCSK9 portion may comprise heavy chain CDR1, CDR2, and CDR3 from any one of SEQ ID NOS: 65-95 and light chain CDR1 CDR2, and CDR3 from any one of SEQ ID NOS: 96-126.

In one embodiment, the anti-PCSK9 portion may comprise a heavy and light chain variable region chosen from the sequences in Group D of Table 1 above. Alternatively, the anti-PCSK9 portion may comprise a heavy and light chain variable region with CDRs identical to a heavy and light chain variable region from Group D of Table 1 above. Additionally, the anti-PCSK9 portion may comprise a heavy chain variable region chosen from SEQ ID NOS: 127-218 and a light chain variable region chosen from SEQ ID NOS: 219-311. Alternatively, the anti-PCSK9 portion may comprise heavy chain CDR1, CDR2, and CDR3 from any one of SEQ ID NOS: 127-218 and light chain CDR1 CDR2, and CDR3 from any one of SEQ ID NOS: 219-311.

In one embodiment, the anti-PCSK9 portion may comprise a heavy and light chain variable region chosen from the sequences in Group E of Table 1 above. Alternatively, the anti-PCSK9 portion may comprise a heavy and light chain variable region with CDRs identical to a heavy and light chain variable region from Group E of Table 1 above. Additionally, the anti-PCSK9 portion may comprise a heavy chain variable region chosen from SEQ ID NOS: 312-317 and a light chain variable region chosen from SEQ ID NOS: 318-323. Alternatively, the anti-PCSK9 portion may comprise heavy chain CDR1, CDR2, and CDR3 from any one of SEQ ID NOS: 312-317 and light chain CDR1, CDR2, and CDR3 from any one of SEQ ID NOS: 318-323.

In one embodiment, the anti-PCSK9 portion may comprise a heavy and light chain variable region chosen from the sequences in Group F of Table 1 above. Alternatively, the anti-PCSK9 portion may comprise a heavy and light chain variable region with CDRs identical to a heavy and light chain variable region from Group F of Table 1 above. Additionally, the anti-PCSK9 portion may comprise a heavy chain variable region chosen from SEQ ID NO: 324 and a light chain variable region chosen from SEQ ID NO: 325. Alternatively, the anti-PCSK9 portion may comprise heavy chain CDR1, CDR2, and CDR3 from any one of SEQ ID NOS: 324 and light chain CDR1, CDR2, and CDR3 from any one of SEQ ID NOS: 325.

In one embodiment, the anti-PCSK9 portion may comprise a heavy and light chain variable region chosen from the sequences in Group G of Table 1 above. Alternatively, the anti-PCSK9 portion may comprise a heavy and light chain variable region with CDRs identical to a heavy and light chain variable region from Group G of Table 1 above. Additionally, the anti-PCSK9 portion may comprise a heavy chain variable region chosen from SEQ ID NOS: 326, 339 340, or 343-400 and a light chain variable region chosen from SEQ ID NOS: 327, 341, or 342. Alternatively, the anti-PCSK9 portion may comprise heavy chain CDR1, CDR2, and CDR3 from any one of SEQ ID NOS: 326, 339, 340, or 343-400 and light chain CDR1, CDR2, and CDR3 from any one of SEQ ID NOS: 327, 341, or 342. Further, the anti-PCSK9 portion may comprise heavy chain CDR1, CDR2, and CDR3 from SEQ ID NOS: 328 (HC CDR1) 329 (HC CDR2), 331 (HC CDR2), 330 (HC CDR3), 332 (HC CDR3) and light chain CDR1 CDR2, and CDR3 from SEQ ID NOS: 333 (LC CDR1), 334 (LC CDR2), 333 (LC CDR3), 336 (LC CDR1), (LC CDR2), and 338 (LC CDR3). In one embodiment the anti-PCSK9 portion may comprise a heavy variable region comprising the amino acid sequence of SEQ ID NO: 491 and light chain variable region comprising the amino acid sequence of SEQ ID NO: 492. Alternatively, the anti-PCSK9 portion may comprise heavy chain CDR1, CDR2, and CDR3 from SEQ ID NOS: 493-495 and light chain CDR1, CDR2, and CDR3 from SEQ ID NOS: 496-498.

In other embodiments, the antibody portion may comprise antibodies other than an anti-PCSK9 antibody (e.g., an anti-B7-H1 antibody). In one embodiment, the anti-B7-H1 antibody may comprise a heavy variable region comprising the amino acid sequence of SEQ ID NO: 422 and light chain variable region comprising the amino acid sequence of SEQ ID NO: 423.

2. Antibody or Antigen-Binding Fragments

As used herein, the term antibody or antigen-binding fragment thereof is used in the broadest sense. It may be man-made such as monoclonal antibodies (mAbs) produced by conventional hybridoma technology, recombinant technology and/or a functional fragment thereof. It may include both intact immunoglobulin molecules for example a polyclonal antibody, a monoclonal antibody (mAb), a monospecific antibody, a bispecific antibody, a polyspecific antibody, a human antibody, a humanized antibody, an animal antibody (e.g. camelid antibody), chimeric antibodies, as well as portions, fragments, regions, peptides and derivatives thereof (provided by any known technique, such as, but not limited to, enzymatic cleavage, peptide synthesis, or recombinant techniques), such as, for example, immunoglobulin devoid of light chains, Fab, Fab', F (ab')$_2$, Fv, scFv, antibody fragment, diabody, Fd, CDR regions, or any portion or peptide sequence of the antibody that is capable of binding antigen or epitope. In one embodiment, the functional part is a single chain antibody, a single chain variable fragment (scFv), a Fab fragment, or a F(ab')$_2$, fragment.

An antibody or functional part is said to be "capable of binding" a molecule if it is capable of specifically reacting with the molecule to thereby bind the molecule to the antibody. Antibody fragments or portions may lack the Fc fragment of intact antibody, clear more rapidly from the circulation, and may have less non-specific tissue binding than an intact antibody. Examples of antibody may be produced from intact antibodies using methods well known in the art, for example by proteolytic cleavage with enzymes such as papain (to produce Fab fragments) or pepsin (to produce F(ab')$_2$, fragments). Portions of antibodies may be made by any of the above methods, or may be made by expressing a portion of the recombinant molecule. For example, the CDR region(s) of a recombinant antibody may be isolated and subcloned into an appropriate expression vector.

In one embodiment, an antibody or functional part is a human antibody. The use of human antibodies for human therapy may diminish the chance of side effects due to an immunological reaction in a human individual against non-human sequences. In another embodiment, the antibody or functional part is humanized. In another embodiment, an antibody or functional part is a chimeric antibody. This way, sequences of interest, such as for instance a binding site of interest, can be included into an antibody or functional part.

In one embodiment, the antibody may have an IgG, IgA, IgM, or IgE isotype. In one embodiment, the antibody is an IgG. In one aspect, the anti-PCSK9 antibody or antigen-binding fragment thereof may be an IgG1.

3. Modifications to the Constant Domain

In one embodiment, the anti-PCSK9 antibody or antigen binding fragment comprises an Fc region. It will be understood that Fc region as used herein includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et al. supra. Fc may refer to this region in isolation, or this region in the context of an antibody, antibody fragment, or Fc fusion protein.

In one embodiment, the anti-PCSK9 antibody or antigen-binding portion thereof has a variant Fc region having reduced effector function (e.g., reduced ADCC and/or CDC). In one embodiment, the Fc region has no detectable effector function. In one embodiment, the Fc region comprises at least one non-native amino acid at one or more positions chosen from 234, 235, and 331, as numbered by the EU index as set forth in Kabat. In a specific embodiment, the present invention provides an Fc variant, wherein the Fc region comprises at least one non-native amino acid chosen from 234F, 235F, 235Y, and 331S, as numbered by the EU index as set forth in Kabat. In a further specific embodiment, an Fc variant of the invention comprises the 234F, 235F, and 331S amino acid residues, as numbered by the EU index as set forth in Kabat. In another specific embodiment, an Fc variant of the invention comprises the 234F, 235Y, and 331S amino acid residues, as numbered by the EU index as set forth in Kabat. In a particular embodiment, the anti-PCSK9 antibody or antigen-binding portion thereof has a variant Fc region, wherein the variant comprises a phenylalanine (F) residue at position 234, a phenylalanine (F) residue or a glutamic acid (E) residue at position 235 and a serine (S) residue at position 331, as numbered by the EU index as set forth in Kabat. Such mutation combinations are hereinafter referred to as the triple mutant (TM).

The serine228proline mutation (S228P), as numbered by the EU index as set forth in Kabat, hereinafter referred to as the P mutation, has been reported to increase the stability of a particular IgG4 molecule (Lu et al., J Pharmaceutical Sciences 97(2):960-969, 2008). Note: In Lu et al. it is referred to as position 241 because therein they use the Kabat numbering system, not the "EU index" as set forth in Kabat.

This P mutation may be combined with L235E to further knock out ADCC. This combination of mutations is hereinafter referred to as the double mutation (DM).

B. GLP-1 Moiety

The fusion molecule contains a GLP-1 moiety. GLP-1 may also be referenced by the synonym glucagon-like peptide-1. By GLP-1 we also reference Exendin-4, which is a GLP-1 analog. In one embodiment, the GLP-1 moiety provides glucose control and/or weight loss benefits.

In one embodiment, the full length GLP-1 molecule may be used in the fusion protein. In another embodiment, a fragment of GLP-1 may be used as a GLP-1 moiety in the fusion protein.

In one embodiment, the GLP-1 moiety has a pair of cysteine residues that allows for a disulphide bridge. In one embodiment, the cysteine is an engineered cysteine compared to the parental sequence. In one embodiment, the cysteine is an E18C mutation.

In one embodiment, the GLP-1 potency is reduced at the human GLP-1 receptor compared to wild type GLP-1 (e.g., SEQ ID NO: 29) or a GLP-1 analog (e.g., SEQ ID NO: 12). In another embodiment, the GLP-1 potency at the human GLP-1 receptor is at least about 10×, 20×, 30×, 40×, 50×, 60×, 100×, 125×, 150×, 175×, 200×, or 225× lower than wildtype GLP-1 or a GLP-1 analog. In another embodiment, the potency is reduced by similar amounts as compared to dulaglutide. The GLP-1 potency may be reduced to allow for saturation of PCSK9 while reducing side effects. In one embodiment, the GLP-1 moiety may have at least one mutation that reduces the potency of the GLP-1 moiety. In one embodiment, this offers benefits of reducing side effects, including, but not limited to nausea. In one embodiment, the mutation is a point mutation. In one embodiment, the point mutation is chosen from V19A, G2V, E15A, or L26I with respect to Exendin-4.

In one embodiment, the GLP-1 moiety is comprises any one of SEQ ID NOS: 3, 7, 12, 13, or 28-42. In another embodiment, the GLP-1 moiety is a fragment of any one of SEQ ID NOS: 3, 7, 12, 13, or 28-42 comprising at least 10, 15, 20, or 25 amino acids. In a further embodiment, the GLP-1 moiety comprises a sequence which is at least at least 70%, 75%, 80%, 85%, 90%, 95%, 96%, 97%, 98%, or 99% identical to any one of SEQ ID NOS: 3, 7, 12, 13, or 28-42. In a further embodiment, the GLP-1 moiety comprises a sequence which has 1, 2, 3, 4, 5, or 6 mutations as compared to any one of SEQ ID NOS: 3, 7, 12, 13, or 28-42.

C. Fusion and Linkers

In one embodiment, the GLP-1 moiety is fused directly or indirectly to the light chain of the anti-PCSK9 antibody or antigen binding fragment. In another embodiment, the GLP-1 moiety is fused directly or indirectly to the heavy chain of the anti-PCSK9 antibody or antigen binding fragment.

In one embodiment, a linker may be used to construct a fusion between the anti-PCSK9 antibody or antigen-binding fragment and the GLP-1 moiety. In another embodiment, the anti-PCSK9 antibody or antigen-binding fragment may be directly conjugated to the GLP-1 moiety.

If a linker is used, the linker may be chosen from any suitable linker for fusion proteins. In one embodiment, the linker may comprise a GGGGS (SEQ ID NO: 27) repeat, either alone or in combination with other amino acids, either as one, two, three, or four sets of repeats. In one embodiment, the linker may comprise other combinations of G and S, either alone or in combination with other amino acids. In some embodiments, the linker has a C-terminal Alanine (A).

In one embodiment, a specific linker may be chosen from GGGGSGGGGSGGGGSA (SEQ ID NO: 4). In one embodiment, the linker allows for a disulfide bridge to form between the C terminus of the GLP-1 moiety and another portion of the GLP-1 molecule, but not with the antibody portion. In such an instance, a linker with limited flexibility may prevent undesired disulfide bridging to the antibody portion.

In one embodiment, the linker is at least 70%, 75%, 80%, 85%, 90%, 95%, 96%, 97%, 98%, or 99% identical to SEQ ID NO: 4.

In one embodiment, the cysteine:cysteine disulfide bridge is formed by making a cysteine substitution mutation in the GLP-1 moiety. In one embodiment, the mutation is E18C.

II. Nucleic Acids Encoding Fusion Molecules

The present embodiments further provides an isolated, synthetic, or recombinant nucleic acid sequence encoding any of the fusion molecules described in section I above. Such nucleic acids encode the heavy and light chain sequences set forth herein. Alternatively, such nucleic acids include the anti-PCSK9 antibody or antigen-binding portion fused to the GLP-1 moiety portion. Due to the degeneracy of the nucleic acid code, multiple nucleic acids will encode the same amino acid and all are encompassed herein.

III. Methods of Making Fusion Molecules, Formulation, and Pharmaceutical Compositions One embodiment includes a method of producing the fusion molecule by culturing host cells under conditions wherein a nucleic acid is expressed to produce the fusion molecule, followed by recovering the fusion molecule. A variety of cell lines may be used for expressing the fusion molecule, including, but not limited to, mammalian cell lines. In one embodiment, the cell lines may be human. In another embodiment, bacterial or insect cell lines may be used. In one embodiment, the cell lines include Chinese hamster ovary (CHO) cells, variants of CHO cells (for example DG44), 293 cells, and NSO cells. In another embodiment, cell lines include VERY, BHK, Hela, COS, MDCK, 293F, 293T, 3T3, W138, BT483, Hs578T, Sp2/0, HTB2, BT2O, T47D, CRL7O3O, and HsS78Bst cells.

Recombinant expression utilizes construction of an expression vector containing a polynucleotide that encodes the fusion molecule. Once a polynucleotide has been obtained, a vector for the production of the fusion molecule may be produced by recombinant DNA technology well known in the art. Expression vectors may include appropriate transcriptional and translational control signals. This may be accomplished using in vitro recombinant DNA techniques, synthetic techniques, and in vivo genetic recombination. In one embodiment, a replicable vector comprises a nucleic acid sequence encoding an antibody or functional part operably linked to a heterologous promoter.

A variety of host-expression vector systems may be utilized to express the fusion molecule as described in U.S. Pat. No. 5,807,715. For example, mammalian cells such as Chinese hamster ovary cells (CHO), in conjunction with a vector such as the major intermediate early gene promoter element from human cytomegalovirus, are an effective expression system for antibodies (Foecking et al., Gene, 45:101 (1986); and Cockett et al., Bio/Technology, 8:2 (1990)). In addition, a host cell strain may be chosen which modulates the expression of inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the protein of the invention. To this end, eukaryotic host cells which possess the cellular machinery for proper processing of the primary transcript, glycosylation, and phosphorylation of the gene product may be used.

In bacterial systems, a number of expression vectors may be selected depending upon the use intended for the fusion molecule being expressed. For example, when a large quantity of such fusion molecule is to be produced, for the generation of pharmaceutical compositions comprising the fusion molecule, vectors which direct the expression of high levels of fusion protein products that are readily purified may be desirable. Such vectors include, but are not limited to, the *E. coli* expression vector pUR278 (Ruther et al., EMBO, 12:1791 (1983)), in which the coding sequence may be ligated individually into the vector in frame with the lac Z coding region so that a fusion protein is produced; pIN vectors (Inouye & Inouye, 1985, Nucleic Acids Res. 13:3101-3109 (1985); Van Heeke & Schuster, 1989, J. Biol. Chem., 24:5503-5509 (1989)); and the like. pGEX vectors may also be used to express foreign polypeptides as fusion proteins with glutathione-S-transferase (GST). In general, such fusion proteins are soluble and can easily be purified from lysed cells by adsorption and binding to glutathione-agarose affinity matrix followed by elution in the presence of free glutathione. The pGEX vectors are designed to introduce a thrombin and/or factor Xa protease cleavage sites into the expressed polypeptide so that the cloned target gene product can be released from the GST moiety.

In an insect system, Autographa californica nuclear polyhedrosis virus (AcNPV) is used as a vector to express foreign genes. The virus grows in Spodoptera frugiperda cells. The protein coding sequence may be cloned individually into non-essential regions (for example, the polyhedrin gene) of the virus and placed under control of an AcNPV promoter (for example, the polyhedrin promoter).

In mammalian host cells, a number of virus based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion into a non-essential region of the viral genome (e.g., region E1 or E3) will result in a recombinant virus that is viable and capable of expressing the antibody or functional part in infected hosts (e.g., see, Logan & Shenk, Proc. Natl. Acad. Sci. USA, 81:355-359 (1984)). Specific initiation signals may also be required for efficient translation of inserted antibody or functional part coding sequences. These signals include the ATG initiation codon and adjacent sequences. Furthermore, the initiation codon should generally be in frame with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol., 153:51-544(1987)).

Stable expression can be used for long-term, high-yield production of recombinant proteins. For example, cell lines which stably express the fusion molecule may be generated. Host cells can be transformed with an appropriately engineered vector comprising expression control elements (e.g., promoter, enhancer, transcription terminators, polyadenylation sites, etc.), and a selectable marker gene. Following the introduction of the foreign DNA, cells may be allowed to grow for 1-2 days in an enriched media, and then are switched to a selective media. The selectable marker in the recombinant plasmid confers resistance to the selection and allows cells that stably integrated the plasmid into their chromosomes to grow and form foci which in turn can be cloned and expanded into cell lines. Plasmids that encode the fusion molecule can be used to introduce the gene/cDNA into any cell line suitable for production in culture.

A number of selection systems may be used, including, but not limited to, the herpes simplex virus thymidine kinase (Wigler et al., Cell, 11:223 (1977)), hypoxanthineguanine phosphoribosyltransferase (Szybalska & Szybalski, Proc. Natl. Acad. Sci. USA, 48:202 (1992)), and adenine phosphoribosyltransferase (Lowy et al., Cell, 22:8-17 (1980)) genes can be employed in tk-, hgprt- or aprT-cells, respectively. Also, antimetabolite resistance can be used as the basis of selection for the following genes: dhfr, which confers resistance to methotrexate (Wigler et al., Natl. Acad. Sci. USA, 77:357 (1980); O'Hare et al., Proc. Natl. Acad. Sci. USA, 78:1527 (1981)); gpt, which confers resistance to mycophenolic acid (Mulligan & Berg, Proc. Natl. Acad. Sci. USA, 78:2072 (1981)); neo, which confers resistance to the aminoglycoside G-418 (Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIB TECH 11(5):155-2 15 (1993)); and hygro, which confers resistance to hygromycin (Santerre et al., Gene, 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds.), Current Protocols in Human Genetics, John Wiley & Sons, NY (1994); Colberre-Garapin et al., 1981, J. Mol. Biol., 150:1.

Once the fusion molecule has been produced by recombinant expression, it may be purified by any method known in the art for purification, for example, by chromatography (e.g., ion exchange, affinity, particularly by affinity for the specific antigens Protein A or Protein G, and sizing column chromatography), centrifugation, differential solubility, or by any other standard technique for the purification of proteins.

Further provided are compositions, e.g., pharmaceutical compositions, that contain an effective amount of a dual active fusion molecule as provided herein, formulated for the treatment of metabolic diseases, e.g., Type 2 diabetes.

Compositions of the disclosure can be formulated according to known methods. Suitable preparation methods are described, for example, in *Remington's Pharmaceutical Sciences,* 19th Edition, A. R. Gennaro, ed., Mack Publishing Co., Easton, Pa. (1995), which is incorporated herein by reference in its entirety. Composition can be in a variety of forms, including, but not limited to an aqueous solution, an emulsion, a gel, a suspension, lyophilized form, or any other form known in the art. In addition, the composition can contain pharmaceutically acceptable additives including, for example, diluents, binders, stabilizers, and preservatives. Once formulated, compositions of the disclosure can be administered directly to the subject.

Carriers that can be used with compositions of the disclosure are well known in the art, and include, without limitation, e.g., thyroglobulin, albumins such as human serum albumin, tetanus toxoid, and polyamino acids such as poly L-lysine, poly L-glutamic acid, influenza, hepatitis B virus core protein, and the like. A variety of aqueous carriers can be used, e.g., water, buffered water, 0.8% saline, 0.3% glycine, hyaluronic acid and the like. Compositions can be sterilized by conventional, well known sterilization techniques, or can be sterile filtered. A resulting composition can be packaged for use as is, or lyophilized, the lyophilized preparation being combined with a sterile solution prior to administration. Compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamineoleate, etc.

IV. Methods for Use of the Anti-PCSK9~GLP-1 Fusion Molecule and Kits

The anti-PCSK9~GLP-1 fusion may be used to treat diabetes or TType 2 diabetes. In one embodiment, the patient has TType 2 diabetes. In one embodiment, the patient has a high cardiovascular risk profile. In another embodiment, the patient has both TType 2 diabetes and a high cardiovascular risk profile. By high cardiovascular risk profile, it means that the patient is at higher risk for a cardiovascular event due to one or more factors: high cholesterol, high LDL cholesterol, low HDL cholesterol, high blood pressure, atherosclerosis, obesity, prior cardiovascular event (including angina, heart attack, transient ischemic attack, stroke, etc.), family history of cardiovascular event, smoking, high triglycerides, lack of physical activity, poorly controlled blood sugars, and the like.

In other embodiments, the anti-PCSK9~GLP-1 fusion may be used to treat other disease including but not limited to NASH, obesity, hypercholesterolemia, and major adverse cardiovascular events (MACE) including but not limited to acute coronary syndrome (ACS), stroke, heart failure, and malignant dysrhythmia.

In one embodiment, the fusion molecule has increased stability upon administration. In one embodiment, the increased stability is demonstrated by comparing it to a benchmark control compound dulaglutide, a GLP-1 analog fused with an Fc fragment, in an in vivo administration to mice.

In one embodiment, the fusion molecule as increased potency at the GLP-1 receptor. In one embodiment, the decreased potency is demonstrated at the human GLP-1 receptor over the benchmark control compound dulaglutide and/or wild type GLP-1.

In some embodiments, the fusion molecule promotes weight loss in a subject.

In one embodiment, the fusion molecule is administered by injection.

In other embodiments, the present disclosure provides kits comprising dual active fusion molecules, which can be used to perform the methods described herein. In certain aspects, a kit comprises a dual active fusion molecule disclosed herein in one or more containers. A kit as provided herein can contain additional compositions for combination therapies. One skilled in the art will readily recognize that the disclosed dual active fusion molecules can be readily incorporated into one of the established kit formats that are well known in the art.

Reference will now be made in detail to the present exemplary embodiments, examples of which are illustrated in the accompanying drawings. Wherever possible, the same reference numbers will be used throughout the drawings to refer to the same or like parts. Other embodiments will be apparent to those skilled in the art from consideration of the specification and practice disclosed herein. The embodiments are further explained in the following examples. These examples do not limit the scope of the claims, but merely serve to clarify certain embodiments. It is intended that the specification and examples be considered as exemplary only, with a true scope and spirit being indicated by the following claims.

EXAMPLES

Example 1. Antibody Optimisation

The anti-PCSK9 antibody PC9#2 (SEQ ID NOs. 8 and 9 for the variable heavy and light chains respectively) has been optimised to:

1_ Reduce the immunogenicity risk by reverting amino acids to the ones corresponding to the closest human germline sequence without significantly impacting the binding to PCSK9 antigen.

2_ Remove pH-dependent binding to PCSK9 by mutating histidine residues VH_52, VL_30 and VL_50 (Kabat numbering).

3_ Improve affinity for human PCSK9 at physiological pH in order to efficiently engage with the target and achieve sufficient free PCSK9 suppression following administration of PCSK9/GLP-1 peptide antibody fusion molecules.

A) Germlining

The amino acid sequences of the VH and VL domains of the anti-PCSK9 antibody PC9#2 were aligned to the known human germline sequences in the VBASE database (Tomlinson, 1997; http://vbase.mrc-cpe.cam.ac.uk/), and the closest human germline was identified by sequence similarity to be 1-46 (DP-7) (SEQ ID 417) and VK1 O18 O8 (DPK1) (SEQ ID 418) for the variable heavy and light chains respectively. FIGS. 1E and 1F are showing an alignment of PC9#2 variable domains with those germline sequences.

A structure model of the anti-PCSK9 PC9#2 antibody in complex with human PCSK9 antigen has been generated using the primary amino acid sequence of PC9#2 variable domains and previously described crystal structure of human PCSK9 in complex with another anti-PCSK9 antibody deposited in the Protein Data Bank using PBD ID code 3SQO (Liang et al., 2012, J. Pharm. Exp. Ther., Vol. 340, p 228-236).

Using that structure model, the following residues were identified as non-contacting with PCSK9 antigen but nonetheless solvent-exposed: Arg56, Asn58, Glu61, Lys64 and Ser65 in the variable heavy chain as well as Arg24 in the variable light chain (Kabat numbering). Because those residues are different from the closest germline sequences and might be solvent-exposed, they can present some immunogenicity risks. Without being bound by theory, mutating those residues should not significantly impact the ability of the antibody to strongly bind PCSK9 as they should not contribute to the interaction network between the antibody and its antigen.

Mutations R56S, N58S, E61Q, K64Q and S65G were then introduced in PC9#2 heavy chain sequence as well as K24Q in the light chain using standard molecular biology techniques to generate the antibody PC9#2_FG of SEQ ID 5 and 6 for the variable heavy and light chains respectively.

Anti-PCSK9 PC9#2 and PC9#2_FG were produced as human IgG1-TM antibodies as described in Example 2 and characterised for binding to human PCSK9 using Biacore as described in Example 17. Kinetic parameters at pH 7.4 for those compounds are summarised in Table 2. Both antibodies exhibit similar on-rate, off-rate and affinity for human PCSK9 demonstrating that the germlining mutagenesis had no impact on antigen binding.

TABLE 2

Kinetic parameters for human PCSK9 at physiological pH of germlined and non-germlined version of PC9#2antibody

| Compound | ka (1/Ms) | kd (1/s) | KD (M) |
|---|---|---|---|
| PC9#2 | 2.70E+05 | 5.10E−04 | 1.89E−09 |
| PC9#2_FG | 3.03E+05 | 5.40E−04 | 1.78E−09 |

B) Removing pH Dependent Binding and Improving Affinity for Human PCSK9

Anti-PCSK9 antibodies PC9#2 and PC9#2_FG exhibit pH-dependent binding properties as they bind strongly to human PCSK9 antigen at physiological pH but rapidly dissociate from their target at acidic pH. That feature should enable the antibodies to dissociate from PCSK9 in the acidic compartment of endosome in order to be recycled at cell surface rather than being sent to lysosome for degradation. This should ultimately translate into a longer antibody in vivo half-life.

Table 3 are comparing off-rate (kd) for those two compound with human PCSK9 at pH7.4 (physiological) and 6.0 (acidic) determined by Biacore as described in Example 17 but with the following modifications. After antibody capture onto the CM5 chip, human PCSK9 antigen diluted to concentrations ranging from 1 nM to 200 nM in running buffer pH7.4 (10 mM sodium phosphate pH 7.4, 150 mM sodium chloride, 1 mg/mL BSA, 0.05% Tween20) were injected for 10 minutes. After the association phase, running buffer at pH7.4 or pH6.0 were injected for 10 minutes dissociation phase. Global dissociation rates were calculated using a 1:1 binding kinetics model.

TABLE 3

Dissociation constant (kd) at physiological and acidic pH of germlined and non-germlined version of PC9#2antibody.

| Compound | kd (1/s) pH 7.4 | kd (1/s) pH 6.0 | kd ratio |
|---|---|---|---|
| PC9#2 | 5.10E−04 | 3.24E−03 | 6.4 |
| PC9#2_FG | 5.40E−04 | 6.47E−03 | 12 |

Long antibody in vivo half-life is not desirable for PCSK9/GLP-1 fusion molecules as it might lead to the accumulation of drug metabolites able to bind PCSK9 but degraded in the GLP-1 analogue peptide and thus unable to activate the GLP-1 receptor.

In addition, genetic fusion of a GLP-1 analogue peptide in front of the light chain of the anti-PCSK9 PC9#2 was slightly impacting the affinity of the compound for human PCSK9 (19 nM) compared to PC9#2 antibody (7 nM) as shown in Example 5, Table 11. Affinity maturation of PC9#2_FG was then required in order to counterbalance the negative impact of GLP-1 analogue light chain fusion on affinity for human PCSK9 antigen.

To remove pH-dependent binding, histidine residues in position 52 of the heavy chain as well as in position 30 and 50 of the light chain need to be mutated. Based on the structure model described above and subsequent analysis of PC9#2 in complex with human PCSK9, the following mutations were identified as potentially beneficial for antibody binding to PCSK9 and could lead to an affinity improvement: heavy chain H52K or H52S, light chain H30Y, H30K or H30S and light chain H50Y or H50S.

Combination of all those mutations in the sequence of PC9#2_FG were generated using standard molecular biology techniques in order to produce optimised antibodies. Table 4 is summarising the different compounds resulting from the combination experiment.

TABLE 4

PC9#2_FG mutations to generate optimised antibodies

| # | VH_H52 | VL_H30 | VL_H50 | Antibody name | SEQ ID |
|---|---|---|---|---|---|
| 1 | K | Y | Y | HS1 | 424 and 425 |
| 2 | K | Y | S | HS2 | 426 and 427 |
| 3 | K | K | Y | HS3 | 428 and 429 |
| 4 | K | K | S | HS4 | 430 and 431 |
| 5 | K | S | Y | / |  |
| 6 | K | S | S | HS5 | 432 and 433 |
| 7 | S | Y | Y | HS6 | 434 and 435 |
| 8 | S | Y | S | HS7 | 436 and 437 |
| 9 | S | K | Y | HS8 | 438 and 439 |
| 10 | S | K | S | HS9 | 1 and 2 |
| 11 | S | S | Y | / |  |
| 12 | S | S | S | HS10 | 442 and 443 |

Combination of H30S and H50Y mutations in PC9#2_FG light chain failed to deliver and compound #5 and #11 have subsequently not been generated.

Antibodies were produced as human IgG1-TM as described in Example 2 and tested for their ability to block the binding of PC9#2 to human PCSK9 using an epitope competition assay as described in Example 3. Data are summarised in Table 5 and show that HS7, HS9 and HS10 have an IC50 at least 10-fold lower compared to the parent antibody PC9#2_FG suggesting that those antibodies may have a significantly better affinity for PCSK9 than PC9#2_FG.

TABLE 5

Inhibition of PC9#2 binding to human PCSK9 using anti-PCSK9 antibodies as competition reagent.

| Antibody | IC50 (M) | Ratio over PC9#2_FG |
|---|---|---|
| HS1 | 5.6E−10 | 1.3 |
| HS2 | 9.3E−11 | 7.8 |
| HS3 | 7.0E−10 | 1.0 |
| HS4 | 1.2E−10 | 6.1 |
| HS5 | 2.2E−10 | 3.3 |
| HS6 | 1.7E−10 | 4.3 |
| HS7 | 6.3E−11 | 11.6 |
| HS8 | 1.6E−10 | 4.6 |
| HS9 | 6.6E−11 | 11.1 |
| HS10 | 7.0E−11 | 10.4 |
| PC9#2_FG | 7.3E−10 | 1.0 |

Antibody HS9 has been further characterised and compared to the parental antibody PC9#2_FG for its binding parameters to human PCSK9 at physiological pH by Biacore as described in Example 17. As shown in Table 6, engineered anti-PCSK9 antibody HS9 displays a 3-fold improvement in affinity for human PCSK9 compared to PC9#2_FG at physiological pH, mainly due to a reduction in off-rate (kd).

TABLE 6

Kinetic parameters for human PCSK9 at physiological pH of engineered antibody HS9 compared to PC9#2_FG

| Antibody | ka (1/Ms) | kd (1/s) | KD (M) |
|---|---|---|---|
| PC9#2_FG | 3.09E+05 | 6.57E−04 | 2.13E−09 |
| HS9 | 3.81E+05 | 2.57E−04 | 6.75E−10 |

In a separate experiment, pH dependent binding of HS9 anti-PCSK9 antibody has been compared to PC9#2_FG using Biacore as described above. Table 7 is showing the dissociation constant (kd) at physiological and acidic pH for those two compounds. Contrary to PC9#2_FG which dissociates more rapidly at pH6.0 than at pH7.4, HS9 displays a lower kd at acidic than at physiological pH demonstrating that it is dissociating from PCSK9 more slowly at pH6.0 than at pH7.4.

TABLE 7

Dissociation constant (kd) at physiological and acidic pH of engineered antibody HS9 compared to PC9#2_FG.

| Antibody | kd (1/s) pH 7.4 | kd (1/s) pH 6.0 | ratio kd |
|---|---|---|---|
| PC9#2_FG | 6.50E−04 | 7.40E−03 | 11.4 |
| HS9 | 2.04E−04 | 9.82E−05 | 0.5 |

Example 2. Preparation of a Dual Action Fusion Molecule

A dual action fusion molecule was made according with a large-scale structure as shown in FIG. 1A of: GLP-1 moiety—Linker—Antibody Light Chain. SEQ ID NO: 3 was used as the GLP-1 moiety, SEQ ID NO: 4 was used as the linker, and SEQ ID NO: 1 and 2, were used as the heavy and light chain respectively.

In this embodiment, the N-terminal end of GLP-1 analogue peptides was free in order to most efficiently engage and activate the GLP-1 receptor; peptides were fused to the N-terminal of antibody variable domains. A linker sequence was used in many constructs between the end of the peptide and the start of variable domain in order to minimize the impact of the fusion on peptide and/or antibody activities. Peptides were fused either at the heavy chain or the light chain of antibodies in order to obtain two peptide moieties per fusion molecule. Large scale structure of such fusions are shown FIG. 1B (heavy chain fusion) and 1C (light chain fusion). In some embodiments, peptides may be fused at both the heavy and light chains to display four peptide moieties per fusion molecule (shown prophetically in FIG. 1D).

Genes coding for GLP-1 analogue peptides in fusion with antibody variable domains were built by overlapping PCR using standard methods. Unique restriction sites were incorporated at the 5' and 3' end of the DNA fragment to enable cloning in the expression vectors.

The VH domain, with or without a peptide/linker fusion, was cloned into a vector containing the human heavy chain constant domains and regulatory elements to express whole IgG1 triple mutant (IgG1-TM) heavy chain in mammalian cells. IgG1-TM format is similar to human IgG1 but Fc sequence incorporating mutations L234F, L235E and P331S to reduce its ability to trigger antibody-dependent cell-mediated cytotoxicity and complement-dependent cytotoxicity (Oganesyan V. et al., 2008, Acta Cryst., D64: 700-704). The VL domain, with or without peptide/linker fusion, was cloned into a vector for the expression of the human light chain constant domains and regulatory elements to express whole IgG light chain in mammalian cells. An OriP fragment was included in the heavy and light chain expression vectors to facilitate use with CHO cells and to allow episomal replication.

To obtain IgGs and peptide antibody fusions, the heavy and light chain expressing vectors were transiently transfected into 30 mL (small scale) or 400 mL (medium scale) of CHO mammalian cells. Table 8 is summarizing the different products that can be obtained by co-transfection of the heavy and light chain expressing vectors with or without a peptide/linker fusion.

TABLE 8

Product description when using heavy and light chain vectors co-transfection

| # | Heavy chain vector | Light chain vector | Product |
|---|---|---|---|
| 1 | VH without peptide fusion | VL without peptide fusion | IgG |
| 2 | VH with peptide fusion | VL without peptide fusion | Peptide/antibody VH fusion (FIG. 1B) |
| 3 | VH without peptide fusion | VL with peptide fusion | Peptide/antibody VL fusion (FIG. 1C) |
| 4 | VH with peptide fusion | VL with peptide fusion | Peptide/antibody VH + VL (shown prophetically in FIG. 1D) |

Compounds were expressed and secreted into the medium. Harvests were pooled and filtered before compound purification using Protein A chromatography. Culture supernatants were loaded on a column of appropriate size of MabSelectSure (GE Healthcare Life Sciences) and washed with 1×DPBS (Gibco). Bound compound was eluted from the column using 0.1 M Sodium Citrate pH 3.0 and neutralised by the addition of Tris-HCl pH 9.0. For small scale transfection, eluted material was buffer exchanged into 1×DPBS using PD10 columns (GE Healthcare). For medium scale transfection, eluted material was further purified by Size Exclusion Chromatography (SEC) using either a HiLoad 16/600 Superdex 200 prep grade column (GE Healthcare) for sample volumes of up to 5 ml or a HiLoad 26/600 Superdex 200 column (GE Healthcare) for sample volumes of up to 12 ml. Isocratic elution was performed using 1×DPBS as the running buffer.

Compound concentration was determined spectrophotometrically using an extinction coefficient based on the amino acid sequence according to the protocol in Mach, H. et al., Statistical determination of the average values of the extinction coefficients of tryptophan and tyrosine in native proteins, Anal Biochem, 200(1):74-80 (1992). Purified compounds were analysed for aggregation and degradation using SEC-HPLC and SDS-PAGE. SEC-HPLC was performed by loading 70 μL of sample onto a TSKgel G3000SWXL 7.8 mm×300 mm column (Tosoh Bioscience) using a flow rate of 1 mL/min and 0.1M Sodium Phosphate Dibasic anhydrous plus 0.1M Sodium Sulphate at pH 6.8 as running buffer. SDS-PAGE is run by loading 2 μg protein on a Nu PAGE® 4%-12% Bis-Tris (Invitrogen) using 1× Nu PAGE® MES SDS Running Buffer (Invitrogen). Compounds from medium scale transfections were further characterized for integrity by Electro-Spray Ionisation Mass Spectrometry (ESI-MS) and tested for endotoxin level using the Limulus Amebocyte Lysate (LAL) Kinetic-QCL (Lonza). For ESI-MS analysis, samples were prepared at 1 mg/mL in 10 mM Tris-HCl pH 8.0. A 30 minutes reduction at 37° C. using 10 mM DTT was carried out prior analysis. Data were acquired using a Waters ACQUITY UPLC® I-Class system coupled to a Waters SYNAPT G1 QTOF Mass Spectrometer, operated using MassLynx software. The mobile phases used were highly purified water plus 0.01% trifluoroacidic acid (TFA), 0.1% formic acid (A) and acetonitrile +0.01% TFA, 0.1% FA (B). Separation between heavy and light chain was achieved using a 2.1 mm×50 mm Waters BEH300 C4 column, heated at 60° C. The flow rate was set at 0.3 mL/min, with 22 minutes total run time. Samples (10 pmol) were injected onto the column and MS data were acquired in positive ion mode, using the following electrospray source parameters: capillary voltage: 3.4 kV, 81° C. source temperature: 81° C., desolvation temperature: 24° C. Data were acquired between 500 and 4500 Da.

Example 3. In Vitro Characterization of a GLP-1 Analogue in Genetic Fusion with Anti-PCSK9 Antibodies To evaluate the feasibility of generating dual activity molecules by genetic fusion between GLP-1 receptor agonist peptides and anti-PCSK9 antibodies, the GLP-1 analogue peptide of SEQ ID NO:28 was fused using a linker of SEQ ID NO:4 to the heavy or light chain variable domains of seven different previously identified anti-PCSK9 antibodies.

1_ PC9#1 with antibody variable heavy chain of SEQ ID NO:10 and antibody variable light chain of SEQ ID NO:11.

2_ PC9#2 with antibody variable heavy chain of SEQ ID NO:8 and antibody variable light chain of SEQ ID NO:9.

3_ PC9#3 with antibody variable heavy chain of SEQ ID NO: 404 and antibody variable light chain of SEQ ID NO: 405.

4_ PC9#4 with antibody variable heavy chain of SEQ ID NO: 406 and antibody variable light chain of SEQ ID NO: 407.

5_ PC9#5 with antibody variable heavy chain of SEQ ID NO: 408 and antibody variable light chain of SEQ ID NO: 409.

6_ PC9#6 with antibody variable heavy chain of SEQ ID NO: 410 and antibody variable light chain of SEQ ID NO: 411.

7_ PC9#7 with antibody variable heavy chain of SEQ ID NO: 412 and antibody variable light chain of SEQ ID NO:413.

PCSK9 activity of each peptide-antibody fusions was assessed using Homogenous Time Resolved Fluorescence (HTRF) epitope competition assays. In these assays a fluorescence resonance energy transfer (FRET) complex is formed between Streptavidin Cryptate, biotinylated-PCSK9 and a fluorescently (DyLight 650) labelled anti-PCSK9 antibody. Unlabelled peptide-antibody fusions that bind the same or overlapping epitopes of PCSK9 as that bound by the fluorescently labelled antibody will compete resulting in a reduction in FRET signal.

Labeling of the anti-PCSK9 antibodies was carried out using a DyLight-650 (Thermo Scientific 84536) according to the manufacturer instructions. For the assay all samples and reagents were prepared in assay buffer containing 1× Phosphate Buffered Saline, 0.1% BSA (Sigma A9576) and 0.4M Potassium Fluoride. Test samples of peptide-antibody fusions or control antibodies were prepared in 384 well polypropylene plates by 3-fold serial dilutions. Samples (5 µl) or assay buffer (total binding control wells) were transferred to a 384-well assay plate (Costar 3676) and incubated for 4 hours at room temperature with 1 nM Streptavidin Cryptate (Cisbio 61SAXLB), 0.05-0.5 nM biotinylated-PCSK9 and 0.1-2 nM Dy650 labelled anti PCSK9 antibody in a 20 µl total assay volume. Non-specific binding (NSB) control wells were set up with the biotinylated PCSK9 omitted. Time resolved fluorescence emission at 665 nm and 620 nm was measured following excitation at 320 nm using the Perkin Elmer Envision. The ratio of the 665 nm counts/620 nm counts was calculated and multiplied by 10000 to give HTRF Counts. Delta F % was then calculated using the following equation.

$$\text{Delta F \%} = \left(\frac{\text{Sample } HTRF \text{ Counts} - NSBHTRF \text{ Counts}}{NSB\ HTRF \text{ Counts}}\right) \times 100$$

The results were expressed as % specific binding according to the following equation:

$$\% \text{ Specific Binding} = \left(\frac{(\text{Sample Delta F \%} - NSB \text{ Delta F \%})}{(\text{Total Binding Delta F \%} - NSB \text{ Delta F \%})}\right) \times 100$$

FIGS. 2A-G and FIGS. 3A-G showing the inhibition of human PCSK9 binding to anti-PCSK9 antibodies using a titration of unlabelled heavy chain or light chain peptide antibody fusions respectively. Isotype match irrelevant antibody NIP228 IgG1-TM alone (Control#1) or in fusion to the heavy (Control#2) or light chain (Control#3) with a GLP-1 analogue peptide of SEQ ID NO:28 using a linker of SEQ ID NO:4 were used as negative controls.

Potency of each peptide antibody fusion at human GLP-1 receptor was assessed using a cAMP production assay. Stable cell lines expressing human GLP-1 receptor was generated in CHO cells by standard methods. GLP-1 receptor activation by tested compounds will result in downstream production of cAMP second messenger that can be measured in a functional activity assay. Low protein binding 384-well plates (Greiner) were used to perform eleven 1 in 4 serial dilutions of test compound that were made in assay medium (0.1% bovine serum albumin in Hanks Balanced Salt Solution (GIBCO or Sigma), containing 0.5 mM IBMX (Sigma)). All sample dilutions were made in duplicate. A frozen cryo-vial of cells expressing human GLP-1 receptor was thawed rapidly in a water-bath, transferred to pre-warmed assay media and spun at 240 xg for 5 minutes. Cells were then re-suspended in assay buffer at the optimized concentration of $1 \times 10^5$ cells/mL and dispensed at 5 uL per well to black shallow-well u-bottom 384-well plates (Corning). 5 µL of test compound was transferred from the dilution plate to the cell plate and incubated at room temperature for 30 minutes. cAMP levels were measured the cAMP dynamic 2 HTRF kit (Cisbio), following the two step protocol as per manufacturer's recommendations. Briefly, anti-cAMP cryptate (donor fluorophore) and cAMP-d2 (acceptor fluorophore) were made up separately by diluting each 1/20 in conjugate & lysis buffer provided in the kit. 5 uL of anti-cAMP cryptate was added to all wells of the assay plate and 5 uL of cAMP-d2 added to all wells except non-specific binding wells, to which only conjugate and lysis buffer was added. Plates were incubated at room temperature for one hour and then read on an Envision (Perkin Elmer) using excitation wavelength of 320 nm and emission wavelengths of 620 nm and 665 nm. Data was transformed to % Delta F as described in manufacturer's guidelines and analyzed by unconstrained 4-parameter logistic fit of data, curve mid-point to determine $EC_{50}$.

Activation of the human GLP-1 receptor by heavy chain (A) or light chain (B) peptide antibody fusions are shown in FIGS. 4A-B, respectively. Free human GLP-1 peptide (Bachem) and irrelevant isotype match NIP228 human IgG1-TM without peptide were used as positive and negative controls respectively.

To conclude, all tested fusions were able to compete with anti-PCSK9 antibodies for binding to human PCSK9 as well as activating the human GLP-1 receptor. Those fusion molecules between a GLP-1 analogue peptide and different anti-PCSK9 antibodies display dual activity and can be used to provide combined pharmacology.

Example 4. In Vivo Stability of Existing GLP-1 Analogues in Antibody Fusion

Without target-mediated clearance, human IgGs have a long circulating half-life in man of around 21 days. This is notably due to the rescue of internalised antibodies by FcRn receptor. After non-specific uptake by cells, antibodies can bind to FcRn in the acidic environment of endosomes and be directed to the cell surface and back into circulation rather than to lysosomes for degradation.

In order to achieve maximum efficacy, GLP-1 analogue peptide in fusion with anti-PCSK9 antibody molecules should display adequate in vivo activity half-life for both activation of the GLP-1 receptor and PCSK9 suppression mediated by the peptide and the antibody moieties respectively. For instance if the peptide is quickly inactivated after injection, a majority of the product will only be functional for PCSK9 suppression and will not properly engage with the GLP-1 receptor over time to provide efficient glucose control through the dosing period.

In order to assess in vivo stability of existing GLP-1 analogue peptides when in antibody fusion, the following fusions were generated:

1: A GLP-1 analogue peptide of SEQ ID NO:28 was fused using a linker of SEQ ID NO:4 to the heavy chain of the irrelevant NIP228 human IgG1-TM antibody of SEQ ID NO: 414 and 415 (compound NIP228_GLP-1_VH).

2: Exendin-4 peptide, a GLP-1 analogue derived from Gila monster' saliva, of SEQ ID NO:12 was fused using a linker of SEQ ID NO:4 to the light chain of the anti-PCSK9 antibody PC9#2 of SEQ ID NO 9 (compound PC9#2_Exe4_VL).

3: A GLP-1 analogue peptide of SEQ ID NO:28 was fused using a linker of SEQ ID NO:4 to human IgG4 Fc fragment of SEQ ID NO: 416 (compound GLP-1-Fc)

4: A GLP-1 analogue peptide of SEQ ID NO:28 was fused using a linker of SEQ ID NO:4 to the light chain of the anti-PCSK9 antibody PC9#2 of SEQ ID NO 9 (compound PC9#2_GLP-1_VL).

All compounds are active at the human GLP-1 receptor in vitro and display $EC_{50}$ in the cAMP assay described in Example 3 of 2.08E-10 M, 1.12E-10 M, 1.12E-10 M and 1.03E-10 M for NIP228_GLP-1_VH, PC9#2_Exe4_VL, GLP-1-Fc and PC9#2_GLP-1_VL respectively.

Compounds NIP228_GLP-1_VH and PC9#2_Exe4_VL were injected intravenously to rat and serum or plasma samples were collected at several timepoints post-injection. Compound concentration in serum or plasma (exposure) and concentration in active compound for GLP-1 activity were determined for each sample. Comparison between decline over time of total compound (exposure) and active compound at GLP-1 receptor provides an assessment of the in vivo stability for the GLP-1 analogue peptide in antibody fusion.

Levels of total human IgG1 antibody in rat plasma or serum were quantified by a generic sandwich enzyme-linked immunosorbent assay (ELISA) method using the Gyrolab platform (Gyros AB). Human IgG1 was captured by a biotinylated monoclonal anti-human IgG1 antibody (clone JDC-10, Southern Biotech, for plasma samples or in-house clone TM446 for serum samples) at 100 ug/mL and detected by an Alexa-labelled monoclonal anti-human IgG1 antibody at 25 nM (BD Pharmingen clone G18-145 for plasma samples) or 10 nM (the Binding Site AU003CUS01 for serum samples) on Gyrolab Bioaffy 200 CD. Standards, controls, plasma or serum samples, wash solution, capture and detection antibodies were added to a 0.2 mL 96-well PCR plate (Thermo Scientific) according to the Gyrolab method and loaded onto the machine with the CD200 plate. All samples were analyzed in duplicate. The mean response of each human IgG standard was plotted against concentration and the points were fit using a 5-parameter weighted logistic model using the Gyrolab Evaluator software.

The concentration of active peptide-antibody fusion at human GLP-1 receptor in rat samples was estimated using an ex-vivo cAMP cell based assay. Reference compounds were spiked into naïve rat serum or plasma at a known concentration to be used as a standard. All samples were serially diluted in assay medium and examined using the cAMP dynamic 2 HTRF kit (Cisbio) as described in Example 3 for serum samples or using the LANCE® Ultra cAMP Detection Kit (Perkin Elmer) for plasma samples.

Test samples were plotted using the same top concentration as the equivalent reference. The $EC_{50}$ values obtained could then be used to calculate the Sample Ratio (Sample $EC_{50}$/$EC_{50}$ reference compound) and then the estimated concentration in active GLP-1 compound (known top concentration of reference compound spiked into rat plasma or serum/Sample Ratio). Rat serum or plasma alone has a quenching effect on the cryptate donor signal and gives concentration-dependent activation of cAMP that can be diluted out. Any tested compound must therefore possess cAMP activity above that of the rat serum or plasma baseline (termed the limit of detection) in order to have an observable effect in the activity assay.

Figure 5A:
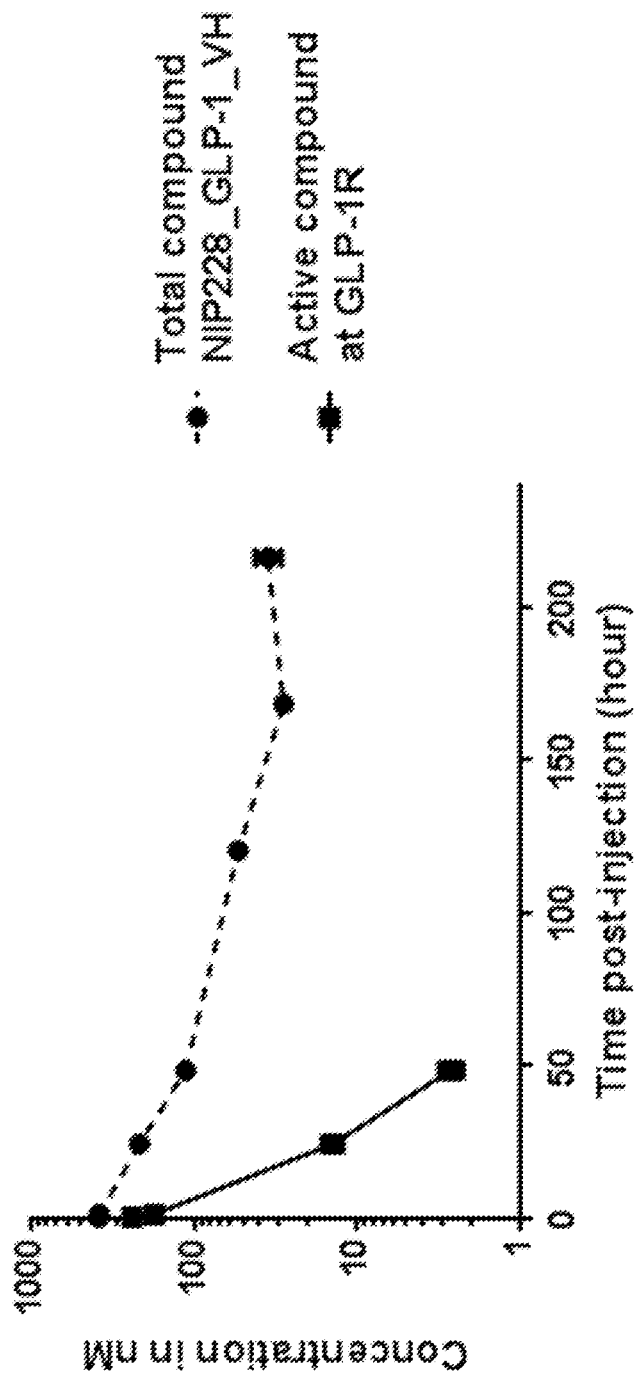
FIG. 5A illustrates stability in rat for a GLP-1 analogue in heavy chain fusion with the control antibody NIP228.
Figure 9:
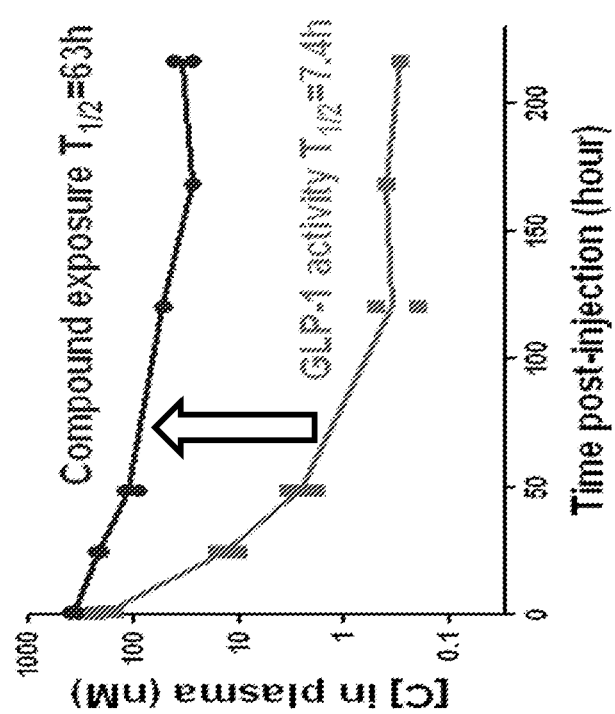
FIG. 9 shows stability in rat of NIP228_GLP1_VH, a GLP-1 analogue in heavy chain fusion with the control antibody NIP228).

Compound NIP228_GLP-1_VH was injected at 2 mg/kg in three Wistar rats (Charles River) and blood samples for each animal were collected in EDTA tubes containing dPP4 inhibitor at 2 minutes, 1 h, 24 h, 48 h, 120 h, 168 h and 216 h post injection. Total compound and concentration in active GLP-1 compound in rat plasma over time are shown in FIGS. 5A and 9. Concentration of active compound in samples collected after 48 h cannot be determined as they were below the lower limit of quantification of the assay.

Compound PC9#2_Exe4_VL was injected at 1 mg/kg in three CD rats (Charles River) and blood samples were collected in plain tubes containing dPP4 inhibitor at 30 minutes, 6 h, 24 h, 48 h, 96 h, 240 h and 336 h post injection. Serum samples were prepared by leaving the tubes on the bench for 30 minutes followed by 2 minutes centrifugation at 13000 rpm. Exposure and concentration in active GLP-1 compound in rat serum over time is shown in FIG. 5B. Concentration of active compound in samples collected after 48 h cannot be accurately determined as they were below the lower limit of quantification of the assay.

In vivo half-life in rat of NIP228_GLP-1_VH and PC9#2_Exe4_VL for both exposure and active compound at GLP-1 receptor are presented in Table 9.

TABLE 9

Compound and active GLP-1 in vivo half-life in rat of existing GLP-1 analogues in antibody fusion

| Compound | Experimental design | Compound in vivo half life (h) | Active GLP-1 in vivo half life (h) |
|---|---|---|---|
| NIP228_GLP-1_VH | 2 mg/kg IV in Wistar rats | 63 | 7.4 |
| PC9_2_Exe4_VL | 1 mg/kg IV in CD rats | 88 | 5.7 |

For both NIP228_GLP-1_VH and PC9#2_Exe4_VL compounds, activity at GLP-1 receptor is loss much quicker than the compound itself demonstrating in vivo peptide instability.

Compounds GLP-1-Fc and PC9#2_GLP-1_VL were injected intravenously to healthy C57/B6 mice (7-8 weeks old, females, Charles River) and plasma samples were collected at several timepoints. Compound concentration in plasma (exposure) and concentration in active compound for GLP-1 activity were determined for each sample as described above.

GLP-1-Fc was injected at 1 mg/kg. Groups of three mice were sacrificed at each of the following time points: pre-injection, 2 minutes, 1 h, 6 h, 24 h, 48 h, 72 h and 96 h post injection. Blood for each animal were collected in EDTA tubes containing dPP4 inhibitor. Plasma samples were then centrifuged at 14000 rpm for 5 min at 4° C. and stored at −80° C. pending analysis.

PC9#2_GLP-1_VL was injected at 5 mg/kg and mice were sacrificed at each of the following time points: pre-injection, 5 minutes, 6.5 h, 24 h, 72 h and 168 h post injection. Samples were treated as described above.

Figure 5C:
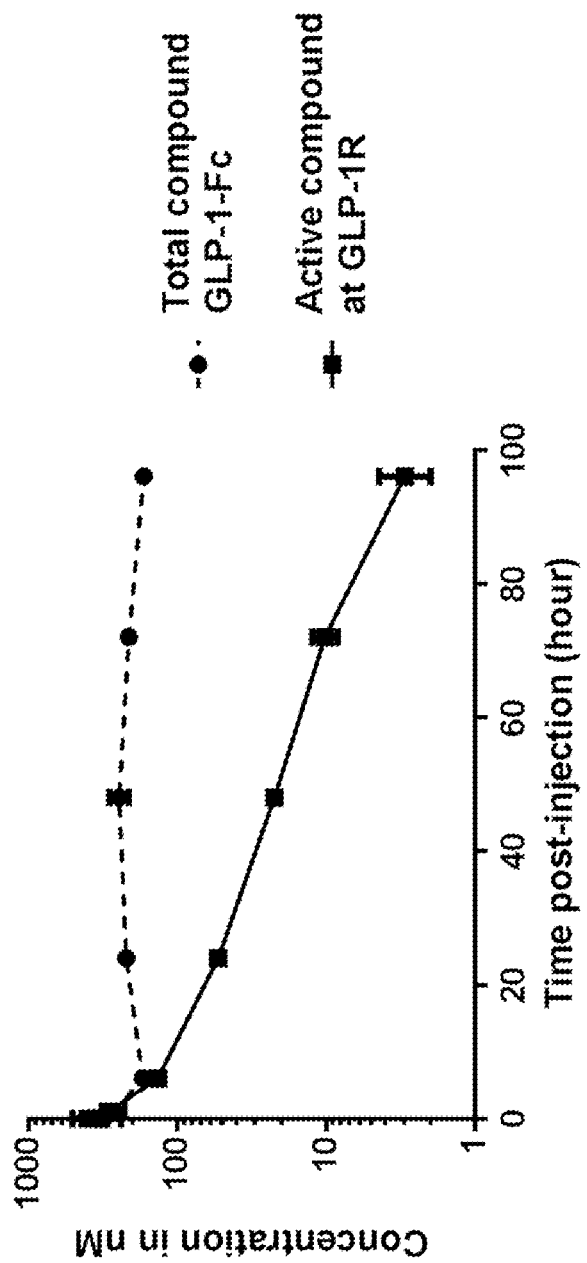
FIG. 5C demonstrates stability in mice for a GLP-1 analogue in fusion with human IgG4 Fc fragment.
Figure 5D:
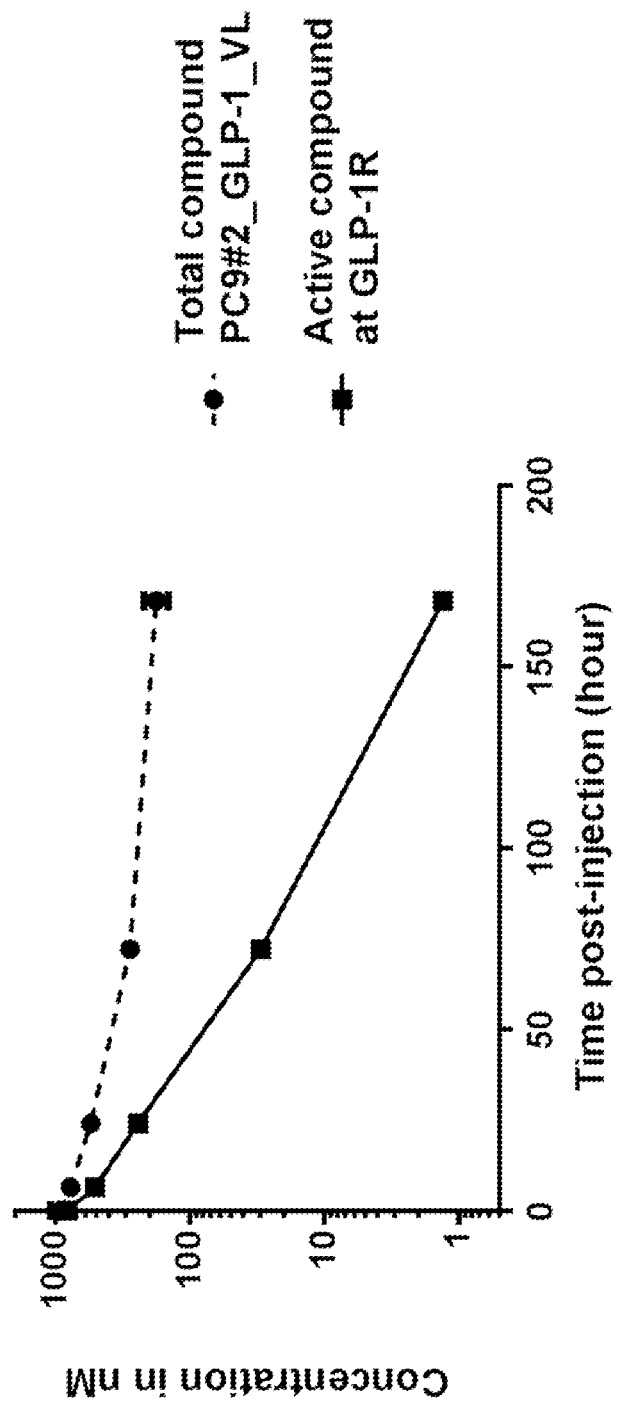
FIG. 5D demonstrates stability in mice for a GLP-1 analogue in light chain fusion with the anti-PCSK9 antibody PC9#2.
Figure 10:
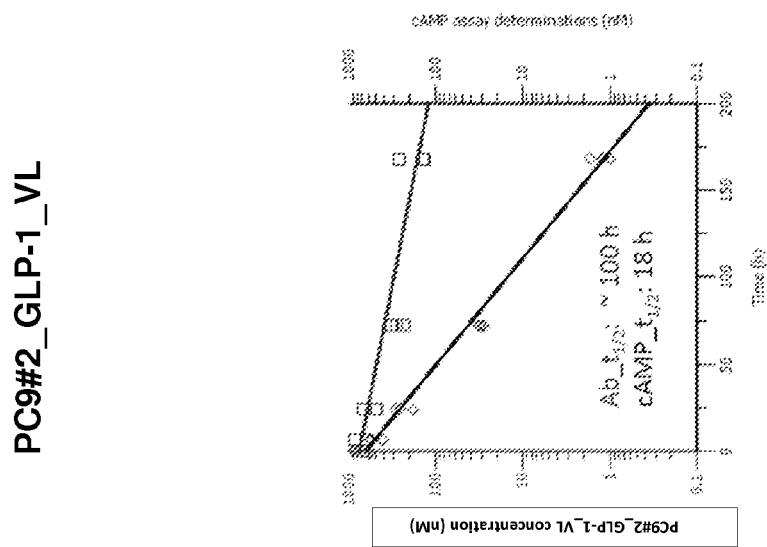
FIG. 10 shows stability in mice of PC9#2_GLP-1_VL, a GLP-1 analogue in light chain fusion with the anti-PCSK9 antibody PC9#2.

Exposure and concentration in active GLP-1 compound in mouse plasma over time for GLP-1-Fc are shown in FIGS. 5C and 14A and PC9#2_GLP-1_VL are shown in FIGS. 5D and 10, respectively.

In vivo half-life in mice of GLP-1-Fc and PC9#2_GLP-1_VL for both exposure and active GLP-1 are presented in Table 10.

TABLE 10

Compound and active GLP-1 in vivo half-life in mice of existing GLP-1 analogues in antibody or Fc fusion

| Compound | Experimental design | Compound in vivo half life (h) | Active GLP-1 in vivo half life (h) |
|---|---|---|---|
| GLP-1-Fc | 1 mg/kg in C57/B6 mice | ~100 | 16 |
| PC9#2_GLP-1_VL | 5 mg/kg in C57/B6 mice | ~100 | 18 |

As observed for NIP228_GLP-1_VH and PC9#2_Exe4_VL in rat, activity at GLP-1 receptor for both GLP-1-Fc and PC9#2_GLP-1_VL following injection in mice is loss quicker than the compound itself, demonstrating in vivo peptide instability.

Quick inactivation for both GLP-1 analogues of SEQ ID NO:28 and SEQ ID NO:12 will impact efficient glucose control for PCSK9/GLP-1 fusion molecules and GLP-1 analogue peptides with better in vivo stability need to be engineered.

Example 5. Affinity for huPCSK9

Figure 6:
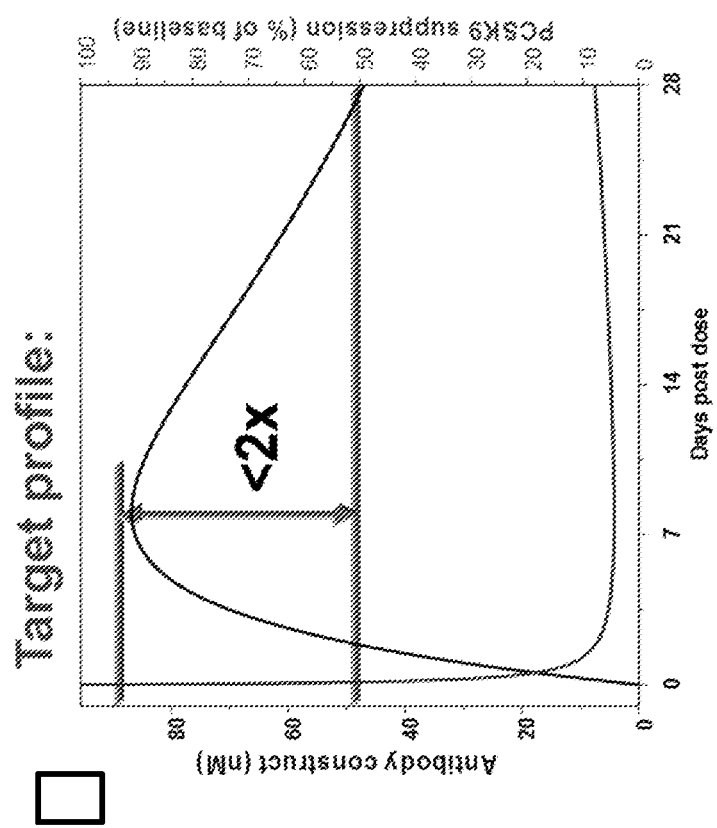
FIG. 6 demonstrates a potential target profile to guide PCSK9 affinity and GLP-1 potency.

The PCSK9 antibody was used as a benchmark control. Data are presented in Table 11 and a visual representation of the PC9#2_GLP1 molecule and the anti-PC9#2 antibody used as a benchmark control are shown in FIG. 8. A visualization of a potential target profile to guide PCSK9 affinity and GLP-1 potency is provided in FIG. 6.

Association (ka or kon), dissociation (kd or koff) and equilibrium dissociation constants (KD) for PCSK9 binding were determined at 25° C. by Surface Plasmon Resonance (SPR) using the Biacore 2000 biosensor (GE Healthcare).

A Protein G surface was first created on a CM5 sensor chip (GE Healthcare). Human antibodies were then captured on the chip surface before injecting different concentrations of human, cynomolgus or rat PCSK9. Global dissociation rates were first calculated followed by global on-rate calculations both using a 1:1 binding kinetics model.

TABLE 11

Affinity for huPCSK9 (Biacore)

| Test Compound | Kd (nM) | $k_{on}$ ($M^{-1} \cdot s^{-1}$) | $k_{off}$ ($s^{-1}$) |
|---|---|---|---|
| PC9#2 (SEQ ID NO. 8 & 9) | 7 | 7.8E+04 | 5.5E−04 |
| PC9#2_GLP1 (SEQ ID NO: 8, 9, 4, & 28) (with the light chain fusion SEQ ID NO: 43) | 19 | 2.7E+04 | 5.0E−04 |
| x change | 2.7 | 2.9 | 0.9 |

This demonstrates that the fusion is only marginally impacting PCSK9 binding.

Additionally, the dual action fusion molecule HS9_DSB7 was tested in a Biacore assay as described in Example 17 to determine its affinity for human PCSK9. The PCSK9 antibody alone (PC9_2_FG_HS#9 of SEQ ID 1 and 2 for heavy and light chain respectively) was used as a benchmark control. Table 12 provides the data. This data demonstrates that the fusion is only marginally impacting PCSK9 binding across species (human (Hu), cynomolgus monkeys (Cy) and rat).

TABLE 12

Affinity for huPCSK9, CyPCSK9, and RatPCSK9 (Biacore)

| Summary | Hu | | | Cy | | | Rat | | |
|---|---|---|---|---|---|---|---|---|---|
| | ka ($M^{-1} \cdot s^{-1}$) | kd ($s^{-1}$) | KD (M) | ka ($M^{-1} \cdot s^{-1}$) | kd ($s^{-1}$) | KD (M) | ka ($M^{-1} \cdot s^{-1}$) | kd ($s^{-1}$) | KD (M) |
| PC9_2_FG_HS#9 | 3.47E+05 | 3.65E−04 | 1.05E−09 | 3.19E+05 | 3.74E−04 | 1.17E−09 | 9.69E+05 | 3.45E−04 | 3.56E−10 |
| HS9_DSB7 | 1.46E+05 | 2.87E−04 | 1.97E−09 | 9.49E+04 | 2.84E−04 | 2.99E−09 | 5.07E+05 | 2.67E−04 | 5.27E−10 |

Example 6. GLP-1 Potency in cAMP Cell-Based Assay

PC9#2_GLP-1 was tested in a cAMP cell-based assay to determine its potency as described in Example 3. The GLP1 peptide alone was used as a control and GLP-1Fc was used as a benchmark. Data are presented in Table 13 and a visual representation of the PC9#2_GLP1 molecule and the GLP-1 Fc used as a benchmark control are shown in FIG. 8.

TABLE 13

GLP-1 Potency in cAMP Cell-Based Assay

| Test Compound | EC50 (pm) | x change |
| --- | --- | --- |
| PC9#2_GLP1 (SEQ ID NO: 8, 9, 4, & 28) | 290 | 2.4 |
| GLP1-Fc ( | 120 | 1 |
| GLP1 peptide (SEQ ID NO: 29) | 15 | 0.1 |

This data demonstrates that there was no significant loss of GLP-1 potency compared to the benchmark molecule GLP-1-Fc following the fusion of the GLP-1 analogue peptide to the light chain of the anti-PCSK9 antibody PC9#2.

Example 7. Dulaglutide: A Benchmark Molecule

FIG. 14A provides stability in rat of GLP-1-Fc benchmark. Benchmark molecule is a GLP-1 moiety fusion to an Fc portion of an antibody, as shown in FIG. 14A.

Compounds GLP-1-Fc was injected intravenously to healthy C57/B6 mice (7-8 weeks old, females, Charles River) and plasma samples were collected at several timepoints. Compound concentration in plasma (exposure) and concentration in active compound for GLP-1 activity were determined for each sample as described in Example 4.

GLP-1-Fc was injected at 1 mg/kg. Groups of three mice were sacrificed at each of the following time points: pre-injection, 2 minutes, 1 h, 6 h, 24 h, 48 h, 72 h and 96 h post injection. Blood for each animal were collected in EDTA tubes containing dPP4 inhibitor. Plasma samples were then centrifuged at 14000 rpm for 5 min at 4° C. and stored at −80° C. pending analysis.

GLP-1 activity is lost at a quicker rate than the compound, demonstrating peptide instability. The line with the squares corresponds to the serum concentration of GLP-1-Fc and the line with the circles corresponds to the activity of GLP-1-Fc for the same samples. See FIG. 14A.

Example 8. Fusion Molecules with Enhanced In Vivo Stability Profiles

A) Evaluating GLP-1 Analogue Peptides in Antibody Fusion with Enhanced In Vivo Stability Profiles To improve in vivo peptide stability of antibody fusion molecules, steric hindrance was engineered around the peptide to protect it from degradation. This was done either by introducing a bulky sugar motif or by engineering an inter molecular disulphide bridge.

It has been demonstrated that addition of N-glycosylation consensus motifs can increase in vivo stability and duration of action of proteins (Elliott S. et al., Nat. Biotech., 2003, 21, 414-421). GLP-1 analogue peptides incorporating an extra N-glycosylation motif, NxS or NxT where x can be any amino acid except proline, at the C-terminus of the peptide or in the linker between the peptide and the antibody have been engineered in fusion with the light chain of anti-PCSK9 antibody PC9#2 (antibody light chain, SEQ ID NO: 9). Peptide and linker amino acid sequence for eight of those compounds (named NGS for N-Glysosylation Site) are shown in FIG. 7A. Amino acid changes to generate the glycosylation motif are shown in bold underlined.

Among those eight compounds, only PC9_2_GLP-1_NGS#7 shows a high glycosylation yield by SDS-PAGE. This was detected by an increase in the molecular weight of the light chain compared to the control compound without the glycosylation consensus sequence, and with no visible lower molecular band corresponding to the non-glycosylated light chain product. Glycosylation for PC9_2_GLP-1_NGS#7 was further confirmed by ESI mass spectrometry.

It has also been shown that introducing an inter-disulphide bond could be a successful approach to improve in vivo stability of GLP-1 analogues as free peptide (Li Y. et al., Peptides, 2011, 21, 1303-1312).

Exendin-4 peptide variants incorporating two cysteine residues to form the disulphide bridge as well as, if appropriate, a glycine C-terminus cap in order to facilitate the bonding were fused to the light chain of anti-PCSK9 antibody PC9#2 (SEQ ID NO: 9). Peptide amino acid sequence for the three compounds initially generated (named DSB for DiSulphide Bridge) are shown in FIG. 7B (as SEQ ID NOs: 30-32). Cysteine residues are shown in black, other mutated residues are shown as underline and additional glycine residues at the C-terminus cap are shown in grey.

For DSB#1 variant, the first cysteine was engineered in position 9 instead of an aspartic acid and using a C-terminus cap, incorporating the second cysteine, of sequence:

(SEQ ID NO: 401)
GGGGGGGGGGCGG.

For DSB#2 variant, the first cysteine was engineered in position 4 instead of a glycine and using a C-terminus cap, incorporating the second cysteine, of sequence:

(SEQ ID NO: 402)
GGGGGGGGGGGCG.

For DSB#3 variant, the first cysteine was engineered in position 18 instead of an alanine but no C-terminus cap was used. The second cysteine was introduced at position 39 of the Exendin-4 sequence instead of a serine. Proline 38 was also changed into a glycine to generate more flexibility in the tryptophan cage of Exendin-4 in order to facilitate the formation of the disulphide bridge.

PC9_2_Exe4_DSB#2 in light chain fusion does not express significantly in mammalian cells and was not further characterised but sufficient amount of PC9_2_Exe4_DSB#1 and PC9_2_Exe4_DSB#3 were obtained. Integrity and identity of the fusions were confirmed by ESI mass spectrometry before in vivo experiments.

In vivo stability of PC9_2_GLP-1_NGS#7, PC9_2_Exe4_DSB#1 and PC9_2_Exe4_DSB#3 was assessed in mouse by following both compound exposure and concentration in active GLP-1 over time as described in Example 4.

Healthy C57/B6 mice (7-8 weeks old, females, Charles River) received one single intravenous (IV) dose of PC9_2_GLP-1_NGS#7 at 40 mg/kg, PC9_2_Exe4_DSB#1 at 10.8 mg/kg or PC9_2_Exe4_DSB#3 at 5 mg/kg. Groups of three mice were sacrificed at each of the following time points: pre-injection, 5 minutes, 6 h, 24 h, 72 h and 168 h post injection and blood for each animal were collected in EDTA tubes containing dPP4 inhibitor. Plasma samples were then centrifuged at 14000 rpm for 5 min at 4° C. and stored at −80° C. pending analysis.

All three compounds are active at the human GLP-1 receptor in vitro but display different $EC_{50}$ in the cAMP assay: $1.94^{-8}$M, $5.25^{-9}$ M and $3.25^{-10}$M for PC9_2_GLP-1_NGS#7, PC9_2_Exe4_DSB#1 and PC9_2_Exe4_DSB#3 respectively. Doses were adjusted as much as possible based on potency to generate a signal above the lower limit of quantification in the cAMP ex-vivo assay in order to calculate concentration in active GLP-1 compound over a significant period of time.

Figure 12:
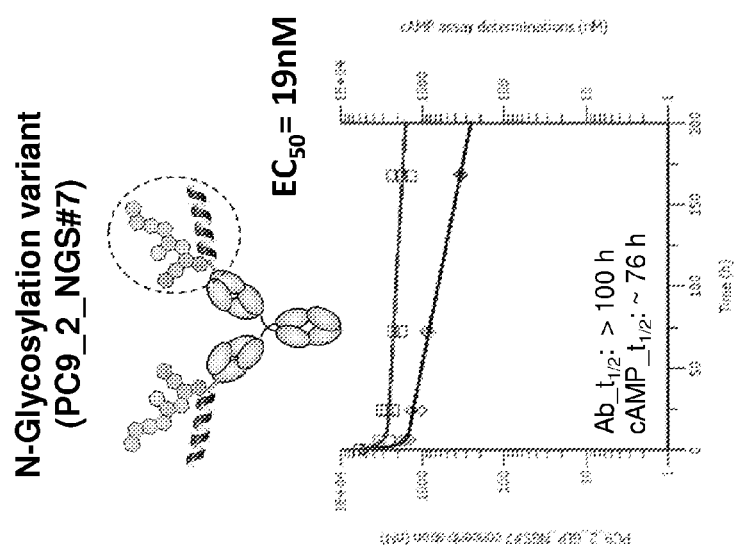
FIG. 12 shows stability in mice of PC9#2_NGS#7, GLP-1 analogue NGS#7 in light chain fusion with the anti-PCSK9 antibody PC9#2.
Figure 13A:
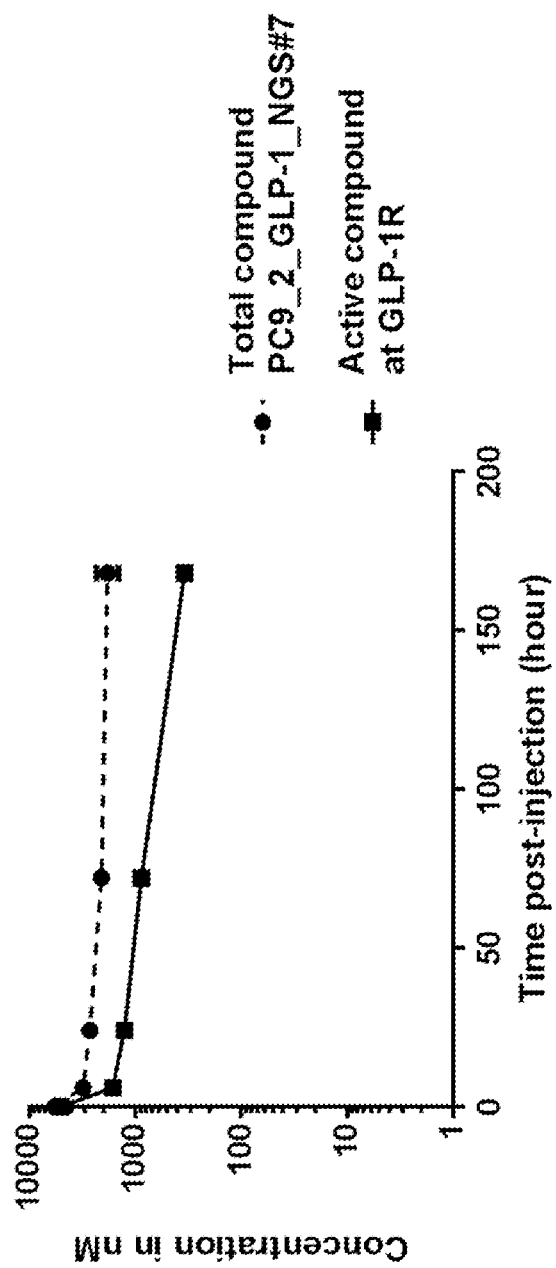
FIG. 13A illustrates stability in mice for GLP-1 analogue NGS#7 in light chain fusion with the anti-PCSK9 antibody PC9#2.
Figure 13B:
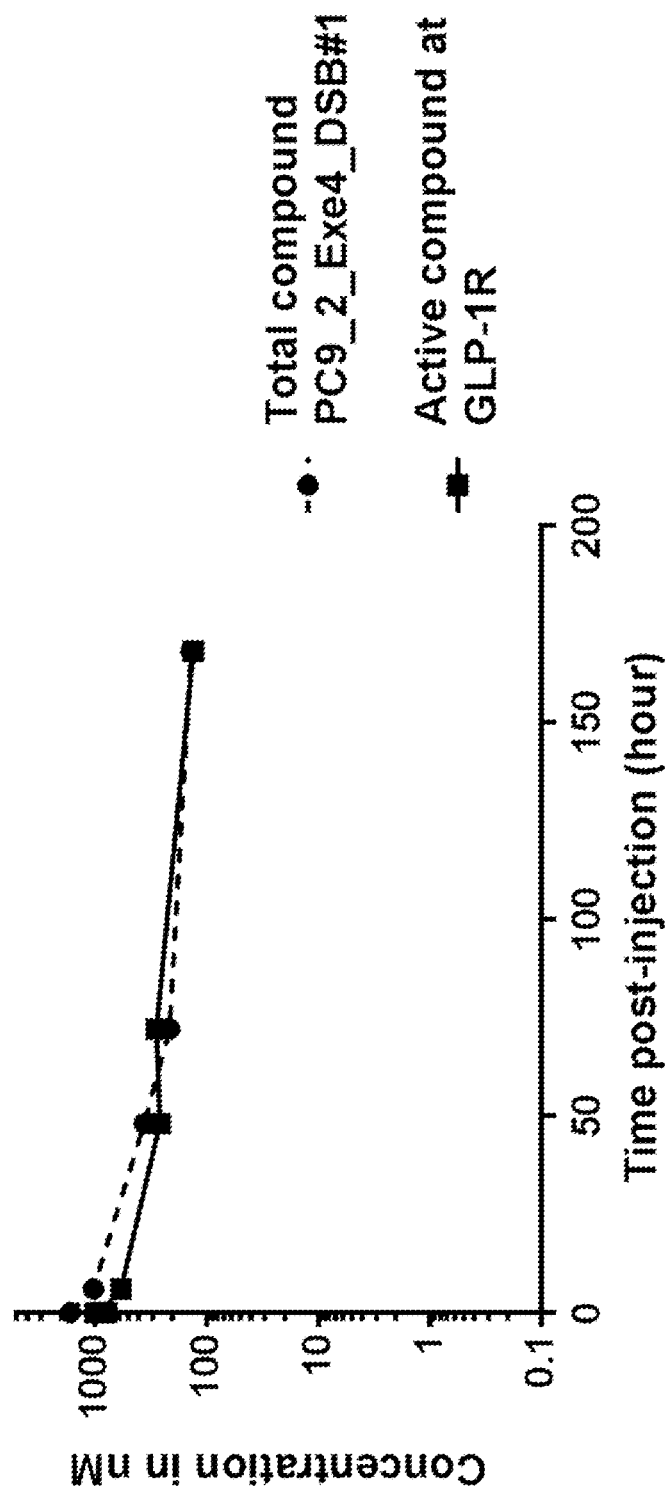
FIG. 13B shows stability in mice for Exendin-4 analogue DSB#1 in light chain fusion with the anti-PCSK9 antibody PC9#2.
Figure 13C:
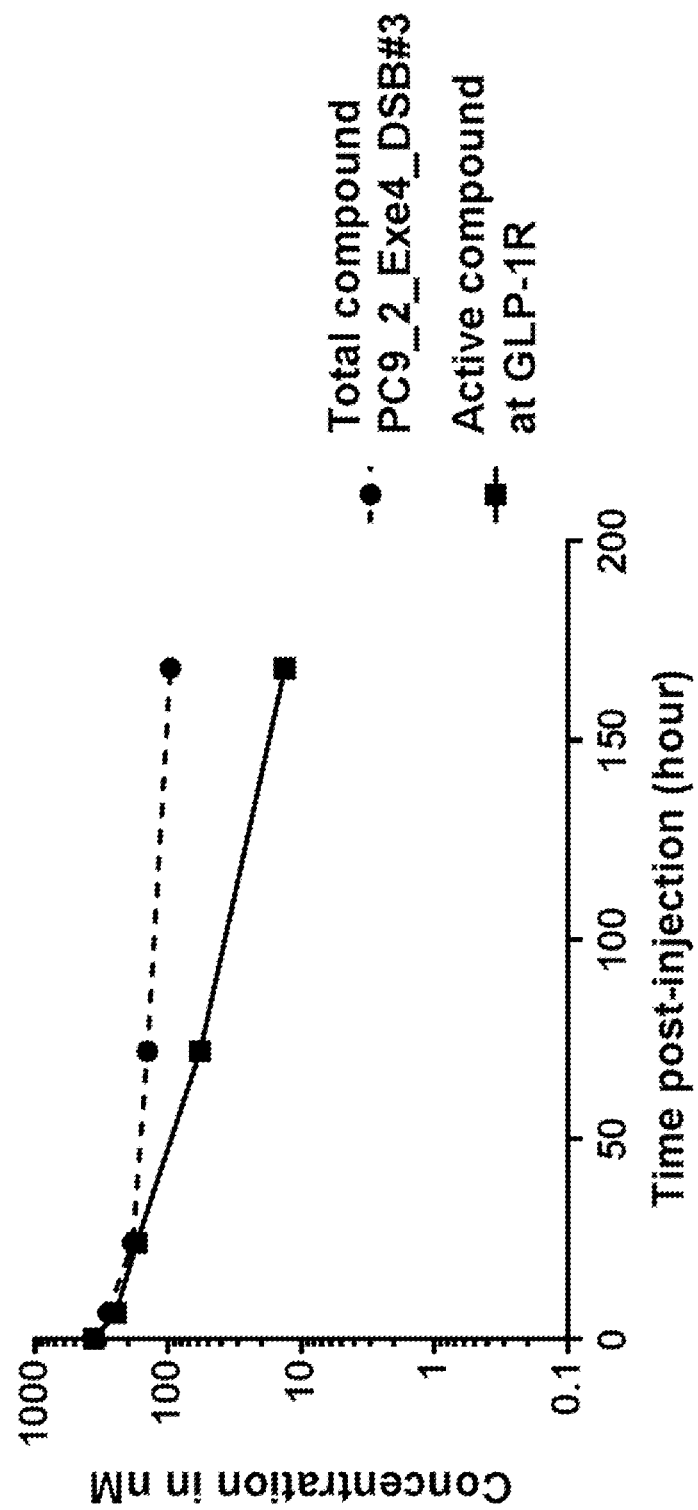
FIG. 13C illustrates stability in mice for Exendin-4 analogue DSB#3 in light chain fusion with the anti-PCSK9 antibody PC9#2.
Figure 14B:
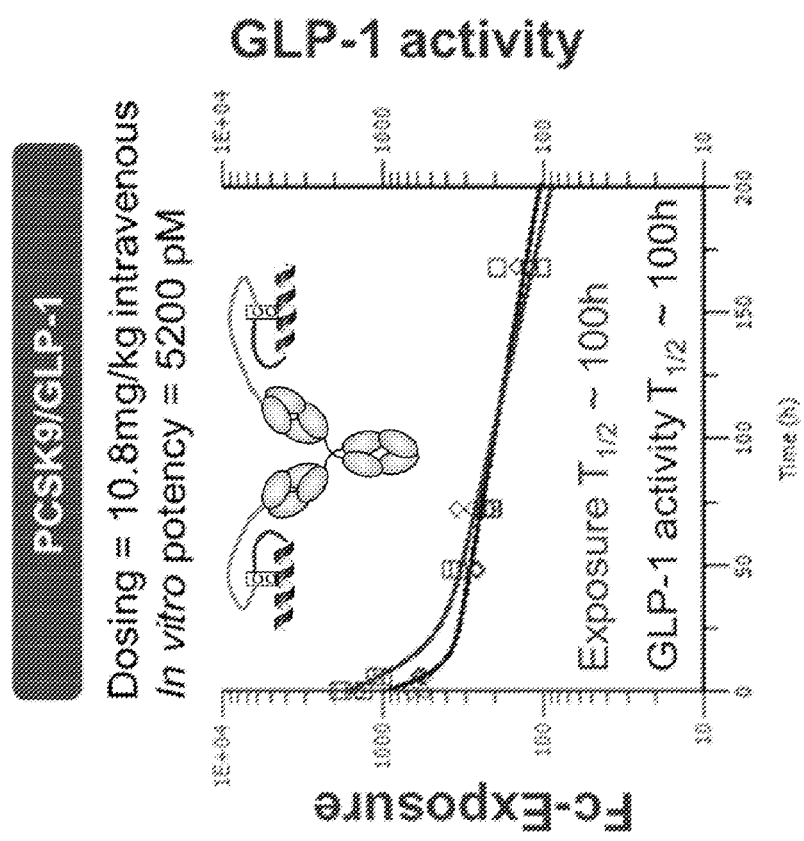
FIG. 14B shows stability in mice for Exendin-4 analogue DSB#1 in light chain fusion with the anti-PCSK9 antibody PC9#2. Open squares: concentration of test molecule in serum over time; open diamonds concentration of "active" test molecule (as measured by GLP-1 activity) over time for the same samples.

Exposure and concentration in active GLP-1 compound in mouse plasma over time for PC9_2_GLP-1_NGS#7 are shown in FIGS. 12 and 13A, PC9_2_Exe4_DSB#1 are shown in FIGS. 13B and 14B, and PC9_2_Exe4_DSB#3 fusion molecules are shown in FIGS. 11 and 13C, respectively.

In vivo half-life of PC9_2_GLP-1_NGS#7, PC9_2_Exe4_DSB#1 and PC9_2_Exe4_DSB#3 for both exposure and active GLP-1 are presented in Table 14.

TABLE 14

Compound and active GLP-1 in vivo half-life of engineered GLP-1 analogues in antibody fusion

| Compound | Experimental design | Compound in vivo half life (h) | Active GLP-1 in vivo half life (h) |
|---|---|---|---|
| PC9_2_GLP-1_NGS#7 | 40 mg/kg IV in C57/B6 mice | ~100 | 76 |
| PC9_2_Exe4_DSB#1 | 10.8 mg/kg IV in C57/B6 mice | ~100 | ~100 |
| PC9_2_Exe4_DSB#3 | 5 mg/kg IV in C57/B6 mice | ~100 | 36 |

Compared to parent molecules NIP228_GLP-1_VH and PC9#2_Exe4_VL (Table 9), all three compounds have improved in vivo stability for GLP-1 activity with half-life of 76 h, around 100 h and 36 h for PC9_2_GLP-1_NGS#7, PC9_2_Exe4_DSB#1 and PC9_2_Exe4_DSB#3 respectively.

Quite interestingly, PC9_2_Exe4_DSB#1 appears fully stable in mice for up to 7 days with no observed loss of GLP-1 activity when compared to compound exposure (FIG. 13B).

Such data are suggesting that generating steric hindrance around GLP-1 analogues can increase in vivo activity half-life of the peptide in antibody fusion.

B) Evaluating Fusion Molecules with Enhanced In Vivo Stability Profiles

The protocol discussed in Example 4 and 8A was followed to administer various compounds to mice and to plot the concentration of the compounds in the plasma over time. Compound potency (EC50) at human GLP-1 receptor was determined using the cAMP assay as described in Example 3.

Fusion molecule optimization was guided through an in vivo PK/stability assessment. As shown in FIGS. 14A, 11 and 12, peptide engineering produced fusion molecules with enhanced in vivo stability profiles. Benefits were seen with disulfide bridge stabilization for which there was longer retention of activity with minimum impact on potency at GLP-1 receptor. NGS#7 also has an improved stability profile but a low potency (19 nM) compared to DSB#3 (340 pM).

FIG. 14A shows a GLP-1-Fc benchmark molecule with an $EC_{50}$ of 100 pm.

FIG. 11 shows a disulfide bridged variant (PC9_2_DSB#3) (SEQ ID NO: 49 and SEQ ID NO: 8) with an $EC_{50}$ of 340 pM.

FIG. 12 shows an n-glycosylation variant (PC9_2_NGS#7) (SEQ ID NO: 50 and SEQ ID NO: 8) with an $EC_{50}$ of 19 nM.

In vivo half-life for those compounds are presented in Table 15.

TABLE 15

Compound and active GLP-1 in vivo half-life of engineered GLP-1 analogues in antibody fusion

| Compound | Experimental design | Compound in vivo half life (h) | Active GLP-1 in vivo half life (h) |
|---|---|---|---|
| GLP-1-Fc | 1 mg/kg in C57/B6 mice | ~100 | 16 |
| PC9_2_Exe4_DSB#3 | 5 mg/kg IV in C57/B6 mice | ~100 | 36 |
| PC9_2_GLP-1_NGS#7 | 40 mg/kg IV in C57/B6 mice | ~100 | 76 |

Example 9. A PCSK9/GLP-1 Fusion Demonstrates an Ideal Stability/Activity Profile The dual action fusion molecule was evaluated for Fc-exposure and GLP-1 activity in a mouse model. Dosing was 10.8 mg/kg intravenously and the in vitro potency was 5200 pM. Protocol was as described in Example 8. The data were compared to the GLP-1 Fc benchmark molecule, with dosing of 1 mg/kg intravenously and an in vitro potency of 100 pM. Similar protocol was here used as described in Example 4. Results are shown in FIGS. 14A (dulaglutide) and 14B (PCSK9/GLP-1 fusion PC9_2_DSB#1) (SEQ ID NO: 48 and SEQ ID NO: 8). There was no loss of GLP-1 activity in the mouse for up to 7 days.

Figure 15A:
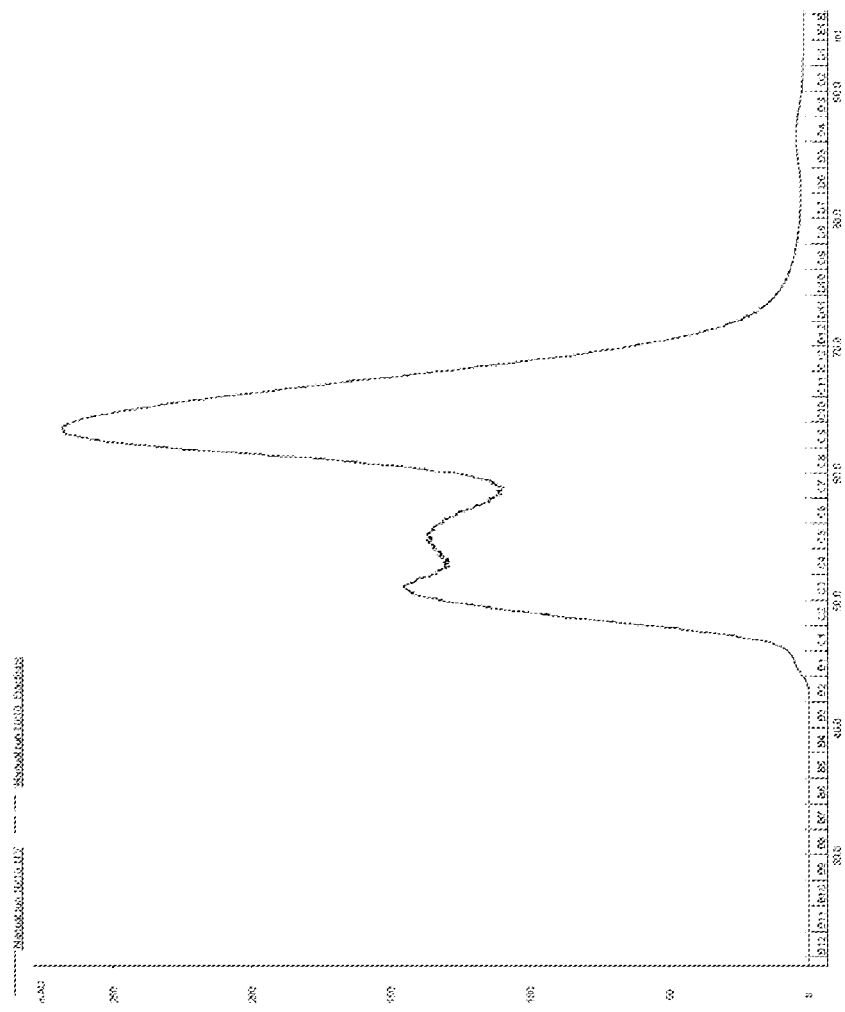
FIG. 15A provides a preparative SEC chromatogram for Exendin-4 analogue DSB#1 in light chain fusion with the anti-PCSK9 antibody PC9#2 after initial protein A purification.
Figure 15B:
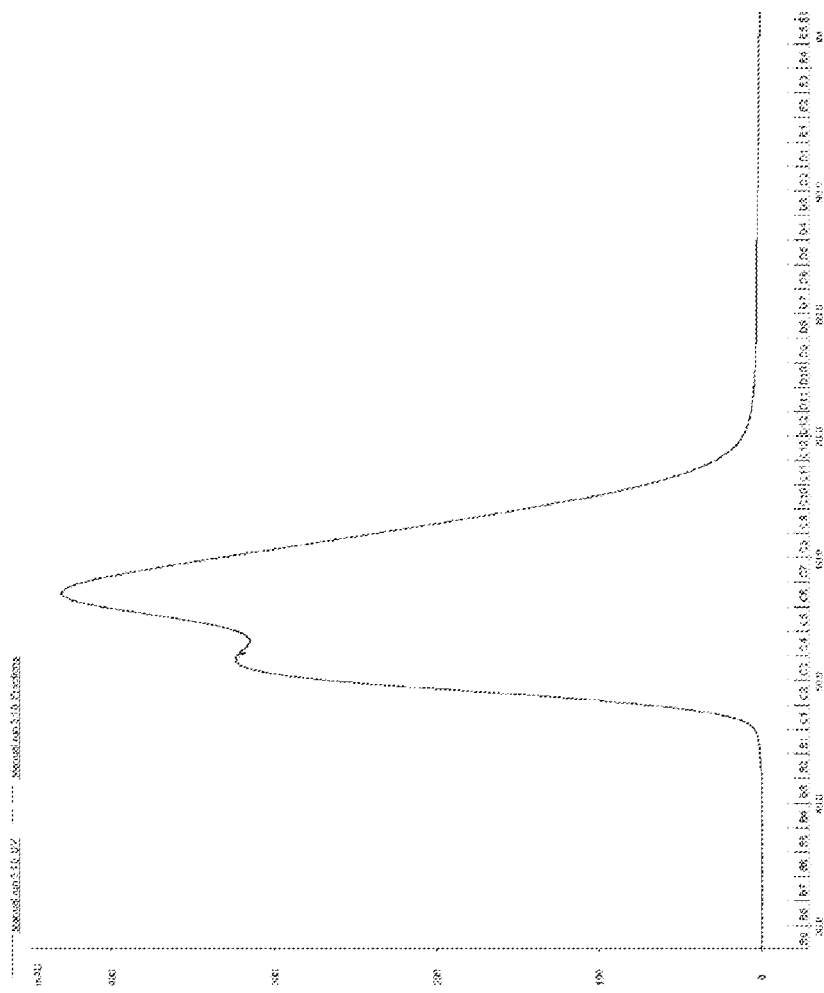
FIG. 15B provides a preparative SEC chromatogram for Exendin-4 analogue DSB#3 in light chain fusion with the anti-PCSK9 antibody PC9#2 after initial protein A purification.

Example 10. Production and Purification of Early GLP-1 Analogue Peptide Antibody Fusions with an Intramolecular Disulphide Bridge Quality of the material post-protein A purification from medium scale batches was poor for PC9_2_Exe4_DSB#1 and PC9_2_Exe4_DSB#3 as lot of aggregates were detected by SEC-HPLC. Preparative Size Exclusion Chromatography using Superdex 200 prep grade columns was then used to further purify the compounds as described in Example 2. Preparative SEC chromatograms for PC9_2_Exe4_DSB#1 and PC9_2_Exe4_DSB#3 are shown in FIGS. 15A and 15B, respectively. A significant proportion (25-40%) of the material is aggregated as shown by additional peaks at early retention time. Fractions containing the monomeric compound were collected to obtain the material used for in vivo testing. See Example 8 and 9.

Scalability of PC9_2_Exe4_DSB#1 production was further assessed by transiently transfected 48.2 L of CHO mammalian cells in wavebags (GE Healthcare). Compound was purified by using a Protein A column followed by two additional purification steps using a mixed-mode resin.

A high level of aggregation (>25%) was detected in the harvest and efficient purification of the monomer product was particularly challenging. Three chromatography steps were required to generate a product at 95.9% purity by SEC-HPLC. This was very detrimental to the purification yield with an overall recovery of around 3.4%. In addition, the titre in harvest was at 104 mg/L which is low compared to monoclonal antibodies using a similar expression system. Production of DSB#1 disulphide bridge GLP-1 analogue in fusion with the light chain of anti-PCSK9 antibody HS9 (SEQ ID NO: 2) gave very similar results.

Example 11. Aggregation

Figure 16:
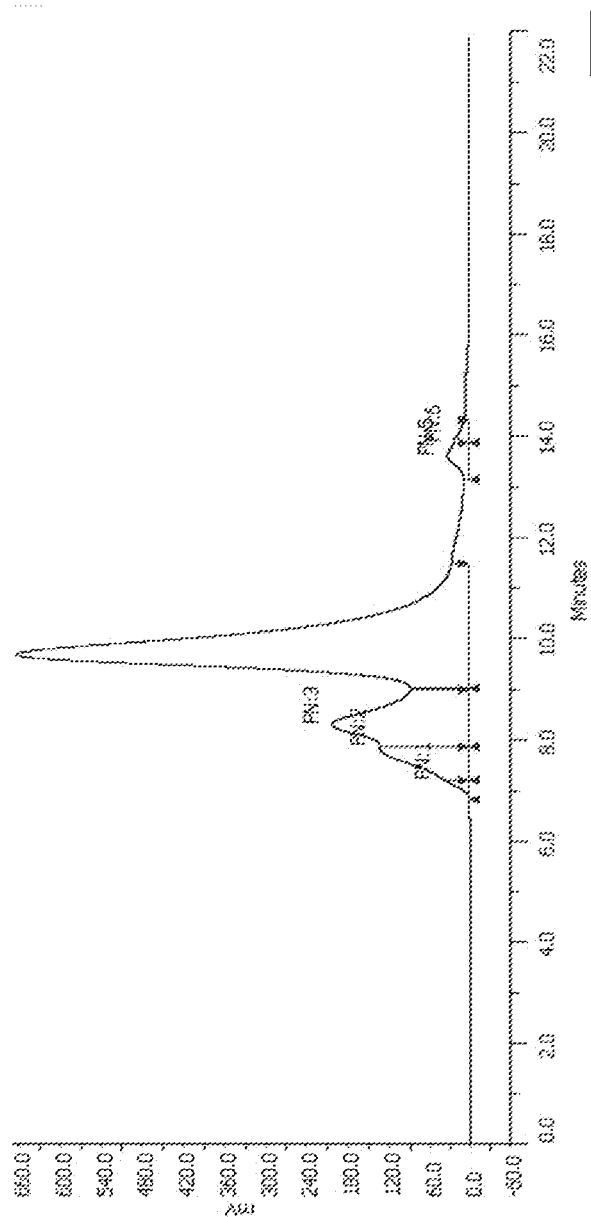
FIG. 16 shows an analytical SEC-HPLC profile of Exendin-4 analogue DSB#1 in light chain fusion with the anti-PCSK9 antibody PC9#2 after initial protein A purification.

The dual action fusion molecule (PCSK9/GLP-1 fusion PC9_2_DSB#1) (SEQ ID NO: 48) has the potential for aggregation and in some embodiments monomer is desired to be selected. Aggregates, detected during an analytical SEC-HPLC following protein A purification as described in Example 2, are shown in FIG. 16. Thus, in some embodiments additional engineering may be desired to improve the monomeric profile.

Example 12. GLP-1 Analogue Peptides in Antibody Fusion with Enhanced Monomeric Profiles Additional Exendin-4 disulphide bridge peptides (DSB) in fusion with the light chain of PC9#2 (SEQ ID NO: 9) were generated in order to improve the monomeric profile during production of the peptide antibody molecule. Different positions of the cysteine bridge as well as length of the glycine rich C-terminus cap and various glycine point mutations in the C-terminus of the Exendin-4 peptide were engineered in order to facilitate the formation of the disulphide bond and ultimately reduce aggregation during production probably due to disulphide scrambling. Peptide engineering work was guided using the 3-D NMR structure of Exendin-4 (Neidigh, J W et al., Biochemistry, 2001, 40, 13188-200.).

Figure 17:
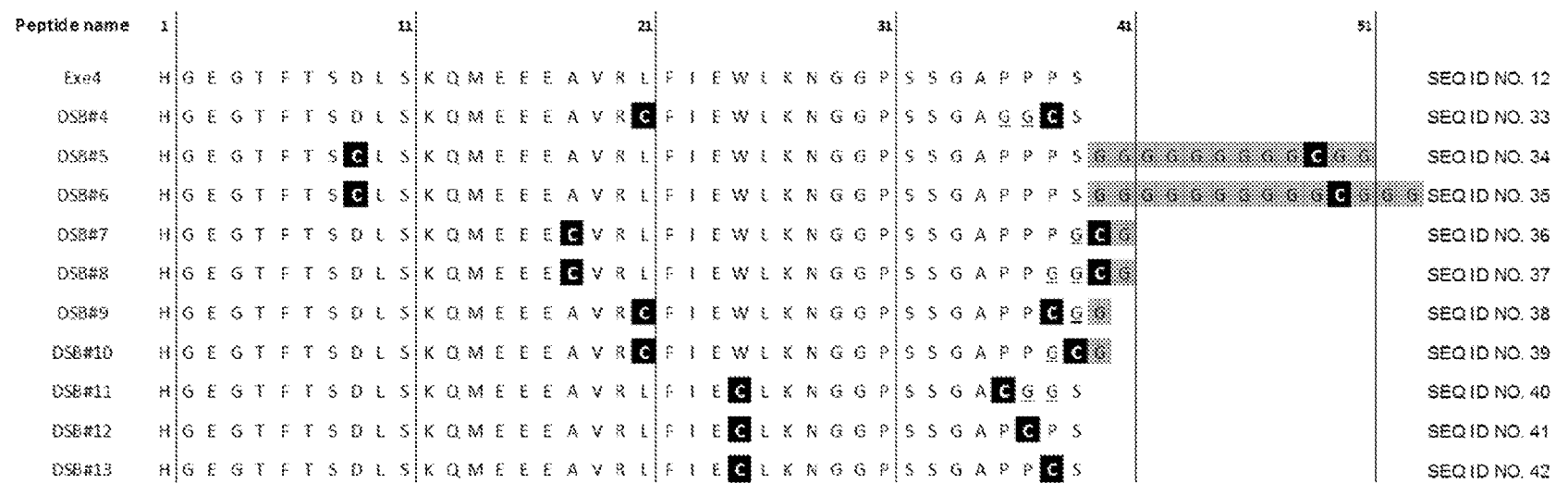

A total of ten DSB peptide anti-PCSK9 fusions were produced at small scale and screened for an improved monomeric profile by SEC-HPLC. Peptide sequences are described in FIG. 17. PC9_2_Exe4_DSB#4 did not significantly express and was not further characterised.

Percentages of aggregate for the nine fusions compared to PC9_2_Exe4_VL and PC9_2_Exe4_DSB#1 determined by analytical SEC-HPLC after protein A purification are described in Table 16.

TABLE 16

Percentage of aggregate post protein A purification for disulphide bridge exendin-4 variants in fusion with the light chain of PCSK9 antibody PC9_2

| # | Compound | % aggregate by analytical SEC |
|---|---|---|
| 1 | PC9_2_Exe4_VL | 2.9 |
| 2 | PC9_2_Exe4_DSB#1 | 26.5 |
| 3 | PC9_2_Exe4_DSB#5 | 20.5 |
| 4 | PC9_2_Exe4_DSB#6 | 23.3 |
| 5 | PC9_2_Exe4_DSB#7 | 5.1 |
| 6 | PC9_2_Exe4_DSB#8 | 51.1 |
| 7 | PC9_2_Exe4_DSB#9 | 7.8 |
| 8 | PC9_2_Exe4_DSB#10 | 7.3 |
| 9 | PC9_2_Exe4_DSB#11 | 7.6 |
| 10 | PC9_2_Exe4_DSB#12 | 20.1 |
| 11 | PC9_2_Exe4_DSB#13 | 17.1 |

Four compounds among the nine tested achieve a percentage aggregate below 10%: PC9_2_Exe4_DSB#7, PC9_2_Exe4_DSB#9, PC9_2_Exe4_DSB#10 and PC9_2_Exe4_DSB#11. PC9_2_Exe4_DSB#7 has the lowest percentage aggregate at 5.1% compared to 26.5% for the early fusion PC9_2_Exe4_DSB#1. Exendin-4 antibody fusion without a disulphide bridge, PC9_2_Exe4_VL, shows 2.9% aggregate.

Figure 18:
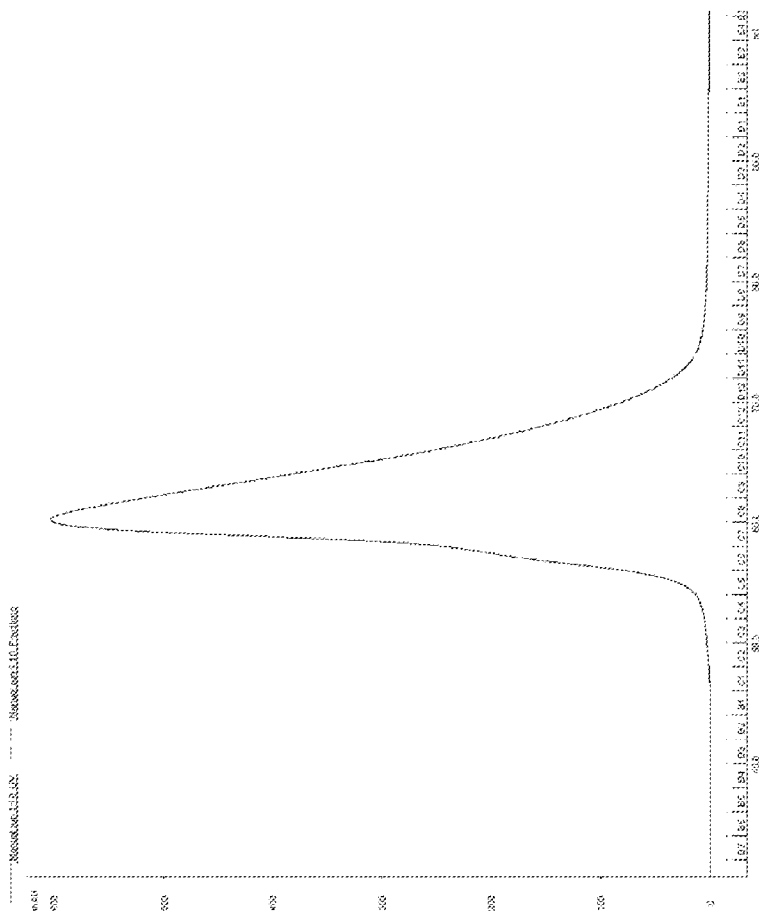
FIG. 18 provides a preparative SEC chromatogram for Exendin-4 analogue DSB#7 in light chain fusion with the anti-PCSK9 antibody PC9#2 after initial protein A purification.
Figure 19:
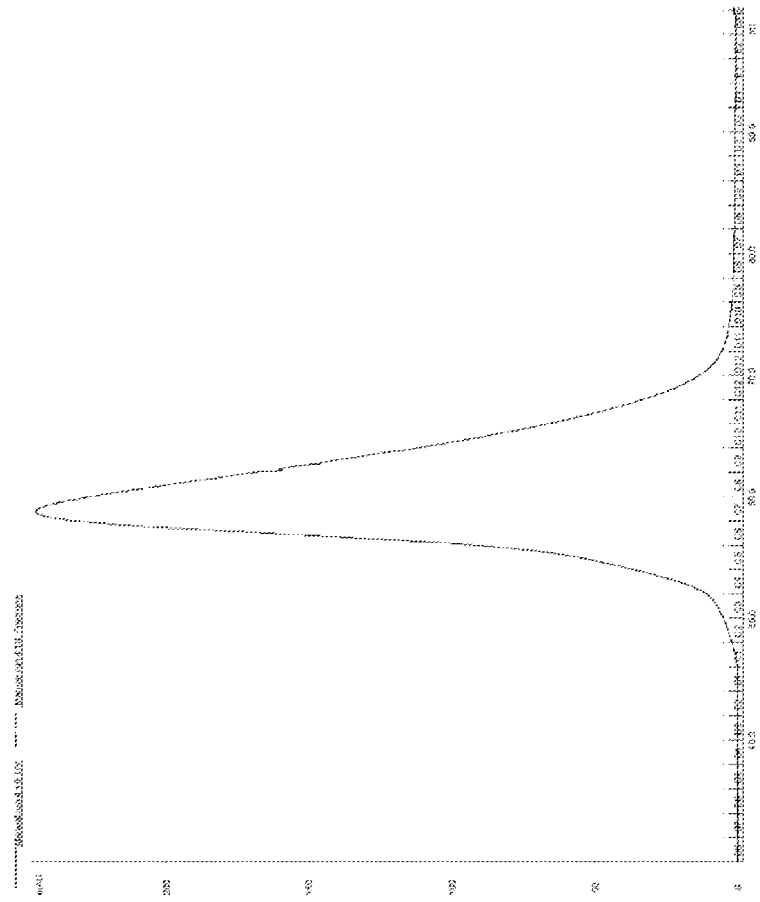
FIG. 19 provides a preparative SEC chromatogram for Exendin-4 analogue DSB#9 in light chain fusion with the anti-PCSK9 antibody PC9#2 after initial protein A purification.

Productions of PC9_2_Exe4_DSB#7 and PC9_2_Exe4_DSB#9 were scaled up to supply material in sufficient quantity to perform in vivo stability experiments. FIGS. 18 and 19 show showing preparative SEC chromatograms of PC9_2_Exe4_DSB#7 and PC9_2_Exe4_DSB#9 respectively following an initial protein A purification as described in Example 2. Unlike PC9_2_Exe4_DSB#1 and PC9_2_Exe4_DSB#3 (FIGS. 15A and B), no significant proportion of aggregates was detected during that purification step.

In order to check that the optimised DSB peptide antibody fusions with an improved monomeric profile do exhibit a superior in vivo stability compared to Exendin-4 antibody fusion, PC9_2_Exe4_DSB#7 and PC9_2_Exe4_DSB#9 were injected intravenously in three CD rats for each compound at 10 mg/kg and 1 mg/kg respectively. Serum samples for each animal were collected at 30 minutes, 6 h, 24 h, 48 h, 96 h, 240 h and 336 h post injection. Compound exposure and concentration in active GLP-1 were measured over time as described in Example 4.

Both compounds are active at the human GLP-1 receptor in the cAMP assay with $EC_{50}$ of 9.45E-10 M for PC9_2_Exe4_DSB#7 and 1.24E-10 M for PC9_2_Exe4_DSB#9. PC9_2_Exe4_DSB#7 is around eight time less potent than PC9_2_Exe4_DSB#9 and as thus been injected at ten time higher a dose to generate a signal above the lower limit of quantification in the cAMP ex-vivo assay over a significant period of time.

Figure 20:
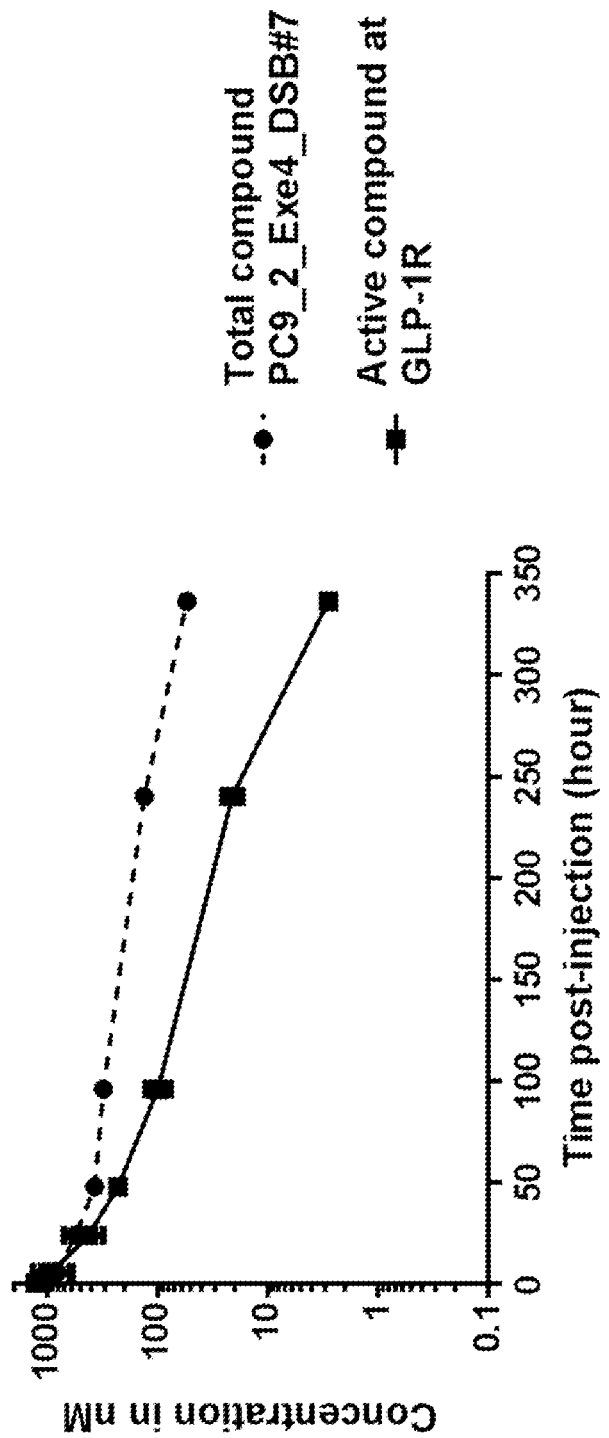
FIG. 20 shows stability in rat for Exendin-4 analogue DSB#7 in light chain fusion with the anti-PCSK9 antibody PC9#2.
Figure 21:
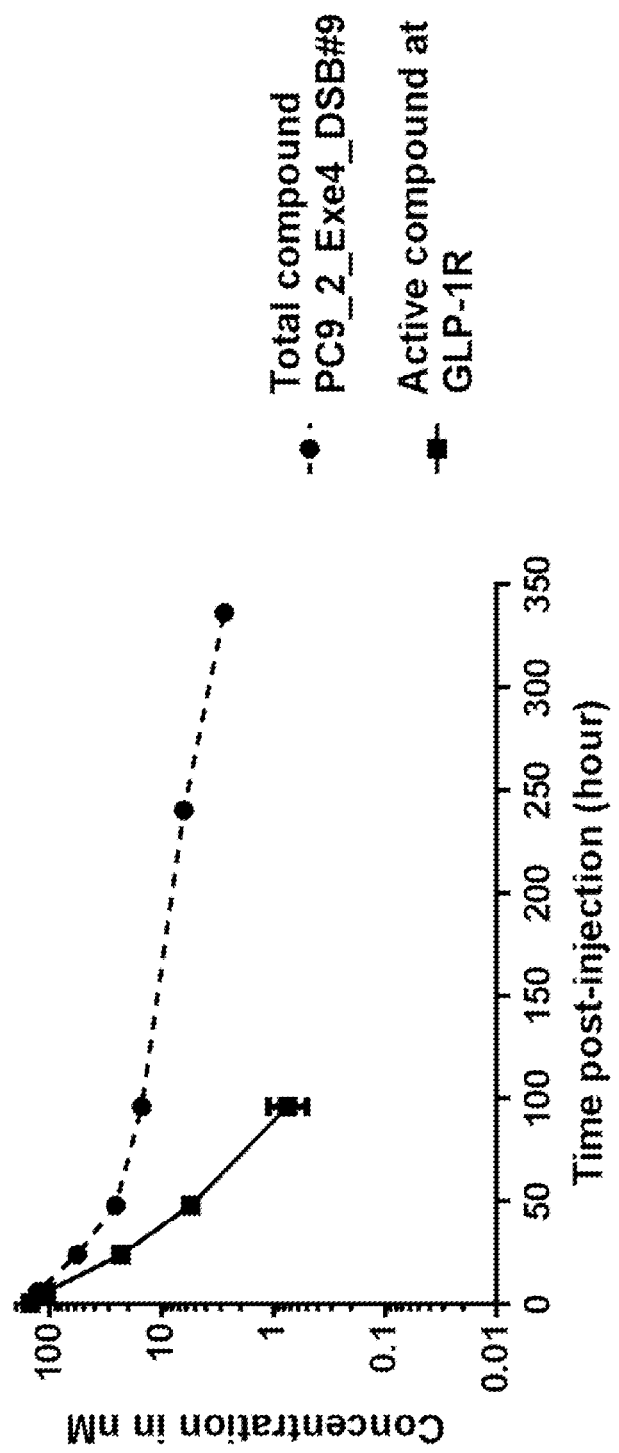
FIG. 21 illustrates stability in rat for Exendin-4 analogue DSB#9 in light chain fusion with the anti-PCSK9 antibody PC9#2.

Exposure and concentration in active GLP-1 compound in rat serum over time for PC9_2_Exe4_DSB#7 and PC9_2_Exe4_DSB#9 fusion molecules are shown in FIGS. 20 and 21, respectively. Concentrations in active GLP-1 were normalised to the exposure at the first time point (30 min) to simplify the analysis.

PC9_2_Exe4_DSB#7 and PC9_2_Exe4_DSB#9 have a half-life for GLP-1 activity of 44.2 h and 12.5 h respectively compared to 5.7 h for the parent Exendin-4 fusion molecule PC9_2_Exe4_VL (see Table 9)). Concentrations of active compound for PC9_2_Exe4_DSB#9 samples collected after 96 h cannot be determined as they were below the lower limit of quantification of the assay.

Those data are demonstrating that both PC9_2_Exe4_DSB#7 and PC9_2_Exe4_DSB#9 have an improved in vivo activity half-life of the GLP-1 analogue peptide when in antibody fusion compared to the parent fusion molecule.

As described above peptide engineering can manage the aggregation profile. Mutations were made in the position of the cysteine bridge in the peptide and the composition and length of the peptide/C terminus of the GLP-1 moiety.

The protocol was as described above.

PCSK9/GLP-1 fusion (PC9_2_DSB#7) (SEQ ID NO: 51 and SEQ ID NO: 8) achieved >90% monomer by SEC-HLPC in small-scale batch. Aggregation was still detected in medium scale batch but to a much lower extended than PCSK9/GLP-1 fusion PC9_2_DSB#1 (SEQ ID NO: 48 and SEQ ID NO: 8).

Figure 23:
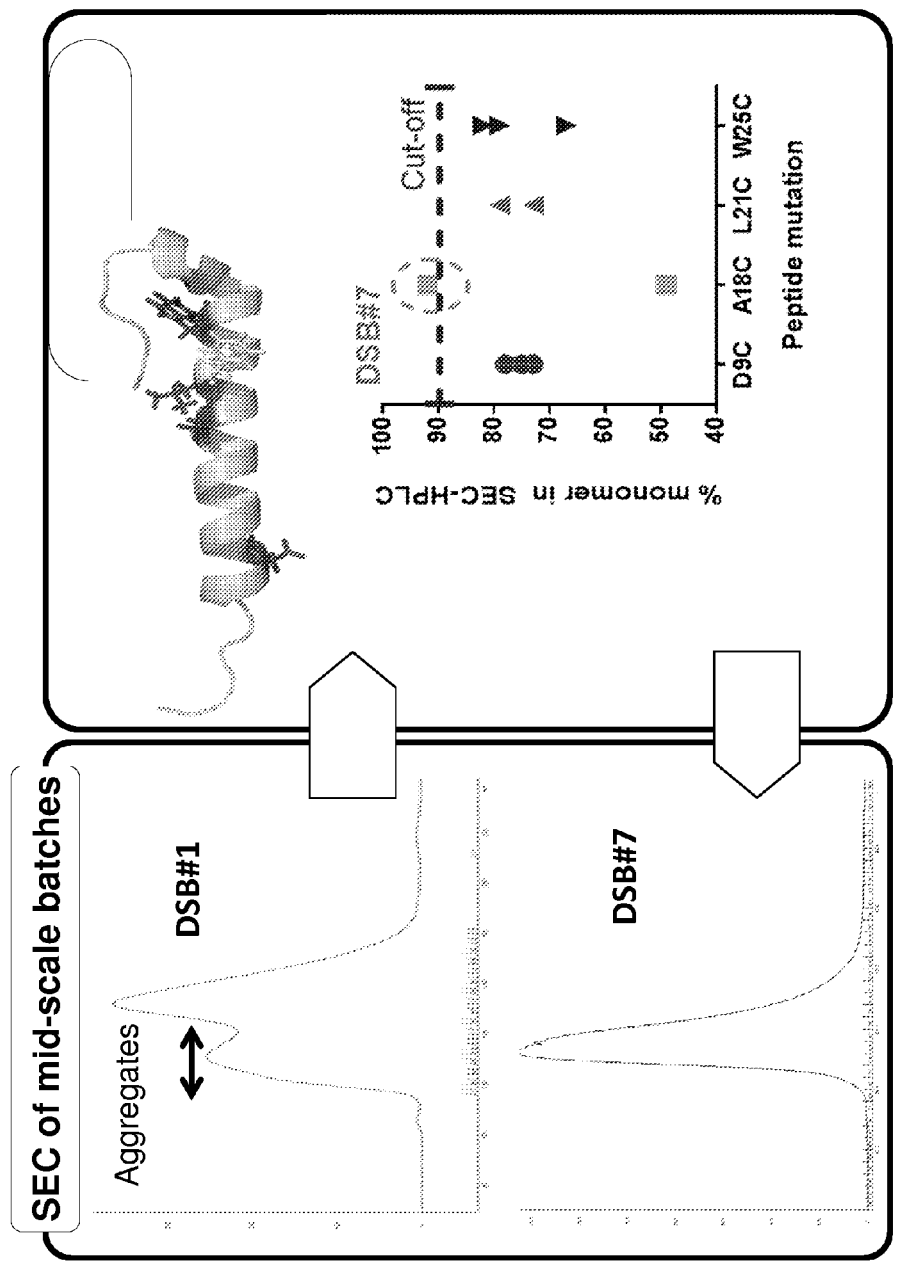
FIG. 23 shows the improved monomeric profile for PC9_2_DSB#7.

Results are presented in FIGS. 15A, 18, 23 and Table 16.

Example 13. Pharmacokinetics and Pharmacodynamics Modeling of GLP-1 Analogue Peptides in Fusion with Anti-PCSK9 Antibodies To guide the design of PCSK9/GLP-1 fusion molecules, a pharmacokinetic (PK)—pharmacodynamic (PD) model has been developed using prior data on the relationship between PCSK9 suppression and affinity of anti-PCSK9 antibodies tested in the clinic as well as data on the approved GLP-1 receptor agonist molecules Liraglutide and Dulaglutide.

Figure 22A:
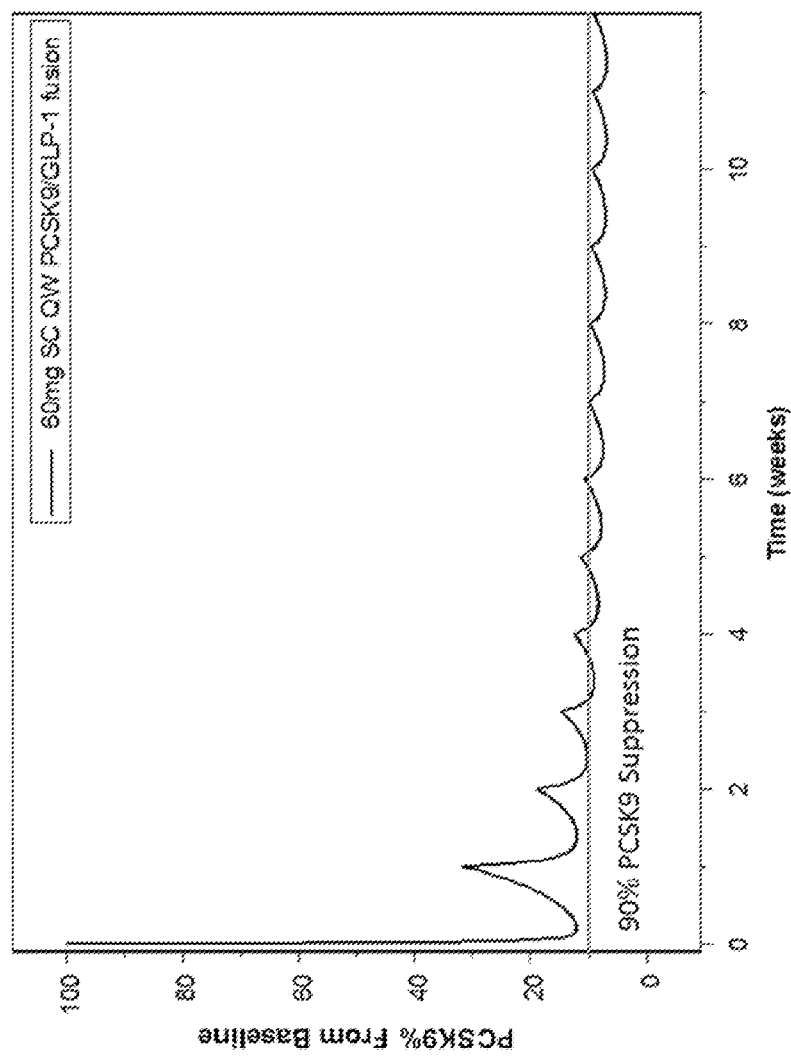
FIG. 22A shows simulation in human of the impact PCSK9/GLP-1 fusion for PCSK9 suppression.

The potency of GLP-1 analogue peptide in fusion with anti-PCSK9 antibody was scanned to identify the optimum range that would result in comparable GLP-1 activity to marketed drugs using a dose able to generate sufficient PCSK9 suppression. Simulations were performed using the pharmacokinetics, plasma protein binding, and receptor affinity properties of Dulaglutide to obtain the potency-normalised GLP-1 activity over time of that compound. For PCSK9/GLP-1 fusion molecule, the PK properties are assumed to be those of a typical human antibody directed towards PCSK9 and the information was derived from compounds in the clinic. These simulations indicate that a 60 mg subcutaneous weekly dose of PCSK9/GLP-1 fusions with an affinity of 3.9 nM for human PCSK9 should result in greater than 90% PCSK9 suppression over the dosing period at steady-state (FIG. 22A).

Figure 22B:
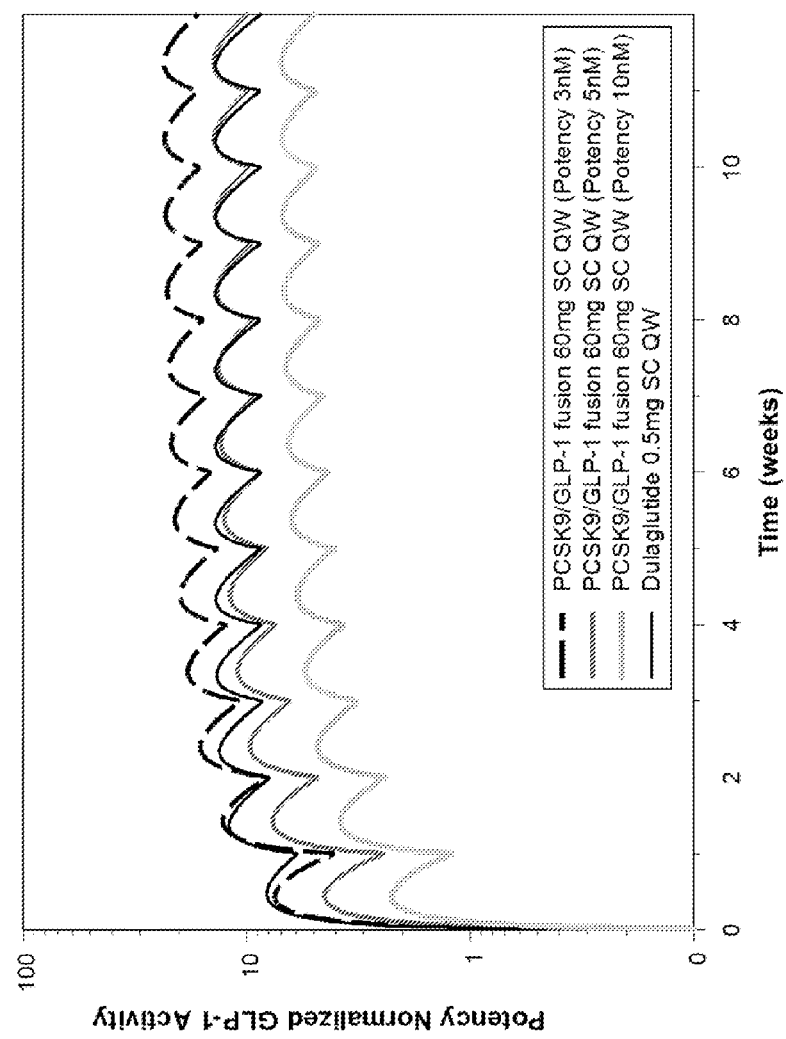
FIG. 22B illustrates simulation in human of PCSK9/GLP-1 fusion molecule for GLP-1 agonism activity compared to Dulaglutide.

Using that dosing regimen, simulations indicate that potency of PCSK9/GLP-1 fusion molecules at human GLP-1 receptor should be within 3-5 nM in order to achieve similar GLP-1 activity compared to existing molecules (FIG. 22B). Potency of Dulaglutide in those simulations was set-up at 80 pM suggesting that potency of PCSK9/GLP1 fusion molecules need to be around 30 to 60 fold lower than Dulaglutide in order to manage nausea side effect associated with GLP-1 receptor agonist molecules at the dose required to efficiently suppress PCSK9.

Example 14. GLP-1 Analogue Peptides with Reduced Potency at the Human GLP-1 Receptor Methods for reducing potency of the GLP-1 peptide or GLP-1 analogues are well known in the art as for instance mutating or introducing non-natural amino acids at key residues in the peptide. Critical residues for binding of GLP-1 peptide to the receptor and activity were notably identified by alanine scanning (Adelhorst, K. et al., J. Bio. Chem., 1994, 269, 6276-6278).

To further demonstrate the feasibility to reduce potency at GLP-1 receptor, a panel of GLP-1 analogues with a mutation or non-natural amino acids in position 2 or 3, using the 7-36 GLP-1 sequence, were synthesized as free peptide and tested for activity at the human GLP-1 receptor in the cAMP in vitro assay as described in Example 3. Data are summarised in Table 17 below. Aib is for 2-aminoisobutyric acid and Orn for ornithine.

TABLE 17

Potency at human GLP-1R in the cAMP assay of GLP-1 point mutant peptides

| # | Peptide | Modification | Potency at huGLP-1R in cAMP assay (nM) | Fold difference in EC50 vs GLP-1 |
|---|---|---|---|---|
| 1 | GLP-1 | / | 0.10 | / |
| 2 | g769 | E3D | 0.10 | 1 |
| 3 | g766 | A2Aib | 0.11 | 1.1 |
| 4 | g770 | A2P | 0.15 | 1.5 |
| 5 | g767 | E3Q | 0.28 | 2.8 |
| 6 | g762 | A2S | 0.29 | 2.9 |
| 7 | g755 | A2H | 0.32 | 3.2 |
| 8 | g752 | A2V | 0.56 | 5.6 |
| 9 | g749 | A2G | 0.63 | 6.3 |
| 10 | g768 | E3N | 0.68 | 6.8 |
| 11 | g751 | A2I | 1.78 | 17.8 |
| 12 | g765 | A2Q | 2.98 | 29.8 |
| 13 | g763 | A2T | 4.30 | 43 |
| 14 | g753 | A2F | 4.30 | 43 |
| 15 | g756 | A2W | 5.46 | 54.6 |
| 16 | g754 | A2Y | 14.4 | 144 |
| 17 | g764 | A2N | 21.0 | 210 |
| 18 | g750 | A2L | 80.0 | 800 |
| 19 | g761 | A2Orn | 86.4 | 864 |
| 20 | g757 | A2E | 103.3 | 1033 |
| 21 | g758 | A2D | >100 | >1000 |
| 22 | g760 | A2R | >80 | >800 |
| 23 | g759 | A2K | >100 | >1000 |

Those data demonstrate that $EC_{50}$ of GLP-1 analogue peptides can be modulated to achieve a defined potency reduction.

Example 15. GLP-1 Analogue Peptides in Antibody Fusion with Reduced Potency at the Human GLP-1 Receptor To reduce the potency of DSB#7 GLP-1 analogue peptide (SEQ ID NO: 13) in fusion with the light chain of the anti-PCSK9 antibody HS9 (SEQ ID NO: 2), point mutations were introduced at position G2, E15, V19, 123 or L26 in the peptide using standard molecular biology techniques. A total of 28 mutants of the peptide antibody fusion molecule were produced and tested for activity at the human GLP-1 receptor using the cAMP assay as described in Example 3. List of the compounds and activity data are presented in Table 18.

TABLE 18

Potency at human GLP-1R and percentage maximum activation compared to GLP-1 of DSB#7 point mutants in light chain fusion of PCSK9 antibody HS9

| # | Compound | Potency at huGLP-1R in cAMP assay (M) | % Max Effect | Fold difference in EC50 vs GLP1-Fc | SEQ ID NO: |
|---|---|---|---|---|---|
| 1 | HS9_DSB7_G2Y | 1.7E−08 | 10 | 603 | 444 |
| 2 | HS9_DSB7_G2V | 1.2E−09 | 93 | 43 | 445 |
| 3 | HS9_DSB7_G2T | 6.3E−09 | 73 | 227 | 446 |
| 4 | HS9_DSB7_G2Q | 1.2E−08 | 86 | 436 | 447 |
| 5 | HS9_DSB7_G2N | 1.9E−08 | 31 | 685 | 448 |
| 6 | HS9_DSB7_G2I | 2.3E−09 | 87 | 81 | 449 |
| 7 | HS9_DSB7_G2F | 5.8E−09 | 69 | 209 | 450 |
| 8 | HS9_DSB7_E15G | 6.8E−09 | 91 | 243 | 451 |
| 9 | HS9_DSB7_E15A | 1.2E−09 | 92 | 42 | 452 |
| 10 | HS9_DSB7_V19T | 4.0E−10 | 95 | 14 | 453 |
| 11 | HS9_DSB7_V19S | 2.7E−09 | 94 | 95 | 454 |
| 12 | HS9_DSB7_V19G | 1.3E−08 | 93 | 479 | 455 |
| 13 | HS9_DSB7_V19A | 1.3E−09 | 96 | 46 | 456 |

TABLE 18-continued

Potency at human GLP-1R and percentage maximum activation compared to GLP-1 of DSB#7 point mutants in light chain fusion of PCSK9 antibody HS9

| # | Compound | Potency at huGLP-1R in cAMP assay (M) | % Max Effect | Fold difference in EC50 vs GLP1-Fc | SEQ ID NO: |
|---|---|---|---|---|---|
| 14 | HS9_DSB7_I23T | Inactive | Inactive | / | 457 |
| 15 | HS9_DSB7_I23S | Inactive | Inactive | / | 458 |
| 16 | HS9_DSB7_I23G | 5.6E−07 | 82 | 2.0E+04 | 459 |
| 17 | HS9_DSB7_I23A | 6.1E−07 | 67 | 2.2E+04 | 460 |
| 18 | HS9_DSB7_L26T | 1.3E−07 | 87 | 4.7E+03 | 461 |
| 19 | HS9_DSB7_L26S | Inactive | Inactive | / | 462 |
| 20 | HS9_DSB7_L26P | 1.4E−06 | 60 | 5.1E+04 | 463 |
| 21 | HS9_DSB7_L26N | 4.3E−06 | 44 | 1.5E+05 | 464 |
| 22 | HS9_DSB7_L26Q | 5.9E−06 | 34 | 2.1E+05 | 465 |
| 23 | HS9_DSB7_L26M | 5.3E−08 | 90 | 1.9E+03 | 466 |
| 24 | HS9_DSB7_L26I | 7.4E−10 | 96 | 27 | 467 |
| 25 | HS9_DSB7_L26H | 8.0E−08 | 87 | 2.9E+03 | 468 |
| 26 | HS9_DSB7_L26G | 2.8E−06 | 81 | 1.0E+05 | 469 |
| 27 | HS9_DSB7_L26E | Inactive | Inactive | / | 470 |
| 28 | HS9_DSB7_L26D | Inactive | Inactive | / | 471 |
| 29 | HS9_DSB7 | 2.1E−10 | 96 | 8 | 472 |
| 30 | GLP1 | 1.9E−11 | 100 | 0.7 | |
| 31 | GLP1-Fc | 2.8E−11 | 99 | 1 | |

Five out of the twenty-eight constructs are inactive. The others compounds display very diverse potency at human GLP1 receptor ranging from 400 pM for HS9_DSB7_V19T to almost 6 uM for HS9_DSB7_L26Q. In addition some compounds, as HS9_DSB7_G2Y or HS9_DSB7_L26Q, are partial agonists: they do not provide the same level of activation at saturating dose compared to GLP-1 peptide.

Based on PKPD modeling in Example 13 the dual activity anti-PCSK9 antibody GLP-1 receptor agonist molecules need to have a potency reduction at human GLP-1 receptor compared to the GLP-1-Fc benchmark of around 30 to 60 fold in order to manage nausea at the dose required to efficiently suppress PCSK9 antigen.

Four peptide antibody fusions (HS9_DSB7_G2V, HS9_DSB7_E15A, HS9_DSB7_V19A and HS9_DSB7_L26I) display a potency between 700 pM and 1.4 nM corresponding to a 25 to 50 fold loss compared to the benchmark GLP1-Fc. All those four compounds are full agonists at human GLP-1 receptor with a percentage of maximum activation greater than 90% compared to the GLP-1 peptide.

Example 16. Characterisation of GLP-1 Analogue Peptides in Fusion with Anti-PCSK9 Antibody A) Developability Assessment of GLP-1 Analogue Peptides in Fusion with Anti-PCSK9 Antibody The four selected peptide antibody fusions at the desired human GLP-1R potency (HS9_DSB7_G2V, HS9_DSB7_EISA, HS9_DSB7_V19A and HS9_DSB7_L26I) were produced in large scale to support further characterisation. To assess propensity of the compounds to aggregate during production, post protein A purification samples were tested by analytical SEC-HPLC. Data are summarised in Table 19.

TABLE 19

SEC-HPLC analysis of peptide/antibody lead molecules following Protein A purification

| # | Compound | % Aggregate | % Monomer | % Truncate |
|---|---|---|---|---|
| 1 | HS9_DSB7_G2V | 25.08 | 74.64 | 0.28 |
| 2 | HS9_DSB7_E15A | 21.04 | 78.6 | 0.36 |
| 3 | HS9_DSB7_V19A | 4.33 | 95.43 | 0.24 |
| 4 | HS9_DSB7_L26I | 5.96 | 93.81 | 0.23 |

Only two out of the four fusions (HS9_DSB7_V19A and HS9_DSB7_L26I) achieve a percentage monomer greater than 90% post protein A purification. HS9_DSB7_V19A presents the best profile with more than 95% monomer. HS9_DSB7_G2V and HS9_DSB7_E15A are significantly prone to aggregation during production with percentage aggregate greater than 20% compared to less than 5% for HS9_DSB7_V19A.

Purified compounds were concentrated using centrifugal spin concentrators with a molecular weight cut-off of 30 kDa to achieve a target concentration of 50 mg/mL in default formulation buffer. Concentration of HS9_DSB7_G2V and HS9_DSB7_E15A was stopped at 38.7 and 33.7 mg/mL respectively as it was noticed that further volume reduction leads to a drop in protein concentration. No such issue was observed during the concentration step of HS9_DSB7_V19A and HS9_DSB7_L26I.

Samples were then incubated at 5° C. or 40° C. for 4 weeks followed by analytical SEC-HPLC in order to assess storage stability. Results are summarized in Table 20.

TABLE 20

Purity and aggregation parameters for purified peptide/antibody lead molecules after 4 weeks incubation at 5° C. or 40° C.

| # | Compound | [C] mg/mL | Purity after 4 weeks at 5° C. (%) | Purity after 4 weeks at 40° C. (%) | Aggregation rate per month at 5° C. (%) | Aggregation rate per month at 40° C. (%) |
|---|---|---|---|---|---|---|
| 1 | HS9_DSB7_G2V | 38.7 * | 88.6 | 77.9 | 1.4 | 9.2 |
| 2 | HS9_DSB7_E15A | 33.7 * | 93.9 | 80.8 | 0.81 | 13.2 |
| 3 | HS9_DSB7_V19A | 52 | 98.7 | 90.1 | 0.3 | 6.3 |
| 4 | HS9_DSB7_L26I | 47.2 | 97 | 87.6 | 0.32 | 7.1 |

Both HS9_DSB7_V19A and HS9_DSB7_L26I display better stability parameters than HS9_DSB7_G2V and HS9_DSB7_E15A. For instance, the first two have an aggregation rate per month at 5° C. of around 0.3% compared to 0.8 and 1.4% for HS9_DSB7_E15A and HS9_DSB7_G2V respectively.

B) Single Intravenous Dose Pharmacokinetics in Rat of GLP-1 Analogue Peptides in Fusion with Anti-PCSK9 Antibody Pharmacokinetic profile of the four selected peptide antibody fusions at the desired human GLP-1R potency was assessed as described in Example 4 following a single intravenous bolus in three CD rats at 60, 53, 58.5 and 60 mg/kg for HS9_DSB7_G2V, HS9_DSB7_E15A, HS9_DSB7_V19A and HS9_DSB7_L26I respectively. A high dose of the compound (above 50 mg/kg) was used to saturate the PCSK9 sink for a significant period of time to determine PK parameters during the linear phase, without any target mediated drug disposition component.

Figure 24:
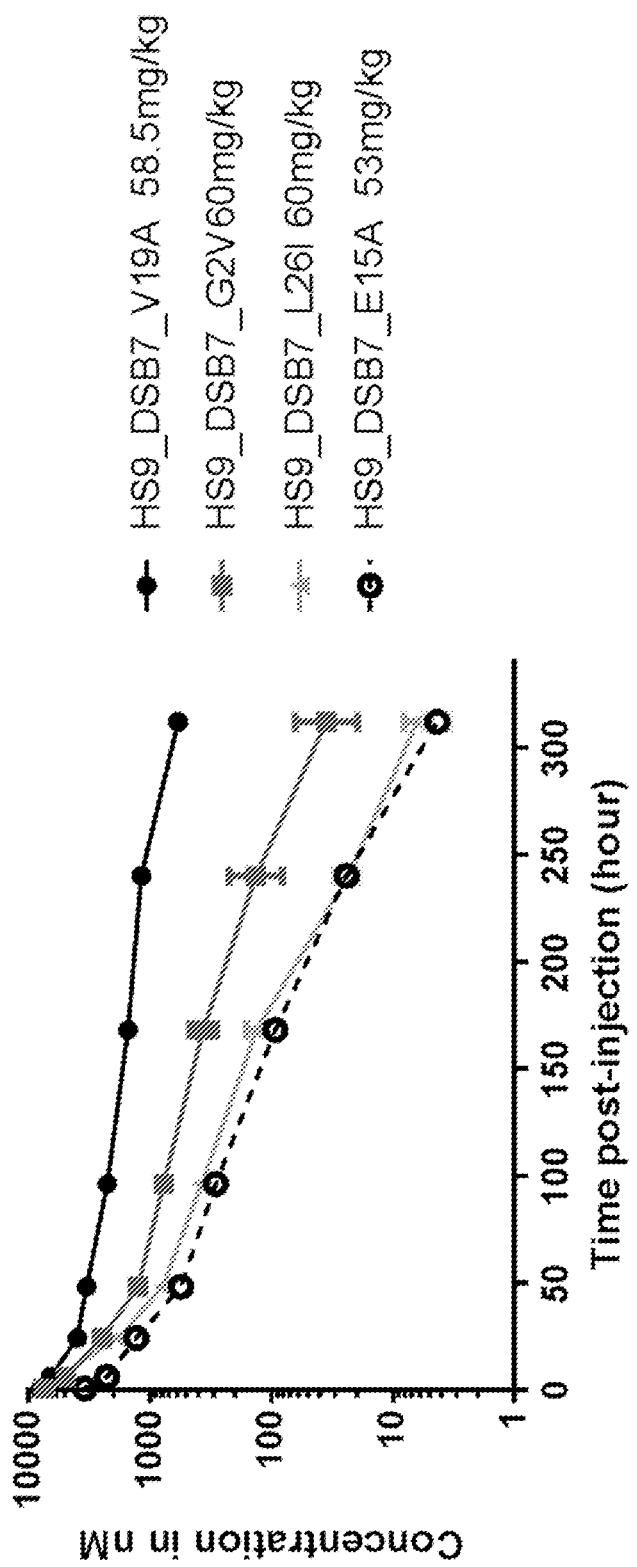
FIG. 24 illustrates the pharmacokinetic profile of peptide/antibody molecules in rats after a single i.v. injection.

Blood samples were collected at 30 minutes, 6 h, 24 h, 48 h, 96 h, 168 h, 240 h and 336 h post injection. Concentrations for the four compounds over time are shown in FIG. 24 and half-life data are summarized in Table 21.

TABLE 21

In vivo half-life of peptide/antibody lead molecules in rats after a single i.v. injection.

| # | Compound | Design | Exposure half-life (h) |
|---|---|---|---|
| 1 | HS9_DSB7_G2V | 60 mg/kg iv in CD rats | 48 |
| 2 | HS9_DSB7_E15A | 53 mg/kg iv in CD rats | 41 |
| 3 | HS9_DSB7_V19A | 58.5 mg/kg iv in CD rats | 128 |
| 4 | HS9_DSB7_L26I | 60 mg/kg iv in CD rats | 39 |

The four fusions molecules have significant different profiles despite being very close in sequence and sharing the same antibody backbone. HS9_DSB7_V19A has the longest in vivo half-life of the four fusions, 128 h compared to for instance only 39 h for HS9_DSB7_L26I.

Example 17. Affinity and Kinetic Parameters Determination for PCSK9 Across Species of GLP-1 Analogue Peptide in Fusion with Anti-PCSK9 Antibody Association (ka), dissociation (kd) and equilibrium dissociation constants (KD) for human, cynomolgus and rat PCSK9 binding to the GLP-1 analogue anti-PCSK9 fusion HS9_DSB7_V19A human IgG1-TM were determined at 25° C. by Surface Plasmon Resonance (SPR) using the Biacore 2000 biosensor (GE Healthcare), essentially as described by Karlsson et al. (J. Immunol. Methods (1991), vol. 145, p. Dear229-40). Anti-PCSK9 antibody PC9#3 human IgG1-TM was used as benchmark (Variable heavy chain of SEQ ID NO: 404 and variable light chain of SEQ ID NO: 405.

A mouse anti-human IgG monoclonal antibody surface was first created using a Human Antibody Capture Kit and CM5 sensor chip (GE Healthcare). Human antibody compounds were captured at a flow rate of 10 μL/minute for 3 minutes. Recombinant human Avi_PCSK9_Flag_His (in-house), cynomolgus Avi_PCSK9_Flag_His (in-house) and His-tagged rat PCSK9 (SinoBiological) were diluted to concentrations ranging from 1 nM to 200 nM in running buffer (10 mM sodium phosphate pH 7.4, 150 mM sodium chloride, 1 mg/mL BSA, 0.05% Tween20) and injected over the chip surface for 10 minutes, followed by running buffer only for a 10 minutes dissociation phase. The surface of the chip was regenerated using 3 M magnesium chloride between each antibody application. Global dissociation rates were first calculated followed by global on-rate calculations both using a 1:1 binding kinetics model.

Results are shown in Table 22.

TABLE 22

Kinetic parameters determined by Biacore of peptide/antibody lead molecule HS9_DSB7_V19A for human, cynomolgus and rat PCSK9 compared to anti-PCSK9 antibody PC9#3

| kinetic parameters | ka (1/Ms) | kd (1/s) | KD (M) |
|---|---|---|---|
| Human PCSK9 | | | |
| PC9#3 | 6.4E+05 | 4.4E−04 | 7.0E−10 |
| HS9_DSB7_V19A | 1.9E+05 | 1.1E−04 | 6.0E−10 |
| Cynomolgus PCSK9 | | | |
| PC9#3 | 4.2E+05 | 4.2E−04 | 1.0E−09 |
| HS9_DSB7_V19A | 1.1E+05 | 1.9E−04 | 1.7E−09 |
| Rat PCSK9 | | | |
| PC9#3 | 9.0E+05 | 4.7E−03 | 5.2E−09 |
| HS9_DSB7_V19A | 3.7E+05 | 2.1E−04 | 5.7E−10 |

Fusion molecule HS9_DSB7_V19A has an affinity at pH7.4 for human PCSK9 of 600 pM very similar to the benchmark anti-PCSK9 antibody PC9#3. Interestingly HS9_DSB7_V19A, with a four time lower dissociation constant, is less prone to dissociate from human PCSK9 compared to PC9#3.

In addition, HS9_DSB7_V19A can strongly bind to cynomolgus and rat PCSK9 at physiological pH with equilibrium dissociation constants close to the human PCSK9 value (1.7 nM and 570 pM respectively).

Example 18. Specificity for PCSK9 Compared to Closely Related Human Proteins of GLP-1 Analogue Peptide in Fusion with Anti-PCSK9 Antibody Specificity for PCSK9 compared to related human proteins of the GLP-1 analogue anti-PCSK9 fusion HS9_DSB7_V19A human IgG1-TM was determined by Dissociation-Enhanced Lanthanide Fluorescent Immunoassay Time Resolved Fluorescence (DELFIA TRF Assay, PerkinElmer). Recombinant human Avi_PCSK9_Flag_His (in-house), GST tagged human PCSK7 (Abnova), GST tagged human MBTPSI (Abnova) and Flag/His tagged human CD86 (in-house) were coated at 10 μg/mL in PBS into 96-well immunoassay plate. After washing, HS9_DSB7_V19A was added to antigen-coated wells at a concentration of 25 μg/mL. Plates were incubated at room temperature for 2 hours before extensive washing. Bound HS9_DSB7_V19A human IgG1-TM was detected using secondary Europium-labelled anti-human IgG antibody (PerkinElmer). Antigen coating to the plates was assessed by using a mouse anti-GST IgG (Abcam) as primary and Europium-labelled anti-mouse IgG (PerkinElmer) as detection for human PCSK7 and human MBTPSI. Human PCSK9 and human CD86 coating was directly assessed using a Europium-labelled anti-His IgG (PerkinElmer).

89

Results showed that HS9_DSB7_V19A human IgG1-TM binds strongly to human PCSK9 but not to human PCSK7, human MBTPSI (PCSK8) or human CD86 (data not shown).

Example 19. Blocking Human PCSK9 Binding to LDL Receptor with GLP-1 Analogue Peptide in Fusion with Anti-PCSK9 Antibody Ability of the GLP-1 analogue anti-PCSK9 fusion HS9_DSB7_V19A to block the binding of human PCSK9 to human LDL receptor was assessed using an ELISA competition assay. Anti-PCSK9 antibody HS9 and irrelevant isotype match NIP228 human IgG1-TM were used as positive and negative controls respectively.

Binding of biotinylated human PCSK9 (in house) at 5 ug/mL in 1× Phosphate Buffered Saline, 3% skimmed milk to human LDL-R (R&D Systems) coated overnight at 10 ug/mL onto 96 well MaxiSorb plate (NUNC) was detected by ELISA using cryptate labelled streptavidin (Perkin Elmer) diluted at 100 ng/mL in Delfia Buffer (Perkin Elmer). That interaction was challenged using a 3-fold serial dilution, starting at 100 ug/mL, of compounds co-incubated for 2 h at room temperature with the biotinylated PCSK9 reagent in the LDL receptor coated wells. Fluorescence signal was read on the Perkin Elmer Envision machine using a 340 nm excitation and 620 nm emission. Percentage of specific binding was calculated by subtracting the background signal obtained with no LDL receptor coated onto the plate normalized with the maximum specific binding signal obtained with no competitor compound minus background level.

Figure 25:
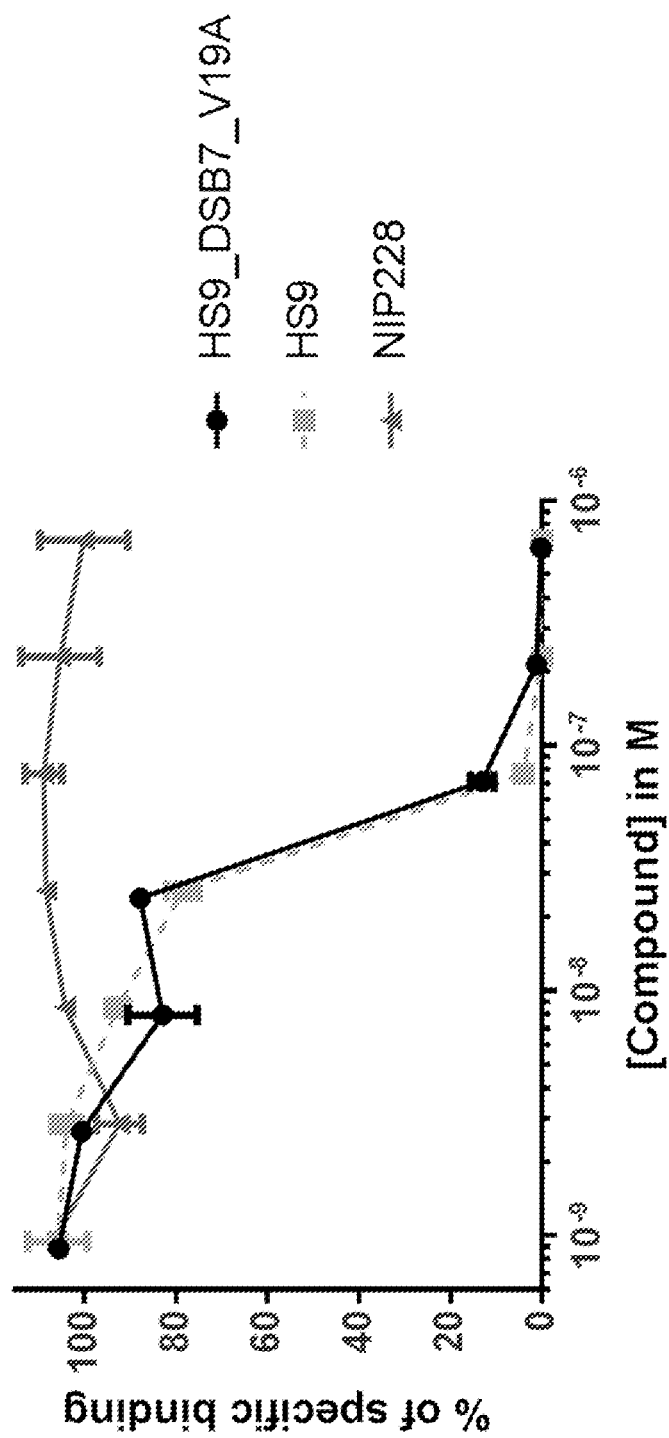
FIG. 25 demonstrates inhibition of human PCSK9 binding to LDL receptor using competition ELISA.

Biochemical inhibition of PCSK9 binding to LDL receptor is presented in FIG. 25.

Fusion molecule HS9_DSB7_V19A can block the binding of biotinylated human PCSK9 to recombinant LDL receptor with similar $IC_{50}$ compared to the positive control anti-PCSK9 antibody HS9 (4.3E-8 and 3.5E-8 M respectively).

Example 20. LDL Uptake by HEPG2 Cells Treated with GLP-1 Analogue Peptide in Fusion with Anti-PCSK9 Antibody Ability of the GLP-1 analogue anti-PCSK9 fusion HS9_DSB7_V19A to block PCSK9 activity and restore LDL uptake was tested in HepG2 hepatic cells as followed. Anti-PCSK9 antibody PC9#2 and irrelevant isotype match NIP228 human IgG1-TM were used as positive and negative controls respectively.

Human HepG2 cells were seeded in black, clear bottom 96-well Greiner plates at a concentration of $2\times10^4$ cells per well in DMEM medium (Gibco) supplemented with 10% lipoprotein deficient serum (Sigma) and incubated at 37° C. (5% $CO_2$) overnight. To complex PCSK9 with the tested compound, 45 nM of human Avi_PCSK9_FLAG_His (in house) was incubated with or without the tested compound at various concentrations in DMEM +10% LPDS for 1 hour at room temperature. All media was removed from the cell plate and the PCSK9/compound mixtures were transferred to the plate and incubated for 1 hour. Bodipy-LDL (Molecular Probes), diluted in DMEM+10% LPDS to a final concentration of 50 nM, was next transferred to the cells and the plate incubated for 5 hours at 37° C. (5% $CO_2$). Cells were washed thoroughly with PBS, stained with the nuclear dye Hoescht and fixed using formaldehyde at a final concentration of 3.7% (v/v). Assay plates were read for cell-associated fluorescence using the Cellomics ArrayScan VTi high content imaging system. Hoescht staining was measured in channel 1 using the BGRFR_386_23 filter and Bodipy-LDL in channel 2 using the BGRFR_485_20 filter. Images were analysed using the Compartmental Analysis v4 algorithm.

Figure 26:
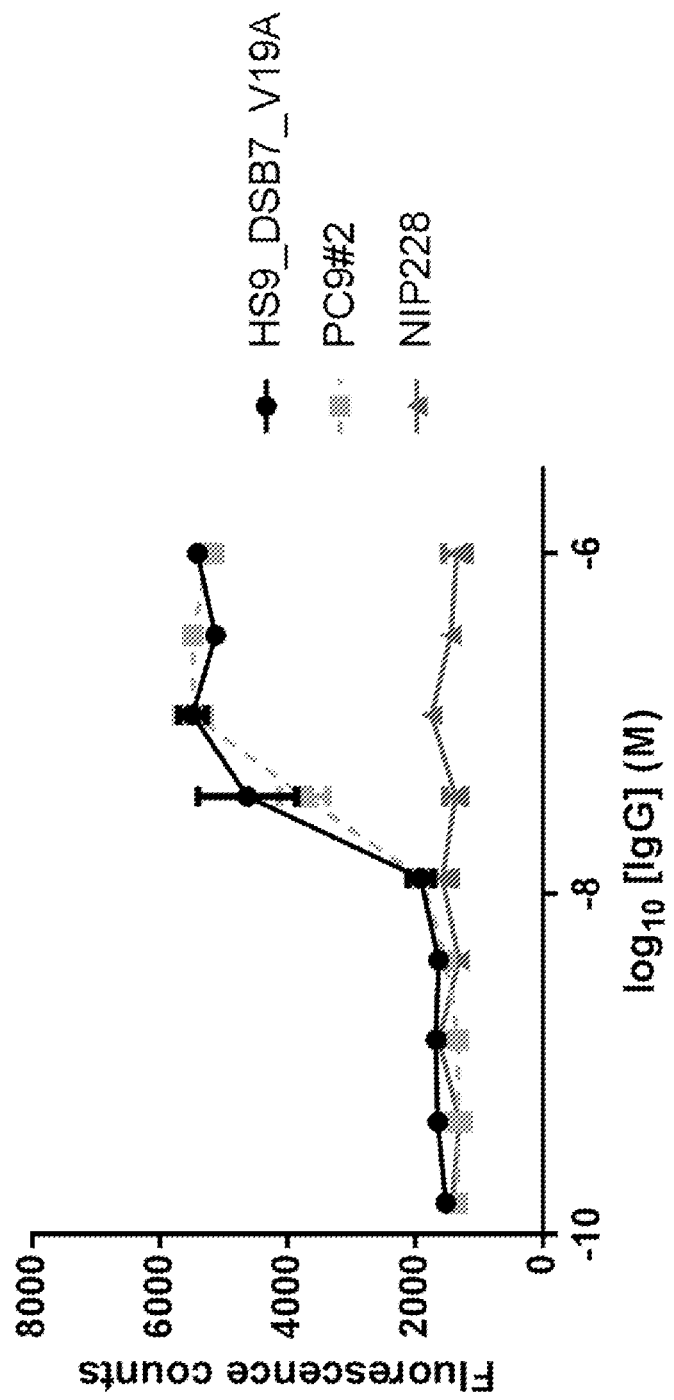
FIG. 26 shows inhibition of human PCSK9-dependent loss of LDL uptake in HepG2 cells.

Inhibition of PCSK9-dependent loss of LDL uptake by HepG2 cells is presented in FIG. 26.

Fusion molecule HS9_DSB7_V19A can restore LDL-uptake by HepG2 cells treated with human PCSK9 with similar $IC_{50}$ compared to the positive control anti-PCSK9 antibody PC9#2 (2.5E-8 and 3.1E-8 M respectively).

Example 21. Potency at GLP-1 Receptors Across Species of GLP-1 Analogue Peptide in Fusion with Anti-PCSK9 Antibody Cross-reactivity of the GLP-1 analogue anti-PCSK9 fusion HS9_DSB7_V19A at human, cynomolgus, mouse and rat GLP-1 receptors was tested in a cAMP production assay as previously described by using stable cell lines overexpressing the receptor of interest. GLP1-Fc fusion (in house) and GLP-1 peptide were used as positive controls.

Potency at the different GLP-1 receptors is summarised in Table 23.

TABLE 23

Potency of lead molecule HS9_DSB7_V19A at GLP-1 receptor across species

| # | Compound | Potency at GLP-1R in cAMP assay across species (M) | | | |
|---|---|---|---|---|---|
| | | human | cynomolgus | mouse | rat |
| 1 | HS9_DSB7_V19A | 3.73E-09 | 5.83-10 | 5.75-10 | 3.83E-11 |
| 2 | GLP1-Fc(Gamma4) | 7.72E-11 | 1.09E-11 | 8.98E-11 | 8.92E-12 |
| 3 | GLP-1 peptide | 1.61E-11 | 1.03E-11 | 2.69E-11 | 9.31E-11 |

Fusion molecule HS9_DSB7_V19A can activate GLP-1 receptor across all the four tested species.

Example 22. Several Compounds were Identified by Reducing Potency at the Human GLP-1 Receptor To reduce DSB7 potency, certain residues in the peptide were mutated. Peptide Ab fusions to SEQ ID NO: 2 with linker SEQ ID NO: 4 at the desired potency, here shown in green triangles, were further analyzed for specificity at human GLP1-R and species cross reactivity. See FIG. 27.

Figure 27:
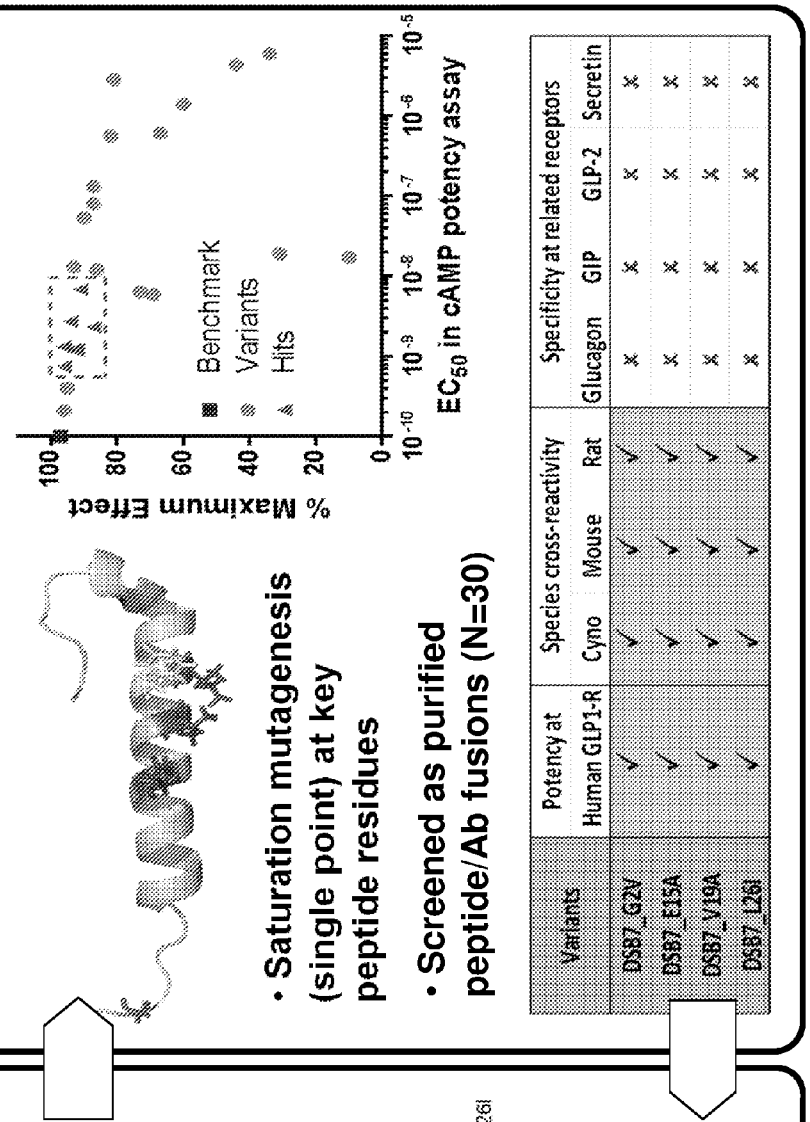
FIG. 27 shows the engineered reduction of potency at the human GLP-1 receptor.

The variants are shown as HS9_DSB7_G2V ($Gly_2 \rightarrow Val$) (SEQ ID NO: 44 and SEQ ID NO: 1); HS9_DSB7_E15A ($Glu_{15} \rightarrow Ala$) (SEQ ID NO: 45 and SEQ ID NO: 1); HS9_DSB7_V19A ($Val19 \rightarrow Ala$) (SEQ ID NO: 47 and SEQ ID NO: 1); HS9_DSB7_L26I ($Leu_{26} \rightarrow Ile$) (SEQ ID NO: 46 and SEQ ID NO:1) (compared to Val$_{19}$→Ala (SEQ ID NO: 3)). These four variants were selected for final characterization. Results are shown in FIG. 27.

Example 23. Fusion Molecule with Reduced Potency

Figure 28A:
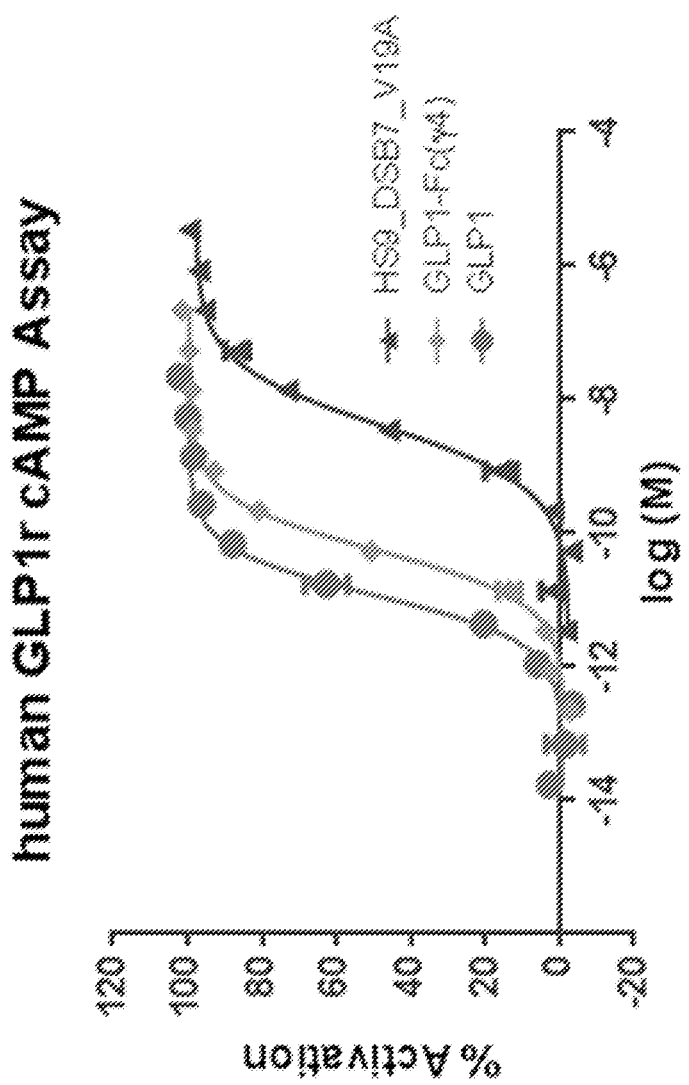
FIG. 28A show a human GLP1r cAMP assay for Exendin-4 GLP-1 analogue DSB7_V19A in light chain fusion with the anti-PCSK9 antibody HS9.

The PCSK9/GLP-1 fusion molecule exhibits the desired potency on the GLP-1 receptor, as shown in FIG. 28A. The potency of this compound has been reduced to minimize nausea. Table 24 shows that HS9_DSB7_V19A has a 57.7 fold reduced potency with respect to dulaglutide. This engineered reduction of potency provides the desired effect of reducing nausea and other untoward effects.

TABLE 24

Fusion Molecule with Reduced Potency

| Sample ID | Mean EC50 (M) | Fold Change Over Benchmark | Max Activation (%) |
|---|---|---|---|
| HS9_DSB7_V19A (heavy chain of SEQ ID NO: 1 and light chain fusion of SEQ ID NO: 47) | 4.4E−09 | 57.7 | 98 |
| GLP-1 (SEQ ID NO: 29) | 1.6E−11 | 0.2 | 100 |
| GLP1-Fc(G4) (dulaglutide) | 7.7E−11 | 1.0 | 100 |

Figure 28B:
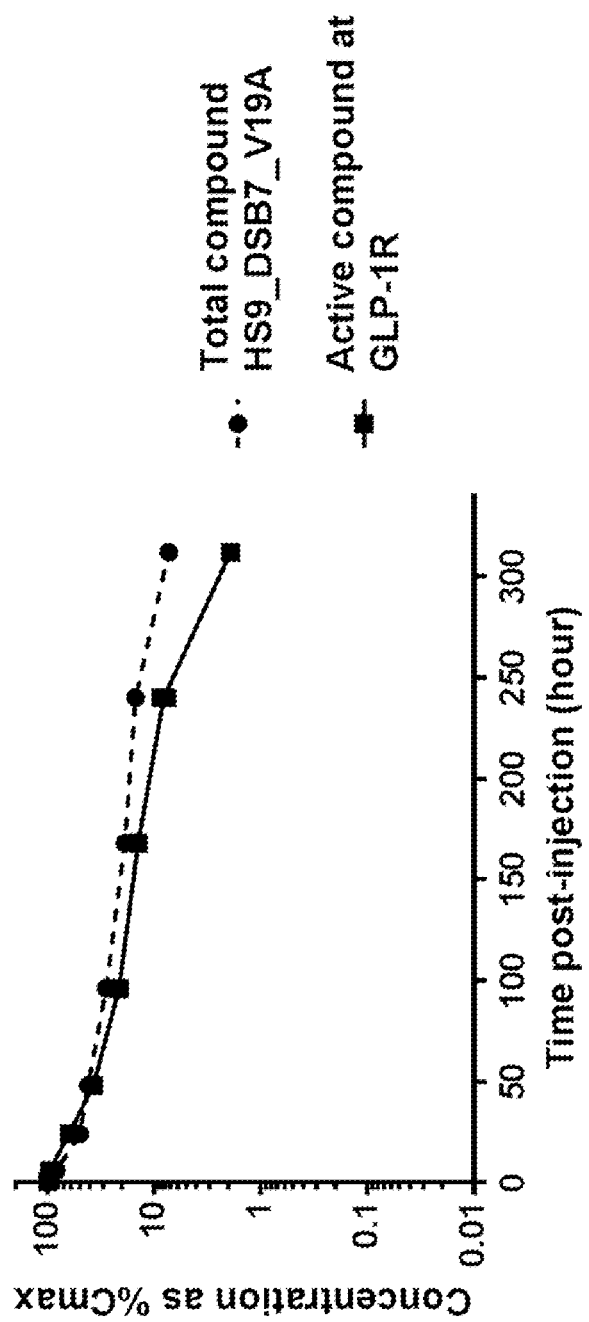
FIG. 28B illustrates the stability in rat for Exendin-4 GLP-1 analogue DSB7_V19A in light chain fusion with the anti-PCSK9 antibody HS9.

PCSK9/GLP-1 fusion of Example 1 exhibits an Ab exposure/GLP-1 activity profile sufficient to enable weekly dosing, for example, as shown in FIG. 28B. pK stability study in rat of 58.5 mg/kg of HS9_DSB7_V19A injected into rat. Concentration of the fusion compound is measured in the serum over time. Samples taken from rat are analyzed for both activity of the test compound and concentration of the test compound in serum. Data from the GLP-1 activity portion is used to back calculate for concentration of "active" compound. The line with closed circles is the concentration of HS9_DSB_V19A and line with closed squares is the concentration of active HS9_DSB_7_V19A (i.e., having GLP-1 activity) for the same samples.

Example 24. Specificity for GLP-1 Receptor Compared to Closely Related Human Receptors of GLP-1 Analogue Peptide in Fusion with Anti-PCSK9 Antibody Specificity of the GLP-1 analogue anti-PCSK9 fusion HS9_DSB7_V19A for GLP-1 receptor compared to related human receptors was tested in a cAMP production assay as previously described by using stable cell lines overexpressing the receptor of interest: glucagon, GIP, GLP-2 and secretin receptors. Specific agonist peptides for each of the four receptors were used as positive controls.

Data are shown in FIGS. 29A-D (A: Glucagon receptor, B: GIP receptor, C: GLP-2 receptor, D: Secretin receptor).

Fusion molecule HS9_DSB7_V19A is specific for GLP-1 receptor and does not activate any of the four tested closely related receptors.

Example 25. Further Characterization of Fusion Molecule Demonstrates a Favorable In Vivo Profile The PCSK9/GLP-1 fusion molecule of Example 2 (HS9_DSB7_V19A (heavy chain of SEQ ID NO: 1 and light chain fusion of SEQ ID NO: 47)) shows superior glucose control and weight loss over time, including at day 7 post dose. Data is shown against dulaglutide and PC9_2_VH and VL (SEQ ID NOS: 8 and 9). Animals were dosed at day 0 with the compounds and then their body weight was measured over time to determine a change in body weight.

The fusion molecule has shown that it binds purified PCSK9 with high affinity, it restores LDLc uptake in HEPG2 cells, stimulates GLP-1R at a desired potency, promotes weight loss and demonstrates favorable exposure/activity profile in rat PK to support weekly dosing and sustained GLP-1 activity in vivo.

Figure 30A:
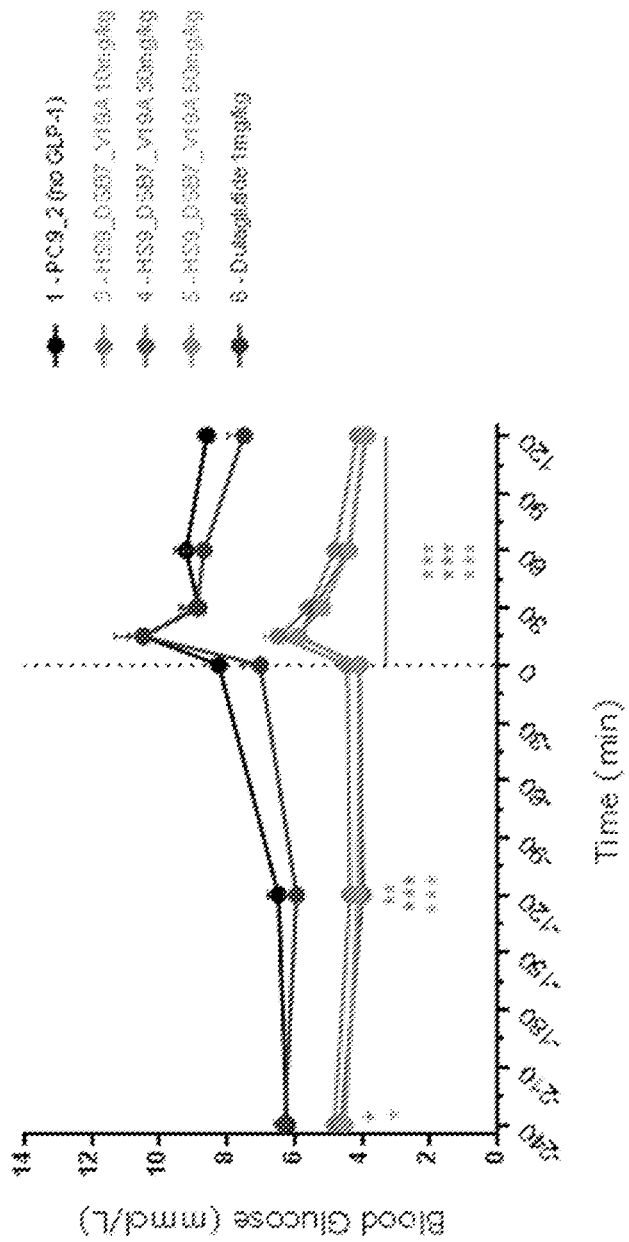
FIGS. 30A-B show superior glucose control (A) and weight loss (B) over time, including at day 7 post dose.
Figure 30B:
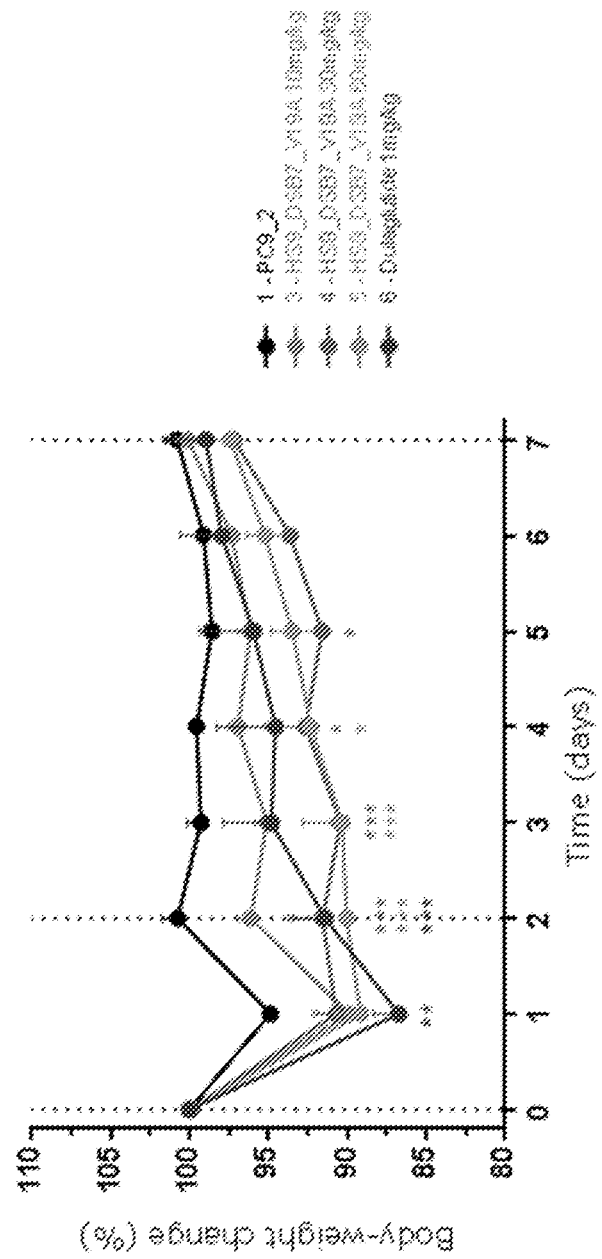

Results are provided in FIGS. 30A-B.

Example 26. Impact of the Linker on the Activities of GLP-1 Analogue Peptide in Fusion With Anti-PCSK9 Antibody The compound HS9_DSB7_V19A has a linker of SEQ ID NO: 4 corresponding to a Gly$_4$Ser motif repeated three times between the peptide moiety and the antibody light chain. To investigate the impact of the linker length between the GLP-1 analogue peptide DSB7_V19A (SEQ ID NO: 3) when fused to the light chain of anti-PCSK9 antibody HS9 (light chain: SEQ ID NO: 2 and heavy chain: SEQ ID NO: 1), three fusions with a reduced linker length were generated: HS9_DSB7_V19A_L2 (SEQ ID NO: 419) having a linker corresponding to the Gly$_4$Ser motif repeat two times (linker: SEQ ID NO: 403), HS9_DSB7_V19A_L1 (SEQ ID NO: 420) having a linker corresponding to the Gly$_4$Ser motif repeat one time (SEQ ID NO. 27) and HS9_DSB7_V19A_L0 with no linker between the peptide and the antibody light chain (SEQ ID NO: 421).

Compounds were tested for both binding to recombinant human PCSK9 by ELISA and activity at the human GLP-1 receptor using the cAMP assay cell based assay as described in Example 4.

Binding ELISA was performed by coating human PCSK9 (in house) at 10 ug/mL in 1× Phosphate Buffered Saline. After plate blocking with 1× Phosphate Buffered Saline, 3% skimmed milk, compounds were added at 100 ug/mL in PBS and incubated for 2 h at room temperature before washing. Bound compounds were detected using cryptate labelled Fc specific anti human IgG (Perkin Elmer) diluted at 100 ng/mL in Delfia Buffer (Perkin Elmer). Fluorescence signal was read on the Perkin Elmer Envision machine using a 340 nm excitation and 620 nm emission. HS9_DSB7_V19A was used as positive control and irrelevant isotype match NIP228 used to determine the background level.

Figure 31:
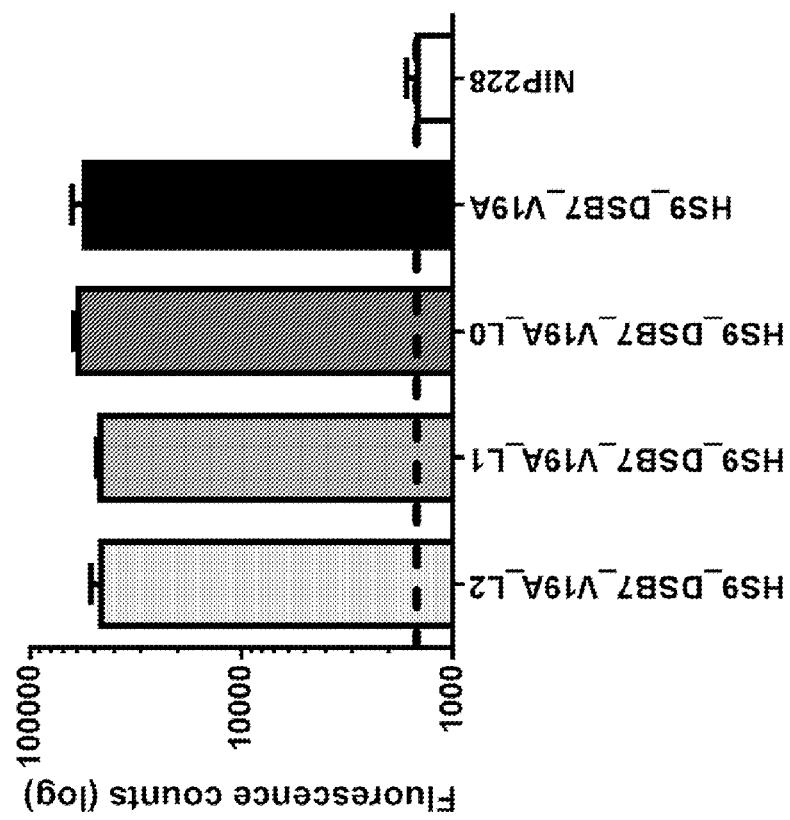
FIG. 31 shows binding to human PCSK9 of HS9 anti-PCSK9 antibody in fusion with GLP-1 analogue peptide DSB7_V19A using different linkers.
Figure 32:
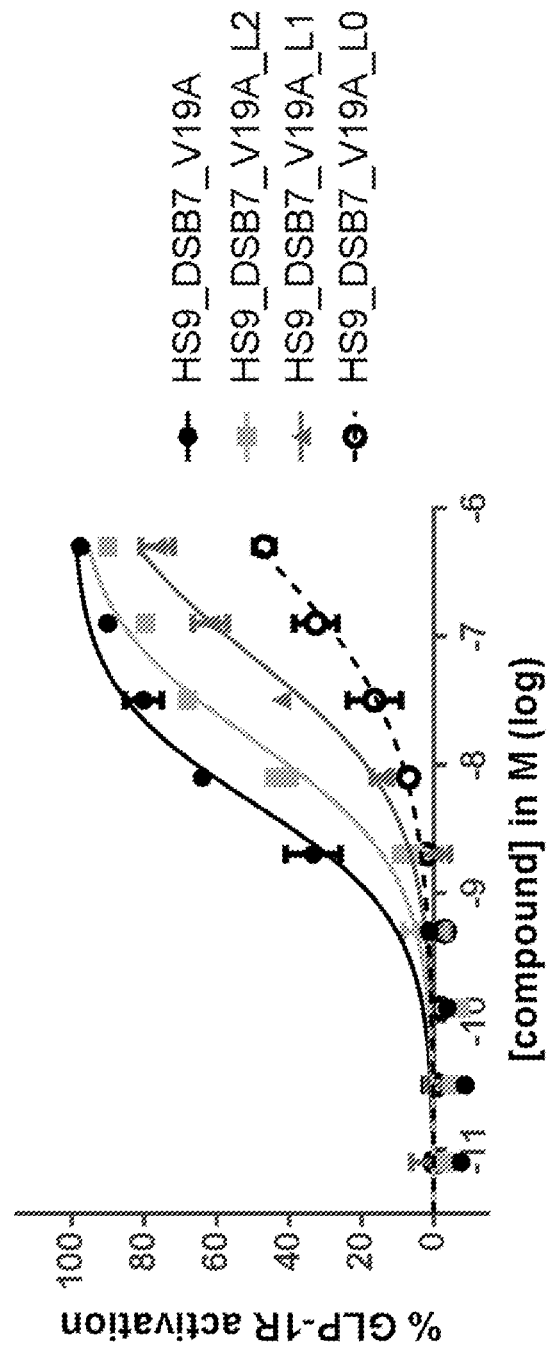
FIG. 32 shows human GLP-1 receptor activation using GLP-1 analogue peptide DSB7_V19A in fusion with anti-PCSK9 antibody HS9 using different linkers.

PCSK9 binding and GLP-1 receptor activation data are shown in FIGS. 31 and 32, respectively.

All additional fusion molecules are able to bind human PCSK9 to a similar level compared to HS9_DSB7_V19A. Tested fusion molecules can also activate human GLP-1 receptor in the cAMP cell based assay but reducing linker length is having a negative impact on compound potency. In that assay, EC$_{50}$ for HS9_DSB7_V19A, HS9_DSB7_V19A_L2, HS9_DSB7_V19A_L1 and HS9_DSB7_V19A_L0 are 5.0 nM, 15.6 nM, 68.7 nM and 537 nM, respectively.

Example 27. In Vitro Characterization of Stable GLP-1 Analogue Peptide in Fusion with Anti-PCSK9 Antibodies The GLP-1 analogue peptide DSB7_V19A of SEQ ID NO: 3) was fused using a linker of SEQ ID NO:4 to the light chain of other anti-PCSK9 antibodies than HS9:

1_ PC9#1 with antibody variable heavy chain of SEQ ID NO:10 and antibody variable light chain of SEQ ID NO:11.

2_ PC9#3 with antibody variable heavy chain of SEQ ID NO:404 and antibody variable light chain of SEQ ID NO:405.

3_ PC9#4 with antibody variable heavy chain of SEQ ID NO:406 and antibody variable light chain of SEQ ID NO:407.

4_ PC9#5 with antibody variable heavy chain of SEQ ID NO:408 and antibody variable light chain of SEQ ID NO:409.

5_ PC9#6 with antibody variable heavy chain of SEQ ID NO:410 and antibody variable light chain of SEQ ID NO:411.

6_ PC9#7 with antibody variable heavy chain of SEQ ID NO:412 and antibody variable light chain of SEQ ID NO:413.

Fusions were tested for both binding to recombinant human PCSK9 by ELISA as described in Example 26 and activity at the human GLP-1 receptor using the cAMP cell based assay as described in Example 4. HS9_DSB7_V19A and NIP228 isotype match were used as positive and negative controls respectively.

Figure 33:
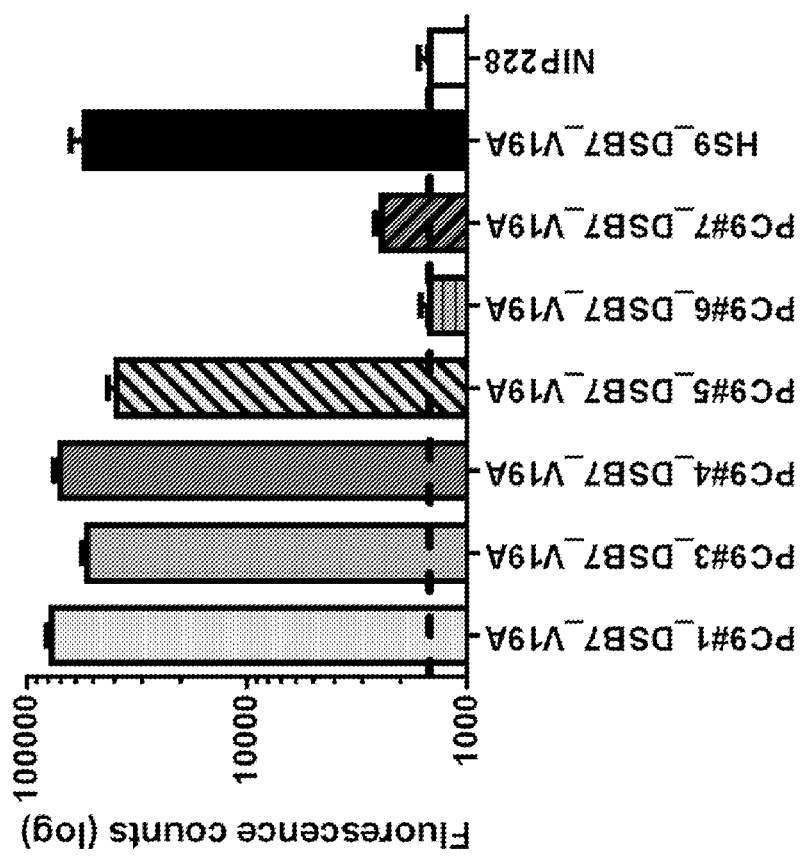
FIG. 33 illustrates binding to human PCSK9 of anti-PCSK9 antibodies in fusion with GLP-1 analogue peptide DSB7_V19A
Figure 34:
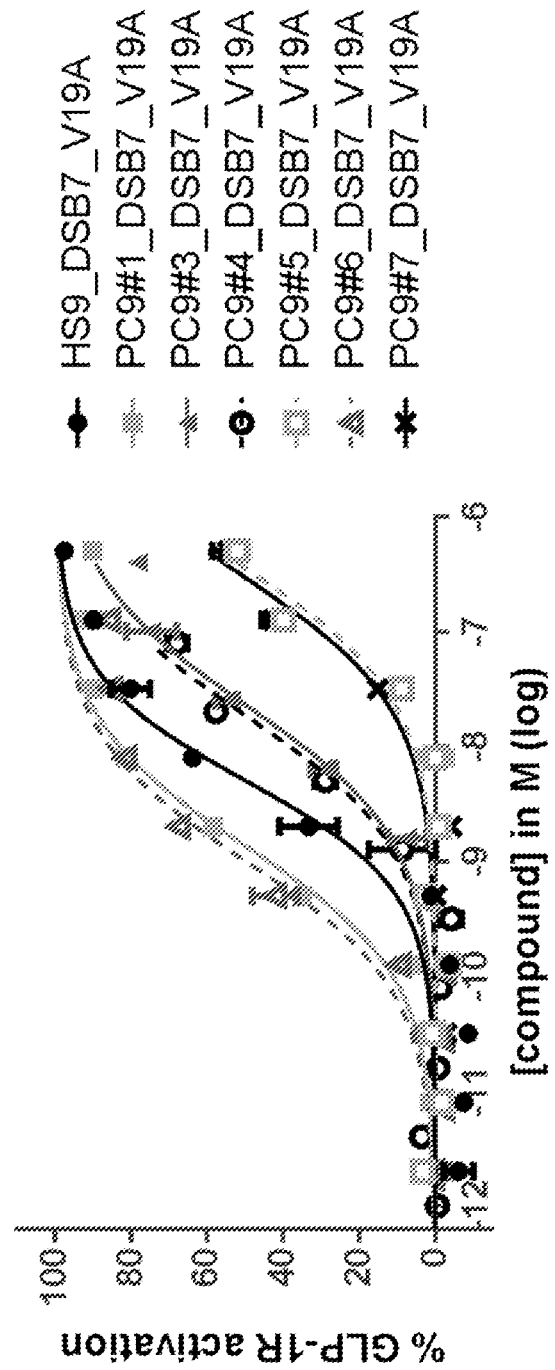
FIG. 34 illustrates human GLP-1 receptor activation using GLP-1 analogue peptide DSB7_V19A in fusion with anti-PCSK9 antibodies FIG. 35 demonstrates binding to human B7-H1 of anti-B7-H1 antibody 2.7A4 in fusion with GLP-1 analogue peptide DSB7_V19A

PCSK9 binding and GLP-1 receptor activation data are shown in FIGS. 33 and 34, respectively.

All seven compounds tested in the human GLP-1 receptor cAMP assay are able to activate the receptor. Potency among the panel is ranging from 1 to 350 nM for PC9#6_DSB7_V19A and PC9#5_DSB7_V19A, respectively. HS9_DSB7_V19A has a potency of 5 nM in that assay.

In addition, all tested fusions are also able to bind strongly to human PCSK9 by ELISA at the exception of PC9#7_DSB7_V19A which binds poorly and PC9#6_DSB7_V19A which does not bind.

Example 28. In Vitro Characterisation of Stable GLP-1 Analogue Peptide in Fusion with an Anti-B7-H1 Antibody The GLP-1 analogue peptide DSB7_V19A of SEQ ID NO: 3 was fused using a linker of SEQ ID NO:4 to the light chain of the anti-B7-H1 antibody 2.7A4 described in patent WO2011066389. Anti B7-H1 antibody 2.7A4 has a variable heavy chain of SEQ ID NO:422 and a variable light chain of SEQ ID NO:423.

Fusion was tested for both binding to recombinant human B7-H1 by ELISA and activity at the human GLP-1 receptor using the cAMP assay cell based assay as described in Example 4.

Binding ELISA was performed by coating human B7-H1 (in house) at 5 ug/mL in 1× Phosphate Buffered Saline. After plate blocking with 1× Phosphate Buffered Saline, 3% skimmed milk, compounds were added at 10 ug/mL in PBS and incubated for 2 h at room temperature before washing. Bound compounds were detected using cryptate labelled Fc specific anti human IgG (Perkin Elmer) as described in Example 25. Anti-B7-H1 antibody 2.7A4 and irrelevant isotype match NIP228 were used as positive and negative control respectively.

Figure 35:
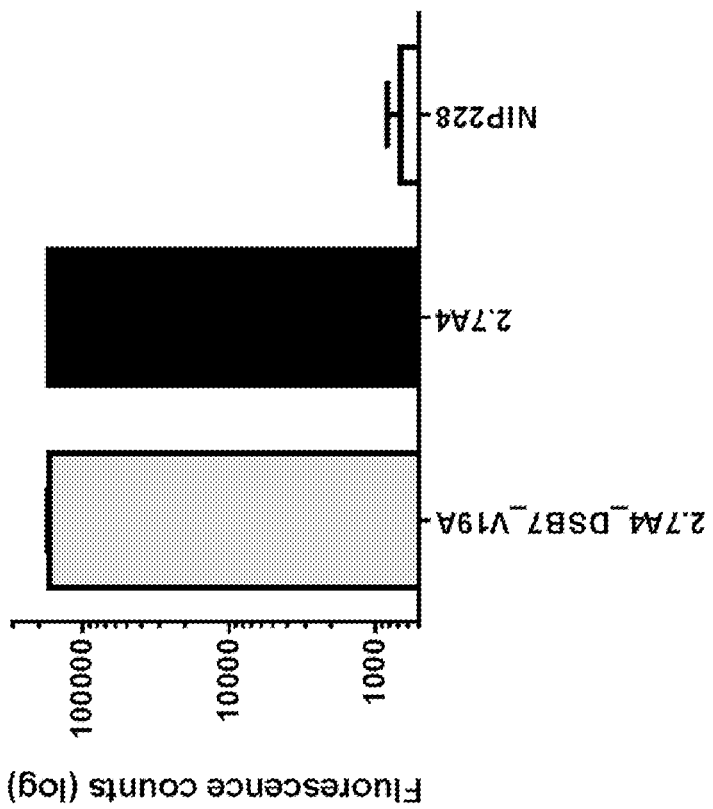
Figure 36:
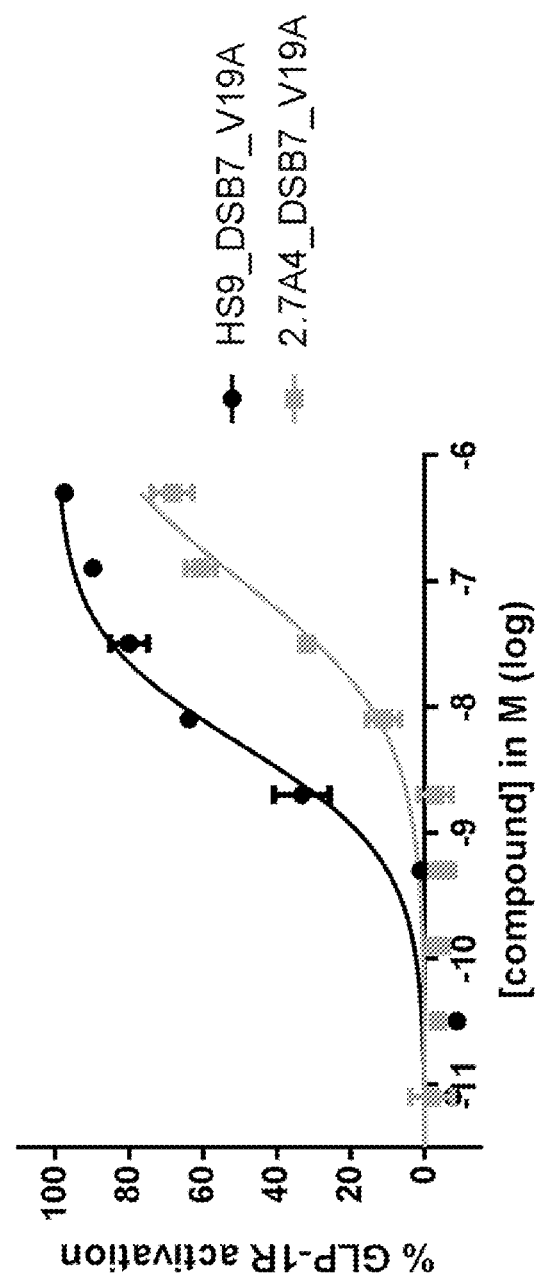
FIG. 36 shows human GLP-1 receptor activation using GLP-1 analogue peptide DSB7_V19A in fusion with anti-B7-H1 antibody 2.7A4.

B7-H1 binding and GLP-1 receptor activation data are shown in FIGS. 35 and 36, respectively.

Fusion 2.7A4 DSB7 V19A is able to bind human B7-H1 to a similar level than the positive control 2.7A4 antibody. The fusion can also activate human GLP-1 receptor in the cAMP cell based assay with a potency of 100 nM compared to 5 nM for HS9_DSB7_V19A.

Example 29. Pharmacokinetics and Pharmacodynamics in Rat of GLP-1 Analogue Peptide in Fusion with Anti-PCSK9 Antibody Following Single Intravenous Dose A PKPD study for the peptide antibody fusion HS9_DSB7_V19A following a single intravenous bolus in CD rats was conducted in order to assess its in vivo stability, by measuring both compound exposure and concentration in active GLP-1, as well as target engagement by measuring concentration in free rat PCSK9.

Fusion molecule was injected at 10, 30 and 60 mg/kg. Anti-PCSK9 mAb HS9, without a peptide attached to it, was used as control and injected at 60 mg/kg. Blood samples were collected at:

1: Pre-dose—0.5 h—6 h—24 h—48 h—96 h and 168 h for the 10 mg/kg treatment group;

2: Pre-dose—0.5 h—24 h—48 h—96 h—168 h and 240 h for the 30 mg/kg treatment group; and 3: Pre-dose—0.5 h—24 h—72 h—168 h—336 h and 504 h for the 60 mg/kg treatment groups.

Concentrations of total human IgG1 antibody (exposure) and of active GLP-1 compound in rat serum samples were quantified as described in Example 4.

Figure 37:
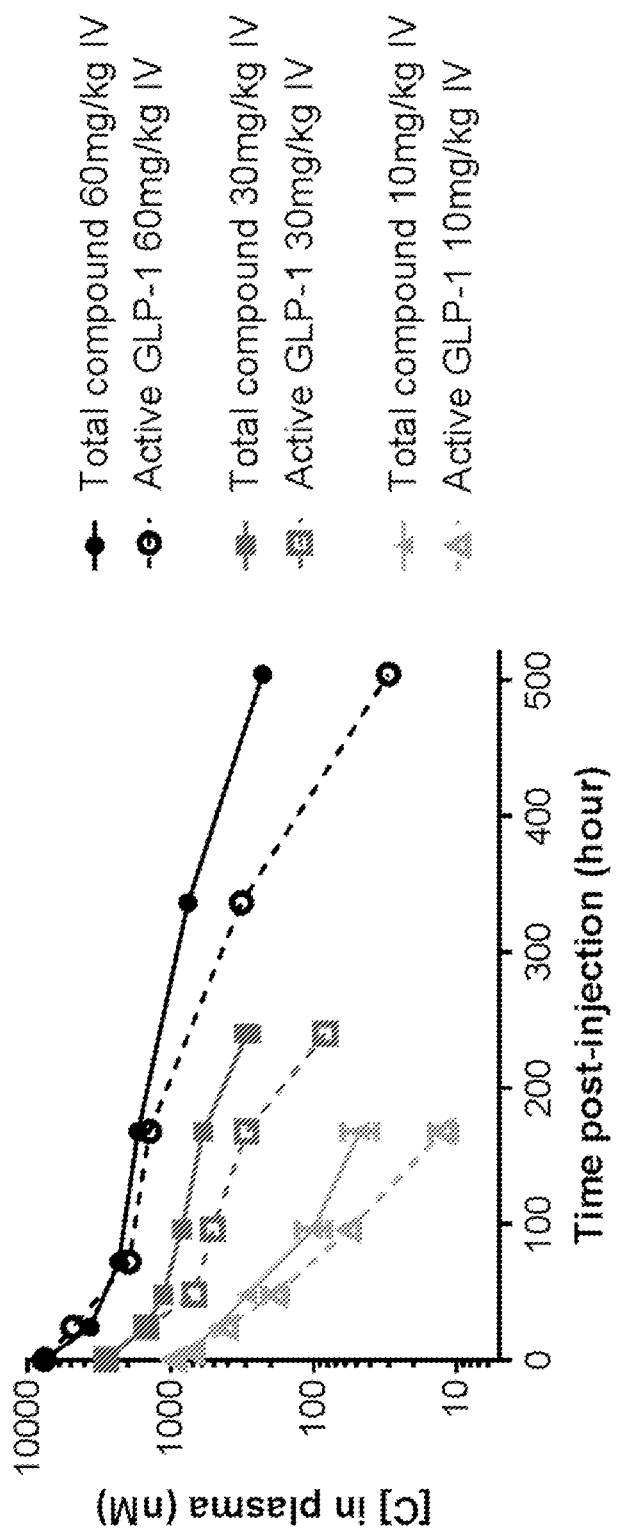
FIG. 37 describes stability in rat for the fusion molecule HS9_DSB7_V19A following a single i.v. injection at 60, 30 or 10 mg/kg.

HS9_DSB7_V19A concentration over time in total and active GLP-1 compound in rat serum for the three tested doses (10, 30 and 60 mg/kg) are shown in FIG. 37.

Area under curve (AUC) for both total compound and active GLP-1 are summarised in Table 25. Calculating the ratio between active GLP-1 and total compound AUC is one way to evaluate in vivo stability. A ratio of one is corresponding to a fully stable compound in the tested conditions.

Data for the parent fusion molecule PC9#2_Exe4 comprising Exendin-4 in light chain fusion with the anti-PCSK9 mAb PC9#2 (See Example 4) have also been included for comparison.

TABLE 25

Total and active GLP-1 AUC0-t following a single IV injection of the fusion molecule HS9_DSB7_V19A compared to the parent fusion molecule PC9#2_Exe4

| Compound | Design | AUC0-t Total (day · nmol) | AUC0-t Active GLP-1 (day · nmol) | Active/ Total AUC Ratio |
|---|---|---|---|---|
| HS9_DSB7_V19A | 10 mg/kg IV | 1595 | 1216 | 0.76 |
| HS9_DSB7_V19A | 30 mg/kg IV | 8702 | 6230 | 0.72 |
| HS9_DSB7_V19A | 60 mg/kg IV | 24535 | 26494 | 1.08 |
| PC9#2_Exe4 | 1 mg/kg IV | 299 | 40 | 0.13 |

HS9_DSB7_V19A displays a greater Active/Total AUC ratio compared to the parent molecule PC9#2_Exe4 demonstrating an improved in vivo stability profile in rat for activity at GLP-1 receptor.

Determination of free rat PCSK9 concentration in serum samples was based on a sandwich ligand binding assay method using the MSD® platform. Free rat PCSK9 was captured using the anti-PCSK9 mAb HS9 that was first non-specifically adsorbed on to the carbon surface of a Standard Bind MSD® plate. Anti-PCSK9 antibody from Abcam (Product Number ab125251) was labelled in-house with MSD® SULFO-TAG™ and used as detection reagent. Plate was then read using the MSD® Sector Imager 6000 (SI6000) instrument.

Figure 38:
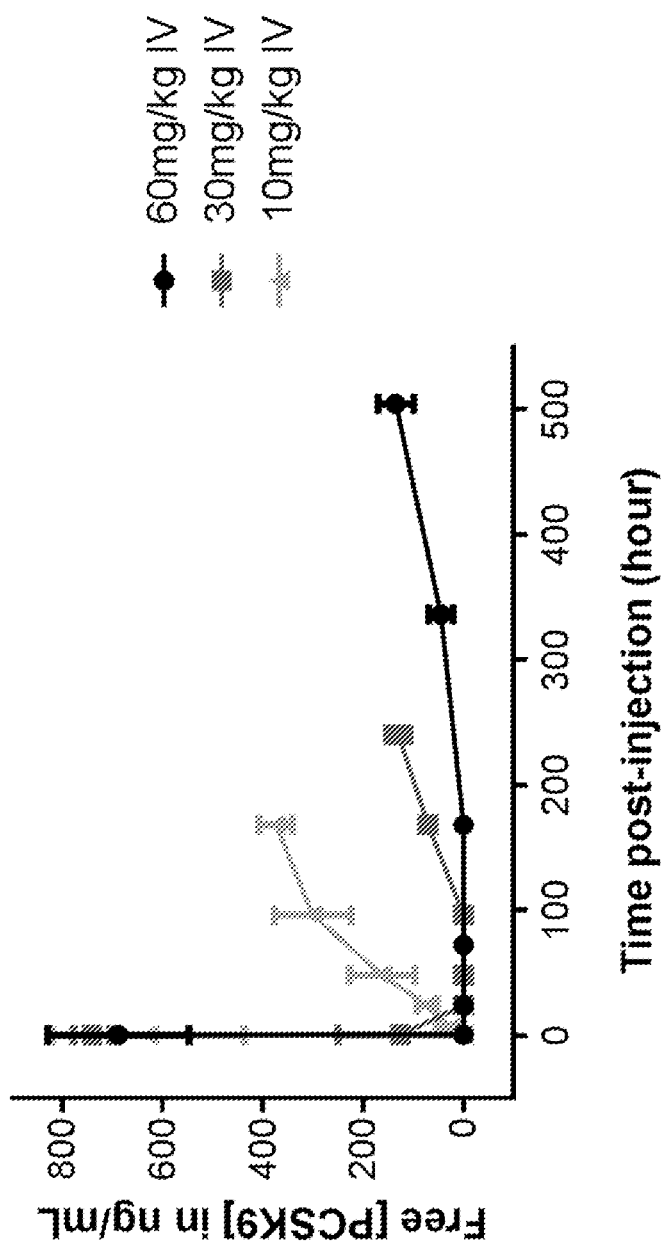
FIG. 38 shows free PCSK9 concentration in rat following a single i.v. injection at 60, 30, or 10 mg/kg of HS9_DSB7_V19A.

Engagement of HS9_DSB7_V19A to rat PCSK9 over time was evaluated by measuring the concentration of free antigen in the rat serum samples. Data for the three dosing groups (10, 30 and 60 mg/kg) are shown in Table 26 and FIG. 38.

TABLE 26

Concentration of Free Antigen in Rat Plasma Samples Over Time

| 10 mg/kg IV | | 30 mg/kg IV | | 60 mg/kg IV | |
| --- | --- | --- | --- | --- | --- |
| Time (h) | Mean free rat [PCSK9] in ng/mL | Time (h) | Mean free rat [PCSK9] in ng/mL | Time (h) | Mean free rat [PCSK9] in ng/mL |
| 0 | 837.2 | 0 | 741.8 | 0 | 688.5 |
| 0.5 | below LLOQ | 0.5 | 125.8 | 0.5 | below LLOQ |
| 6 | 26.7 | 24 | below LLOQ | 24 | below LLOQ |
| 24 | 74.1 | 48 | below LLOQ | 72 | below LLOQ |
| 48 | 162.5 | 96 | below LLOQ | 168 | below LLOQ |
| 96 | 301.0 | 168 | 70.9 | 336 | 45.4 |
| 168 | 374.7 | 240 | 130.3 | 504 | 135.8 |

HS9_DSB7_V19A is able to suppress rat PCSK9 below 90% at all tested doses but the duration of suppression is dose dependent. Free rat PCSK9 is again detectable at 6 h, 168 h and 336 h after injection when HS9_DSB7_V19A is dosed at 10, 30 and 60 mg/kg respectively.

Example 30. Pharmacokinetics and Pharmacodynamics in Rat of GLP-1 Analogue Peptide in Fusion with Anti-PCSK9 Antibody Following Single Subcutaneous Dose A pharmacokinetic study for the GLP-1 analogue peptide antibody fusion HS9_DSB7_V19A following a single subcutaneous bolus at 60 mg/kg in CD rats was performed in order to compare routes of administration and their potential impact on compound exposure and in vivo stability.

Fusion molecule was injected at 40 mg/mL using a 1.5 mL/kg regimen. Blood samples were collected at Pre-dose—6 h—24 h—48 h—96 h—168 h and 240 h.

Concentrations of total human IgG1 antibody and of active GLP-1 compound as well as concentrations in free rat PCSK9 antigen in the serum samples were determined as described in Example 4 and Example 29.

Figure 39:
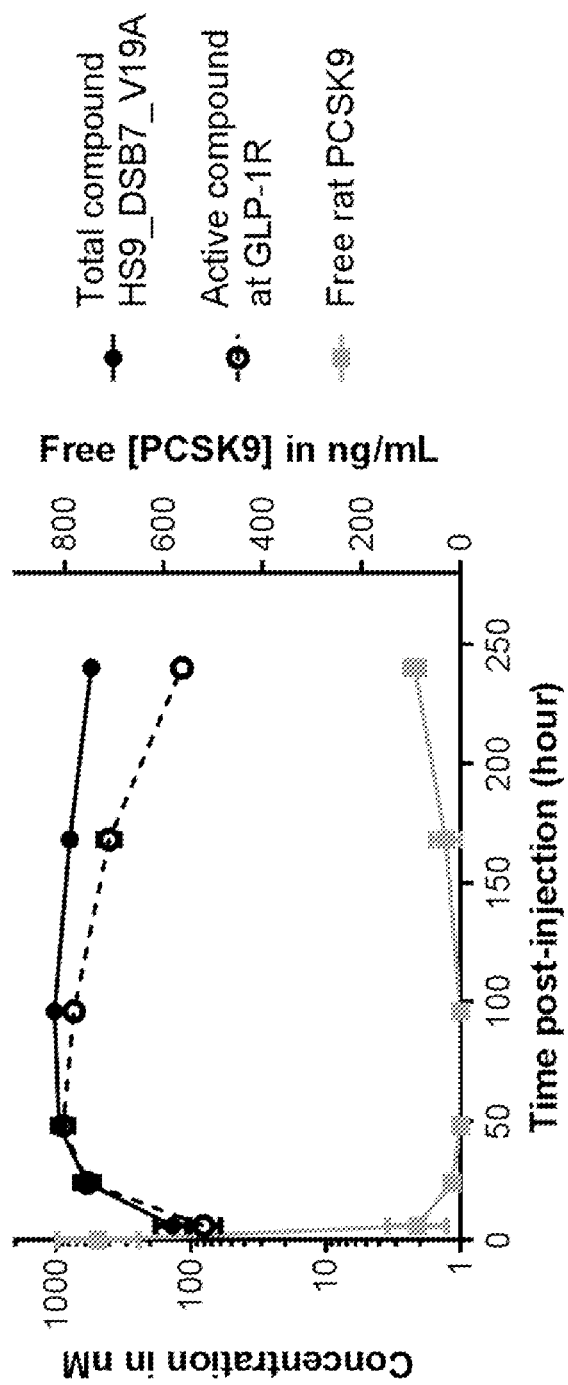
FIG. 39 shows total compound, active compound at GLP-1 receptor and free PCSK9 concentrations in rat following a single subcutaneous injection at 60 mg/kg of HS9_DSB7_V19A.

Total and active compound for HS9_DSB7_V19A and free rat PCSK9 concentrations are shown in FIG. 39. A maximum compound concentration of around 1000 nM was observed between 48 h and 96 h post-injection. Concentration in free rat PCSK9 is dropping sharply below the lower limit of quantification of the assay after compound injection and can be detected again at 168 h.

Area under curve (AUC) for both total and active compound were calculated and compared (Table 27) to model prediction using the data from the single intravenous dose injection described in Example 29. Fraction of absorption and absorption rate were set up to 75% and 0.3 $d^1$ respectively.

TABLE 27

Calculated and predicted Area Under Curve following a single SC injection of the fusion molecule HS9_DSB7_V19A

| | SC data 60 mg/kg | Predicted using IV data |
| --- | --- | --- |
| Exposure AUC0-t (day nmol) | 7815 | 8103 |
| Active GLP-1 AUC0-t (day nmol) | 5796 | 5739 |
| Active/Exposure AUC ratio | 0.74 | 0.71 |

Exposure and active GLP-1 AUC of HS9_DSB7_V19A after a single subcutaneous injection at 60 mg/kg are similar to those predicted using the single intravenous injection data. This demonstrates that a subcutaneous route of injection has no significant impact on in vivo compound stability compared to an intravenous route of administration.

Example 31. Rodent Pharmacology-Antidiabetic Effects of a GLP-1 Analogue Peptide in Fusion with an Anti-PCSK9 Antibody In order to confirm that the engineered nature of the GLP-1 analogue peptide portion of the HS9_DSB7_V19A fusion molecule retained antidiabetic activity in vivo, several; rodent pharmacology studies in normal, obese, and diabetic mouse models were performed.

A) Acute and Semi-Acute Effects of HS9_DSB7_V19A on Glucose Tolerance in C57B16 Mice A single dose of HS9_DSB7_V19A was administered subcutaneously in normal C57B16 mice at either 1 or 50 mg/kg. The efficacy of the GLP-1 analogue component of the fusion molecule was evaluated by multiple glucose challenges (oral glucose tolerance test) at 4, 48, and 168 hours post administration of HS9_DSB7_V19A. Anti-PCSK9 mAb HS9 without a GLP-1 analogue peptide fused to it was administered at 50 mg/kg as a negative control for glucose tolerance, while Liraglutide (Victoza) and a GLP-1 analogue-Fcγ4 fusion (similar to Dulaglutide) were administered at 0.2 and 1 mg/kg, respectively. Due to the short half-life of Liraglutide, this compound was administered 2 hours prior to each glucose challenge while the GLP-1 analogue-Fcγ4 fusion molecule was administered once, at the same time as the HS9_DSB7_V19A test compound.

30 male C57B16 mice from Taconic Denmark were acclimatized for five days before experimentation. On day −1 of the study, animals were randomized into 5 groups based on body weight.

Figure 40A:
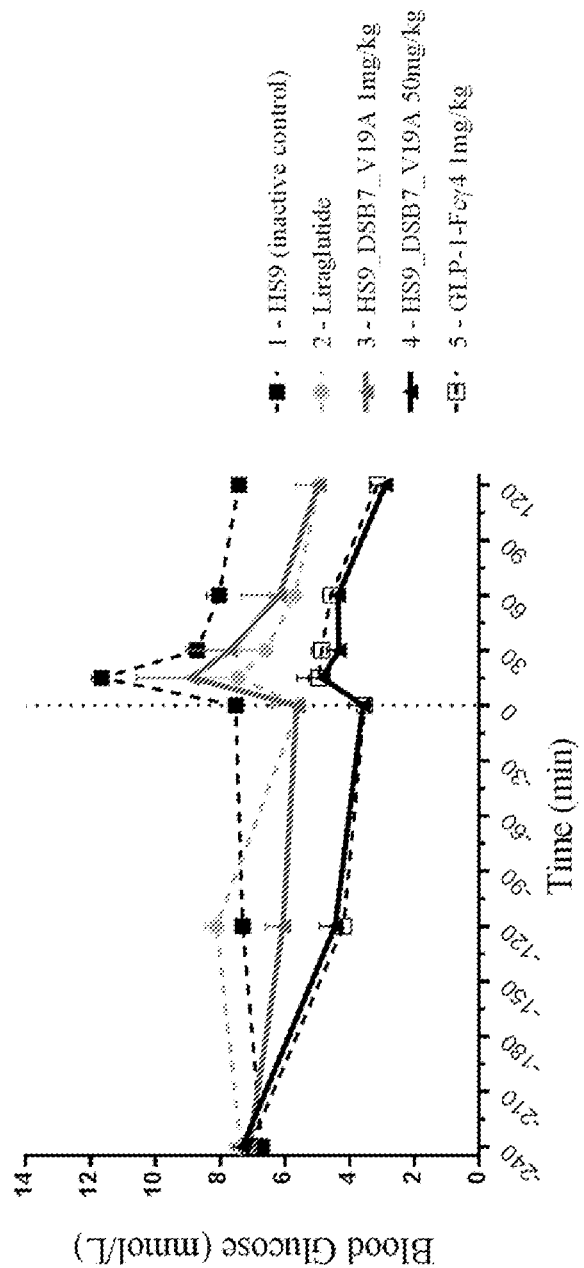
FIGS. 40A-C provides the results from oral glucose tolerance tests (day 0 (A), day 2 (B), day 7 (C), confirming the ability of a single, subcutaneous administration of HS9_DSB7_V19A.
Figure 40B:
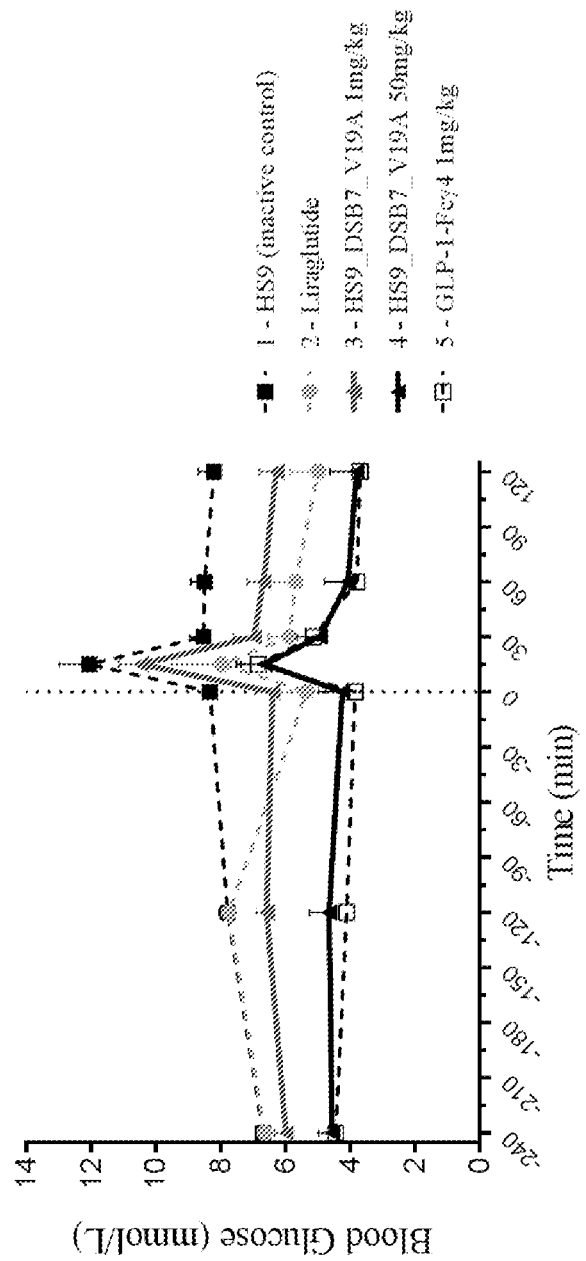
Figure 40C:
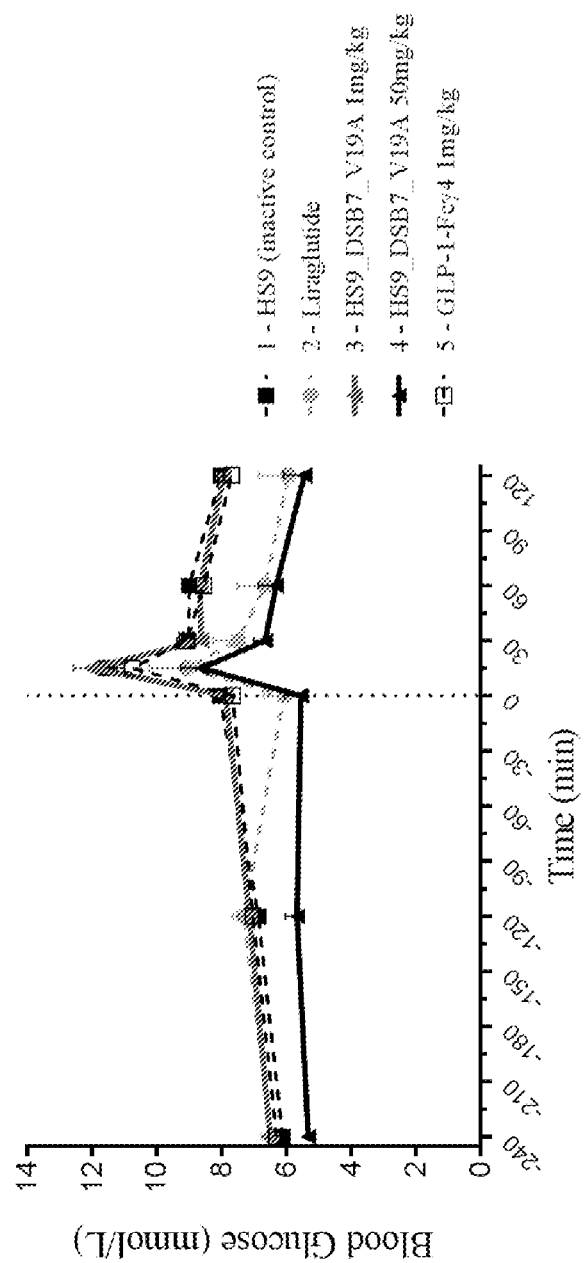

The experimental groups were as follows:

Group 1: Anti-PCSK9 mAb HS9 without GLP-1 analogue peptide component (negative control)—50 mg/kg subcutaneous dose Group 2: Liraglutide (positive control)—0.2 mg/kg subcutaneous dose Group 3: HS9_DSB7_V19A—1 mg/kg subcutaneous dose Group 4: HS9_DSB7_V19A—50 mg/kg subcutaneous dose Group 5: GLP-1 analogue-Fcγ4 fusion—1 mg/kg subcutaneous dose In order to assess efficacy of the GLP-1 analogue component of the fusion molecule over an extended period of time post dosing, 3 Oral Glucose Tolerance Tests (OGTT) were performed at days 0, 2 and 7. Animals were fasted for 4 hours prior to the oral glucose challenge(s). Both doses of HS9_DSB7_V19A, inactive control and GLP-1 analogue- Fcγ4 fusion were administered once, 4 hours prior to the Day 0 OGTT. Liraglutide (positive control) was administered 2 hours prior to each glucose challenge at days 0, day 2 and day 7. At t=0 mice all mice are challenged with an oral glucose load of 2 g/kg glucose. Blood glucose is measured at t=−240, −120 and 0 minutes to establish a baseline and at t=15, 30, 60 and 120 minutes to monitor effects on glucose excursion. The results of the day 0, 2 and 7 OGTTs are presented in FIGS. 40A-C (day 0 (A), day 2 (B), day 7 (C)).

This study confirms the ability of a single, subcutaneous administration of HS9_DSB7_V19A at 50 mg/kg to improve glucose tolerance in normal C57B16 mice for at least 7 days.

Figure 41:
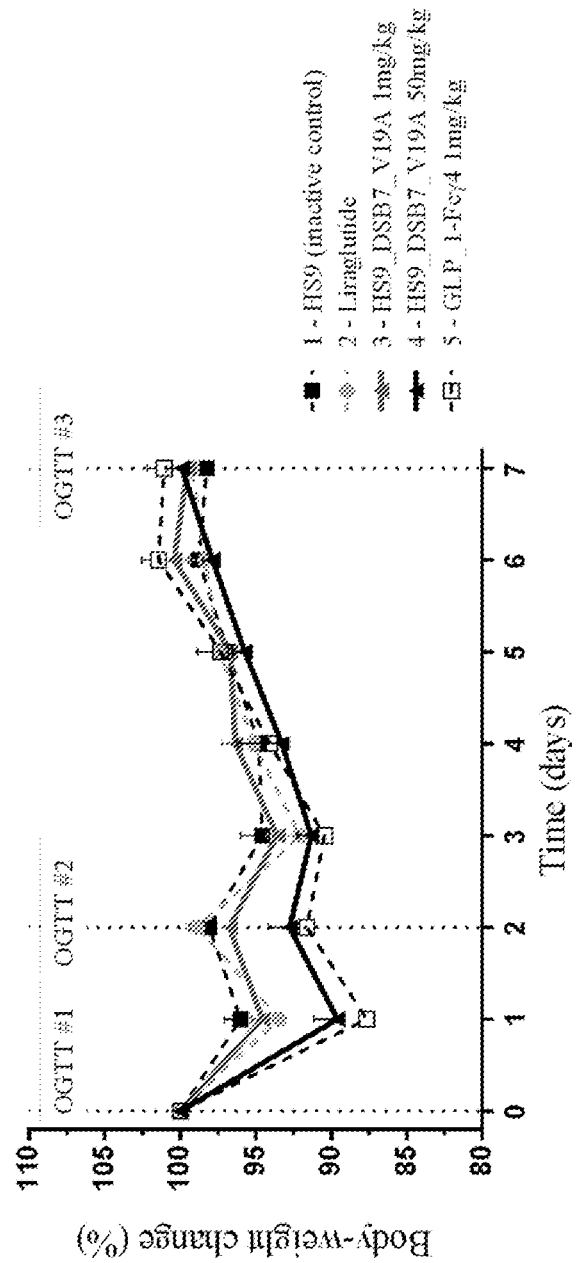
FIG. 41 shows body-weight change over time in the oral glucose tolerance test of FIGS. 40A-C.

As an additional measure of efficacy of the GLP-1 analogue component of the HS9_DSB7_V19A fusion molecule body weights of all were recorded once daily from day −3 to the end of the study. A single, subcutaneous administration of HS9_DSB7_V19A at 50 mg/kg induced a transient reduction in body weight at days 1 and 2. Percent bodyweight change over time is shown in FIG. 41.

B) Acute and semi-acute effects of HS9_DSB7_V19A on glucose tolerance in C57B16 mice-dose response In order to examine a dose response effect and to determine a maximally efficacious dose of HS9_DSB7_V19A on glucose tolerance and body weight reduction in normal C57B16 mice, a study similar in design to that described above was conducted with the following experimental groups and doses:

Group 1: Anti-PCSK9 mAb HS9 without GLP-1 analogue peptide component (negative control)—50 mg/kg subcutaneous dose Group 2: Liraglutide (positive control)—0.2 mg/kg subcutaneous dose Group 3: HS9_DSB7_V19A—10 mg/kg subcutaneous dose Group 4: HS9_DSB7_V19A—30 mg/kg subcutaneous dose Group 5: HS9_DSB7_V19A—60 mg/kg subcutaneous dose Group 6: GLP-1 analogue-Fcγ4 fusion—1 mg/kg subcutaneous dose On day −1 animals were randomized into these 6 groups based on body weight (n=6 animals per group). As previously, OGTTs were performed on Days 0, 2 and 7 and blood glucose was measured at t=−240, −120, 0, 15, 30, 60 and 120 minutes.

Figure 42A:
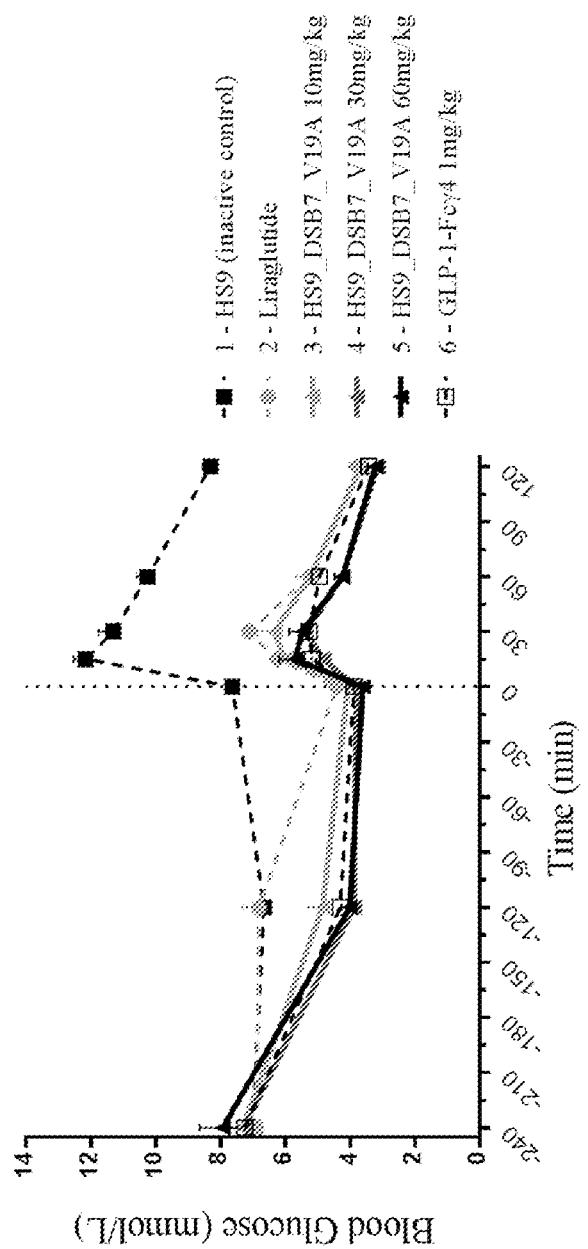
FIGS. 42A-C illustrates the results from oral glucose tolerance tests (day 0 (A), day 2 (B), day 7 (C).
Figure 42B:
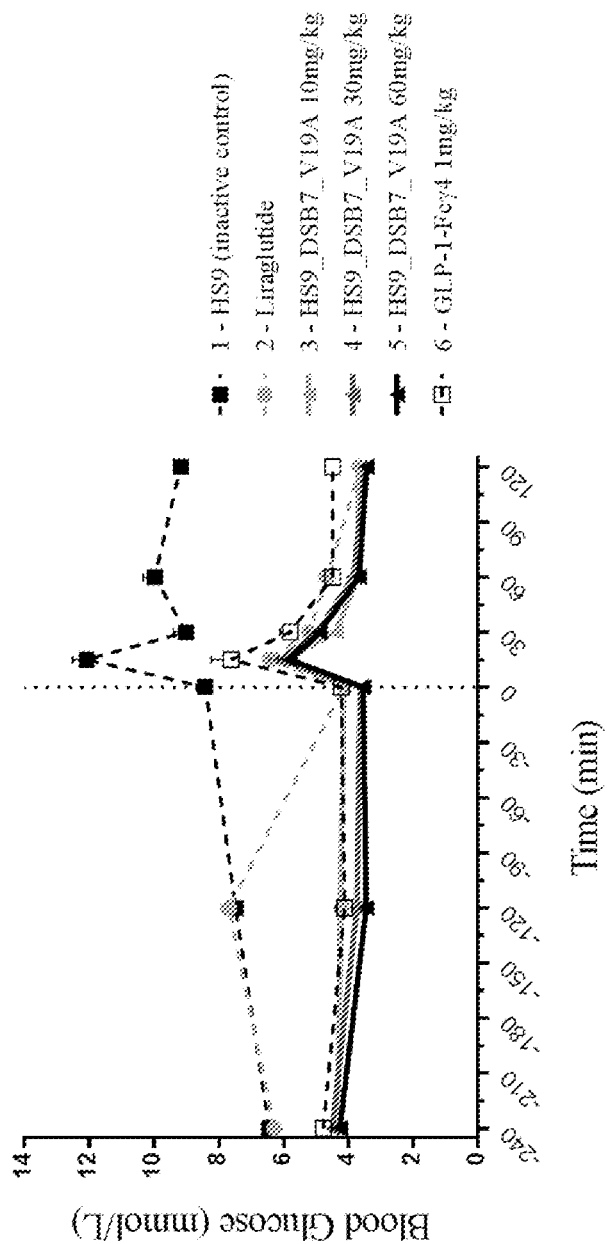
Figure 42C:
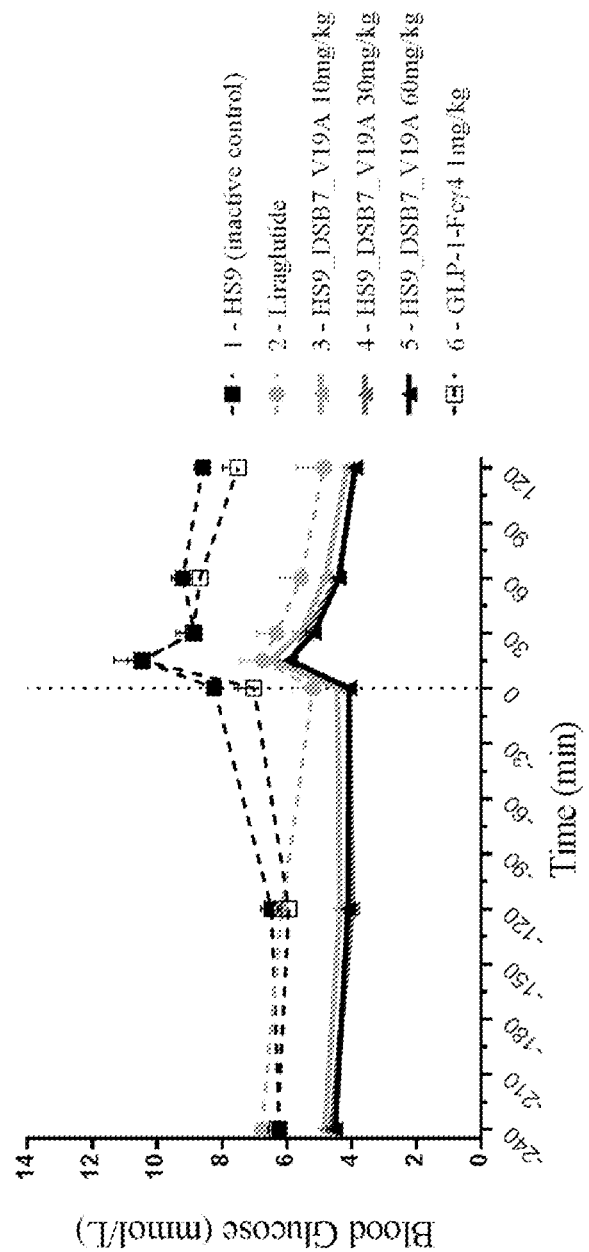

All three doses of HS9_DSB7_V19A resulted in similar levels of improved glucose tolerance at all three time points at which OGTTs were performed. FIGS. 42A-C illustrate the results from this oral glucose tolerance tests (day 0 (A), day 2 (B), day 7 (C)).

Figure 43:
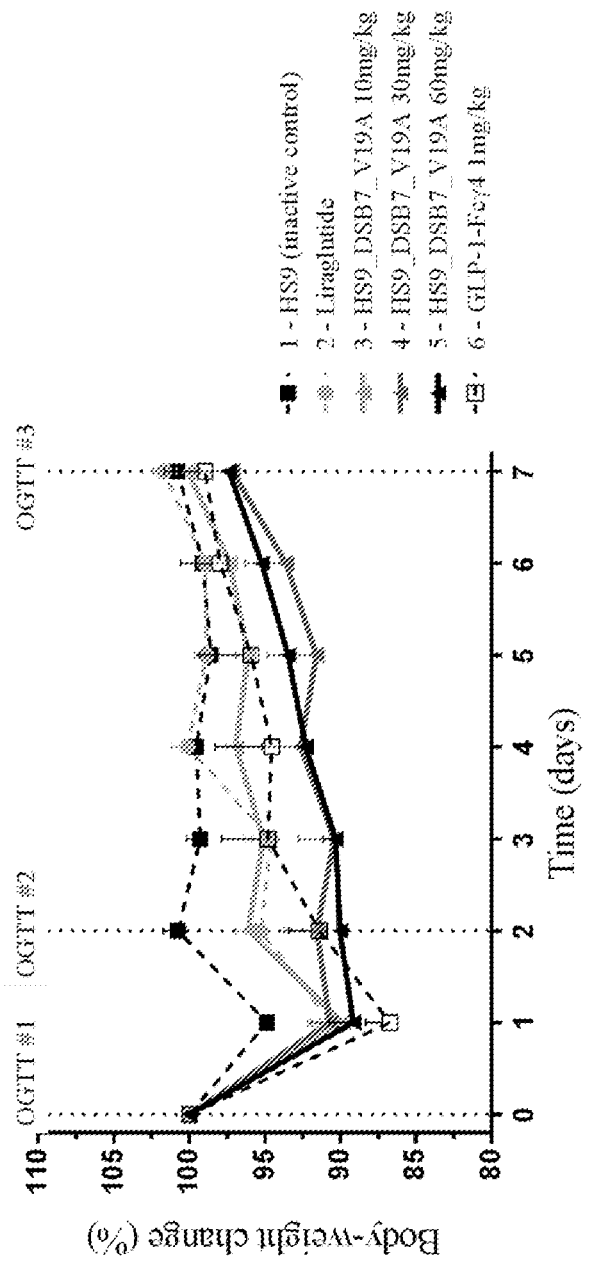
FIG. 43 provides body-weight change over time in the oral glucose tolerance test of FIGS. 42A-C.

In contrast to the lack of a dose response observed for improvements in glucose homeostasis, a clear dose-dependent effect on body weight reduction was observed in this study. FIG. 43.

In this experimental model a single 10 mg/kg dose of HS9_DSB7_V19A generated a maximally efficacious level of improvement in glucose homeostasis in an OGTT performed 7 days post administration while the same dose did not have a statistically significant effect on body weight reduction at any point during the study.

C) Chronic Metabolic Effects of HS9_DSB7_V19A in a Diabetic db/db Mouse Model

In order to confirm the chronic vivo efficacy of HS9_DSB7_V19A on several metabolic parameters in a diabetic model, db/db (leptin receptor deficient) mice were utilized to examine the effects of weekly administration of HS9_DSB7_V19A on fasting glucose, glucose tolerance, body weight reduction and body mass composition.

In this study we examined the chronic metabolic effects of HS9_DSB7_V19A upon weekly dosing via a subcutaneous route. The vehicle control group and the positive control GLP-1 analogue-Fcγ4 fusion molecule were subcutaneously dosed twice weekly. In order to match the number of dosing manipulations to all animals in the study, the groups receiving a weekly dose of HS9_DSB7_V19A were dosed with vehicle on the days the other animals received their second weekly dose of either vehicle (negative control) or positive control GLP-1 analogue-Fcγ4 fusion molecule.

60 male db/db mice from Charles River, Italy were primarily randomized on body weight and glycosylated hemoglobin (HbA1c) and secondarily on 4 hour fasting blood glucose. These animals were randomized into 5 groups (n=12) as follows:

Group 1: Vehicle control group (Phosphate Buffered Saline)—twice weekly (BIW) subcutaneous dosing Group 2: GLP-1 analogue-Fcγ4 fusion (positive control)—1 mg/kg subcutaneous dose—twice weekly subcutaneous dosing Group 3: HS9_DSB7_V19A—30 mg/kg subcutaneous dose—once weekly (QW)

Group 4: HS9_DSB7_V19A—10 mg/kg subcutaneous dose—once weekly (QW)

Group 5: HS9_DSB7_V19A—3 mg/kg subcutaneous dose—once weekly (QW)

The chronic study was run for 28 days post initial dose. Last dose of the BIW groups was on study day 24 whereas the last dose of the QW groups was on study day 21. The major efficacy endpoints of this study are body weight, fasting blood glucose, and glucose tolerance.

Body weight was measured three times weekly during the treatment period.

4 hour fasting blood glucose was measured once weekly at approximately 24 hours post dosing.

Glucose tolerance was measured on study day 22 at approximately 24 hours post dosing by Intraperitoneal glucose tolerance test (IPGTT). Animals were fasted for 4 hours before administration of a 1 g/kg glucose bolus. Blood glucose was measured at t=0, 15, 30, 60, 120, and 180 minutes.

Figure 44:
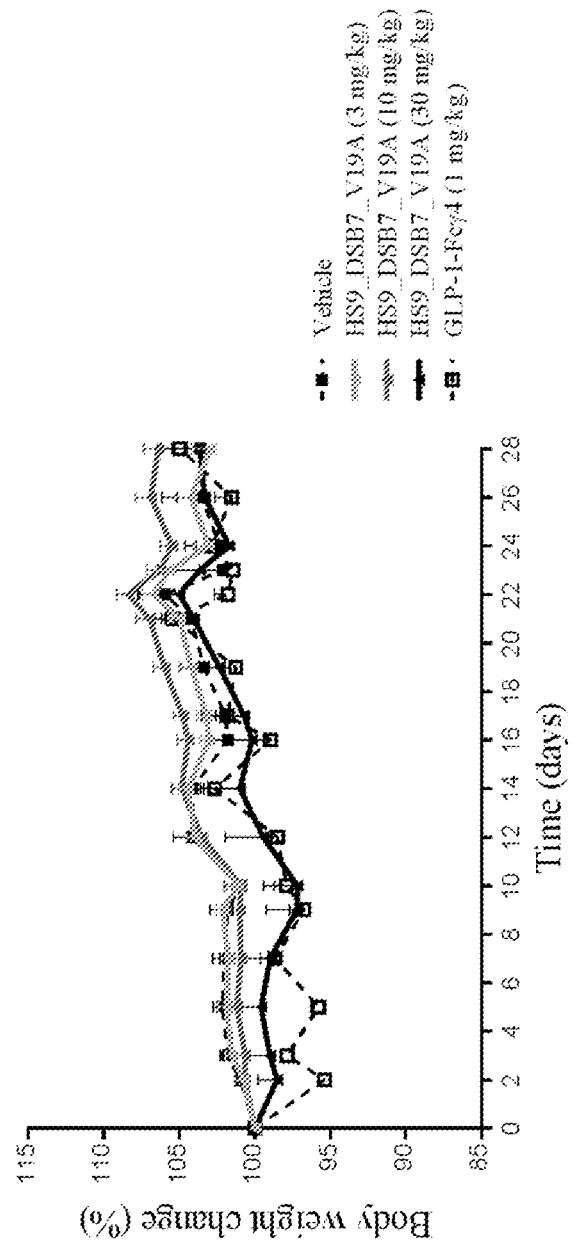
FIG. 44 shows body weight change in an intraperitoneal glucose tolerance test.

Body weight reduction in this study was not significant with the exception of one time point in the positive control GLP-1 analogue-Fcγ4 fusion molecule group. All three doses of HS9_DSB7_V19A did not result in a significant body weight reduction at any time during the course of the 28 day study. FIG. 44.

Figure 45:
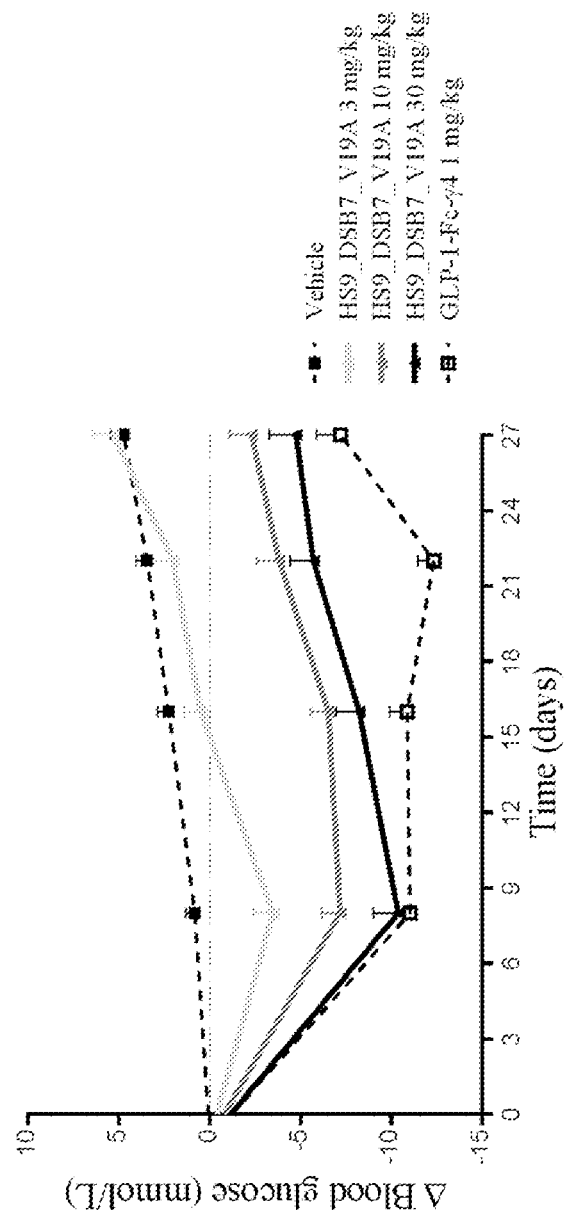
FIG. 45 demonstrates that weekly HS9_DSB7_V19A exhibited a dose dependent reduction in 4 hour fasting blood glucose compared to vehicle control in an intraperitoneal glucose tolerance test.

Weekly HS9_DSB7_V19A exhibited a dose dependent reduction in 4 hour fasting blood glucose as compared to vehicle control. FIG. 45.

Figure 46:
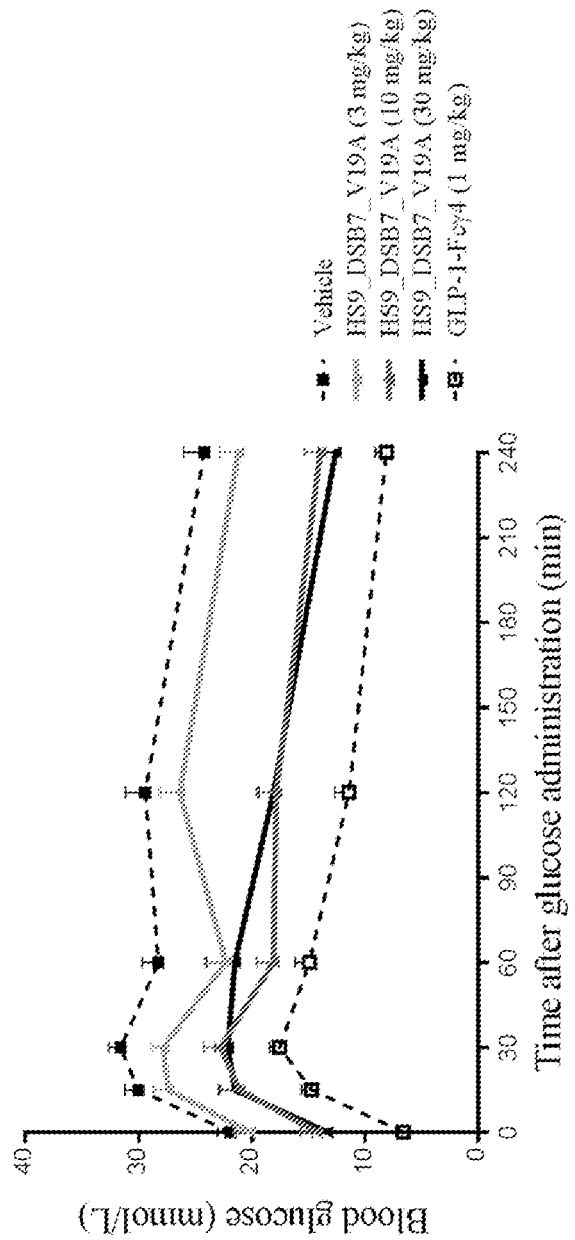
FIG. 46 shows that weekly dosed HS9_DSB7_V19A exhibited a dose dependent improvement in glucose tolerance as assessed by IPGTT at study day 22.

Weekly dosed HS9_DSB7_V19A exhibited a dose dependent improvement in glucose tolerance as assessed by IPGTT at study day 22. FIG. 46.

D) Acute effect of single dose HS9_DSB7_V19A on glucose tolerance in a Diet-Induced Obesity (DIO) mouse model A single dose of HS9_DSB7_V19A was administered subcutaneously in Diet-induced obese (DIO) mice at 0.1, 1 or 10 mg/kg. The efficacy of the GLP-1 analogue component of the fusion molecule was evaluated by separate glucose challenges (intraperitoneal glucose tolerance test) at 4 and 168 hours post administration of HS9_DSB7_V19A. Anti-PCSK9 mAb HS9 without a GLP-1 analogue peptide fused to it was administered once at 10 mg/kg as a negative control for effects on glucose tolerance. As a positive control, the GLP-1 analogue-Fcγ4 fusion (similar to Dulaglutide) used in the previous experiments was administered at 1 mg/kg twice weekly (BIW). In order to simulate the dosing regimen of the positive control GLP-1 analogue-Fcγ4 fusion, all animals in the negative control group and the HS9_DSB7_V19A experimental groups were dosed with vehicle BIW. The study duration was for 21 days following the first dose. Primary endpoint was effects on glucose tolerance in IPGTT on day 0 (4 hours post dose) and Day 7. Secondary endpoint was body weight reduction.

50 Male, 21 week old DIO mice on 60% high fat diet for 15 weeks prior to study start were obtained from Jackson labs (JAX: 380050). Just prior to study start, animals were randomized into 5 groups based on body weight.

The experimental groups (n=10 per group) were as follows:

Group 1: Anti-PCSK9 mAb HS9 without GLP-1 analogue peptide component (negative control)—10 mg/kg subcutaneous dose—single dose Group 2: HS9_DSB7_V19A—0.1 mg/kg subcutaneous dose—single dose Group 3: HS9_DSB7_V19A—1 mg/kg subcutaneous dose—single dose Group 4: HS9_DSB7_V19A—10 mg/kg subcutaneous dose—single dose Group 5: GLP-1 analogue-Fcγ4 fusion—1 mg/kg subcutaneous dose—twice weekly dosing (BIW)

In order to assess efficacy of the GLP-1 analogue component of the fusion molecule over an extended period of time post dosing, two Intraperitoneal Glucose Tolerance Tests (IPGTT) were performed at days 0 and 7. Animals were fasted for 6 hours prior to the IP glucose challenge(s). All three doses of HS9_DSB7_V19A, inactive control and GLP-1 analogue-Fcγ4 fusion were administered once, 4 hours prior to the Day 0 OGTT. The GLP-1 analogue-Fcγ4 fusion was administered on days 0, 3, 7, 10, 14 17 and 21. On day 0 all groups were dosed with test compounds 4 hours prior to the IP glucose challenge while on day 7 the GLP-1 analogue-Fcγ4 fusion was administered 4 hours prior to the IP glucose challenge while all other groups were dosed with vehicle only. For each day in which IPGTTs were performed, at t=0 mice all mice were challenged with an IP glucose load of 1.5 g/kg glucose. Blood glucose was measured at t=−240 and 0 minutes to establish a baseline and at t=15, 30, 45, 60, 90 and 120 minutes to monitor effects on glucose excursion.

The results of the day 0 and 7 IPGTTs are presented in FIGS. 47A-B.

In order to assess effects of the GLP-1 component of HS9_DSB7_V19A on body weight, all animals were weighed daily for the entire course of the study. Effects on body weight are presented in 48A-B.

E) Effects of multiple doses of HS9_DSB7_V19A on body weight in DIO mice.

In order to establish a dose-response in body weight reduction HS9_DSB7_V19A was administered subcutaneously to diet-induced obese mice at 3, 10 and 30 mg/kg once weekly (QW). The duration of the study was 28 days and primary endpoint was body weight reduction. Secondary evaluation of glycemic parameters included analyses included fed glucose throughout the course of the study and measurements of terminal fasting glucose. As in our previous studies in both DIO and db/db mice, the GLP-1 analogue-Fcγ4 fusion was administered subcutaneously, twice weekly (BIW) at 1 mg/kg as a positive control for both glucose control and body weight loss.

Male, 21 week old DIO mice on 60% high fat diet for 15 weeks prior to study start were obtained from Jackson labs (JAX: 380050). Just prior to study start, animals were randomized into 5 groups based on body weight (n=8 animals per group).

The experimental groups (n=8 per group) were as follows:

Group 1: Vehicle control

Group 2: HS9_DSB7_V19A—3 mg/kg subcutaneous dose—once weekly (QW)

Group 3: HS9_DSB7_V19A—10 mg/kg subcutaneous dose—once weekly (QW)

Group 4: HS9_DSB7_V19A—30 mg/kg subcutaneous dose—once weekly (QW)

Group 5: GLP-1 analogue-Fcγ4 fusion—1 mg/kg subcutaneous dose—twice weekly dosing (BIW)

Figure 49:
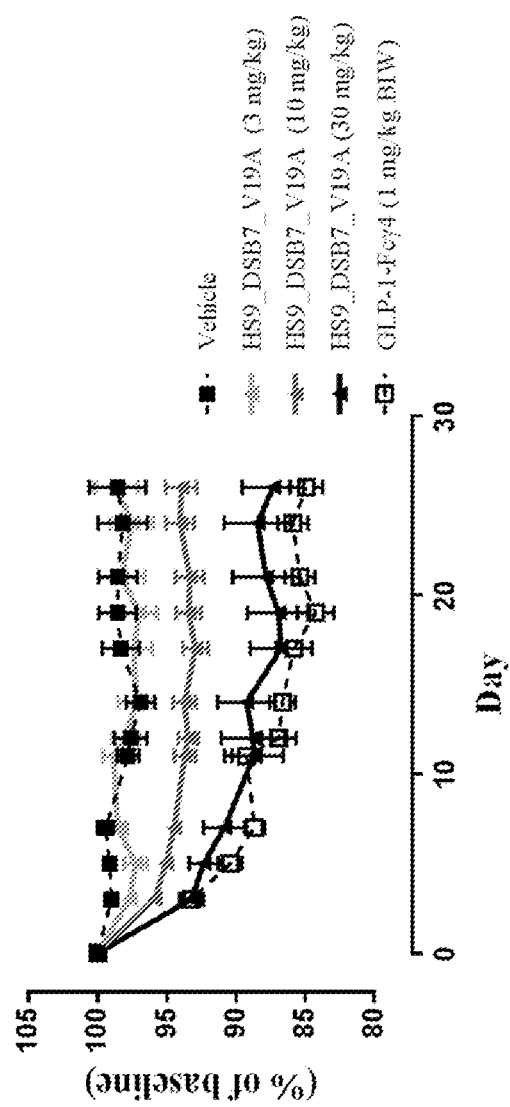
FIG. 49 shows the change in body weight over time in a multiple dose study with HS9_DSB7_V19A.

In order to assess effects of the GLP-1 component of HS9_DSB7_V19A on body weight (the primary endpoint of this study), all animals were weighed daily for the entire course of the study. Effects on body weight are presented in FIG. 49.

As a secondary endpoint and in order to assess effects of the GLP-1 component of HS9_DSB7_V19A on glycemic control in a weekly dose setting, fed glucose was measured at days 0, 7, 11, 14, 21 and 26 and fasting glucose was measured at just prior to study termination (day 28). Results are presented in FIGS. 50A-B.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiments may be practiced in many ways and the claims include any equivalents thereof.

What is claimed is:

1. A dual active fusion molecule for the treatment of diabetes comprising an anti-PCSK9 antibody stably fused to a GLP-1 peptide, wherein the anti-PCSK9 antibody binds a PCSK9 polypeptide and the GLP-1 peptide binds a GLP-1 receptor.

2. The fusion molecule of claim 1, wherein the GLP-1 peptide comprises the amino acid sequence of SEQ ID NO: 3.

3. A method of treating Type 2 Diabetes, cardiovascular disease or metabolic syndrome comprising administering to a subject in need thereof, a fusion molecule of claim 1.

4. A method of promoting weight loss, controlling glucose or reducing LDL in a subject comprising administering to a subject in need thereof, a fusion molecule of claim 1.

5. An isolated polynucleotide encoding the fusion molecule of claim 1.

6. A vector comprising the polynucleotide of claim 5.

7. A host cell comprising the polynucleotide of claim 5.

8. A method of making a fusion molecule, comprising culturing the host cell of claim 7 under conditions allowing expression of the fusion molecule, and recovering the fusion molecule.

9. A pharmaceutical composition comprising the fusion molecule of claim 1, and a carrier.

10. A kit comprising the composition of claim 9.

11. A dual active fusion molecule for the treatment of diabetes comprising an anti-PCSK9 antibody stably fused to a GLP-1 peptide comprising the amino acid sequence of SEQ ID NO: 3, wherein the C-terminus of the GLP-1 peptide is fused via a peptide linker to the anti-PCSK9 antibody, and wherein the anti-PCSK9 antibody binds a PCSK9 polypeptide and the GLP-1 peptide binds a GLP-1 receptor.

12. A dual active fusion molecule comprising an anti-PCSK9 antibody stably fused to a GLP-1 peptide comprising the amino acid sequence of SEQ ID NO: 3, wherein the C-terminus of the GLP-1 peptide is fused via a peptide linker to the anti-PCSK9 antibody, and wherein the anti-PCSK9 antibody binds a PCSK9 polypeptide and the GLP-1 peptide binds a GLP-1 receptor.

13. The dual active fusion molecule of claim 12, wherein the GLP-1 peptide is fused via a peptide linker to the light chain of the anti-PCSK9 antibody.

14. The dual active fusion molecule of claim 13, wherein the light chain of the anti-PCSK9 antibody is at least 90% identical to the amino acid sequence of SEQ ID NO: 2.

15. The dual active fusion molecule of claim 14, wherein the light chain of the anti-PCSK9 antibody comprises the amino acid sequence of SEQ ID NO: 2.

16. The dual active fusion molecule of claim 12, wherein the GLP-1 peptide is fused via a peptide linker to the heavy chain of the anti-PCSK9 antibody.

17. The dual active fusion molecule of claim 16, wherein the heavy chain of the anti-PCSK9 antibody is at least 90% identical to the amino acid sequence of SEQ ID NO: 1.

18. The dual active fusion molecule of claim 17, wherein the heavy chain of the anti-PCSK9 antibody comprises the amino acid sequence of SEQ ID NO: 1.

19. The dual active fusion molecule of claim 12, wherein the light chain of the anti-PCSK9 antibody comprises the amino acid sequence of SEQ ID NO: 2 and the heavy chain of the anti-PCSK9 antibody comprises the amino acid sequence of SEQ ID NO: 1.

20. A dual active fusion molecule for the treatment of diabetes comprising an anti-PCSK9 antibody stably fused to a GLP-1 peptide that has reduced potency at the human GLP-1 receptor compared to a GLP-1 peptide comprising the amino acid sequence of SEQ ID NO: 28 or SEQ ID NO: 29, wherein the C-terminus of the GLP-1 peptide is fused via a peptide linker to the anti-PCSK9 antibody, and wherein the anti-PCSK9 antibody binds a PCSK9 polypeptide and the GLP-1 peptide binds a GLP-1 receptor.

\* \* \* \* \*